United States Patent [19]
Bernstein et al.

[11] Patent Number: 5,521,179
[45] Date of Patent: May 28, 1996

[54] HETEROCYCLIC AMIDES

[75] Inventors: Peter R. Bernstein, Wallingford; Andrew Shaw, Kennett Square, both of Pa.; Royston M. Thomas; Peter Warner, both of Macclesfield, England; Donald J. Wolanin, Orange, Conn.

[73] Assignee: Zeneca Limited, London, England

[21] Appl. No.: 45,009

[22] Filed: Apr. 8, 1993

Related U.S. Application Data

[63] Continuation-in-part of Ser. No. 869,993, Apr. 16, 1992, abandoned.

[30] Foreign Application Priority Data

| Apr. 18, 1991 | [GB] | United Kingdom | 9108357 |
| Apr. 18, 1991 | [GB] | United Kingdom | 9108358 |
| Mar. 12, 1992 | [GB] | United Kingdom | 9205392 |
| Apr. 16, 1992 | [GB] | United Kingdom | 9208379 |
| Apr. 16, 1992 | [GB] | United Kingdom | 9208380 |
| Jul. 8, 1992 | [GB] | United Kingdom | 9214448 |
| Aug. 14, 1992 | [GB] | United Kingdom | 9217362 |
| Aug. 14, 1992 | [GB] | United Kingdom | 9217363 |
| Aug. 14, 1992 | [GB] | United Kingdom | 9217364 |

[51] Int. Cl.$^6$ ............... C07D 237/00; C07D 211/72; C07D 401/00; C07D 215/14

[52] U.S. Cl. ............... 514/235.5; 546/24; 546/193; 546/282.1; 546/282.4; 546/284.4; 546/284.7; 546/283.4; 546/23; 546/272.7; 546/174; 546/175; 546/256; 546/268.4; 546/271.4; 546/271.7; 546/269.7; 546/270.7; 546/270.4; 546/274.1; 546/274.4; 546/292; 546/291; 546/274.7; 546/277.1; 546/278.7; 546/278.4; 546/277.4; 546/277.7; 546/278.1; 546/279.1; 546/281.4; 514/236.8; 514/247; 514/346; 514/349; 544/224; 544/360; 544/362

[58] Field of Search ........................... 546/292, 797, 546/174, 175, 270, 271, 273, 275, 276, 277, 278, 280, 281, 283, 284; 544/224, 360, 362; 514/235.5, 236.8, 247, 346, 349

[56] References Cited

U.S. PATENT DOCUMENTS

| 4,474,778 | 10/1984 | Gordon et al. | 546/297 |
| 4,910,190 | 3/1990 | Bergeson et al. | 546/297 |

FOREIGN PATENT DOCUMENTS

| 0189305A2 | 7/1986 | European Pat. Off. . |
| 0369391 | 5/1990 | European Pat. Off. . |
| 0509769A2 | 10/1992 | European Pat. Off. . |
| 0528633A1 | 2/1993 | European Pat. Off. . |

OTHER PUBLICATIONS

B. Imperali & R. H. Abeles "Inhibition of Serine Preteases by Peptidyl Fluoromethyl Ketones" *Biochemistry* (1986), 25, 3760–3767.

C. P. Sommerhoff et al "Inhibition of Human Neutrophil Elastase by ICI 200,355" *European Journal of Pharmacology*, (1991), 193, 153–158.

*Primary Examiner*—C. Warren Ivy
*Assistant Examiner*—Raymond Compton
*Attorney, Agent, or Firm*—Michael D. Alexander; Ruth H. Newtson; Robert J. Harris

[57] ABSTRACT

The present invention relates to certain novel heterocyclic amides which are 1-pyridylacetamide compounds of formula I, set out herein, which are inhibitors of human leukocyte elastase (HLE), also known as human neutrophil elastase (HNE), making them useful whenever such inhibition is desired, such as for research tools in pharmacological, diagnostic and related studies and in the treatment of diseases in mammals in which HLE is implicated. The invention also includes intermediates useful in the synthesis of these heterocyclic amides, processes for preparing the heterocyclic amides, pharmaceutical compositions containing such heterocyclic amides and methods for their use.

14 Claims, No Drawings

HETEROCYCLIC AMIDES

This application is a continuation-in-part of U.S. Ser. No. 07/869,993, filed Apr. 16, 1992, now abandoned.

The present invention relates to certain heterocyclic amides, in particular, certain 1-pyridylacetamide compounds, which are inhibitors of human leukocyte elastase (HLE), also known as human neutrophil elastase (HNE), making them useful whenever such inhibition is desired, such as for research tools in pharmacological, diagnostic and related studies and in the treatment of diseases in mammals in which HLE is implicated. For example, HLE has been implicated in the pathogenesis of acute respiratory distress syndrome (ARDS), rheumatoid arthritis, atherosclerosis, pulmonary emphysema, and other inflammatory disorders, including airway inflammatory diseases characterized by increased and abnormal airway secretion such as chronic bronchitis and cystic fibrosis. Also, HLE has been implicated in certain vascular diseases and related conditions (and their therapy) in which neutrophil participation is involved or implicated, for example, in hemorrhage associated with acute non-lymphocytic leukemia, as well as in reperfusion injury associated with, for example, myocardial ischaemia and related conditions associated with coronary artery disease such as angina and infarction, cerebrovascular ischaemia such as transient ischaemic attack and stroke, peripheral occlusive vascular disease such as intermittent claudication and critical limb ischaemia, venous insufficiency such as venous hypertension, varicose veins and venous ulceration, as well as impaired reperfusion states such as those associated with reconstructive vascular surgery, thrombolysis and angioplasty. The invention also includes intermediates useful in the synthesis of these heterocyclic amides, processes for preparing the heterocyclic amides, pharmaceutical compositions containing such heterocyclic amides and methods for their use.

In U.S. Pat. No. 4,910,190, of Mar. 20, 1990, assigned to ICI Americas Inc. (now ZENECA Inc.), there is disclosed a series of peptidoyl trifluoromethane derivatives which are HLE inhibitors. Disclosed herein is a series of substituted 2-(2-oxo-1,2-dihydro-1-pyridyl)-N-[ 3,3,3-trifluoro-1-(lower alkyl)-2-oxopropyl]acetamide derivatives, which unexpectedly possess inhibitory properties against HLE, which provides the basis for the present invention.

According to the invention there is provided a Compound of the invention which is a compound of formula I (formula set out, together with other formulae referred to by Roman numerals, following the Examples) wherein:

$R^0$ is (1–5C)alkyl;

R is hydrogen; or

R is an acyl group of formula A.X.CO— in which A.X—, taken together, is hydrogen, trifluoromethyl, 2,2,2-trifluoroethoxy, amino, methoxyamino, 2,2,2-trifluoroethylamino, RbRcN.O—, RaOCONH—, $R^1SO_2NH$—, RaOCO—, RbRcNCO— or RaCO—; or R is an acyl group of formula A.X.C(—J)— in which J is oxygen or sulfur;

X is a direct bond, imino, oxy or thio; and

A is as defined below or

A is tetrahydropyran-4-yl, 1-methylpiperid-4-yl, or 5-methyl-1,3-dioxacyclohex-5-ylmethyl; or R is a sulfonyl group of formula $D.W.SO_2$— in which D.W—, taken together, is hydroxy, amino, di(lower alkyl)amino, 2,2,2-trifluoroethylamino, 2,2,2-trifluoroethyl, 3,3,3-trifluoropropyl or trifluoromethyl; or W is a direct bond, imino, carbonylimino, oxycarbonylimino or iminocarbonylimino; and D is as defined below; or R is a group G as defined below;

The group A, D or G is (1–6C)alkyl, (3–6C)cycloalkyl, (3–6C)cycloalkyl-(1–3C)alkyl, aryl, aryl(1–3C)alkyl, heteroaryl or heteroaryl(1–3C)-alkyl wherein an aryl or heteroaryl moiety may bear one or more halogeno, nitro, methyl or trifluoromethyl groups and further wherein the group A, D or G may bear one or more substituents selected from a group consisting of hydroxy, lower alkoxy, lower acyloxy, COORa, $CH_2$COORa, CONRbRc, $CH_2$CONRbRc, $COO(CH_2)_2$NReRf, cyano, $SO_2R^1$, $CONRdSO_2R^1$, NReRf, NRgCHO, $NRgCOR^2$, $NRgCOOR^2$, NRhCQNRiRj, $NRkSO_2R^3$, $SO_2$NRlRm, $SO_2$NRnCOR$^4$ and $P(O)(ORa)_2$ in which Q is oxygen or sulfur;

Ra–Rn are independently hydrogen, benzyl or lower alkyl; or, independently, a group NRbRc, NReRf, NRiRj or NRlRm is a cyclic radical selected from a group consisting of 1-pyrrolidinyl, piperidino, morpholino or 1-piperazinyl which may bear a lower alkyl substituent at the 4-position; or, independently, a group NReRf is a cyclic radical selected from a group consisting of 2-pyrrolidinon-1-yl, succinimido, oxazolidin-2-on-3-yl, 2-benzoxazolinon-3-yl, phthalimido and cis-hexahydrophthalimido; and $R^1$–$R^4$ are independently trifluoromethyl, (1–6C)alkyl, (3–6C)cycloalkyl, aryl or heteroaryl in which the aryl or heteroaryl may bear one or more substituents selected from a group consisting of lower alkyl, hydroxy, lower alkoxy, halogeno or trifluoromethyl; and Each of $R^5$ and $R^6$ is, independently, hydrogen or lower alkyl; or One of $R^5$ and $R^6$ is hydrogen or methyl and the other of $R^5$ and $R^6$ is a radical of formula B.Y— in which B is aryl or heteroaryl, which aryl or heteroaryl independently may bear one or more of the substituents defined for A, D or G or an aryl or heteroaryl moiety thereof;

Y is a direct bond, methylene, ethylene or trans-vinylene;

provided that no aliphatic carbon is bonded to more than one nitrogen or oxygen, except as part of a cyclic ketal or where the nitrogen bears a carbonyl group; or, for a compound of formula I which is acidic or basic, a pharmaceutically acceptable salt thereof.

In this specification, the following definitions are used, unless otherwise described: Halogeno is fluoro, chloro, bromo or iodo. Alkyl, alkoxy, etc. denote botch straight and branched groups; but reference to an individual radical such "propyl" embraces only the straight chain ("normal") radical, a branched chain isomer such as "isopropyl" being specifically referred to. Lower alkyl and lower alkoxy refer to radicals containing one to about four carbon atoms. Lower acyloxy refers to a radical containing one to about five carbon atoms. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms selected from the group consisting of oxygen, sulfur and nitrogen, as well as a radical of an ortho-fused bicyclic heterocycle of about eight to ten ring atoms derived therefrom, particularly a benz-derivative or one derived by fusing a propenylene, trimethylene or tetramethylene diradical thereto, as well as a stable N-oxide thereof.

It will be appreciated that, owing to the asymmetrically substituted carbon atom at the chiral center indicated by "*" in formula I, a compound of formula I may exist in, and be isolated in, optically active and racemic forms. If a compound of formula I contains an additional chiral element, such compound of formula I may exist in, and be isolated in, the form of a diastereomeric mixture or as a single diastereomer. It is to be understood that the present invention encompasses a compound of formula I as a mixture of diastereomers, as well as in the form of an individual diastereomer, and that the present invention encompasses a compound of formula I as a mixture of enantiomers, as well as in the form of an individual enantiomer. When $R^o$ is isopropyl, a compound of formula I may be viewed as a valyl trifluoromethane derivative. In general, a compound of formula I having the (S)-configuration at the chiral center indicated by "*" which corresponds to the L-alanyl configuration, is preferred as more potent than the corresponding (R)-isomer. Accordingly, it may be preferred to use the compound of formula I in a form which is characterized as containing, for example, at least 95%, 98% or 99% enantiomeric excess (ee) of the (S)-form. However, owing to the interconvertability of the (S)-isomer and the (R)-isomer by the facile epimerization of the chiral center indicated by "*" in formula I, it may be preferred to utilize a compound of formula I as a mixture of the (S)- and (R)-isomers at the center indicated by "*" in formula I.

As will be appreciated by those skilled in the art, a trifluoromethyl ketone of formula I can exist as a solvate, particularly a hydrate; and such a solvate of a compound of formula I is encompassed by the present invention.

A compound of formula I may exhibit polymorphism. The compound may form solvates in addition to a ketone solvate mentioned above. A compound may exist in more than one tautomeric form. It is to be understood, therefore, that the present invention encompasses any racemic or optically-active form, any polymorphic form, any tautomer or any solvate, or any mixture thereof, which form possesses inhibitory properties against HLE, it being well known in the art how to prepare optically active forms (for example, by resolution of the racemic form or by synthesis from optically-active starting materials) and how to determine the inhibitory properties against HLE by the standard tests described hereinafter.

It is preferred that the radicals $R^o$, R, $R^5$ and $R^6$ not contain nor introduce an additional element of chirality into the molecule beyond the chiral center indicated by "*" in formula I.

Particular values are listed below for radicals, substituents and ranges for illustration only and they do not exclude other defined values or other values within defined ranges for the radicals and substituents.

A particular value for $R^o$ is ethyl or isopropyl.

A particular value for D.W—, taken together, is amino, 2,2,2-trifluoroethylamino or 2,2,2-trifluoroethyl.

A particular value for W is a direct bond or imino.

A particular value for G is (1–3C)alkyl, aryl(1–C)alkyl or heteroaryl(1–2C)alkyl which may bear one or more substituents as defined above for G or a part thereof,.

A particular value of (1–6C)alkyl is methyl, ethyl, propyl, isopropyl, butyl, isobutyl, t-butyl, pentyl, 3-methylbutyl, 1-ethylpropyl, hexyl or 4-methylpentyl. A particular value of (3–6C)cycloalkyl is cyclopropyl, cyclopentyl or cyclohexyl. A particular value for the (1–3C)alkyl portion of (3–6C)cycloalkyl-( 1–3C)alkyl, aryl(1–3C)alkyl or heteroaryl(1–3C)alkyl is methylene, ethylene or trimethylene. A particular value for aryl is phenyl, indenyl or naphthyl. A particular value for heteroaryl is furyl, imidazolyl, tetrazolyl, pyridyl (or its N-oxide), thienyl, pyrimidinyl (or its N-oxide), endolyl, quinalyl (or its N-oxide), thiozolyl or pyarzinl. A particular value for lower alkyl is methyl, ethyl, propyl, isopropyl, butyl, isobutyl or t-butyl. A particular value for lower acyloxy is acetoxy. A particular value for lower alkoxy is methoxy, ethoxy, propoxy, isoproxy or t-butoxy. A particular value for halogeno is bromo, chloro or fluoro.

A particular value for COORa is carboxy or methoxycarbonyl. A particular value for CONRbRc is carbamoyl or N,N-dimethylcarbamoyl. A particular value for NRgCHO is formylamino. A particular value for $NRgCOR^2$ is acetylamino or trifluoroacetylamino. A particular value of $CONRdSO_2R^1$ is N-phenylsulfonylcarbamoyl or N-(4-chlorophenylsulfonyl)carbamoyl.

A more particular value for $R^o$ is isopropyl. A more particular value for J is oxygen. A more particular value for X is a direct bond, imino or oxy. A more particular value for A is methyl, ethyl, phenyl, benzyl, phenethyl, pyridyl, thienyl, 5-tetrazolyl, thiazolyl, pyridylmethyl, thenyl, 5-tetrazolylmethyl, 2-(pyridyl)ethyl, 2-(thienyl)ethyl or 2-(thiazolyl)ethyl wherein the phenyl or heteroaryl group may bear one or two halogeno or methyl groups and further wherein the group A may bear a substituent selected from hydroxy, methoxy, t-butoxy, acetoxy, pivaloyloxy, carboxy, methoxycarbonyl, ethoxycarbonyl, carbamoyl, dimethylcarbamoyl, 2-(dimethylamino)ethoxycarbonyl, cyano, methylsulfonyl, phenylsulfonyl, N-methylsulfonylcarbamoyl, N-phenylsulfonylcarbamoyl, amino, dimethylamino, oxazolidin-2-on-3-yl, acetylamino, trifluoroacetylamino, ureido, methylsulfonyl, sulfamoyl, dimethylphosphoryl or diethylphosphoryl. A more particular value for D is methyl, ethyl, isopropyl, tert-butyl, cyclohexyl, phenyl, benzyl, phenethyl, pyridyl, thienyl, 5-tetrazolyl, thiazolyl, quinolyl, pyridylmethyl, thenyl, 5-tetrazolylmethyl, 2-(pyridyl)ethyl, 2-(thienyl)ethyl or 2-(thiazolyl)ethyl wherein the phenyl or heteroaryl group may bear one or two halogeno or methyl groups and further wherein the group D may bear a substituent selected from hydroxy, methoxy, t-butoxy, acetoxy, pivaloyloxy, carboxy, methoxycarbonyl, ethoxycarbonyl, carbamoyl, dimethylcarbamoyl, 2-(dimethylamino)ethoxycarbonyl, cyano, methylsulfonyl, phenylsulfonyl, N-methylsulfonylcarbamoyl, N-phenylsulfonylcarbamoyl, N-(4-chlorophenylsulfonyl)carbamoyl, methylsulfonylamino, amino, dimethylamino, oxazolidin-2-on-3-yl, acetylamino, trifluoroacetylamino, ureido, methylsulfonyl, sulfamoyl, dimethylphosphoryl or diethylphosphoryl. A more particular value for G is methyl, ethyl, benzyl, phenethyl, pyridyl, pyridylmethyl, thenyl, 5-tetrazolylmethyl, or 2-(pyridyl)ethyl, wherein an alkyl carbon may bear an oxo group and wherein the phenyl or heteroaryl group may bear one or two halogeno or methyl groups and further wherein the group G may bear a substituent selected from hydroxy, methoxy, acetoxy, carboxy, methoxycarbonyl, ethoxycarbonyl, carbamoyl, dimethylcarbamoyl, phenylcarbamoyl, pyridylcarbamoyl, methylsulfonylamino, amino, dimethylamino, acetylamino, nicotinoylamino, or trifluoroacetylamino.

A particular value for R is, for example, hydrogen, trifluoroacetyl, hydroxyoxalyl, methoxycarbonyl, ethoxycarbonyl, isopropoxycarbonyl, 4-fluorophenoxycarbonyl, 4-bromophenoxycarbonyl, 4-methoxyphenoxycarbonyl, benzyloxycarbonyl, 4-fluorobenzyloxycarbonyl, 4-pyridylmethoxycarbonyl, 3-methylpyrid-4-ylmethoxycarbonyl, 2,6-dimethylpyrid-4-ylmethoxycarbonyl, 2-pyridylmethoxycarbonyl, 6-methylpyrid-2-ylmethoxycarbonyl, 2-dimethylaminoethoxycarbonyl, acetyl, carbamoylmethylaminocarbonyl, 4-(N-phenylsulfonylcarbamoyl)phenylacetyl, sulfo, aminosulfonyl, dimethylaminosulfonyl, trifluoromethylsulfonyl, methylsulfonyl (which may bear a methoxycarbonyl, carboxy or ethylsulfonyl substituent), methylaminosulfonyl, isopropylaminosulfonyl, butylsulfonyl, butylaminosulfonyl, tert-butylaminosulfonyl, cyclohexylaminosulfonyl, phenylsulfonyl (in which the phenyl may bear a chloro, nitro, amino, acetylamino, trifluoroacetylamino, methoxy, carboxy, N-(4-chlorophenylsulfonyl)carbamoyl, or methylsulfonylamino substituted at the 3- or 4-position), anilino, pyridylsulfonyl, quinolylsulfonyl, benzylsulfonyl (in which the phenyl ring may bear a nitro or amino substituent at the 3- or 4-position), pyridylmethylsulfonyl, 2-(pyridyl)ethylsulfonyl, benzylaminosulfonyl, methyl, ethyl, benzyl, phenethyl or pyridylmethyl.

A more particular value for R is, for example hydrogen, trifluoroacetyl, methoxycarbonyl, 4-bromophenoxycarbonyl, benzyloxycarbonyl or 4-fluorobenzyloxycarbonyl.

One particular group of compounds of formula I is one in which $R^4$, $R^0$ and R have any of the values defined above, $R^5$ is hydrogen and $R^6$ is hydrogen.

Another particular group of compounds of formula I is one in which $R^4$, $R^0$ and R have any of the values defined above, $R^5$ is benzyl, the phenyl ring of which may bear a 3-fluoro, 4-fluoro, 4-trifluoromethyl, 4-methoxycarbonyl, 3-acetoxy, 3-hydroxy, 3-pivaloyloxy, 4-hydroxy, 4-pivaloyloxy, 3-trifluoroacetylamino or 3-amino substituent, and $R^6$ is hydrogen.

A further particular group of compounds of formula I is one in which $R^4$, $R^0$ and R have any of the values defined above $R^5$ is hydrogen, and $R^6$ is 2-furyl, 2-thienyl, 3-pyridyl or phenyl in which the phenyl may bear one or two halogeno, trifluoromethyl, methyl, hydroxy, methoxy, tert-butoxy, methoxycarbonyl or carboxy substituents; and, more particularly, $R^6$ is phenyl, 4-fluorophenyl or 2-thienyl.

Specific compounds of formula I are described in the accompanying Examples. Of these, compounds of particular interest, along with their pharmaceutically acceptable salts, include those described in Examples 35, 49, 157, 159, 178, 211, 235, 236 and 245.

A pharmaceutically acceptable salt of an acidic compound of formula I is one made with a base which affords a pharmaceutically acceptable cation, which includes alkalai metal salts (especially lithium, sodium and potassium), alkaline earth metal salts (especially calcium and magnesium), aluminum salts and ammonium salts, as well as salts made from appropriate organic bases such as triethylamine, morpholine, piperidine and triethanol amine. A pharmaceutically acceptable salt of a basic compound of formula I includes an acid-addition salt made with an acid which provides a pharmaceutically acceptable anion, including for example, a strong acid such as hydrochloric, sulfuric or phosphoric acid.

A compound of formula I may be made by processes which include processes known in the chemical art for the production of structurally analogous heterocyclic and peptidic compounds. Such processes and intermediates for the manufacture of a compound of formula I as defined above are provided as further features of the invention and are illustrated by the following procedures in which the meanings of generic radicals are as defined above:

(A) Oxidizing a corresponding alcohol of formula II. If R is hydrogen or a group G, it will be recognized that protection of the pyridone 3-amino substituent prior to oxidation and removal of the protecting group after oxidation may be preferred or required if the amino group is not stable to the oxidation conditions employed. A convenient method is the use of excess dimethyl sulfoxide and a water soluble carbodimide, with dichloroacetic acid as a catalyst, in a inert solvent such as toluene at about room temperature, for example as described in Example 1. Other methods which may be useful include the use of alkaline aqueous potassium permanganate solution; the use of oxalyl chloride, dimethyl sulfoxide and a tertiary amine; the use of acetic anhydride and dimethyl sulfoxide; the use of chromium trioxide pyridine complex in methylene chloride; and the use of a hypervalent iodine reagent, such as a periodinane, for example 1,1,1-triacetoxy-2,1-benzoxidol-3(3H)—one with trifluoroacetic acid in dichloromethane.

(B) For a compound of formula I which contains an N—H residue, removal by using a conventional method of the nitrogen protecting group of a corresponding compound bearing a conventional nitrogen protecting group to afford the compound of formula I which contains an amino N—H residue, particularly for a compound of formula I in which R is hydrogen, removal of a group from a corresponding compound of formula I, or for a compound of formula I in which R has a value of G, the removal of an activating/protecting group Rx from a corresponding compound of formula Vb. Rx is a group which protects and activates a primary amino group for substitution, such as for example benzyloxycarbonyl or trifluoroacetyl. Conventional methods include, for example, removal of a benzyloxycarbonyl group by hydrogenolysis, removal of a benzyloxycarbonyl or tert-butoxycarbonyl group by treatment with a strong acids, for example with trifluoromethanesulfonic acid in an inert solvent such as dichloromethane, or basic hydrolysis of a trifluoroacetyl group.

(C) For a compound of formula I wherein R is an acyl group, acylation of a corresponding amine of formula I wherein R is hydrogen. Convenient methods include those described below for acylation of an amine of formula IX, for example, when J is oxygen, the use of an activated carboxylic acid derivative, such as an acid halide, the use of a carboxylic acid and a coupling reagent, the use of an isocyanate for a compound wherein X is imino, and the use of a diactivated carbonic acid derivative, for example, carbonyldiimidazole, phosgene, diphosgene (trichloromethyl chloroformate) or triphosgene (bis(trichloromethyl) carbonate) with an alcohol of formula A.OH, a thiol of formula A.SH or an amine of formula A.NH$_2$ and a base, such as triethylamine or, when J is sulfur, the use of an activated thiocarboxylic acid derivative, such as a thioyl chloride or a lower alkyl ester of a dithioic acid, the use of a thioic acid and a coupling reagent, the use of an isothiocyanate for a compound wherein X is imino, and the use of a diactivated thiocarbonic acid derivative, for example, dimethyl trithiocarbonate, with an alcohol of formula A.OH, a thiol of formula A.SH or an amine of formula A.NH$_2$.

(D) For a compound of formula I wherein R is a sulfonyl group, sulfonylation of a corresponding amine of formula I wherein R is hydrogen with a corresponding sulfonic acid of formula D.W.SO$_2$.OH, or an activated derivative thereof, such as an acid halide, particularly a sulfonyl (or sulfamoyl) chloride of formula D.W.SO$_2$.Cl. The sulfonylation is conveniently carried out in an inert solvent or diluent, such as dichloromethane, tetrahydrofuran or toluene, at about ambient temperature, using an organic base such as, for example, triethylamine or pyridine, or an inorganic base, such as sodium or potassium carbonate, as an acid acceptor. If a sulfonyl chloride is not commercially available, it may be obtained by a conventional method.

(E) For a compound of formula I in which R is a group G, substitution of the group L of a corresponding compound of formula G—L, wherein L is a conventional leaving group, such as for example halogeno, methylsulfonyloxy, trifluoromethylsulfonyloxy or diazonium, with a corresponding amine of formula I wherein R is hydrogen, optionally using a conventional catalyst.

(F) For a compound of formula I which bears a hydroxy substituent on an aryl or heteroaryl group, cleaving the alkyl ether or acyloxy ester of a corresponding compound of formula I which bears a lower alkoxy or lower acyloxy substituent on an aryl or heteroaryl group. Convenient methods include, for example, the cleavage of a methoxy group using boron tribromide or pyridinium chloride and the cleavage of a t-butoxy group using trifluoroacetic acid for an alkyl ether, and the acidic or alkaline hydrolysis of an acyloxy group.

(G) For a compound of formula I which bears a group of formula COORa in which Ra is hydrogen (a carboxy group), decomposing the ester group of a corresponding ester made with a conveniently removed acid protecting group, for example a corresponding compound of formula I in which Ra is not hydrogen. The decomposition may be carried out using any one of the variety of procedures well known in organic chemistry, for example basic hydrolysis using lithium or sodium hydroxide, or by hydrogenolysis of a benzyl ester.

(H) For a compound of formula I bearing a moiety of formula COORa, $CH_2COORa$, CONRbRc, $CH_2CONRbRc$, $COO(CH_2)_2NReRf$ or $CONRdSO_2R^1$, acylation of a corresponding compound of formula HORa, HNRbRc, $HO(CH2)_2NReRf$ or $HNRdSO_2R^1$ with a corresponding acid of formula I bearing a moiety of formula COORa in which Ra is hydrogen, or an activated derivative thereof.

(I) For a compound of formula I bearing a lower acyloxy group or a group of formula NRgCHO, $NRgCOR^2$, $NRgCOOR^2$, NRhCQNRiRj or $NRkSO_2R^3$, acylation or sulfonylation of a corresponding compound of formula I bearing a hydroxy group or an amino group of formula NHRg, NHRh or NHRk (i.e. an amino group of formula NReRf is which Re is hydrogen and Rf is Rg, Rh or Rk) with an activated derivative of a corresponding acid of formula HOCHO, $HOCOR^2$, $HOCOOR^2$, HOCQNRiRj (including an isocyanate or isothiocyanate) or $HOSO_2R^3$, respectively using a conventional method.

(J) For a compound of formula I which bears a heteroaryl N-oxide group, oxidation of a corresponding compound of formula I which bears a heteroaryl group using a conventional oxidant, such as for example dioxirane in acetone.

(K) For a compound of formula I which bears a primary amino group, reduction of a corresponding compound bearing a nitro group using a conventional reducing method, such as for example, hydrogenation over a palladium catalyst, or reduction with tin(II) chloride.

Whereafter, for any of the above procedures, when a pharmaceutically acceptable salt of an acidic or basic compound of formula I is required, it may be obtained by reacting the acidic or basic form of such a compound of formula I with a base or acid affording a physiologically acceptable counterion or by any other conventional procedure.

If not commercially available, the necessary starting materials for the above procedures may be made by procedures which are selected from standard techniques of heterocyclic chemistry and peptide chemistry, techniques which are analogous to the synthesis of known, structurally similar compounds, and techniques which are analogous to the above described procedures or the procedures described in the Examples. For uniformity and clarity, compounds herein are represented as the 2-pyridone, rather than the 2-hydroxypyridine, tautomers.

As will be clear to one skilled in the art, a variety of sequences is available for preparation of the starting materials. According to one of the available routes, a key intermediate pyrid-2-one-3-carboxylic acid of formula III may be prepared as shown in Scheme I (set out, together with other Schemes, following Examples) and as described in the Examples. In the Schemes, CBZ represents a benzyloxycarbonyl group.

In general, in a formal sense, a ketone of formula $R^5.CH_2.CO.R^6$ may be formylated then cyclized with cyanoacetamide to afford a pyrid-2-one-3-carbonitrile of formula IV. Methods of preparation of a nitrile of formula IV and related pyridones are described in Example 1, part a (Cyclization Method A), Example 2, part a (Cyclization Method B) and Example 3, part a (Cyclization Method C). Where more than one product is possible from the cyclization reaction, the product selectivity may be controlled by the cyclization (and formylation) method chosen. For example, cyclization of phenylacetone by Cyclization Method A affords 6-methyl-5-phenylpyrid-2-one-3-carbonitrile (Example 60, part a); but cyclization of phenylacetone by Cyclization Method C affords 6-benzylpyrid-2-one-3-carbonitrile (Example 11, part a). Hydrolysis of the cyano group of a compound of formula IV, for example by heating with 48% hydrobromic acid in acetic acid (Hydrolysis Method A, Example 1, part b) or with sodium hydroxide solution in a pressure vessel (Hydrolysis Method B, Example 2, part b), affords a corresponding carboxy derivative of formula III. For a compound in which $R^6$ is B.Y— and Y is ethylene or trans-vinylene, it may be preferred to proceed via an alternative route to an acid of formula III, for example as described in Examples 3 and 12. Thus, cyclization of a ketone of formula $R^5.CH_2.CO.CH_3$ affords a 6-methyl pyridone derivative of formula IVa. Bis-metallation, followed by alkylation with a reagent of, for example, formula $B.CH_2.Br$ affords a corresponding nitrile of formula IV in which Y is ethylene, for example as described in Example 3. Alternatively, for example as described in Example 12, bis-metallation of a 6-methyl pyridone of formula IVa, followed by condensation with an aldehyde of formula B.CHO, affords a pyrid-2-one-3-carbonitrile of formula IVb which may be converted by acid hydrolysis and dehydration into a corresponding pyride-2-one-3-carboxylic acid of formula III in which Y is trans-vinylene.

An acid of formula III may be converted into a corresponding isocyanate of formula VI by a conventional method, for example by using diphenylphosphoryl azide in an inert solvent, as described in Example 1, part c. Conveniently, the isocyanate is not isolated, but is converted into a benzyl urethane of formula VII as also is shown in Scheme I. It will be clear to one skilled in the art that, in general, treatment of an isocyanate of formula VI with a selected alcohol or amine of formula A.X.H in which X is oxy or imino will provide a corresponding product of formula VIIa in which X is oxy or imino, and that the product of formula VIIa may be carried forward to an alcohol of formula II using one of the routes outlined below. (An isocyanate of formula VI may undergo intramolecular cyclization to the oxygen at the pyridone 2-position, thereby forming a corresponding cyclic carbamate, which carbamate similarly may afford a corresponding compound of formula VII or VIIa.)

Elaboration of a substituted amino pyridone of formula VII (or VIIa) into a corresponding intermediate alcohol of formula II may be carried out as outlined in Scheme II. Alkylation of a compound of formula VII with an iodoacetamide derivative, for example as described in Example 1, part d, for a compound in which $R^0$ is isopropyl, affords a 1-substituted pyridone of formula VIII, wherein Rp represents an alcohol protecting group, conveniently t-butyldimethylsilyl. (The corresponding 2-alkoxypyridine resulting from O-alkylation is also obtained. When $R^6$ is subject to hindered rotation, for example when $R^5$ is methyl and $R^6$ is phenyl, as in Example 9, or, for example, when $R^5$ is hydrogen and $R^6$ is 2-chlorophenyl as in Example 21, the ratio of N-alkylated product to O-alkylated product is increased.) If an alcohol of formula II wherein R is benzyloxycarbonyl is required, it may be obtained directly from a compound of formula VIII by removal of the protecting group Rp, such as by the desilylation reaction described in Example 1, part e. When an alcohol of formula II with a different value of R is desired, the benzyloxycarbonyl group of a compound of formula VIII may be removed by a conventional method, for example by hydrogenolysis as described in Example 14, part a, to afford a corresponding 3-amino pyridone of formula IX. For a compound of formula X wherein R is an acyl group, a 3-amino pyridone of formula IX may then be acylated by using a conventional method to afford a corresponding pyridone of formula X. Conventional acylation methods include the use of an acyl halide (for example as described in Example 14, part b, Acylation Method A), the use of a carboxylic acid and a coupling reagent (for example as described in Example 15, part a, Acylation Method B), the use of an isocyanate for a compound wherein X is imino (for example as described in Example 16, part a, Acylation Method C) and the use of triphosgene (bis(trichloromethyl) carbonate) with an alcohol of formula A.OH or an amine of formula A.NH$_2$ and a base, such as for example triethylamine (for example as described in Example 22, part e, Acylation Method D). For a compound of formula X wherein R is a sulfonyl group of formula D.W SO$^2$—, a 3-amino pyridone of formula IX may be sulfonylated by using a conventional method to afford a corresponding pyridone of formula X. Conventional sulfonylation methods include those described above in process (D) for the sulfonylation of an amine of formula I. (Should a portion of bis-sulfonylated product be obtained, treatment with aqueous base at an elevated temperature may be used to remove the more labile second sulfonyl group at a convenient stage in the synthesis; see for example Example 196, parts a.–b.) For a compound of formula X wherein R is a group G, a 3-amino pyridone of formula IX may be subjected to a conventional substitution reaction similar to one described above in process (E) to afford a corresponding pyridone of formula X. Finally, removal of the alcohol protecting group Rp of a compound of formula X affords a corresponding alcohol of formula II. Instead of the deprotection method described in Example 1, part e, it may be preferred to use the alternative buffered deprotection as described in Example 19, part b.

An alternative order of steps to convert a protected compound of formula VIII into a corresponding alcohol of formula II can be used as well. Thus, removal of the alcohol protecting group of a compound of formula VIII affords the corresponding alcohol of formula VIIIa. Deprotection of the amino group of a compound of formula VIIIa affords a corresponding amino alcohol of formula XXVII (see Scheme IV for formula XXVII) which can be converted into a corresponding alcohol of formula II using a conventional procedure.

A different route which obviates the need for an alcohol deprotection step is also shown in Scheme II. Thus, a pyridone of formula VII (or VIIa) may be alkylated, for example with ethyl or t-butyl iodoacetate, to afford a corresponding ester of formula XI, wherein Rq is a conveniently removable acid protecting group, for example ethyl or t-butyl. Removal of the acid protecting group of an ester of formula XI by a conventional method, for example by base catalyzed hydrolysis or by acid catalyzed elimination as described in Example 3, part f, affords a corresponding acid of formula XII. An acid of formula XII may be coupled with 3-amino-1,1,1-trifluoro- 4-methyl-2-pentanol, for example as described in Example 3, part g, to afford a corresponding alcohol of formula VIIIa.

An alternative route for the preparation of an intermediate acid of formula XII, beginning with a ketone of formula $R^5$.CH$_2$.CO.R$^6$ and involving a novel pyridone synthesis, which may be a preferred route, is described in Example 49, parts d.–i., for the conversion of acetophenone into 3-benzyloxycarbonylamino-2-oxo-6-phenyl-1,2-dihydro- 1-pyridylacetic acid. The coupling to provide the corresponding alcohol of formula VIIIa, 2-(3-benzyloxycarbonylamino-2-oxo-6-phenyl- 1,2-dihydro-1-pyridyl)-N-(3,3,3-trifluoro-2-hydroxy-1-isopropylpropyl)acetamide is also described in Example 49.j.

Alternatively, oxidation of an alcohol of formula VIIIa (which is a compound of formula II wherein R is benzyloxycarbonyl), using a method similar to one described in process (A) for oxidation of an alcohol of formula II, affords a corresponding ketone of formula VIIIb (which is a compound of formula I wherein R is benzyloxycarbonyl). Removal of the nitrogen protecting group of a ketone of formula VIIIb by hydrogenolysis or by treatment with a strong acid, for example as described in Example 197.i., affords a corresponding amine of formula I wherein R is hydrogen.

A preferred method for introducing the substituent R when it is a group G, particularly when it is an alkyl or substituted alkyl group, is by the use of a corresponding compound in which the pyridone 3-amino substituent bears an activating/protecting group of formula Rx, for example, benzyloxycarbonyl or trifluoroacetyl. Thus, acylation of a compound of formula I wherein R is hydrogen with trifluoroacetic anhydride affords a corresponding compound of formula Va in which Rx is trifluoroacetyl, which compound also may be prepared by an alternative order of steps via the corresponding compound of formula IX. It will be noted that a compound of formula VIIIb is, itself, a corresponding compound of formula Va in which Rx is benzyloxycarbonyl. Also, each of a compound of formula Va in which Rx is benzyloxycarbonyl or trifluoroacetyl is also a compound of formula I in which R is an acyl group. Alkylation, using a corresponding reagent of formula G.L in which G is alkyl or substituted alkyl, then provides a corresponding intermediate of formula Vb.

Synthesis routes involving a cross coupling reaction to introduce a substituent $R^5$ into intermediate compounds are outlined in Scheme III. These routes may be preferred when $R^5$ has the value B.Y—and Y is methylene, ethylene or trans-vinylene. Thus, a pyridone of formula VII in which $R^5$ is hydrogen may be converted into a corresponding 5-iodo pyridone of formula XXI by treatment with an iodinating agent, for example N-iodosuccinimide. An appropriate halide, for example a bromide of formula B.CH$_2$.Br, may be converted into a corresponding organozinc reagent, for example B.CH$_2$.Zn.Br, by treatment with zinc dust in tetrahydrofuran, and cross-coupled with an iodide of formula XXI using a palladium catalyst, such as dichloro[1,1'-bis-(diphenylphosphino)ferrocene]palladium(II) to afford a corresponding compound of formula VII in which $R^5$ is B.Y—and Y is methylene. A similar cross coupling utilizing a bromide of formula B.Y.Br in which Y is trans-vinylene may be useful to convert an iodide of formula XXI into a corresponding compound of formula VII in which $R^5$ is B.Y— and Y is trans-vinylene. At a convenient point in a synthesis, a compound in which $R^5$ is B.Y— and Y is trans-vinylene may be hydrogenated to afford a corresponding compound in which $R^5$ is B.Y— and Y is ethylene.

Alternatively, an iodide of formula XXI may be alkylated to afford a corresponding iodide of formula XXII or XXIII which may be further cross coupled as described above to provide a corresponding compound of formula VIII or XI.

Alternative synthesis routes in which a 3-nitro pyridone serves as a precursor to a 3-amino pyridone are outlined in Scheme IV. They may be particularly useful when the 3-nitro derivative is readily available, such as when $R^5$ and $R^6$ are hydrogen. Alternatively, beginning with a ketone of formula $R^5.CH_2.CO.R^6$, the corresponding 3-nitropyridone may be prepared as described in Example 185, parts a. and b., beginning with 3-methoxycarbonylacetophenone. Direct reduction of the nitro group, followed by acylation of the amine obtained, provides a pyridone of formula VIIb, which may be converted into a corresponding intermediate of formula II using a route similar to one outlined in Scheme II for a compound of formula VII. Using a different order of steps, the 3-nitro pyridone may be alkylated first to provide an ester of formula XXIV. The ester of formula XXIV may be converted into the corresponding acid of formula XXV. The acid of formula XXV also may be obtained by allylation of the starting 3-nitro pyridone, followed by oxidative cleavage of the 1-allyl group using potassium permanganate. By coupling with the appropriate amino alcohol, an acid of formula XXV may be converted into a nitro alcohol of formula XXVI. A nitro alcohol of formula XXVI may be reduced to afford a corresponding 3-amino pyridone of formula XXVII. Acylation of a 3-amino pyridone of formula XXVII affords a corresponding intermediate alcohol of formula II. In addition, a nitro alcohol of formula XXVI may be oxidized to a corresponding nitro ketone of formula XXVIII. Reduction of the nitro group of a nitro ketone of formula XXVIII affords an amine of formula I wherein R is hydrogen. An analogous route from a nitro compound of formula XXIV involves first reducing the nitro group to afford a corresponding amino compound of formula XXIX. Acylation of a compound of formula XXIX affords a compound of formula XIb, which may be further converted into a corresponding compound of formula II using a similar method to that described in Scheme II for a compound of formula XI, that is, conversion into a corresponding acid of formula XIIb, followed by coupling with a requisite amino alcohol.

For a compound in which R is is a group G, it will be clear that the methodology described above using an activating/protecting group of formula Rx to introduce the substituent R on the pyridone 3-amino group may be utilized analogously at any convenient stage of a synthetic scheme.

The trifluoromethyl amino alcohols required for the synthesis routes described above may be prepared by known routes. For example, 3-amino-1,1,1-trifluoro-4-methyl-2-pentanol (as its hydrochloride salt) conveniently may be obtained as described in U.S. Pat. No. 4,910,190 in Example 4 (as a single diastereomer) or Example 6 (as a single enantiomer of a single diastereomer). If it is desired to carry out a chiral synthesis of a compound of formula I, using the single enantiomer in a substantially enantiomerically pure form and using methods and conditions which avoid epimerization at the center indicated by "*" in formula I provide such a synthesis.

It may be desired optionally to use a protecting group during all or portions of the above described processes; the protecting group then may be removed when the final compound or a required starting material is to be formed. As will be clear to one skilled in the art, the order of steps in the sequences leading to the starting materials and products of the invention may be altered if appropriate considerations relative to coupling methods, racemization, deprotection methods, etc. are followed.

The utility of a compound of the invention or a pharmaceutically acceptable salt thereof (hereinafter, collectively referred to as a "Compound") may be demonstrated by standard tests and clinical studies, including those described below.

INHIBITION MEASUREMENTS

The potency of a Compound to act as an inhibitor of human leukocyte elastase (HLE) on the low molecular weight peptide substrate methoxy-succinyl-alanyl-alanyl-prolyl-valine-p-nitroanilide is determined as described in U.S. Pat. No. 4,910,190. The potency of an inhibitor is evaluated by obtaining a kinetic determination of the dissociation constant, $K_i$, of the complex formed from the interaction of the inhibitor with HLE. If a Compound is found to be a "slow-binding" inhibitor of HLE, special methods of analysis to accurately determine $K_i$ values for the inhibition of HLE are carried out as described in U.S. Pat. No. 4,910,190. In general, the $K_i$ values for Compounds of the invention which were tested are generally on the order of $10^{-7}M$ or much less.

ACUTE LUNG INJURY MODEL

Animal models of emphysema include intratracheal (i.t.) administration of an elastolytic protease to cause a slowly progressive, destructive lesion of the lung. These lesions are normally evaluated a few weeks to a few months after the initial insult. However, these proteases also induce a lesion that is evident in the first few hours. The early lesion is first hemorrhagic, progresses to an inflammatory lesion by the end of the first 24 hours and resolves in the first week post insult. To take advantage of this early lesion, the following model (described in Williams, et al., *American Review of Respiratory Diseases* (1991), 144, 875–883) was used.

Hamsters are first lightly anesthetized with Brevital. Phosphate buffered saline (PBS) pH 7.4, either alone or containing human leukocyte elastase (HLE), is then administered directly into the trachea. Twenty-four hours later the animals are killed and the lungs removed and carefully trimmed of extraneous tissue. Following determination of wet lung weight, the lungs are lavaged with PBS and total lavagable red and white cells recovered are determined. The values for wet lung weights, total lavagable red cells and total lavagable white cells are elevated in a dose-dependent manner following administration of HLE. Compounds that are effective elastase inhibitors can prevent or diminish the severity of the enzyme-induced lesion resulting in lower wet lung weight and reduced values for total lavagable cells, both red and white, relative to administration of HLE alone. Compounds can be evaluated by administering them intratracheally as solutions or suspensions in PBS, either with or at various times prior to the HLE challenge (400 µg), or by dosing them intravenously or orally as solutions at various times prior to the HLE challenge (100 µg) to determine their utility in preventing an HLE lesion. A solution of a Compound is conveniently prepared using 10% polyethylene glycol 400/PBS or 10% polyethylene glycol 400/water. For a Compound which is acidic or basic, base (e.g. sodium hydroxide solution) or acid (e.g. hydrochloric acid) may be added as indicated to achieve solution. Compounds of this invention produced statistically significant reductions in wet lung weight and total lavagable cells relative to HLE alone.

ACUTE HEMORRHAGIC ASSAY

This assay relies on monitoring only the amount of hemorrhage in the lung following intratracheal administration of human neutrophil elastase (HNE). Hemorrhage is quantified by disrupting erythrocytes recovered in lung lavage fluid and comparing that to dilutions of whole hamster blood. The screening protocol, similar to that described in Fletcher et al., *American Review of Respiratory Disease* (1990), 141,672–677, is as follows. Compounds demonstrated to be HNE inhibitors in vitro are conveniently prepared for dosing as described above for the Acute Lung Injury Model. The compounds are then dosed by mouth to male Syrian hamsters at a fixed time, such as 30 or 90 min, prior to intratracheal administration of 50 µg/animal of HNE in 300 µL phosphate buffered saline (PBS) pH 7.4. Four hours after enzyme administration, the animals are killed with an overdose of pentobarbital sodium, the thorax opened and the lungs and trachea removed. The excised lungs are lavaged with three changes of 2 mL normal saline via a tracheal cannula. The recovered lavages are pooled, the volumes (about 5 mL) are recorded and the lavages stored at 4° C. until assayed. For calculation of the amount of blood in each sample, the thawed lavages and a sample of whole hamster blood are sonicated to disrupt erythrocytes and appropriately diluted into individual wells of a 96-well microtiter plate. The optical densities (OD) of the disrupted lavages and blood samples are determined at 405 nm. The (µL blood equivalents)/(mL lavage) are determined by comparing the OD of the test samples with the OD of the standard curve prepared from whole hamster blood. The total µL equivalents of blood recovered is determined by multiplying recovered lavage volume by the (µL blood equivalents)/(mL lavage) for each sample. Results are reported as % inhibition of hemorrhage with respect to PBS treated controls when the test compound is given at a specified dose and time prior to administration of HNE.

No overt toxicity was observed when Compounds of the invention were administered in the above in vivo tests.

It will be appreciated that the implications of a Compound's activity in the Acute Lung Injury Model or Acute Hemorrhagic Assay are not limited to emphysema, but, rather, that the test provides evidence of general in vivo inhibition of HLE.

Compounds of the present invention which were tested exhibited activity in at least one of the tests described above under Inhibition Measurement, Acute Lung Injury Model and Acute Hemorrhagic Assay. It should be noted that, as would be expected in comparison of in vitro and in vivo results, there was not always a direct correlation between the activities of the compounds measured as $K_i$ values in the Inhibition Measurement test and the reduced values for total lavagable cells and wet lung weights relative to the administration of HLE alone obtained in the Acute Lung Injury Model test or inhibition of hemorrhage in the Acute Hemorragic Assay.

According to a further feature of the invention, there is provided a pharmaceutical composition comprising a pharmaceutically effective amount of a Compound and a pharmaceutically acceptable diluent or carrier. As noted above, another feature of the invention is a method of using a Compound of the invention in the treatment of a disease or condition in a mammal, especially a human, in which HLE is implicated.

A Compound of the present invention may be administered to a warm-blooded animal, particularly a human, in need thereof for treatment of a disease in which HLE is implicated, in the form of a conventional pharmaceutical composition, for example as generally disclosed in U.S. Pat. No. 4,910,190. The preferred mode of administration may be via a powdered or liquid aerosol. In a powdered aerosol, a Compound of the invention may be administered in the same manner as cromolyn sodium via a 'Spinhaler' (a trademark) turbo-inhaler device obtained from Fisons Corp. of Bedford, Mass. at a rate of about 0.1 to 50 mg per capsule, 1 to 8 capsules being administered daily for an average human. Each capsule to be used in the turbo-inhaler contains the required amount of a Compound of the invention with the remainder of the 20 mg capsule being a pharmaceutically acceptable carrier such as lactose. In a liquid aerosol, a Compound of the invention may be administered using a nebulizer such as, for example, a 'Retec' (trademark) nebulizer, in which the solution is nebulized with compressed air. The aerosol may be administered, for example, at the rate of one to about eight times per day as follows: A nebulizer is filled with a solution of a Compound, for example 3.5 mL of solution containing 10 mg/mL; the solution in the nebulizer is nebulized with compressed air; and the patient breathes normally (tidal volume) for eight minutes with the nebulizer in his mouth.

Alternatively, the mode of administration may be oral or parenteral, including subcutaneous deposit by means of an osmotic pump. A compound of the invention may be conventionally formulated in an oral or parenteral dosage form by compounding about 10 to 250 mg per unit of dosage with conventional vehicle, excipient, binder, preservative, stabilizer, flavor or the like as called for by accepted pharmaceutical practice, e.g. as described in U.S. Pat. No. 3,755,340. For parenteral administration, a 1 to 10 mL intravenous, intramuscular or subcutaneous injection would be given containing about 0.02 mg to 10 mg/kg of body weight of a compound of the invention 3 or 4 times daily. The injection would contain a compound of the invention in an aqueous isotonic sterile solution or suspension optionally with a preservative such as phenol or a solubilizing agent such as ethylenediaminetetraacetic acid (EDTA).

For parenteral administration or use in an aerosol, an 10 mg/mL aqueous formulation of an acidic Compound may be prepared, for example by dissolving the Compound (10 mg), dibasic sodium phosphate heptahydrate, USP (11.97 mg), monobasic sodium phosphate, USP (0.74 mg), sodium chloride, USP (4.50 mg) and sufficient 1N sodium hydroxide solution or 0.05M monobasic sodium phosphate solution to achieve pH 7.0–7.5 in sufficient water for injection, USP to afford 1.0 mL (1.01 g), followed by aseptic filtration, and sterile storage using standard procedures.

In general, a Compound of the invention will be administered to humans at a daily dose in the range of, for example, 5 to 100 mg of the Compound by aerosol or 50 to 1000 mg intravenously, or a combination of the two. However, it readily will be understood that it may be necessary to vary the dose of the Compound administered in accordance with well known medical practice to take account of the nature and severity of the disease under treatment, concurrent therapy, and the age, weight and sex of the patient receiving treatment. It similarly will be understood that generally equivalent amounts of a pharmaceutically acceptable salt of the Compound also may be used. Protocols for the administration of an HLE inhibitor and evaluation of the patients are described in the European Patent Applications with Publication Numbers 458535, 458536, 458537, and 463811 for the treatment or prevention of cystic fibrosis, ARDS, bronchitis, and hemorrhage associated with acute non-lymphocytic leukemia or its therapy, respectively;

and a Compound of the invention may be used similarly for the treatment of those diseases and conditions either alone or in combination with another therapeutic agent customarily indicated for the treatment of the particular condition. For therapeutic or prophylactic treatment of a vascular disease or related condition in a mammal in which neutrophils are involved or implicated, a Compound of the invention may conveniently be administered by a parenteral route,, either alone or simultaneously or sequentially with other therapeutically active agents customarily administered for the condition.

The invention will now be illustrated by the following non-limiting examples in which, unless stated otherwise:

(i) temperatures are given in degrees Celsius (° C.); operations were carried out at room or ambient temperature, that is, at a temperature in the range of 18°–25° C.;

(ii) organic solutions were dried over anhydrous sodium sulfate; evaporation of solvent was carried out using a rotary evaporator under reduced pressure (600–4000 pascals; 4.5–30 mm Hg) with a bath temperature of up to 60° C.;

(iii) chromatography means 'flash chromatography' (method of Still) carried out on Merck Kieselgel (Art 9385 from E. Merck, Darmstadt, Germany); if "acidic silica gel" is indicated, material custom prepared by J. T. Baker Chemical Co., Phillipsburg, N.J., USA, and having a pH of about 6 when slurried in water was used; reversed phase chromatography means flash chromatography over octadecylsilane (ODS) coated support having a particle diameter of 32–74μ, know as "PREP-40-ODS" (Art 731740-100 from Bodman Chemicals, Aston, Pa., USA); thin layer chromatography (TLC) was carried out on 0.25 mm silica gel GHLF plates (Art 21521 from Analtech, Newark, Del., USA); reversed phase-TLC (RP-TLC) was carried out Whatman $MKC_{18}F$ plates (Art 4803-110 from Bodman Chemicals);

(iv) in general, the course of reactions was followed by TLC and reaction times are given for illustration only;

(v) melting points are uncorrected and (dec) indicates decomposition; the melting points given are those obtained for the materials prepared as described; polymorphism may result in isolation of materials with different melting points in some preparations;

(vi) final products had satisfactory nuclear magnetic resonance (NMR) spectra;

(vii) yields are given for illustration only and are not necessarily those which may be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 250 MHz using DMSO-$d_6$ (or DMSO-$d_6$/$D_2O$, indicated herein as DMSO/$D_2O$) as solvent; conventional abbreviations for signal shape are used; for AB spectra the directly observed shifts are reported;

(ix) chemical symbols have their usual meanings; SI units and symbols are used;

(x) reduced pressures are given as absolute pressures in pascals (Pa); elevated pressures are given as gauge pressures in bars;

(xi) solvent ratios are given in volume:volume (v/v) terms; and (xii) mass spectra (MS) were run with an electron energy of 70 electron volts in the chemical ionizaton mode using a direct exposure probe; where indicated ionization was effected by electron impact (EI) or fast atom bombardment (FAB); generally, only peaks which indicate the parent mass are reported.

EXAMPLE 1

2-(3-Benzyloxycarbonylamino-2-oxo-6-phenyl-1,2-dihydro-1-pyridyl)-N-(3,3,3-trifluoro-1-isopropyl-2-oxopropyl)acetamide.

A solution of 2-(3-benzyloxycarbonylamino-2-oxo-6-phenyl- 1,2-dihydro-1-pyridyl)-N-(3,3,3-trifluoro-2-hydroxy-1-isopropylpropyl)acetamide (0.78 g) in dry dimethyl sulfoxide (4 mL) and toluene (4 mL) was treated with 1-(3-dimethylaminopropyl)-3-ethylcarbodiimide hydrochloride (2.81 g) and dichloroacetic acid (0.48 mL). After overnight stirring, the reaction mixture was diluted with ethyl acetate (100 mL); washed successively with 10% hydrochloric acid (twice), saturated aqueous sodium bicarbonate (twice) and brine; dried; and evaporated to give an off-white solid (0.75 g). Flash chromatography, eluting with dichloromethane:ethyl acetate (95:5), and drying overnight in a vacuum oven gave the title compound as an off-white solid (0.53 g); TLC: $R_f$=0.29, dichloromethane:ethyl acetate (20:1); HPLC: $t_R$=7.19, FR=3.0, column A, solvent system A; NMR: 0.83 (d,3, J=6.8), 0.89 (d,3, J=6.7), 2.10–2.21 (m,1), 4.46 (d,1, J=16), 4.54 (d,1, J=16), 4.63 (t,1, J=6), 5.19 (s,2), 6.23 (d,1, J=7.6), 7.33–7.49 (m,10), 7.92 (d,1, J=7.6), 8.55 (s,1), 8.74 (d,1, J=7.0); MS: m/z=530(M+1).

Analysis for $C_{27}H_{26}F_3N_3O_5$:

Calculated: C, 61.24; H, 4.95; N, 7.94

Found: C, 61.17; H, 5.06; N, 7.91

The intermediate 2-(3-benzyloxycarbonylamino-2-oxo-6-phenyl- 1,2-dihydro-1-pyridyl)-N-(3,3,3-trifluoro-2-hydroxy-1-isopropylpropyl)acetamide may be prepared as follows:

a. 6-Phenylpyrid-2-one-3-carbonitrile.

A solution of acetophenone (30.6 g) and N,N-dimethylformamide dimethyl acetal (94% by weight; 100 g) in acetonitrile was heated under reflux overnight. The reaction mixture was cooled, evaporated and dried overnight under vacuum to give a yellow semi-solid (36.68 g). To a solution of this material in dimethylformamide (400 mL) were added cyanoacetamide (19.4 g) and sodium methoxide (27.18 g). The red-orange solution was heated for 5 h at 100° C., cooled, diluted with water (1200 mL), and acidified to about pH 5 with 10% hydrochloric acid. The yellow precipitate was filtered and dried overnight under vacuum at 40° C. to yield 6-phenylpyrid-2-one-3-carbonitrile (35.28 g); TLC: $R_f$=0.21, dichloromethane:methanol (50:1); 300 MHz NMR: 6.77 (broad d,1, J=6), 7.55 (m,3), 7.80 (m,2), 8.20 (dd,1, J=0.8, J=7); MS: m/z=197(M+1).

Analysis for $C_{12}H_8N_2O$:

Calculated: C, 73.46; H, 4.11; N, 14.28

Found: C, 73.09; H, 4.11; N, 14.24

The method of 2-pyridone preparation described above in Example 1.a. is denoted herein as Cyclization Method A.

b. 6-Phenylpyrid-2-one-3-carboxylic acid.

A suspension of 6-phenylpyrid-2-one-3-carbonitrile (8.54 g) in a mixture of glacial acetic acid (100 mL) and 48% aqueous hydrobromic acid (50 mL) was heated under reflux overnight, cooled, diluted with water (50 mL) and brought to about pH 5 with 10% NaOH. The precipitate was filtered, washed succesively with 10% hydrochloric acid and water, and dried overnight under vacuum to afford 6-phenylpyrid-2-one-3-carboxylic acid (8.49 g); 300 MHz NMR: 7.02 (d,1, J=7.6), 7.58 (m,3), 7.85 (m,2), 8.42 (d,1, J=7.6); MS: m/z=216(M+1).

The method of hydrolysis of the 3-cyano group to a 3-carboxy group described above in Example 1.b. is denoted herein as Hydrolysis Method A.

c. 3-Benzyloxycarbonylamino-6-phenylpyrid-2-one.

To 6-phenylpyrid-2-one-3-carboxylic acid (10 g), suspended in dry dioxane (260 mL), triethylamine (7.8 mL) was added dropwise rapidly with stirring followed by diphenylphosphoryl azide (11.1 mL). The suspension was heated under reflux for 4 h using a preheated 120° C. oil bath. Benzyl alcohol (9.58 mL) was then added and the mixture stirred under reflux overnight. The suspension was cooled and evaporated. The resulting semisolid was suspended in water (600 mL) and filtered. The solid filter cake was washed with 10% hydrochloric acid (twice), saturated aqueous sodium bicarbonate and water. Trituration with chloroform turned the solid into an oil which was solidified with ether prior to suctioning off the solvents. Recrystallization from chloroform (600 mL) and methanol (450 mL) yielded a yellow solid (2.42 g), which was triturated with ether and dried under vacuum at 40° C. The mother liquor was evaporated, and the residue was recrystallized from chloroform. The total amount of 3-benzyloxycarbonylamino-6-phenylpyrid-2-one isolated was 4.75 g; TLC: $R_f$=0.76, chloroform:methanol (20:1), $R_f$=0.32, dichloromethane:ethyl acetate (10:1); 300 MHz NMR: 5.19 (s,2), 6.61 (d,1, J=7.6), 7.33–7.49 (m,8), 7.70 (m,2), 7.93 (d,1, J=7.6), 8.47 (s,1).

d. 2-(3-Benzyloxycarbonylamino-2-oxo-6-phenyl-1,2-dihydro-1-pyridyl)-N-(2-tert-butyldimethylsilyloxy-3,3,3-trifluoro-1-isopropylpropyl)acetamide.

3-Benzyloxycarbonylamino-6-phenylpyrid-2-one (1.7 g) was added to a suspension of NaH (0.14 g) in dry dimethylformamide (50 mL). After 15 min stirring, the turbid, orange solution was treated with N-(2-tert-butyldimethylsilyloxy-3,3,3-trifluoro-1-isopropylpropyl)- 2-iodoacetamide (2.65 g) and the mixture was stirred overnight. The mixture was diluted with 10% hydrochloric acid (125 mL) and extracted with ethyl acetate (2 times 150 mL). The combined extracts were washed with 10% hydrochloric acid and water (twice), dried and evaporated to an orange-brown glass. Purification by flash chromatography (gradient elution, 1%–4% ethyl acetate in dichloromethane) and overnight drying under vacuum yielded the N-alkylated product 2-(3-benzyloxycarbonylamino-2-oxo-6-phenyl-1,2-dihydro-1-pyridyl)-N-(2-tert-butyldimethylsilyloxy-3,3,3-trifluoro-1-isopropylpropyl)acetamide (0.97 g, 28%); TLC: $R_f$=0.35, dichloromethane:ethyl acetate (97:3); 300 MHz NMR: 0.08 (s,3), 0.10 (s, 3), 0.81 (d,3, J=6.6), 0.86 (s,9), 0.93 (d,3, J=6.6), 1.67–1.78 (m,1), 3.81 (t,1, J=10), 4.22–4.40 (m,2), 4.64 (broad d,1, J=15), 5.19 (s,2), 6.22 (d,1, J=7.6), 7.33–7.48 (m,10), 7.63 (d,1, J=9.9), 7.92 (d,1, J=7.6), 8.53 (s,1). Also obtained was the O-alkylated product 2-(3-benzyloxycarbonylamino-6-phenylpyrid-2-yloxy)-N-(2-tert-butyldimethylsilyloxy- 3,3,3-trifluoro-1-isopropylpropyl)acetamide (2.11 g, 62%); TLC: $R_f$=0.61, dichloromethane:ethyl acetate (97:3), 300 MHz NMR: 0.01 (s,3), 0.07 (s,3), 0.75 (s,9), 0.77 (d,3, J=6.6), 0.89 (d,3, J=6.6), 1.67–1.81 (m,1), 3.84 (t,1, J=10), 4.26 (m,1), 4.81 (d,1, J=15), 5.14 (d,1, J=15), 5.20 (s,2), 7.35–7.48 (m,9), 7.62 (d,1, J= 8), 7.99 (dd,2, J=1.6, J=8.4), 8.12 (d,1, J=8), 9.31 (s,1); MS: m/z=646(M+1). (A mixed fraction (0.25 g, 7%) was also obtained).

e. 2-(3-Benzyloxycarbonylamino-2-oxo-6-phenyl-1,2-dihydro-1-pyridyl)-N- (3,3,3-trifluoro-2-hydroxy-1-isopropylpropyl)acetamide.

A solution 2-(3-benzyloxycarbonylamino-2-oxo-6-phenyl-1,2-dihydro- 1-pyridyl)-N-(2-tert-butyldimethylsilyloxy-3,3,3-trifluoro-1-isopropylpropyl)acetamide (0.96 g) in dry tetrahydrofuran (8 mL) was treated with tetrabutylammonium fluoride (1M in tetrahydrofuran; 1.62 mL) and the mixture was stirred for 4.5 h. The reaction mixture was diluted with ethyl acetate (75 mL), washed with water (twice) and brine, dried and evaporated to yield a yellow foam. Purification by flash chromatography, eluting with ethyl acetate:chloroform (first 5:95, then 10:90), and overnight drying under vacuum gave 2-(3-benzyloxycarbonylamino- 2-oxo-6-phenyl-1,2-dihydro-1-pyridyl)-N-(3,3,3-trifluoro- 2-hydroxy-1-isopropylpropyl)acetamide as a white solid (0.793 g); TLC: $R_f$=0.19, chloroform:ethyl acetate (20:1); 300 MHz NMR: 0.81 (d,3, J=6.7), 0.88 (d,3, J=6.7), 1.67–1.84 (m,1), 3.82 (t,1, J=8.8), 4.0–4.17 (m,1), 4.34 (d,1, J=15), 4.50 (m,1), 5.18 (s,2), 6.20 (d,1, J=7.7), 6.49 (d,1, J=7), 7.31–7.47 (m,10), 7.86 (d,1, J=9.7), 7.91 (d,1 J=7.7), 8.53 (s,1); MS: m/z=532(M+1).

The iodide used in step d. was prepared as follows:

f. 2-Chloro-N-(3,3,3-trifluoro-2-hydroxy-1-isopropylpropyl)acetamide.

To a solution of 3-amino-1,1,1-trifluoro-4-methyl-2-pentanol hydrochloride (20 g) in distilled tetrahydrofuran (480 mL) under nitrogen was added 4-methylmorpholine (21.8 mL) resulting in a white precipitate. A solution of chloroacetyl chloride (7.7 mL) in distilled tetrahydrofuran (40 mL) was added dropwise over 1 hour, and the mixture was stirred overnight. The mixture was diluted with ethyl acetate and filtered to remove undissolved solids. The filtrate was washed with 10% hydrochloric acid, water, saturated aqueous sodium bicarbonate and brine. The solid that had been filtered was dissolved in water, the aqueous phase was extracted with ethyl acetate (twice), and the extracts were washed as the first extract had been. The organic phases were combined, dried, and evaporated to give 2-chloro-N-(3,3,3-trifluoro-2-hydroxy-1-isopropyl-propyl)acetamide as an oil (23.8 g); TLC: $R_f$=0.70, dichloromethane:methanol (95:5); MS: m/z=248(M+1 for $^{35}$Cl).

g. N-(2-tert-Butyldimethylsilyloxy-3,3,3-trifluoro-1-isopropylpropyl)- 2-chloroacetamide.

2-Chloro-N-(3,3,3-trifluoro-2-hydroxy-1-isopropylpropyl)acetamide prepared as above (23.79 g) and used directly was dissolved in dichloromethane (96 mL), and 2,6-lutidine (22.5 mL) was added. tert-Butyldimethylsilyl trillate (33 mL) was added rapidly dropwise. The reaction exothermed vigorously, producing white smoke. Cooling is advised. The mixture was stirred overnight; diluted with ethyl acetate (500 mL); and washed with 10% hydrochloric acid (twice), saturated aqueous sodium bicarbonate, and brine. The ethyl acetate solution was adsorbed onto silica gel (120 mL) by evaporation, and chromatographed, eluting with hexane:ethyl acetate (gradient, 100:0, 93:7, 85:15 and 80:20), to afford N-(2-tert-butyldimethylsilyloxy- 3,3,3-trifluoro-1-isopropylpropyl)-2-chloroacetamide as a white solid (20.49 g); TLC: $R_f$=0.19, hexane:ethyl acetate (9:1);

MS: m/z=362(M+1, $^{35}$Cl).

h. N-(2-tert-Butyldimethylsilyloxy-3,3,3-trifluoro-1-isopropylpropyl)- 2-iodoacetamide.

N-(2-tert-Butyldimethylsilyloxy-3,3,3-trifluoro-1-isopropylpropyl)- 2-chloroacetamide (15.56 g) was added to a solution of NaI (19.3 g) in acetone (130 mL). The mixture was stirred overnight and the yellow reaction mixture was diluted with water (180 mL). The resulting precipitate was filtered; washed with water and saturated aqueous sodium thiosulfate; and dried under vacuum at 40° C. overnight. After spectral data indicated the presence of starting material, the product was subjected to another iteration of the above reaction conditions. The subsequent work-up was identical except that no sodium thiosulfate wash was performed. Purification by chromatography, eluting with hexane:ethyl acetate (gradient, 80:20 and 50:50), and drying under vacuum afforded N-(2-tert-butyldimethylsilyloxy-3,3,3-trifluoro-1-isopropylpropyl)-2-iodoacetamide (17.91 g); TLC: $R_f$=0.30, hexane:ethyl acetate (9:1); MS: m/z=454(M+1).

EXAMPLE 2

2-[3-Benzyloxycarbonylamino-6-(4-methoxyphenyl)-2-oxo-1,2-dihydro-1-pyridyl]-N-(3,3,3-trifluoro-1-isopropyl-2-oxopropyl)acetamide.

Using a similar procedure to that described in Example 1, using dichloromethane:ethyl acetate:ethanol (100:3:0.5) for elution in the chromatography, 2-[3-benzyloxycarbonylamino-6-(4-methoxyphenyl)- 2-oxo-1,2-dihydro-1-pyridyl]-N-(3,3,3-trifluoro-2-hydroxy-1-isopropylpropyl)acetamide was oxidized to afford the title compound; TLC: $R_f$=0.16, dichloromethane:ethyl acetate:ethanol (92:3:5); HPLC: $t_R$=6.82, FR=2, column A, acetonitrile:water (1:1); MS: m/z=560(M+1).

Analysis for $C_{28}H_{28}F_3N_3O_6$:

Calculated: C, 60.13; H, 5.04; N, 7.51

Found: C, 59.85; H, 5.19; N, 7.13

The intermediate 2-[3-benzyloxycarbonylamino-6-(4-methoxyphenyl)- 2-oxo-1,2-dihydro-1-pyridyl]-N-(3,3,3-trifluoro-2-hydroxy- 1-isopropylpropyl)acetamide may be prepared as follows:

a. 6-(4-Methoxyphenyl)pyrid-2-one-3-carbonitrile.

To a stirred mixture of dry tetrahydrofuran (60 mL), dry ether (60 mL), and sodium methoxide (8.95 g) a solution of ethyl formate (11.55 g), 4'-methoxyacetophenone (10.06 g), and dry tetrahydrofuran (90 mL) was added dropwise over 35 min. After addition was complete, the addition funnel was replaced with a reflux condenser and the mixture was warmed to 40° C. (bath) for 3 h. The condenser was then replaced with a distillation head the mixture was heated to 90° C. (bath); and most of the solvents were distilled from the mixture. The remaining solvents were evaporated and the cooled residue was dissolved in water (240 mL) and acetic acid was added to adjust the solution to pH 9. Cyanoacetamide (10.06 g) was added to the solution and the mixture was heated at 90° C. for 18 h. After the mixture was cooled, the solvent was decanted from the gummy residue. The residue was sequentially triturated with aqueous 10% hydrochloric acid and chloroform to give a solid which was filtered, washed with ether, and dried under vacuum to give 6-(4-methoxyphenyl)pyrid-2-one- 3-carbonitrile (2.97 g); TLC: $R_f$=0.50, methanol:dichloromethane (4:96); MS: m/z=227(M+1).

The method of 2-pyridone preparation described above in Example 2.a. is denoted herein as Cyclization Method B.

b. 6-(4-Methoxyphenyl)pyrid-2-one-3-carboxylic acid.

A suspension of 6-(4-methoxyphenyl)pyrid-2-one-3-carbonitrile (2.95 g) in 50% NaOH (w/w; 13 mL) was heated at 140° C. overnight in a sealed pressure vessel. The reaction mixture was cooled to room temperature and allowed to stand for 24 h. The reaction mixture was diluted with water (150 mL) and acidified to pH 1 with concentrated hydrochloric acid. The solids were collected by filtration, washed with water (three times), and dried in a vacuum oven at 40° C. overnight. The dried 6-(4-methoxyphenyl)pyrid-2-one-3-carboxylic acid (3.22 g) required no further purification; MS: m/z=246(M+1).

The method of hydrolysis of the 3-cyano group to a 3-carboxy group described above in Example 2.b. is denoted herein as Hydrolysis Method B.

c. 3-Benzyloxycarbonylamino-6-(4-methoxyphenyl)pyrid-2-one.

Using a similar procedure to that described in Example 1.c., 6-(4-methoxyphenyl)pyrid-2-one-3-carboxylic acid was treated with diphenylphosphoryl azide, followed by benzyl alcohol. The crude solid was suspended in dichloromethane and washed with 10% hydrochloric acid. Filtration of the solids afforded a crude product which was further purified by trituration with chloroform to afford slightly impure urethane. Washing the initial dichloromethane solution with saturated sodium bicarbonate afforded an additional precipitation of pure urethane. Evaporation of the remaining dichloromethane solution, followed by trituration of the residue with chloroform, afforded an additional portion of pure urethane, which was combined with the other pure portion. The urethane was washed with hot water and dried under vacuum to afford 3-benzyloxycarbonylamino-6-(4-methoxyphenyl)pyrid- 2-one; TLC: $R_f$=0.56, dichloromethane:ethyl acetate:ethanol (95:3:2); MS: m/z=351(M+1).

d. 2-[3-Benzyloxycarbonylamino-6-(4-methoxyphenyl)-2-oxo-1,2-dihydro-1-pyridyl]-N-(2-tert-butyldimethylsilyloxy-3,3,3-trifluoro- 1-isopropylpropyl)acetamide.

Using a similar procedure to that described in Example 1.d., but using two successive purifications by flash chromatography, eluting with ethyl acetate:dichloromethane (initially 1.5:100, then 2.5:100 in the second chromatography), 3-benzyloxycarbonylamino-6-( 4-methoxyphenyl)pyrid-2-one was converted into 2-[3-benzyloxycarbonylamino- 6-(4-methoxyphenyl)-2-oxo-1,2-dihydro-1-pyridyl]-N-( 2-tert-butyldimethylsilyloxy-3,3,3-trifluoro-1-isopropylpropyl)acetamide; TLC: $R_f$=0.26, ethyl acetate:dichloromethane (3:97); MS: m/z=676(M+1).

e. 2-[3-Benzyloxycarbonylamino-6-(4-methoxyphenyl)-2-oxo-1,2-dihydro-1-pyridyl]-N-(3,3,3-trifluoro-2-hydroxy-1-isopropylpropyl)acetamide.

Using a similar procedure to that described in Example 1.e., but omitting the chromatography, 2-[3-benzyloxycarbonylamino-6-(4-methoxyphenyl)- 2-oxo-1,2-dihydro-1-pyridyl]-N-(2-tert-butyldimethylsilyloxy- 3,3,3-trifluoro-1-isopropylpropyl)acetamide was converted into 2-[3-benzyloxycarbonylamino-6-(4-methoxyphenyl)-2-oxo-1,2-dihydro- 1-pyridyl]-N-(3,3,3-trifluoro-2-hydroxy-1-isopropylpropyl)acetamide; TLC: $R_f$=0.52, ethyl acetate:dichloromethane (3:97); MS: m/z=562(M+1).

EXAMPLE 3

2-(3-Benzyloxycarbonylamino-2-oxo-6-phenethyl-1,2-dihydro-1-pyridyl)-N-(3,3,3-trifluoro-1-isopropyl-2-oxopropyl)acetamide.

Using a similar procedure to that described in Example 1, using ethyl acetate:dichloromethane (5:95) as the chromatography solvent, 2-(3-benzyloxycarbonylamino-2-oxo-6-phenethyl-1,2-dihydro- 1-pyridyl)-N-(3,3,3-trifluoro-2-hydroxy-1-isopropylpropyl)acetamide was oxidized to afford the title product; HPLC: $t_R$=6.16, FR=2.0, column A, water:acetonitrile (2:3); MS: m/z=558(M+1). Analysis for $C_{29}H_{30}F_3N_3O_5$:

Calculated: C, 62.57; H, 5.42; N, 7.54
Found: C, 62.31; H, 5.47; N, 7.42

The starting material alcohol used for the above preparation was prepared as follows:

a. 6-Methylpyrid-2-one-3-carbonitrile.

To a mixture of sodium methoxide (46.5 g) in dry ether (950 mL), stirred with a mechanical stirrer and cooled with an ice bath, was added a mixture of acetone (distilled from $K_2CO_3$ under nitrogen, 46.5 g) and ethyl formate (distilled from $P_2O_5$ under nitrogen, 59.6 g) dropwise over 1 hour. When addition was complete, the cooling bath was removed and the reaction mixture was warmed to room temperature over 1 hour. The reflux condenser was replaced with a condenser set for distillation, and volatile materials were distilled by heating with an oil bath which was not allowed to rise above 60° C. To the solid residue were added a solution of cyanoacetamide (67.0 g) in water (400 mL) and piperidine acetate (prepared by adding piperidine to a solution of 8 mL of glacial acetic acid in 20 mL of water until the solution was basic to litmus). The flask was fitted with a reflux condenser, and the mixture was heated for 2 h under reflux. The mixture was cooled to room temperature and acidified to pH 5 with glacial acetic acid. After standing overnight at room temperature, the mixture was cooled in an ice bath for about about 45 min; and the yellow solid product was filtered, washed with ice water (four times) and dried in a vacuum oven at 80° C. overnight. Crystallization from 50% (v/v) ethanol yielded 6-methylpyrid-2-one-3-carbonitrile as a yellow solid (52.6 g); TLC: $R_f$=0.29, chloroform:methanol (95:5);

NMR: 2.27 (s,3), 6.20 (d,1, J=7.4), 8.01 (d,1, J=7.4); MS: m/z=135(M+1).

The method of 2-pyridone preparation described above in Example 3.a. is denoted herein as Cyclization Method C.

b. 6-Phenethylpyrid-2-one-3-carbonitrile.

Using a similar procedure to that described below in Example 12.a., but using benzyl bromide in place of benzaldehyde, 6-methylpyrid-2-one-3-carbonitrile was alkylated to provide 6-phenethylpyrid-2-one-3-carbonitrile, which was washed with isopropanol and ether and dried under vacuum; TLC: $R_f$=0.49, methanol:chloroform (3:97); MS: m/z=225(M+1).

c. 6-Phenethylpyrid-2-one-3-carboxylic acid.

Using Hydrolysis Method A, 6-phenethylpyrid-2-one-3-carbonitrile was hydrolyzed to 6-phenethylpyrid-2-one-3-carboxylic acid, which was filtered, washed with water and dried under vacuum; MS: m/z=244(M+1).

d. 3-Benzyloxycarbonylamino-6-phenethylpyrid-2-one.

Using a similar method to that described in Example 1.c., isolating the product by filtration, washing with ethyl acetate, and drying under vacuum, 6-phenethylpyrid-2-one-3-carboxylic acid was converted into 3-benzyloxycarbonylamino-6-phenethylpyrid-2-one; TLC: $R_f$=0.48, methanol:chloroform (4:96); MS: m/z=349(M+1).

e. tert-Butyl (3-Benzyloxycarbonylamino-2-oxo-6-phenethyl-1,2-dihydro- 1-pyridyl)acetate.

Using a similar procedure to that of Example 1.d., above, 3-benzyloxycarbonylamino-6-phenethylpyrid-2-one (1.64 g) was suspended in dry dimethylformamide (20 mL) and to this suspension was added NaH (0.22 g of a 60% mineral oil dispersion). The mixture was stirred for 1.5 h, at which point all solids were in solution. tert-Butyl bromoacetate (0.92 g) was added, and the mixture was stirred overnight. The mixture was diluted with water (100 mL) and extracted with ethyl acetate (four times). The extracts were washed with brine, dried and evaporated. The residue was purified by chromatography, eluting with methanol:dichloromethane (0:100 then 3:97), to give tert-butyl (3-benzyloxycarbonylamino-2-oxo-6-phenethyl-1,2-dihydro- 1-pyridyl)acetate (0.578 g); TLC: $R_f$=0.17, dichloromethane; MS: m/z= 463(M+1).

NOTE: Also isolated from the chromatography was the corresponding O-alkylated product (0.512 g); TLC: $R_f$=0.61, dichloromethane.

f. (3-Benzyloxycarbonylamino-2-oxo-6-phenethyl-1,2-dihydro-1-pyridyl)acetic acid.

To a solution of tert-butyl (3-benzyloxycarbonylamino-2-oxo- 6-phenethyl-1,2-dihydro-1-pyridyl)acetate (0.554 g) in dichloromethane (distilled from CaH) was added trifluoroacetic acid (1.50 ml); and the mixture was stirred overnight, evaporated, and dried under vacuum to afford (3-benzyloxycarbonylamino-2-oxo-6-phenethyl- 1,2-dihydro-1-pyridyl)acetic acid; MS: m/z=407(M+1).

g. 2-(3-Benzyloxycarbonylamino-2-oxo-6-phenethyl-1,2-dihydro-1-pyridyl)-N-(3,3,3-trifluoro-2-hydroxy-1-isopropylpropyl) acetamide.

(3-Benzyloxycarbonylamino-2-oxo-6-phenethyl-1,2-dihydro-1-pyridyl)acetic acid (0.50 g) was dissolved in dry tetrahydrofuran (15 mL) along with 3-amino-1,1,1-trifluoro-4-methyl-2-pentanol hydrochloride (0.25 g), 1-(3-dimethylaminopropyl)-3-ethylcarbodiimide hydrochloride (0.23 g), 4-methylmorpholine (0.27 g) and 1-hydroxybenzotriazole hydrate (0.47 g). The mixture was stirred for 2 days. The reaction mixture was evaporated and the residue partitioned between ethyl acetate (50 mL) and 10% hydrochloric acid (25 mL). The layers were separated and the organics were washed with 10% hydrochloric acid, saturated sodium bicarbonate (twice) and brine; dried and evaporated to a foam. Chromatography, eluting with methanol:dichloromethane (4:96), gave 2-(3-benzyloxycarbonylamino-2-oxo-6-phenethyl-1,2-dihydro-1-pyridyl)-N-(3,3,3-trifluoro-2-hydroxy-1-isopropyl)acetamide (0.51 g); TLC: $R_f$=0.48, methanol:dichloromethane (4:96); MS: m/z=560(M+1).

EXAMPLES 4–12

Using similar procedures to that described in Example 1, the following compounds of formula I wherein $R^0$ is isopropyl, R is benzyloxycarbonyl and $R^5$ and $R^6$ have the indicated values were prepared by oxidation of the corresponding alcohols of formula II:

EXAMPLE 4

$R^5$=hydrogen, $R^6$=3-pyridyl: Chromatography solvent: methanol:dichloromethane (1.5:98.5); TLC: $R_f$=0.24, methanol:dichloromethane (3:97); HPLC: $t_R$=6.80, FR=2.0, column A, water:acetonitrile (1:1); MS: m/z=531(M+1).

Analysis for $C_{26}H_{25}F_3N_4O_5 \cdot 0.25\ H_2O$:

Calculated: C, 58.37; H, 4.80; N, 10.47

Found: C, 58.36; H, 4.89, N, 10.27

An alternative synthesis for this compound is described in Example 170.

EXAMPLE 5

$R^5$=hydrogen, $R^6$=4-chlorophenyl: Chromatography solvent: chloroform:ethyl acetate (20:1); TLC: Rf=0.29, chloroform:ethyl acetate (20:1); MS: m/z=564(M+1 for $^{35}$Cl).

Analysis for $C_{27}H_{25}ClF_3N_3O_5$:

Calculated: C, 57.50; H, 4.47; N, 7.45

Found: C, 57.45; H, 4.66; N, 7.47

EXAMPLE 6

$R^5$=hydrogen, $R^6$=3-tert-butoxyphenyl: Chromatography solvent: ethanol:ethyl acetate:dichloromethane (0.25:2.5:97.25); TLC: Rf=0.59, methanol:ethyl acetate:dichloromethane (2:3:95); HPLC: $t_R$=5.54, FR=2.0, column A; water:acetonitrile (2:3); MS: m/z=602(M+1).

Analysis for $C_{31}H_{34}F_3N_3O_6 \cdot 0.5\ H_2O$:

Calculated: C, 60.98; H, 5.78; N, 6.88

Found: C, 60.96; H, 5.69; N, 6.66

EXAMPLE 7

$R^5$=hydrogen, $R^6$=4-methylphenyl: Chromatography solvent (chromatographed twice): ethanol:ethyl acetate:dichloromethane (0.5:5:94.5—first time) then (0.25:2.5:97.25—second time); TLC: $R_f$=0.21, ethanol:ethyl acetate:dichloromethane (0.5:5:94.5); HPLC: $t_R$=8.27, FR=1, column A, water:acetonitrile (2:3); MS: m/z=544(M+1).

Analysis for $C_{28}H_{28}F_3N_3O_5$:

Calculated: C, 61.87; H, 5.19; N, 7.73

Found: C, 61.62; H, 5.21; N, 7.58

EXAMPLE 8

$R^5$=hydrogen, $R^6$=3-chlorophenyl: Chromatography solvent: dichloromethane:ethyl acetate (gradient, 50:1 then 50:2); HPLC: $t_R$=9.36, FR=2.0, column A, water:acetonitrile (1:1); MS: m/z=564(M+1 for $^{35}$Cl).

Analysis for $C_{27}H_{25}ClF_3N_3 \cdot 0.2\ H_2O$:

Calculated: C, 57.13; H, 4.52; N, 7.40

Found: C, 57.07; H, 4.55; N, 7.30

EXAMPLE 9

$R^5$=methyl, $R^6$=phenyl: Chromatography solvent: dichloromethane:ethyl acetate:ethanol (95:5:1); TLC: $R_f$=0.57, dichlomethane:ethyl actate:ethanol; HPLC: $t_R$=5.84, FR=3.0, column A, water:acetonitrile (1:1); MS: m/z=544(M+1).

Analysis for $C_{28}H_{28}F_3N_3O_5 \cdot 0.35\ H_2O$:

Calculated: 61.16; H, 5.26; N, 7.73

Found: 61.13; H, 5.31; N, 7.53

EXAMPLE 10

$R^5$=hydrogen $R^6$=3,5-dimethoxyphenyl: Chromatography solvent: ethanol:ethyl acetate:dichloromethane (gradient, 0:0:1, 0:2:98, 1:2:98); TLC: $R_f$=0.32, ethanol:ethyl acetate:dichloromethane (1:2:97); HPLC: $t_R$=6.44, FR=3.0, column A, water:acetonitrile (1:1); MS: m/z=590(M+1).

Analysis for $C_{29}H_{30}F_3N_3O_7$:

Calculated: C, 59.07; H, 5.13; N, 7.13

Found: C, 58.80; H, 5.16; N, 6.96

EXAMPLE 11

$R^5$=hydrogen, $R^6$=benzyl: Chromatography solvent: chloroform:ethyl acetate (gradient, 30:1 to 20:1); TLC: $R_f$=0.31, chloroform:methanol (50:1); MS: m/z=544(M+1).

Analysis for $C_{28}H_{28}F_3N_3O_5 \cdot 0.4\ H_2O$:

Calculated: C, 61.06; H, 5.27; N, 7.63

Found: C, 61.08; H, 5.26; N, 7.54

EXAMPLE 12

$R^5$=hydrogen, $R^6$=trans-styryl: Chromatography solvent: ethyl acetate:dichloromethane (5:95); TLC: $R_f$=0.46, ethyl acetate:dichloromethane (1:9); HPLC: $t_R$=6.48, FR=2, column A, water:acetonitrile (2:3); MS: m/z=556(M+1).

Analysis for $C_{29}H_{28}F_3N_3O_5$:

Calculated: C, 62.70; H, 5.08; N, 7.56

Found: C, 62.64; H, 5.18; N, 7.55

The corresponding alcohols of formula II for Examples 4–12 were prepared as follows:

EXAMPLES 4.a.–11.a.

Pyrid-2-one-3-carbonitriles bearing the substituents $R^5$ at the 5-position and $R^6$ at the 6-position were prepared from the corresponding ketones of formula $R^5.CH_2.CO.R^6$ using similar procedures to those of the indicated Cyclization Methods described above:

EXAMPLE 4.a.

$R^5$=hydrogen, $R^6$=3-pyridyl: Cyclization Method A; MS: m/z=198(M+1).

EXAMPLE 5.a.

$R^5$=hydrogen, $R^6$=4-chlorophenyl: Cyclization Method A; TLC: $R_f$=0.17, chloroform:methanol (50:1); MS: m/z=231(M+1 for $^{35}$Cl).

EXAMPLE 6.a.:

$R^5$=hydrogen, $R^6$=3-tert-butoxyphenyl: Cyclization Method A; chromatographed:, eluting with ethyl acetate-:dichloromethane (10:90) followed by trituration with ethyl acetate and precipitation of additional material by adding hexane to the ethyl acetate supernatant; MS: m/z=269(M+1).

The 3'-tert-butoxyacetophenone used for the cyclization was prepared as follows:

A mixture of 3'-hydroxyacetophenone (22.64 g), isobutylene (300 mL) and concentrated $H_2SO_4$ (1 mL) in dry dichloromethane (310 mL) was stirred in a sealed pressure vessel at room temperature for 3 days. After the reaction vessel was vented, the organic phase was washed (10% NaOH, water and brine), dried and evaporated to an oil (25.95 g) which was purified by chromatography, eluting with dichloromethane:ethyl acetate, to give 3'-tert-butoxyacetophenone (22.62 g); TLC: $R_f$=0.55, ethyl acetate:dichloromethane (3:97); MS: m/z=193(M+1).

EXAMPLE 7.a.

$R^5$=hydrogen, $R^6$=4-methylphenyl: Cyclization Method B; after the reaction mixture was filtered at about pH 8, the collected solid was first stirred with 10% hydrochloric acid then triturated with chloroform and ether before air drying; TLC: $R_f$=0.43, chloroform:methanol (20:1); MS: m/z=211(M+1).

EXAMPLE 8.a.

$R^5$=hydrogen, $R^6$=3-chlorophenyl: Cyclization Method A; triturated with ether; TLC: $R_f$=0.22, dichloromethane:methanol (95:5); MS: m/z=231(M+1).

EXAMPLE 9.a.

$R^5$=methyl, $R^6$=phenyl: Cyclization Method A; 300 MHz NMR: 1.96 (s,3), 7.46–7.54 (m,5), 8.15 (s,1), 12.53 (broad s, 1); MS: m/z=211(M+1).

EXAMPLE 10.a $R^5$=hydrogen, $R^6$=3,5-dimethoxyphenyl: Cyclization Method B; TLC: $R_f$=0.44, methanol:dichloromethane (2:98); MS: m/z=257(M+1).

EXAMPLE 11.a.

$R^5$=hydrogen, $R^6$=benzyl: Cyclization Method C; recrystallized from hot ethanol, washed with ether; TLC: $R_f$=0.44, chloroform:methanol (20:1); 300 MHz NMR: 3.90 (s,2), 6.16 (d,1, J=7), 7.32 (m,5), 8.03 (d,1, J=7), 12.8 (broad, 1); MS: m/z=211(M+1).

Analysis for $C_{13}H_{10}N_2O$:
Calculated: C, 74.27; H, 4.79, N, 13.32
Found: C, 74.20; H, 5.01, N, 13.31

EXAMPLE 12.a.

$R^5$=hydrogen, $R^6$=trans-styryl: A solution of dry diisopropylamine (6.6 mL, 4.77 g) in dry tetrahydrofuran (200 mL) under nitrogen in a 500 mL round-bottomed flask was cooled with a –78° C. bath. A solution of n-butyl lithium (2.14M in hexanes; 19.0 mL) was added, and the resultant solution was stirred at –78° C. for 20 min. 6-Methylpyrid-2-one-3-carbonitrile (2.50 g) was added as a solid. After 5 min of stirring at –78° C., the mixture was allowed to warm to 0° C. After the mixture was stirred for 2.5 h at 0° C., a solution of freshly distilled benzaldehyde (1.90 mL; 1.98 g) in dry tetrahydrofuran (4 mL) was added via syringe; and the orange reaction mixture was stirred at 0° C. for 2 h before warming to room temperature and stirring overnight. The mixture was evaporated, and the residue dissolved in water (100 mL). The aqueous phase was washed with ether and petroleum ether. Acidification with 10% hydrochloric acid to about pH 3 gave 6-(2-hydroxy-2-phenylethyl)pyrid-2-one-3-carbonitrile as a yellow solid (3.17 g) which was collected by filtration, washed with isopropanol and ether, dried under vacuum, and used in the next step without purification; MS: m/z=241(M+1).

EXAMPLES 4.b.–11.b.

Pyrid-2-one-3-carboxylic acids bearing the substituents $R^5$ at the 5-position and $R^6$ at the 6-position were prepared from the corresponding pyrid-2-one-3-carbonitriles using similar procedures to those of the Hydrolysis Methods described above:

EXAMPLE 4.b.

$R^5$=hydrogen, $R^6$=3-pyridyl: Hydrolysis Method A; MS: m/z=217(M+1).

EXAMPLE 5.b.

$R^5$=hydrogen, $R^6$=4-chlorophenyl: Hydrolysis Method A; TLC: $R_f$=0.33, chloroform:methanol:acetic acid (50:1:trace); MS: m/z=250(M+1 for $^{35}Cl$).

EXAMPLE 6.b.

$R^5$=hydrogen, $R^6$=3-tert-butoxyphenyl: Hydrolysis Method B; MS: m/z=288(M+1).

EXAMPLE 7.b.

$R^5$=Hydrogen, $R^6$=4-methylphenyl: Hydrolysis Method A; TLC: $R_f$=0.41, chloroform:methanol:acetic acid (20:1:0.1); MS: m/z=230(M+1).

EXAMPLE 8.b.

$R^5$=Hydrogen, $R^6$=3-chlorophenyl: Hydrolysis Method A; TLC: $R_f$=0.99, chloroform:methanol:acetic acid (85:10:5); MS: m/z=250(M+1 for $^{35}Cl$).

EXAMPLE 9.b.

$R^5$=methyl, $R^6$=phenyl: Hydrolysis Method A; TLC: $R_f$=0.34, chloroform:methanol (20:1); MS: m/z=230(M+1).

EXAMPLE 10.b.

$R^5$=Hydrogen, $R^6$=3,5-dimethoxyphenyl: Hydrolysis Method B; MS: m/z=276(M+1).

EXAMPLE 11.b.

$R^5$=hydrogen, $R^6$=benzyl: Hydrolysis Method A; TLC: $R_f$=0.42, dichloromethane:methanol:acetic acid (50:1:trace); MS: m/z=230(M+1).

EXAMPLE 12.b.

6-(2-Hydroxy-2-phenylethyl)pyrid-2-one-3-carbonitrile prepared according to the procedure of Example 12.a. (3.12 g) was suspended in glacial acetic acid (27 mL) and 48% hydrobromic acid (13 mL). The mixture was heated at reflux overnight, cooled and evaporated. The residue was suspended in water and made basic with 50% NaOH. Undissolved solids were removed by filtration. The filtrate was brought to about pH 3 with concentrated HCl. The precipitate which formed was collected by filtration, washed with water and dried under vacuum overnight to afford trans-6-styrylpyrid- 2-one-3-carboxylic acid (1.58 g) which was used in the next step without further purification; MS: m/z=242(M+1).

EXAMPLES 4.c.–12.c.

Using similar procedures to that described above in Example 1.c., except omitting the trituration, 3-benzyloxycarbonylaminopyrid- 2-ones bearing the substituents $R^5$ at the 5-position and $R^6$ at the 6-position were prepared from the corresponding pyrid-2-one-3-carboxylic acids:

EXAMPLE 4.c.

$R^5$=hydrogen, $R^6$=3-pyridyl: TLC: $R_f$=0.70, chloroform:methanol (9:1); MS: m/z=322(M+1).

EXAMPLE 5.c.

$R^5$=hydrogen, $R^6$=4-chlorophenyl: Purified by chromatography, eluting with chloroform:methanol (50:1), or by crystallization from chloroform; TLC: $R_f$=0.72, chloroform:methanol (20:1); MS: m/z=355(M+1 for $^{35}$Cl).

EXAMPLE 6.c.

$R^5$=hydrogen, $R^6$=3-tert-butoxyphenyl: Purified by chromatography, eluting with ethyl acetate:dichloromethane (3:97); TLC: $R_f$=0.67, methanol:chloroform (4:96); MS: m/z=393(M+1).

EXAMPLE 7.c.

$R^5$=hydrogen, $R^6$=4-methylphenyl: Purification by trituration with chloroform; TLC: $R_f$=0.14, chloroform:ethyl acetate (50:1); MS: m/z=335(M+1).

EXAMPLE 8.c.

$R^5$=hydrogen, $R^6$=3-chlorophenyl: Purification by recrystallization from hot ethanol and chloroform; TLC: $R_f$=0.57, dichloromethane:methanol (95:5); MS: m/z=355(M+1).

EXAMPLE 9.c.

$R^5$=methyl, $R^6$=phenyl: Purified by chromatography, eluting with chloroform:methanol (50:1); TLC: $R_f$=0.35, chloroform:methanol (50:1); MS: m/z=335(M+1).

EXAMPLE 10.c $R^5$=hydrogen, $R^6$=3,5-dimethoxyphenyl: Purified by chromatography, eluting with ethanol:ethyl acetate:dichloromethane (1:2:97), followed by trituration with ether; TLC: $R_f$=0.48, ethanol:ethyl acetate:dichloromethane (2:3:95); MS: m/z=381(M+1).

EXAMPLE 11.c.

$R^5$=hydrogen, $R^6$=benzyl: Purified by recrystallization from ethanol; TLC: $R_f$=0.75, chloroform:methanol (20:1), $R_f$=0.10, hexane:ethyl acetate (3:1); MS: m/z=335(M+1).

EXAMPLE 12.c.

$R^5$=hydrogen, $R^6$=trans-styryl: filtered and dried under vacuum; MS: m/z=347(M+1).

EXAMPLES 4.d.–12.d.

Using similar procedures to that described above in Example 1.d., 2-(3-benzyloxycarbonylamino-2-oxo-1,2-dihydro-1-pyridyl)-N-(2-tert-butyldimethylsilyloxy- 3,3,3-trifluoro-1-isopropylpropyl)acetamides bearing the substituents $R^5$ at the 5-position of the pyridyl ring and $R^6$ at the 6-position of the pyridyl ring were prepared from the corresponding 3-benzyloxycarbonylaminopyrid-2-ones and N-(2-tert-butyldimethylsilyloxy-3,3,3-trifluoro-1-isopropylpropyl)- 2-iodoacetamide:

EXAMPLE 4.d.

$R^5$=hydrogen, $R^6$=3-pyridyl: Chromatography solvent: methanol:chloroform (0.5:99.5); TLC: $R_f$=0.37, methanol:dichloromethane (2:98); MS: m/z=647(M+1).

EXAMPLE 5.d.

$R^5$=hydrogen, $R^6$=4-chlorophenyl: Chromatography solvent: dichloromethane:ethyl acetate (100:1 then 50:1); TLC: $R_f$=0.23, dichloromethane:ethyl acetate (50:1); MS: m/z=680(M+1 for $^{35}$Cl).

EXAMPLE 6 d.

$R^5$=hydrogen, $R^6$=3-tert-butoxyphenyl: Purified by three successive chromatographies, eluting with (1) chloroform, (2) ethanol:ethyl acetate:dichloromethane (0.5:0.5:99), and (3) ethanol:ethyl acetate:dichloromethane (0.25:0.5:99.25), which resulted in a product which still contained a small amount of the O-alkylated isomer and was used for Example 6.e.; TLC: $R_f$=0.31, methanol:ethyl acetate:dichloromethane (0.5:1:98.5); MS: m/z=718(M+1).

EXAMPLE 7.d.

$R^5$=hydrogen, $R^6$=4-methylphenyl: Chromatography solvent: ethanol:ethyl acetate:dichloromethane (0.25:2:97.75); TLC: $R_f$=0.25, ethyl acetate:dichloromethane (3:97); MS: m/z=660(M+1).

EXAMPLE 8.d.

$R^5$=hydrogen, $R^6$=3-chlorophenyl: Purified by three successive chromatographies, eluting with (1) chloroform:ethyl acetate:methanol (75:1:0.5), (2) chloroform:ethyl acetate:acetic acid (50:1:0.15), and (3) dichloromethane:ethyl acetate (70:1 then 60:1); TLC (of crude reaction mixture): $R_f$=0.40, chloroform:ethyl acetate (50:1); MS: m/z=681(M+1 for $^{35}$Cl).

EXAMPLE 9.d $R^5$=methyl, $R^6$=phenyl: Chromatography solvent: chloroform:ethyl acetate:methanol (50:1:0 then 75:1:0.5); TLC: $R_f$=0.31, chloroform:ethyl acetate (50:1); MS: m/z=660(M+1).

EXAMPLE 10.d.

$R^5$=hydrogen, $R^6$=3,5-dimethoxyphenyl: Chromatography solvent: dichloromethane:ethyl acetate:ethanol (98:2:0.5) which afforded a mixture of N- and O-alkylated products which was carried through to the next step before separation; TLC: $R_f$=0.36 (N-alkylated) and 0.43 (O-alkylated), dichloromethane:ethyl acetate:ethanol (97:2:1); MS: m/z=706(M+1).

EXAMPLE 11.d.

$R^5$=hydrogen; $R^6$=benzyl: Chromatography solvent: chloroform:ethyl acetate (20:1); TLC: $R_f$=0.53, hexane:ethyl acetate (3:1); MS: m/z=660 (M+1).

EXAMPLE 12.d.

$R^5$=hydrogen, $R^6$=trans-styryl: Chromatography solvent: methanol:ethyl acetate:dichloromethane (successively: 0:1:99, 0:5:95, 0:15:85, 5:0:95); TLC: $R_f$=0.51, ethyl acetate:dichloromethane (5:95).

EXAMPLES 4.e.–12.e.

Using similar procedures to that described above in Example 1.e., 2-(3-benzyloxycarbonylamino-2-oxo-1,2-dihydro-1-pyridyl)-N-( 3,3,3-trifluoro-2-hydroxy-1-isopropylpropyl)acetamides bearing the substituents $R^5$ at the 5-position of the pyridyl ring and $R^6$ at the 6-position of the pyridyl ring were prepared from the corresponding 2-(3-benzyloxyaminocarbonylamino-2-oxo-1,2-dihydro-1-pyridyl)-N-(2-tert-butyldimethylsilyloxy- 3,3,3-trifluoro-1-isopropylpropyl)acetamides:

EXAMPLE 4.e $R^5$=Hydrogen, $R^6$=3-pyridyl: Isolated and dried without chromatography; TLC: $R_f$=0.15, methanol:dichloromethane (2:98); MS: m/z=533(M+1).

EXAMPLE 5.e.

$R^5$=hydrogen, $R^6$=4-chlorophenyl: Chromatography solvent: chloroform:ethyl acetate (20:1 then 10:1); TLC: $R_f$=0.17, chloroform:ethyl acetate (20:1); MS: m/z=566(M+1 for $^{35}$Cl).

EXAMPLE 6.e.

$R^5$=Hydrogen; $R^6$=3-tert-butoxyphenyl: Chromatography solvent: methanol:ethyl acetate:dichloromethane (0.5:4:95.5); TLC: $R_f$=0.18, methanol:ethyl acetate:dichloromethane (1:4:95); MS: m/z=604(M+1).

EXAMPLE 7.e.

$R^5$=hydrogen, $R^6$=4-methylphenyl: Chromatography solvent: ethanol:ethyl acetate:dichloromethane (1:3:96); TLC: $R_f$=0.19, ethanol:ethyl acetate:dichloromethane (1:4:95).

EXAMPLE 8.e.

$R^5$=hydrogen, $R^6$=3-chlorophenyl: Purified by washing with water and brine and drying under vacuum; TLC (of crude reaction mixture): $R_f$=0.15, chloroform:methanol (50:1); MS: m/z=566(M+1 for $^{35}$Cl).

EXAMPLE 9.e.

$R^5$=methyl, $R^6$=phenyl: Isolated directly, not further purified; TLC: $R_f$=0.32, dichloromethane:ethyl acetate (9:1); MS: m/z=546(M+1).

EXAMPLE 10.e.

$R^5$=hydrogen, $R^6$=3,5-dimethoxyphenyl: Chromatography solvent: ethanol:ethyl acetate:dichloromethane (0.5:2:97.5); TLC: $R_f$=0.22, ethanol:ethyl acetate:dichloromethane (1:2:97); MS: m/z=592(M+1).

EXAMPLE 11.e.

$R^5$=hydrogen, $R^6$=benzyl: Chromatography solvent: chloroform:methanol (20:1); TLC: $R_f$=0.26, chloroform:methanol (50:1); MS: m/z=546(M+1).

EXAMPLE 12.e.

$R^5$=hydrogen, $R^6$=trans-styryl: Chromatography solvent: ethyl acetate:dichloromethane (1:9); TLC: $R_f$=0.33, ethyl acetate:dichloromethane (1:9); MS: m/z=558(M+1).

EXAMPLE 13

2-[3-Benzyloxycarbonylamino-6-(3-hydroxyphenyl)-2-oxo-1,2-dihydro-1-pyridyl]
-N-(3,3,3-trifluoro-1-isopropyl-2-oxopropyl)acetamide.

To a solution of 2-[3-benzyloxycarbonylamino-6-(3-tert-butoxyphenyl)- 2-oxo-1,2-dihydro-1-pyridyl]-N-(3,3,3-trifluoro-1-isopropyl- 2-oxopropyl)acetamide (78 mg) in dry dichloromethane (3 mL) was added trifluoroacetic acid (57 mg). After 5 h the reaction was incomplete, and additional trifluoroacetic acid (57 mg) was added. After 18 h the reaction mixture was diluted with dichloromethane (50 mL), washed with water and brine, dried, and evaporated to a crude oil which was purified by chromatography, eluting with ethanol:ethyl acetate:dichloromethane (0.5:5:94.5), to give the title compound as a white solid (60 mg); TLC: $R_f$=0.15, ethanol:ethyl acetate:dichloromethane (0.5:5:94.5); HPLC: $t_R$=6.04, FR=2.0, column A, water:acetonitrile (55:45); MS: m/z=546(M+1).

Analysis for $C_{27}H_{26}F_3N_3O_6$:

Calculated: C, 59.44; H, 4.80; N, 7.70

Found: C, 59.58; H, 4.91; N, 7.41

EXAMPLE 14

2-(2-Oxo-6-phenyl-3-phenylacetylamino-1,2-dihydro- 1-pyridyl)-N-(3,3,3-trifluoro-1-isopropyl-2-oxopropyl)acetamide.

Using a similar procedure to that described in Example 1, using methanol:dichloromethane (1:99) as the chromatography solvent, 2-(2-oxo-6-phenyl-3-phenylacetylamino-1,2-dihydro-1-pyridyl)-N-(3,3,3-trifluoro- 2-hydroxy-1-isopropylpropyl)acetamide was oxidized to afford the title product; HPLC: $t_R$=6.92, FR=2.0, column A, water:acetonitrile (55:45); MS: m/z=514(M+1).

Analysis for $C_{27}H_{26}F_3N_3O_4$:

Calculated: C, 63.15; H, 5.10; N, 8.18

Found: C, 63.03; H, 4.98; N, 8.02

The starting material alcohol used for the above preparation was prepared as follows:

a. 2-(3-Amino-2-oxo-6-phenyl-1,2-dihydro-1-pyridyl)-N-(2-tert-butyl-dimethylsilyloxy-3,3,3-trifluoro-1-isopropylpropyl)acetamide.

To a solution of 2-(3-benzyloxycarbonylamino-2-oxo-6-phenyl- 1,2-dihydro-1-pyridyl)-N-(2-tert-butyldimethylsilyloxy-3,3,3-trifluoro- 1-isopropylpropyl)acetamide (2.41 g) in dry tetrahydrofuran (8 mL) was added 10% (w/w) palladium-on-carbon (0.50 g) in dry tetrahydrofuran (8 mL) under nitrogen. This mixture was stirred under hydrogen at atmospheric pressure for 5 h. The catalyst was removed by filtration through a plug of diatomaceous earth and the plug was washed with ethanol. The filtrate was evaporated and dried under vacuum to give 2-(3-amino-2-oxo-6-phenyl-1, 2-dihydro-1-pyridyl)-N-( 2-tert-butyldimethylsilyloxy-3,3, 3-trifluoro-1-isopropylpropyl)acetamide (1.78 g); TLC: $R_f$=0.06, ethyl acetate:dichloromethane (6:94); MS: m/z= 512(M+1).

Alternatively, the 3-amino-6-phenylpyridone may be prepared from the 3-benzyloxycarbonyl-6-(2-chlorophenyl)pyridone as follows: To a solution of 2-[3-benzyloxycarbonylamino-6-(2-chlorophenyl)-2-oxo- 1,2-dihydro-1-pyridyl]-N-(2-tert-butyldimethylsilyloxy-3,3,3-trifluoro-1-isopropylpropyl)acetamide (Example 21.d.) (0.35 g) in dry tetrahydrofuran (3 mL) was added 10% (w/w) palladium-on-carbon (91 mg). This mixture was stirred under hydrogen at atmospheric pressure overnight. The catalyst was removed by filtration through a plug of diatomaceous earth and the plug was washed with tetrahydrofuran. The filtrate was evaporated and dried under vacuum to give a white powder (0.28 g). To a solution of this powder in absolute ethanol (3 mL) was added sodium methoxide (30 mg), and the mixture was stirred until dissolution of all solid had occurred. To the solution was added 10% (w/w) palladium-on-carbon (90 mg), and the mixture was stirred under hydrogen at atmospheric pressure overnight. The catalyst was removed by filtration through a plug of diatomaceous earth and the plug was washed with ethanol. The filtrate was evaporated and the residue was partitioned between chloroform and water. The organic layer was washed with brine, dried and evaporated to give 2-(3-amino-2-oxo- 6-phenyl-1,2-dihydro-1-pyridyl)-N-(2-tert-butyldimethylsilyloxy-3,3,3-trifluoro-1-isopropyl-propyl)acetamide as a white solid (0.23 g).

b. N-(2-tert-Butyldimethylsilyloxy-3,3,3-trifluoro-1-isopropylpropyl)- 2-(2-oxo-6-phenyl-3-phenylacetylamino-1,2-dihydro-1-pyridyl)acetamide.

A 25 mL flask was charged with 2-(3-amino-2-oxo-6-phenyl- 1,2-dihydro-1-pyridyl)-N-(2-tert-butyldimethylsilyloxy-3,3,3-trifluoro- 1-isopropylpropyl)acetamide (0.301 g) dissolved in freshly distilled tetrahydrofuran (6 mL) under nitrogen. Triethylamine (0.09 mL) was added, followed by phenylacetyl chloride (0.08 mL). The cloudy, yellowish solution was stirred overnight; diluted with ethyl acetate (50 mL); washed with 10% hydrochloric acid (three times), saturated aqueous sodium bicarbonate (three times) and brine; dried; and evaporated to give an oil which solidified under vacuum. The soft solid was purified by chromatography, eluting with ethyl acetate:dichloromethane (3:97), to afford N-(2-tert-butyldimethylsilyloxy- 3,3,3-trifluoro-1-isopropylpropyl)-2-(2-oxo-6-phenyl-3-phenylacetylamino-1,2-dihydro-1-pyridyl)acetamide (0.272 g); TLC: $R_f$=0.54, methanol:dichloromethane (1:99); MS: m/z=630(M+1).

The above described acylation using an acid chloride is denoted herein as Acylation Method A.

c. 2-(2-Oxo-6-phenyl-3-phenylacetylamino-1,2-dihydro-1-pyridyl)-N-(3,3,3-trifluoro-2-hydroxy-1-iso-propylpropyl)acetamide.

Using a similar procedure to that described in Example 1.e., diluting the reaction mixture with ethyl acetate, washing it with water, and evaporating it, N-(2-tert-butyldimethylsilyloxy-3,3,3-trifluoro- 1-isopropylpropyl)-2-(2-oxo-6-phenyl-3-phenylacetylamino- 1,2-dihydro-1-pyridyl)acetamide was converted into 2-(2-oxo-6-phenyl-3-phenylacetylamino-1,2-dihydro-1-pyridyl)-N-(3,3,3-trifluoro-2-hydroxy- 1-isopropylpropyl)acetamide; TLC: $R_f$=0.23, methanol:dichloromethane (1:99); MS: m/z= 516(M+1).

EXAMPLE 15

2-[3-(4-Methoxyphenyl)acetylamino-2-oxo-6-phenyl-1,2-dihydro-1-pyridyl] -N-(3,3,3-trifluoro-1-iso-propyl-2-oxopropyl) acetamide.

Using a similar procedure to that described in Example 1, preadsorbing the crude product onto silica gel before chromatography, eluting with methanol:ethyl acetate:dichloromethane (0.5:5:94.5), 2-[3-(4-methoxyphenyl)acetylamino-2-oxo-6-phenyl-1,2-dihydro-1-pyridyl] -N-(3,3,3-trifluoro-2-hydroxy-1-isopropylpropyl)acetamide was oxidized to afford the title product; HPLC: $t_R$=6.18, FR=2.0, column A, water:acetonitrile (55:45); MS: m/z=544(M+1).

Analysis for $C_{28}H_{28}F_3N_3O_5 \cdot 0.5\ H_2O$:

Calculated: C, 60.86; H, 5.29; N, 7.60

Found: C, 60.85; H, 5.36; N, 7.43

The starting material alcohol for the above preparation was prepared as follows:

a. N-(2-tert-Butyldimethylsilyloxy-3,3,3-trifluoro-1-isopropylpropyl)- 2-[3-(4-methoxyphenyl)acetylamino-2-oxo-6-phenyl-1,2-dihydro- 1-pyridyl]acetamide.

To 2-(3-amino-2-oxo-6-phenyl-1,2-dihydro-1-pyridyl)-N-( 2-tert-butyldimethylsilyloxy-3,3,3-trifluoro-1-isopropylpropyl)acetamide (0.295 g) suspended in redistilled tetrahydrofuran (5 mL) was added 4-methoxyphenylacetic acid (0.97 g), followed by 1-hydroxybenzotriazole hydrate (0.156 g) and 1-(3-dimethylaminopropyl)- 3-ethylcarbodiimide hydrochloride (0.123 g). The reaction was shown by TLC to be incomplete after overnight stirring; therefore, triethylamine (0.08 mL) and 4-dimethylaminopyridine (catalytic amount) were added to the mixture. After stirring 1 h, additional acid (0.098 g), 1-(3-dimethylaminopropylpropyl)-3-ethylcarbodiimide hydrochloride (0.123 g), triethylamine (0.08 mL), and 1-hydroxybenzotriazole (0.156 g) were added. Additional tetrahydrofuran (2 mL) was added to facilitate stirring. After stirring overnight TLC indicated little change in the reaction mixture which was diluted with ethyl acetate (50 mL); washed with water (twice), saturated aqueous sodium bicarbonate (three times) and brine; dried; and evaporated. Purification by chromatography, eluting with ethanol:ethyl acetate:dichloromethane (0.5:5:94.5) gave N-(2-tert-butyldimethylsilyloxy- 3,3,3-trifluoro-1-isopropylpropyl)-2-[3-( 4-methoxyphenyl)acetylamino-2-oxo-6-phenyl-1,2-dihydro-1-pyridyl]acetamide (0.235 g); TLC (of crude reaction mixture): $R_f$=0.88, methanol:dichloromethane (4:96); MS: m/z=660(M+1).

The above described acylation using 1-(3-dimethylaminopropyl)- 3-ethylcarbodiimide for the coupling of an acid with a 3-aminopyridyl derivative is denoted herein as Acylation Method B.

b. 2-[3-(4-Methoxyphenyl)acetylamino-2-oxo-6-phenyl-1,2-dihydro-1-pyridyl] -N-(3,3,3-trifluoro-2-hydroxy-1-isopropylpropyl) acetamide.

Using a similar procedure to that described in Example 1.e., diluting the reaction mixture with ethyl acetate, washing it with water (3 times) and brine, drying it, and evaporating it, N-(2-tert-butyldimethylsilyloxy- 3,3,3-trifluoro-1-isopropylpropyl)-2-[3-(4-methoxyphenyl)acetylamino-2-oxo-6-phenyl-1,2-dihydro-1-pyridyl]acetamide was converted into 2-[3-(4-methoxyphenyl)acetylamino-2-oxo-6-phenyl-1,2-dihydro-1-pyridyl]-N-(3,3,3-trifluoro-2-hydroxy-1-isopropylpropyl)acetamide; TLC: $R_f$=0.18, ethyl acetate:dichloromethane (1:9); MS: m/z=546(M+1).

EXAMPLES 16–19

Using similar procedures to that described in Example 1, the following compounds of formula I wherein $R^0$ is isopropyl, R is the indicated acyl group, $R^5$ is hydrogen and $R^6$ is phenyl were prepared by oxidation of the corresponding alcohols of formula II:

EXAMPLE 16

R=benzylaminocarbonyl: Chromatography solvent: acetic acid:ethyl acetate:dichloromethane (0.5:10:89.5); TLC: $R_f$=0.23, acetic acid:ethyl acetate:dichloromethane (0.5:10:89.5); HPLC: $t_R$=8.35, FR=1.0, column A, water:acetonitrile (1:1); MS: m/z=529(M+1).

Analysis for $C_{27}H_{27}F_3N_4O_4 \cdot 1.0\ CH_3COOH$:

Calculated: C, 59.18; H, 5.31; N, 9.52

Found: C, 59.18; H, 5.30; N, 9.62

EXAMPLE 17

R=4-methoxybenzoyl: Chromatography solvent: ethyl acetate:dichloromethane (5:95 then 10:90), the crude product was preadsorbed onto diatomaceous earth and placed atop the column before elution; HPLC: $t_R$=4.84, FR=2.0, column A, water:acetonitrile (1:1); MS: m/z=530(m+1).

Analysis for $C_{27}H_{26}F_3N_3O_5$:

Calculated: C, 61.24; H, 4.95; N, 7.94

Found: C, 60.93; H, 5.01; N, 7.79

EXAMPLE 18

R=(3,4-dimethoxyphenyl)acetyl: Chromatography solvent: ethyl acetate:dichloromethane (2:98); TLC: $R_f$=0.34, ethyl acetate:dichloromethane (3:97); HPLC: $t_R$=6.89, FR=2.0, column A, water:acetonitrile (55:45); MS: m/z= 574(M+1).

Analysis for $C_{29}H_{30}F_3N_3O_6$:

Calculated: C, 60.73, H, 5.27, N, 7.33

Found: C, 60.57; H, 5.52, N, 7.17

EXAMPLE 19

R=phenoxycarbonyl: Chromatography solvent: ethyl acetate:dichloromethane (5:95); HPLC: $t_R$=8.26, FR=2.0, column A, water:acetonitrile (55:45); MS: m/z=516(M+1).

Analysis for $C_{26}H_{24}F_3N_3O_5 \cdot 0.3\ H_2O$:

Calculated: C, 59.95; H, 4.76; N, 8.06

Found: C, 59.93; H, 4.86; N, 7.80

The corresponding alcohols of formula II for Examples 16–19 were prepared as follows:

EXAMPLES 16.a.–19.a.

2-(3-Acylamino-2-oxo-6-phenyl-1,2-dihyro-1-pyridyl)-N-( 2-tert-butyldimethylsilyloxy-3,3,3-trifluoro-1-isopropylpropyl)acetamides having the indicated acyl group R were prepared from 2-(3-amino-2-oxo-6-phenyl-1,2-dihydro-1-pyridyl)-N-(2-tert-butyldimethylsilyloxy- 3,3,3-trifluoro-1-isopropylpropyl)acetamide as follows:

EXAMPLE 16.a.

R=benzylaminocarbonyl: To a solution of 2-(3-amino-2-oxo-6-phenyl-1,2-dihydro-1-pyridyl)-N-(2-tert-butyldimethylsilyloxy- 3,3,3-trifluoro-1-isopropylpropyl)acetamide (300 mg) in dry tetrahydrofuran (10 mL) was added benzyl isocyanate (86 mg). After 20 h triethyl amine (65 mg) and benzyl isocyanate (43 mg) were added. After another 18 h the reaction mixture was diluted with ethyl acetate and 10% hydrochloric acid. The organic portion was separated, washed with 10% hydrochloric acid and brine, and evaporated to give a crude oil. The reaction was found to be incomplete. To a solution of the recovered oil in dry tetrahydrofuran (6 mL) was added triethyl amine (80 mg) and benzyl isocyanate (86 mg). The solution was heated under reflux for 6 h and stirred 18 h. The reaction mixture was diluted with ethyl acetate; washed with saturated aqueous sodium bicarbonate, 10% hydrochloric acid and brine; dried; evaporated; and dried under vacuum to give a crude solid. Purification by chromatography, eluting with ethanol:ethyl acetate:dichloromethane (0.25:3:96.75), gave N-(2-tert-butyldimethylsilyloxy-3,3,3-trifluoro- 1-isopropylpropyl)-2-[2-oxo-6-phenyl-3-(3-benzylureido)-1,2-dihydro- 1-pyridyl]acetamide (295 mg); TLC: $R_f$=0.20, ethanol:ethyl acetate:dichloromethane (0.5:4:95.5); MS: m/z=645(M+1).

The above described acylation using an isocyanate is denoted herein as Acylation Method C.

EXAMPLE 17.a.

R=4-methoxybenzoyl: Acylation Method A using 4-methoxybenzoyl chloride; chromatography solvent: acetone:dichloromethane (2:98); TLC (of crude product): $R_f$=0.43, methanol:dichloromethane (1:99); MS: m/z= 646(m+1).

EXAMPLE 18.a.

R=(3,4-dimethoxyphenyl)acetyl: Acylation Method A using (3,4-dimethoxyphenyl)acetyl chloride; chromatography solvent: ethanol:ethyl acetate:dichloromethane (0.5:5:95); TLC: $R_f$=0.40, ethanol:ethyl acetate:dichloromethane (0.5:5:95); MS: m/z=690(M+1).

EXAMPLE 19.a.

R=phenoxycarbonyl: Acylation Method A using phenyl chloroformate; chromatography solvent: ethyl acetate:dichloromethane (3:97); TLC (of crude product): $R_f$=0.96, methanol:dichloromethane (3:97); MS: m/z=632(M+1).

EXAMPLES 16.b.–19.b.

2-(3-Acylamino-2-oxo-6-phenyl-1,2-dihydro-1-pyridyl)-N-( 3,3,3-trifluoro-2-hydroxy-isopropylpropyl)acetamides of formula II having the indicated acyl group R, $R^0$ as isopropyl, $R^5$ as hydrogen and $R^6$ as phenyl were prepared by cleavage of the corresponding silyl ethers described above. The cleavage was carried out using a similar procedure to that described in Example I.e. for Examples 16.b.–18.b.

EXAMPLE 16.b.

R=benzylaminocarbonyl: Chromatography solvent: ethanol:ethyl acetate:dichloromethane (1:3:96 then 2:4:94); TLC: $R_f$=0.10, ethanol:ethyl acetate:dichloromethane (2:4:94); MS: m/z=531(M+1).

EXAMPLE 17.b.

R=4-methoxybenzoyl: Chromatography solvent: methanol:dichloromethane (2:98), the crude product was preadsorbed onto diatomaceous earth and placed atop the column before elution; TLC (of crude product): $R_f$=0.45, methanol:dichloromethane (3:97); MS: m/z=532(m+1).

EXAMPLE 18.b.

R=(3,4-dimethoxyphenyl)acetyl: TLC: $R_f$=0.41; methanol:dichloromethane (1:2.0); MS: m/z=576(M+1).

EXAMPLE 19.b.

R=phenoxycarbonyl: Tetra-n-butylammonium fluoride (1.0M in tetrahydrofuran, 0.34 mL) and glacial acetic acid (0.02 mL) were added to dry tetrahydrofuran (1 mL). A solution of N-(2-tert-butyldimethylsilyloxy-3,3,3-trifluoro-1-isopropylpropyl)- 2-(2-oxo-3-phenoxycarbonylamino-6-phenyl-1,2,-dihydro-1-pyridyl)acetamide in dry tetrahydrofuran (2 mL) was added to the reaction vessel, and the addition syringe was washed out with an additional 2 mL tetrahydrofuran. The reaction mixture was stirred for 3 h; diluted with ethyl acetate (50 mL); washed with water and brine; dried and evaporated to an oil which was purified by flash chromatography, eluting with dichloromethane:ethyl acetate (90:10), to afford 2-(2-oxo-3-phenoxycarbonylamino-6-phenyl-1,2-dihydro-1-pyridyl)-N-( 3,3,3-trifluoro-2-hydroxy-1-isopropylpropyl)acetamide as a white solid (0.110 g); TLC: $R_f$=0.30, ethyl acetate:dichloromethane (1:9); MS: m/z=518(M+1).

EXAMPLE 20

2-[3-(4-Hydroxyphenyl)acetylamino-2-oxo-6-phenyl-1,2-dihydro-1-pyridyl]
-N-(3,3,3-trifluoro-1-isopropyl-2-oxopropyl) acetamide.

2-[3-(4-Methoxyphenyl)acetylamino-2-oxo-6-phenyl-1,2-dihydro- 1-pyridyl]-N-(3,3,3-trifluoro-1-isopropyl-2-oxopropylacetamide (65 mg) was suspended in dry dichloromethane (1.5 mL) and cooled in an ice-water bath. To this, suspension was added $BBr_3$ (1M in dichloromethane, 0.4 mL). The mixture was stirred for 5.5 h in the cold bath and at room temperature for 19 h. Additional $BBr_3$ (0.14 mL) was added after the reaction was found to be incomplete. After 5 h the mixture was diluted with water and extracted with dichloromethane. The combined extracts were washed with water and brine, dried, and evaporated to yield a crude oil which was purified by chromatography, eluting with ethanol:dichloromethane (gradient 1:99 to 2:98), to give the title compound (50 mg); TLC: $R_f$=0.38, ethanol:dichloromethane (3:97); HPLC: $t_R$=5.45, FR=2.0, column A, water:acetonitrile (3:2); MS: m/z=530(M+1).

Analysis for $C_{27}H_{26}F_3N_3O_5 \cdot 0.1\ H_2O$:

Calculated: C, 61.04; H, 4.97; N, 7.91

Found: C, 61.03; H, 5.16; N, 7.66

EXAMPLE 21

2-[3-Benzyloxycarbonylamino-6-(2-chlorophenyl)-2-oxo-1,2-dihydro-1-pyridyl]
-N-(3,3,3-trifluoro-1-isopropyl-2-oxopropyl)acetamide.

Using a similar procedure to that described in Example 1, using chloroform:ethyl acetate (50:1) for elution in the chromatography, 2-[3-benzyloxycarbonylamino-6-(2-chlorophenyl)-2-oxo- 1,2-dihydro-1-pyridyl]-N-(3,3,3-trifluoro-2-hydroxy-1-isopropylpropyl)acetamide was oxidized to afford the title compound; TLC: $R_f$=0.16, chloroform:ethyl acetate (50:1); HPLC: $t_R$=7.08 and 8.22, FR=2, column A, acetonitrile:water (1:1); MS: m/z=560(M+1, $^{35}$Cl).

Analysis for $C_{27}H_{25}ClF_3N_3O_5$:

Calculated: C, 56.60; H, 4.58; N, 7.33

Found: C, 56.70; H, 4.73; N, 6.95

The intermediate 2-[3-benzyloxycarbonyl-amino-6-(2-chlorophenyl)- 2-oxo-1,2-dihydro-1-pyridyl]-N-(3,3,3-trifluoro-2-hydroxy-1-isopropylpropyl)acetamide may be prepared as follows:

a. 6-(2-Chlorophenyl)pyrid-2-one-3-carbonitrile.

Using a similar method to that described in Example 1.a., except heating the solution under reflux using an oil bath at 140° C. following the addition of cyanoacetamide and sodium methoxide, and trituration of the initial precipitate with ether, 6-(2-chlorophenyl)pyrid- 2-one-3-carbonitrile was obtained; TLC: $R_f$=0.39, chloroform:methanol (20:1); MS: m/z=231(M+1, $^{35}$Cl).

b. 6-(2-Chlorophenyl)pyrid-2-one-3-carboxylic acid.

Using Hydrolysis Method A, 6-(2-chlorophenyl)pyrid-2-one-3-carbonitrile was converted into 6-(2-chlorophenyl)pyrid-2-one-3-carboxylic acid; TLC: $R_f$=0.37; MS: m/z=250(M+1, $^{35}$Cl).

c. 3-Benzyloxycarbonylamino-6-(2-chlorophenyl) pyrid-2-one.

Using a similar procedure to that described in Example 1.c., 6-(2-chlorophenyl)pyrid-2-one-3-carboxylic acid was converted into 3-benzyloxycarbonylamino-6-(2-chlorophenyl)pyrid-2-one; TLC: $R_f$=0.24, chloroform:ethyl acetate (50:1); MS: m/z=355(M+1, $^{35}$Cl).

d.
2-[3-Benzyloxycarbonylamino-6-(2-chlorophenyl)-2-oxo-1,2-dihydro-1-pyridyl]-N-(2-tert-butyldimethylsilyloxy-3,3,3-trifluoro-1-isopropylpropyl)acetamide.

Using a similar procedure to that described in Example 1.d., but using dichloromethane:hexanes (1:1, then 2:1) for flash chromatography, 3-benzyloxycarbonylamino-6-(2-chlorophenyl)pyrid-2-one was converted into 2-[3-benzyloxycarbonylamino-6-(2-chlorophenyl)- 2-oxo-1,2-dihydro-1-pyridyl]-N-(2-tert-butyldimethylsilyloxy-3,3,3-trifluoro-1-isopropylpropyl)acetamide; TLC: $R_f$=0.34, chloroform:ethyl acetate (50:1); MS: m/z=680(M+1, $^{35}$Cl).

e.
2-[3-Benzyloxycarbonylamino-6-(2-chlorophenyl)-2-oxo-1,2-dihydro-1-pyridyl]-N-(3,3,3-trifluoro-2-hydroxy-1-isopropylpropyl)acetamide.

Using a similar procedure to that described in Example 1.e., 2-[3-benzyloxycarbonylamino-6-(2-chlorophenyl)-2-oxo-1,2-dihydro-1-pyridyl] -N-(2-tert-butyldimethylsilyloxy-3,3,3-trifluoro-1-isopropylpropyl)acetamide was converted into 2-[3-benzyloxycarbonylamino-6-(2-chlorophenyl)-2-oxo-1,2-dihydro-1-pyridyl]-N-(3,3,3-trifluoro-2-hydroxy-1-isopropylpropyl)acetamide; TLC: $R_f$=0.42 and 0.45, dichloromethane:methanol (95:5); MS: m/z=566(M+1, $^{35}$Cl).

EXAMPLE 22

2-[2-Oxo-6-phenyl-3-(4-pyridylmethoxycarbonylamino)-1,2-dihydro-1-pyridyl]-N-(3,3,3-trifluoro-1-isopropyl-2-oxopropyl)acetamide.

Using a similar method to that described in Example 1, using chloroform:methanol (gradient, 40:1, 30:1, 20:1) for elution in the chromatography, 2-[2-oxo-6-phenyl-3-(4-pyridylmethoxycarbonylamino)- 1,2-dihydro-1-pyridyl]-N-(3,3,3-trifluoro-2-hydroxy-1-isopropylpropyl)acetamide was oxidized to afford the title compound; TLC: $R_f$=0.29, chloroform:methanol (20:1); MS: m/z=531(m+1).

Analysis for $C_{26}H_{25}F_3N_4O_5$:

Calculated: C, 58.86; H, 4.75; N, 10.56

Found: C, 58.88; H, 5.08; N, 10.11

The intermediate 2-[2-oxo-6-phenyl-3-(4-pyridylmethoxycarbonylamino)- 1,2-dihydro-1-pyridyl]-N-(3,3,3-trifluoro-2-hydroxy-1-isopropylpropyl)acetamide may be prepared as follows:

a. 6-(2-Chlorophenyl)pyrid-2-one-3-carbonitrile.

To a 5 liter, 3-necked flask equipped with a mechanical stirrer, thermometer, reflux condenser capped with a nitrogen inlet, and a heating mantle were added o-chloroacetophenone (305.8 g, 1.98 mol), N,N-dimethylformamide dimethyl acetal (707.0 g, 5.93 mol), and acetonitrile (dried over molecular sieves, 3.0 L) at room temperature, giving an orange solution. The mixture was heated gradually to reflux (83° C.) over 1.5 hours, then maintained at reflux for 18 hours. After the dark red solution was cooled to room temperature, the acetonitrile was evaporated, leaving a heavy red oil. The oil was redissolved in toluene (1 L). The toluene was evaporated to afford the crude enamine which was further dried under high vacuum overnight to afford 2'-chloro-3-dimethylaminopropenophenone (422 g, quantitative) which was used without further purification.

To a 12-liter, 3-necked flask equipped with a mechanical stirrer, a Claisen adapter holding a thermometer and a reflux condenser capped with a nitrogen inlet, and a heating mantle were added the crude enamine (422 g, 1.98 mol) and N,N-dimethylformamide (dried over molecular sieves, 4.0 L), giving a reddish-brown solution. Cyanoacetamide (189.2 g, 2.25 mol) was added as a dry solid and washed down with N,N-dimethylformamide (500 mL). Lastly, sodium methoxide (235.1 g, 4.35 mol) was added as a dry solid and washed down with N,N-dimethylformamide (500 mL). The mixture was heated gradually over 4 hours to 130° C., then maintained at 135–140° C. for 16 hours. The effluent line from the nitrogen bubbler was trapped through a solution of 3N HCl (2 L). The cooled reaction mixture was evaporated under pump vacuum (bath temperature 50° C.) until approximately 4 liters of N,N-dimethylformamide was removed. The residue was poured into ice/water (6 L) with vigorous stirring. The pH was adjusted to pH 5 by portionwise addition of concentrated hydrochloric acid (300 mL). This produced a suspension of reddish-orange solid. The solid was collected by suction filtration, washed with cold water (2×1.5 L) followed by ether (3×500 mL), leaving a pinkish-tan powder which was dried in the vacuum oven at 60° C. to afford 6-(2-chlorophenyl)pyrid- 2-one-3-carbonitrile (205.5 g, 44.3%); mp 242°–245° C. (dec).

b. 6-(2-Chlorophenyl)pyrid-2-one-3-carboxylic acid.

To a 5 liter, 3-necked flask equipped with a mechanical stirrer, thermometer, reflux condenser capped with a nitrogen inlet, and a heating mantle were added 6-(2-chlorophenyl)pyrid-2-one-3-carbonitrile (205.5 g, 0.891 mol), 48% hydrobromic acid (1500 mL), and glacial acetic acid (1500 mL) at ambient temperature. The golden-brown suspension was heated gradually over a four hour period to gentle reflux (117° C.). During this time, all solids dissolved giving a dark brown solution. The reaction mixture was maintained at reflux for 20 hours, then cooled to room temperature and evaporated until approximately 2 liters of distillate were collected. The remaining suspension was poured into ice/water (5 L) with vigorous stirring, precipitating a tan solid. The solid was collected by suction filtration, washed with cold water (2×1.5 L) and dried in the vacuum oven at 60° C. to afford 6-(2-chlorophenyl)pyrid-2-one-3-carboxylic acid (189.7 g, 85.3%); mp 234° C. (dec).

c. 3-Benzyloxycarbonylamino-6-(2-chlorophenyl)pyrid-2-one.

To a 5 liter, 3-necked flask equipped with a mechanical stirrer, a Claisen adaptor holding a thermometer and a reflux condenser capped with a nitrogen inlet, and a heating mantle were added 6-(2-chlorophenyl)pyrid-2-one-3-carboxylic acid (189.7 g, 0.760 mol) and dioxane (dried over molecular sieves, 3.0 L) at ambient temperature, giving a tan suspension. Triethylamine (92.3 g, 0.910 mol) was added in one portion and caused the solids to dissolve. Diphenylphosphoryl azide (232.0 g, 0.843 mol) was added in one portion and washed down with dioxane (100 mL). The reaction mixture was heated gradually over one hour to reflux (103° C.). At approximately 70° C., nitrogen evolution began as the intermediate acylazide began to decompose. The reaction mixture was heated at reflux for two hours (until nitrogen evolution ceased) and then was cooled to 90° C. Benzyl alcohol (dried over molecular sieves, 169.0 g, 1.563 mol) was added in one portion. The reaction mixture was heated at reflux for 45 hours. After this time, the reaction was checked by TLC using two different solvent systems: A. Dichloromethane:methanol:acetic acid (95:5:trace), $R_f$(starting acid)=0.55, $R_f$(benzyl alcohol)=0.80, $R_f$(product)=0.80;

and B. Dichloromethane:ethyl acetate (9:1), $R_f$(starting acid)=0–0.15, $R_f$(benzyl alcohol)=0.6, $R_f$(product)=0.4. The reaction appeared complete by TLC; so the mixture was cooled to ambient temperature and stirred overnight. During this time, a crop of tan crystals precipitated. The material was collected by suction filtration, washed with dioxane (200 mL) and ether (2×200 mL), then dried to afford crude product (148.0 g). The filtrate was evaporated and the residue was redissolved in methylene chloride (4 L), and washed with aqueous sodium bicarbonate solution (2×800 mL) and brine (1 L), dried (MgSO$_4$), and evaporated leaving a brown semisolid which was triturated with ether and filtered to afford a second crop of crude product (72.5 g). Both fractions of material were shown by NMR to be contaminated with benzyl alcohol and triethylamine hydrochloride. The combined crude material (220.5 g) was stirred for five hours in a mixture of methylene chloride (2.5 L) and 1N hydrochloric acid (1 L), then filtered. The solid was washed with water (3×500 mL) and ether (2×300 mL) to afford pure product (158.0 g). The organic phases were separated from the filtrates and evaporated. The residual solid was pressure filtered through a silica gel plug (eluent: dichloromethane:ethyl acetae, 3:1) to afford a second fraction of pure product (26.5 g). Thus was obtained 3-benzyloxycarbonylamino-6-(2-chlorophenyl)pyrid-2-one (184.5 g, 68.4%); mp 213°–215° C.

d. 2-[3-Benzyloxycarbonylamino-6-(2-chlorophenyl)-2-oxo-1,2-dihydro- 1-pyridyl]-N-(2-tert-butyldimethylsilyloxy-3,3,3-trifluoro- 1-isopropylpropyl)acetamide.

To a 5 liter, 3-necked flask equipped with a mechanical stirrer, thermometer, and a nitrogen inlet were added 3-benzyloxycarbonylamino- 6-(2-chlorophenyl)pyrid-2-one (158.0 g, 0.445 mol) and N,N-dimethyformamide (dried over molecular sieves, 3.0 L) giving a tan suspension. Sodium hydride (60% mineral oil dispersion, 19.6 g, 0.490 mol) was added in one portion at ambient temperature. The reaction mixture was stirred at room temperature for 1.5 h, gradually becoming a clear amber solution; then it was was cooled with an ice/water bath to 5° C. N-(2-tert-butyldimethylsilyloxy-3,3,3-trifluoro- 1-isopropylpropyl)-2-iodoacetamide (222.5 g, 0.490 mol) was added in one portion as a dry solid and washed down with N,N-dimethylformamide (200 mL). The reaction flask was packed in ice and the mixture stirred over the weekend (50 h), gradually warming to room temperature. For analysis of the reaction mixture an aliquot was partitioned between 1N hydrochloric acid and ethyl acetate for TLC: dichloromethane:ethyl acetate (95:5), $R_f$(starting pyridone)=0.15, $R_f$(N-alkyated pyridone)=0.70, $R_f$(O-alkylated pyridone)=0.75. The reaction mixture was treated with water (100 mL) and acetic acid (25 mL) to neutralize any excess sodium hydride; then it was evaporated under pump vacuum at a bath temperature of 35° C. to remove most of the N,N-dimethylformamide. The residue was diluted with water (4 L) yielding a gummy precipitate. The aqueous mixture was extracted with ethyl acetate (1 L, followed by 4×500 mL). The combined extracts were washed successively with 1N hydrochloric acid (2×500 mL), saturated sodium bicarbonate solution (2×500 mL), and brine (500 mL); dried (MgSO$_4$), and evaporated to yield a thick amber syrup which was then pumped down under high vacuum. The crude syrup was redissolved in a mixture of hexane (1000 mL) and ether (200 mL) and seeded with authentic product. Crystallization ensued, and the mixture was stirred periodically with a spatula to complete the crystallization. The mixture was allowed to stand overnight at room temperature before collecting the crystals. The crystals were suction filtered, washed with ether/hexane (1:9) (3×200 mL) then dried in the vacuum oven at 50° C. to yield the N-alkylated product 2-[3-benzyloxycarbonylamino-6-(2-chlorophenyl)-2-oxo-1,2-dihydro- 1-pyridyl]-N-(2-tert-butyldimethylsilyloxy-3,3,3-trifluoro- 1-isopropylpropyl)acetamide as off-white crystals (193.5 g, 63.9%); mp 139°–141° C.

The filtrates were evaporated to an oil (138 g). This material was purified by column chromatography using gradient elution with ethyl acetate (0%–10%) in methylene chloride to afford a small second fraction of pure N-alkylated product (15.2 g, 5.0%). Also isolated was a fraction of the O-alkylated isomeric product (77.4 g, 25.5%) as a heavy yellow syrup.

e. 2-(3-Amino-2-oxo-6-phenyl-1,2-dihydro-1-pyridyl)-N-(2-tert-butyldimethylsilyloxy- 3,3,3-trifluoro-1-isopropylpropyl)acetamide.

2-[3-Benzyloxycarbonylamino-6-(2-chlorophenyl)-2-oxo-1,2-dihydro- 1-pyridyl]-N-(2-tert-butyldimethylsilyloxy-3,3,3-trifluoro- 1-isopropylpropyl)acetamide (100.0 g, 0.147 mol), 10% (w/w) palladium on carbon catalyst (10.0 g), and absolute ethanol (1200 mL), were charged under a nitrogen blanket into a 2-L stainless steel hydrogenation bottle. The mixture was shaken under a hydrogen atmosphere (3.4 bar) for 6 hours. Hydrogen uptake stopped after approximately two hours. The reaction mixture was checked by TLC, eluting with dichloromethane:methanol (97:3) which showed all of the starting material ($R_f$=0.85) to be consumed, essentially a single spot for the intermediate 3-amino-6-(2-chlorophenyl) product ($R_f$=0.55), and a trace spot for the final 3-amino-6-phenyl reduction product ($R_f$= 0.48).

Sodium methoxide (8.10 g, 0.150 mol) was added to the reaction mixture. The hydrogenation bottle was placed back on the shaker, and the hydrogenation continued overnight (18 hours). TLC analysis at this time indicated a single spot ($R_f$=0.50). The reaction mixture was suction filtered through a pad of diatomaceous earth to remove the catalyst. The catalyst was washed thoroughly with ethanol (4×200 mL). The filtrate was evaporated to dryness, leaving a quantitative yield of the crude product.

After a total of 208.7 g of starting material was hydrogenolyzed in this manner, the combined crude product (160 g) was redissolved in methylene chloride:ethyl acetate (1:1) (5 L), washed with water (2×800 mL) and brine (800 mL), dried (MgSO$_4$), and evaporated to afford a glossy, off-white solid which was triturated with hexane:ether (4:1, 500 mL) to provide 2-(3-amino-2-oxo-6-phenyl- 1,2-dihydro-1-pyridyl)-N-(2-tert-butyldimethylsilyloxy-3,3,3-trifluoro-1-isopropyl-propyl)acetamide as a white glossy solid (144.8 g, 92.2%); mp 146°–148° C.

f. N-(2-tert-Butyldimethylsilyloxy-3,3,3-trifluoro-1-isopropyl-propyl)- 2-[2-oxo-6-phenyl-3-(4-pyridylmethoxycarbonylamino)- 1,2-dihydro-1-pyridyl]acetamide.

To a solution of 2-(3-amino-2-oxo-6-phenyl-1,2-dihydro-1-pyridyl)-N-( 2-tert-butyldimethylsilyloxy-3,3,3-trifluoro-1-isopropylpropyl)acetamide (1.00 g) in dry methylene chloride (17 mL) was added dry triethylamine (1.91 mL). The resultant solution was cooled to 0° C. and was treated with a solution of triphosgene (288 mg) in methylene chloride (3 mL) over 5 min. The addition syringe was washed with 2 mL fresh methylene chloride which was then added to the reaction mixture. The reaction mixture was stirred at 0° C. for 45 min, at which time 4-pyridylcarbinol (688 mg) was added as a solid. Stirring was continued 1 h at 0° C. then overnight at room temperature. The mixture was diluted with methylene chloride, washed (saturated sodium bicarbonate solution), dried and evaporated to a brown foam. Purification by flash chromatography, eluting with methylene chloride:methanol (50:1) gave N-(2-tert-butyldimethylsilyloxy- 3,3,3-trifluoro-1-isopropylpropyl)-2-[2-oxo-6-phenyl- 3-(4-pyridylmethoxycarbonylamino)-1,2-dihydro-1-pyridyl]acetamide as a yellow-brown solid (1.18 g); TLC: $R_f$=0.36, eluted twice with dichloromethane:methanol (50:1); MS: m/z=647(M+1).

The above described acylation, using triphosgene, triethylamine and an alcohol of formula A.OH or an amine of formula A.NH$_2$, is denoted herein as Acylation Method D.

g. 2-[2-Oxo-6-phenyl-3-(4-pyridylmethoxycarbonylamino)-1,2-dihydro- 1-pyridyl]-N-(3,3,3-trifluoro-2-hydroxy-1-isopropylpropyl)acetamide.

Using a similar procedure to that described in Example 1.e., purifying the crude product by trituration with ethyl acetate, N-(2-tert-butyldimethylsilyloxy-3,3,3-trifluoro-1-isopropyl-propyl)- 2-[2-oxo-6-phenyl-3-(4-pyridylmethoxycarbonylamino)- 1,2-dihydro-1-pyridyl]acetamide was converted into 2-[2-oxo-6-phenyl- 3-(4-pyridylmethoxycarbonylamino)-1,2-dihydro-1-pyridyl]-N-( 3,3,3-trifluoro-2-hydroxy-1 -isopropylpropyl)acetamide; TLC: $R_f$=0.23, chloroform:methanol (20:1); ms: m/z=533(M+1).

EXAMPLES 23–34

Using similar procedures to that described in Example 1, the following compounds of formula I wherein $R^0$ is isopropyl, R is the indicated acyl group, $R^5$ is hydrogen and $R^6$ is phenyl were prepared by oxidation of the corresponding alcohols of formula II.

The corresponding alcohols of formula II for Examples 23–34 were prepared as follows:

Examples 23.a.–34.a.

2-(3-Acylamino-2-oxo-6-phenyl-1,2-dihydro-1-pyridyl)- N-( 2-tert-butyldimethylsilyloxy-3,3,3-trifluoro-1-isopropylpropyl)aceramides having the indicated acyl group R were prepared from 2-(3-amino-2-oxo-6-phenyl-1,2-dihydro-1-pyridyl)-N-(2-tert-butyl-dimethylsilyloxy- 3,3,3-trifluoro-1-isopropylpropyl)acetamide using triphosgene, triethylamine and an alcohol of formula A.OH or an amine of formula A.NH$_2$ by Acylation Method D, as described in Example 22.f., except as otherwise noted. Certain of the requisite pyridylcarbinols of formula A.OH which were not commerically available were prepared by the method of Katz et al. (R. B. Katz, J. Mistry, and M. B. Mitchell, Synthetic Communications (1989) 19, 317) with the following modified work up: The crude reation mixture was evaporated and the residue partitioned between ethyl acetate and water. The pH was adjusted to 7 by addition of saturated aqueous sodium bicarbonate. The phases were separated and the aqueous further extracted with ethyl acetate. The total organic phase was dried (MgSO$_4$), evaporated and purified as described for each individual alcohol.

Examples 23.b.–34.b.

2-(3-Acylamino-2-oxo-6-phenyl-1,2-dihydro-1-pyridyl)-N-( 3,3,3-trifluoro-2-hydroxy-1-isopropylpropyl)acetamides of formula II having the corresponding acyl group R, $R^0$ as isopropyl, $R^5$ as hydrogen and $R^6$ as phenyl were prepared by cleavage of the corresponding silyl ethers described above using a similar procedure to that described in Example 1.e., except as noted.

Example 23: R=3-pyridylmethoxycarbonyl: Chromatography solvent: dichloromethane:ethyl acetate (first column, gradient 97:3, 95:5; second column, gradient 100:0, 50:50, 30:70), then trituration with petroleum ether; TLC: $R_f$=0.33, dichloromethane:methanol (95:5); HPLC: $t_R$=6.15, FR=0.5, column A, water:acetonitrile (1:1); MS: m/z=531(M+1).

Analysis for $C_{26}H_{25}F_3N_4O_5$: Calculated: C, 58.87; H, 4.75; N, 10.56 Found: C, 58.51; H, 4.98; N, 10.58

Example 23.a.: Chromatography solvent: dichloromethane:methanol (gradient, 100:0 to 97:3); TLC: $R_f$=0.28, dichloromethane:methanol (95:5); MS: m/z= 647(M+1).

Example 23.b.: Not chromatographed, but recrystallized from boiling methanol; TLC: $R_f$=0.60, eluted twice, first dichloromethane:methanol (95:5), then dichloromethane:ethyl acetate (6:4); MS: m/z=533(M+1).

Example 24: R=2-pyridylmethoxycarbonyl: Chromatography solvent: chloroform:methanol (40:1); TLC: $R_f$=0.30; chloroform:methanol (20:1); HPLC: $t_R$=6.73, FR=1, column A, water:acetonitrile (1:1); MS: m/z=531(M+1). Analysis for $C_{26}H_{25}F_3N_4O_5 \cdot 0.1\ H_2O$: Calculated: C, 58.67; H, 4.77; N, 10.53 Found: C, 58.42; H, 4.78; N, 10.51

Example 24.a.: Chromatography solvent: dichloromethane:methanol (50:1); TLC: $R_f$=0.28, chloroform:methanol (50:1); MS: m/z=647(M+1).

Example 24.b.: Not chromatographed, but triturated with ethyl acetate; TLC: $R_f$=0.24, chloroform:methanol (20:1); MS: m/z=533(M+1).

Example 25: R=4-methoxypyrid-2-ylmethoxycarbonyl: Chromatography solvent: dichloromethane:methanol (gradient, 95.5:0.5 to 97.0:3.0); TLC: $R_f$=0.35, dichloromethane:methanol (95:5); NMR: 0.77–0.91 (m,6), 2.1–2.3 (m,1), 3.88 (s,3), 4.07–4.66 (m,3), 5.18 (s,2), 6.20–6.25 (m,1), 6.93 (d,1), 7.17 (d,1), 7.34–7.50 (m,5), 7.93 (d,1, J=8.7), 8.36 (d,1, J=5.7), 8.76 (d,1, J=6.9), 8.84 (d,1); MS: m/z=561(M+1).

Analysis for $C_{27}H_{27}F_3N_4O_6 \cdot 1.0\ H_2O$: Calculated: C, 56.05; H, 5.05; N, 9.68 Found: C, 56.03; H, 4.90; N, 9.58

Example 25.a.: Chromatography solvent: dichloromethane:methanol (gradient, 99.5:0.5 to 97:3); TLC: $R_f$=0.30, dichloromethane:methanol (98:2); MS: m/z= 677(M+1).

4-Methoxypyrid-2-ylcarbinol was prepared by the method of Katz, et al. and purified by chromatography, eluting with dichloromethane:methanol (95:5); TLC: $R_f$=0.45, dichloromethane:methanol (9:1); 300 MHz NMR: 3.82 (s,3), 4.50 (d,2), 5.40 (t,1), 6.81 (dd,1), 7.00 (d,1), 8.28 (d,1); MS: m/z=140(M+1).

Example 25.b.: Isolated and used without further purification; TLC: $R_f$=0.25, dichloromethane:methanol (95:5); MS: m/z=563(M+1).

Example 26: R=2,6-dimethylpyrid-4-ylmethoxycarbonyl: Omitting chromatography, but triturating with dichloromethane to afford a white solid; TLC: $R_f$=0.40, dichloromethane:methanol (95:5); 300 MHz NMR: 0.77–0.90 (m,6), 2.07–2.33 (m,1), 2.41 (s,6), 4.07–4.67 (m,3), 5.14 (s,2), 6.19–6.22 (m,1), 6.90 (s,2), 7.37–7.53 (m,5), 7.70 (d,1, J=10.1), 7.89–7.93 (dd,1), 8.73–8.76 (m,1); MS: m/z= 559(M+1).

Analysis for $C_{28}H_{29}F_3N_4O_5 \cdot 1.2\ H_2O$: Calculated: C, 57.96; H, 5.45; N, 9.65 Found: C, 57.97; H, 5.24; N. 9.60

Example 26.a.: Chromatography solvent: dichloromethane:methanol (gradient, 99.5:0.5 to 97:3); TLC: $R_f$=0.35, dichloromethane:methanol (98:2); MS: m/z= 675(M+1).

2,6-Dimethylpyrid-4-ylcarbinol was prepared by the method of Katz et al. and purified by trituration with diethyl ether, TLC: $R_f$=0.20; dichloromethane:methanol (96:4); 300 MHz NMR: 2.38 (s,6), 4.44 (d,2), 5.30 (t,1), 6.94 (s,1); MS: m/z=138(M+1).

Example 26.b.: Chromatography solvent: dichloromethane:methanol (gradient, 99.5:0.5 to 97.5:2.5); TLC: $R_f$=0.40, dichloromethane:methanol (95:5); 300 MHz NMR: 0.80–0.90 (dd,6), 1.67–1.90 (m,1), 2.41 (s,6), 3.83 (t,1), 1.09 (q,1), 4.30–4.63 (m,2), 5.14 (s,2), 6.20 (d,1, J=7.6), 6.49 (d,1, J=6.7), 7.10 (s,2), 7.39–7.43 (m,5), 7.84–7.92 (m,2), 8.76 (s,1); MS: m/z=561(M+1).

Example 27: R=4-cyanopyrid-2-ylmethoxycarbonyl: Omitting the chromatography, but triturating with dichloromethane:methanol (95:5) to afford a white solid; TLC: $R_f$=0.50, dichloromethane:methanol (95:5); 300 MHz NMR: 0.82–0.95 (m,6), 2.13–2.40 (m,1), 4.09–4.67 (m,3), 5.33 (s,2), 6.23–6.28 (m,1), 7.38–7.51 (m,5), 7.75 (d,1, J=10.6), 7.86 (d,1), 7.99 (d,1, J=7.6), 8.2 (d,1), 8.86 (d,1), 9.07 (s,1); MS: m/z=556(M+1).

Analysis for $C_{27}H_{24}F_3N_5O_5 \cdot 1.0\ H_2O$: Calculated: C, 56.54; H, 4.56; N, 12.21 Found: C, 56.40; H, 4.52; N, 12.05

Example 27.a.: Chromatography solvent: dichloromethane:methanol (gradient, 99.5:0.5 to 97:3); TLC: $R_f$=0.65, dichloromethane:methanol; (95:5) MS: m/z=672(M+1).

4-Cyanopyrid-2-ylcarbinol was prepared by the method of Katz et al. and purified by chromatography, eluting with dichloromethane:methanol (95:5); TLC: $R_f$=0.20, dichloromethane:methanol (96:4); NMR: 4.62 (d,2), 5.65 (t,2), 7.73 (d,1), 7.80 (s,1), 8.75 (d,1); MS: m/z=135(M+1).

Example 27.b.: Chromatography solvent: dichloromethane:methanol (gradient, 99.5:0.5 to 95:5); TLC: $R_f$=0.50, dichloromethane:methanol (95:5); 300 MHz NMR: 0.83 (d,3), 0.90 (d,3), 1.67–1.87 (m,1), 3.83 (t,1), 4:10 (q,1), 4.30–4.63 (m,2), 5.29 (s,2), 6.21 (d,1, J=7.7), 6.50 (d,1, J=6.9), 7.37–7.47 (m,5), 7.81–7.96 (m,3), 8.19 (s,1), 8.82 (d,1), 9.04 (s,1); MS: m/z=558(M+1).

Example 28: R=4-methylpyrid-2-ylmethoxycarbonyl: Chromatography solvent: dichloromethane:methanol (98:2), using three successive columns to afford a pale yellow solid; TLC: $R_f$=0.10; dichloromethane:methanol (96:4); 300 MHz NMR: 0.78– 0.91 (m,6), 2.22 (broad s,1), 2.34 (s,3), 4.03–4.66 (m,3), 5.20 (s,2), 6.22 (d,1), 7.16 (d,1), 7.37–7.48 (m,5), 7.93 (d,1), 8.40 (d,1), 8.72 (s,1); MS: m/z=545(M+1).

Analysis for $C_{27}H_{27}F_3N_4O_5 \cdot 1.5\ H_2O$: Calculated: C, 56.74; H, 5.29; N, 9.80 Found: C, 56.60; H, 5.10; N, 9.59

Example 28.a.: Chromatography solvent: dichloromethane:methanol (gradient, 97.5:2.5 to 95:5); TLC: $R_f$=0.10, dichloromethane:methanol (99:1); MS: m/z=661(M+1).

4-Methylpyrid-2-ylcarbinol was prepared by the method of Katz, et al. and purified by chromatography, eluting with dichloromethane:methanol (95:5); TLC: $R_f$=0.15; dichloromethane:methanol (96:4); 300 MHz NMR: 2.31 (s,3), 4.51 (d,2), 5.35 (t,1), 7.07 (d,1), 7.29 (s,1), 8.31 (d,1); MS: m/z=124(M+1).

Example 28.b.: Isolated and used without further purification; TLC: $R_f$=0.25, dichloromethane:methanol (96.4); 300 MHz NMR: 0.86 (d,3), 0.93 (d,3), 1.73–1.88 (m,1), 2.38 (s,3), 3.86 (m,1), 4.14 (m,1), 4.33 (broad d,1), 4.60 (broad d,1), 5.24 (s,2), 6.25 (d,1), 6.56 (d,1), 7.20 (d,1), 7.35–7.57 (m,6), 7.94 (d,1), 7.97 (d,1), 8.75 (s,1); MS: m/z=547(M+1).

Example 29: R=2-(2-pyridyl)ethylaminocarbonyl: Chromatography solvent: dichloromethane:methanol (gradient, 99.5:0.5 to 97:3); TLC: $R_f$=0.35, dichloromethane:methanol (95:5); 300 MHz NMR: 0.78–0.90 (m,6), 2.11–2.30 (m,1), 2.88 (t,2), 3.47 (q, 1), 4.03–4.67 (m,3), 6.12–6.17 (m,1), 7.13–7.46 (m,8), 7.68–7.75 (m,1), 8.08 (dd,1), 8.35 (s,1), 8.50–8.52 (m,1), 8.73 (d,1, J=7.1); MS: m/z=544(M+1).

Analysis for $C_{27}H_{28}F_3N_5O_4 \cdot 0.3\ H_2O$: Calculated: C, 59.07; H, 5.25; N, 12.75 Found: C, 58.98; H, 5.23; N, 12.65

Example 29.a.: Chromatography solvent: dichloromethane:methanol (gradient, 99.5:0..5 to 97:3); TLC: $R_f$=0.30, dichloromethane:methanol (95:5); 300 MHz NMR: 0.78–0.90 (m,6), 2.11–2.30 (m,1), 2.88 (t,2), 3.47 (q,1), 4.03–4.67 (m,3), 6.12–6.17 (m,1), 7.13–7.46 (m,8), 7.68–7.75 (m,1), 8.08 (dd,1), 8.35 (s,1), 8.50–8.52 (m,1), 8.73 (d,1, J=7.1); MS: m/z=660(M+1).

Example 29.b.: Chromatography solvent: dichloromethane:methanol (gradient, 99:1 to 95:5); TLC: $R_f$=0.50, dichloromethane:methanol (9:1); 300 MHz NMR: 0.81 (d,3, J=6.7), 0.88 (d,3, J=6.7), 1.63–1.83 (m,1), 2.97 (t,2), 3.4–3.57 (d,1), 3.82 (t,1), 4.00–4.17 (m,1), 4.20–4.57 (m,2), 6.12 (d,1, J=7.7), 6.46 (d,1, J=6.8), 7.10–7.53 (m,5), 7.67–7.90 (m,2), 8.05 (d,1, J=7.7), 8.35 (s,1), 8.50 (s,1); MS: m/z=546(M+1).

Example 30: R=2-pyridylmethylaminocarbonyl: Chromatography solvent: dichloromethane:ethyl acetate:methanol (gradient 100:0:0 to 30:69:1); TLC: $R_f$=0.28, dichloromethane:methanol (95:5); MS: m/z=530(M+1).

Analysis for $C_{26}H_{26}F_3N_5O_4$: Calculated: C, 59.98; H, 4.95; N, 13.23 Found: C, 59.22; H, 5.32; N, 12.87

Example 30.a.: Except the reaction mixture was worked up after five hours; chromatography solvent: dichloromethane:ethyl acetate (gradient, 100:0 then 1:1); TLC: $R_f$=0.18, dichloromethane:methanol (95:5); MS: m/z=646(M+1).

Example 30.b.: Isolated and used without further purification; TLC: $R_f$=0.19, dichloromethane:methanol (95:5); MS: m/z=532(M+1).

Example 31: R=4-pyridylaminocarbonyl: Chromatography solvent: dichloromethane:methanol (95:5) after preadsorption onto silica gel and packing in dichloromethane; TLC: $R_f$=0.09, dichloromethane:methanol (95:5); HPLC: $t_R$=26.60, FR=1.0, column A, water:acetonitrile (1:1); MS: m/z=516(M+1).

Analysis for $C_{25}H_{24}F_3N_5O_4 \cdot 1.7\ H_2O$: Calculated: C, 54.98; H, 5.06; N, 12.82 Found: C, 55.27; H, 4.88; N, 12.39

Example 31.a.: Except the reaction mixture was stirred overnight, then heated under reflux for 3 hours, then diluted with ethyl acetate, resulting in the precipitation of a solid (triethylamine hydrochloride) which was filtered and washed with ethyl acetate. The ethyl acetate solution was washed (saturated sodium bicarbonate solution, then brine) and the aqueous phases back-washed with ethyl acetate. The combined ethyl acetate solution was dried and evaporated before chromatography. Chromatography solvent: dichloromethane:methanol (gradient, 100:0, then 97:3); TLC: $R_f$=0.17, dichloromethane:methanol (95:5); MS: m/z=632(M+1).

Example 31.b.: Except the reaction mixture was diluted with ethyl acetate and washed (saturated sodium bicarbonate solution), which resulted in crystallization. The solid product was filtered and dried under vacuum; TLC: $R_f$=0.27, dichloromethane:methanol (95:5); MS: m/z=518(M+1); 424 (base peak, loss of 4-pyridylamino).

Example 32: R=2-morpholinoethoxycarbonyl: Except that the reaction mixture was partitioned between ethyl acetate and saturated sodium bicarbonate solution before the organic phase was washed (brine), dried, evaporated and purified by chromatography; chromatography solvent:

dichloromethane:methanol (gradient, 100:0, 98:2, 97:3, to 95:5), then the product was dried under vacuum; TLC: $R_f$=0.14, dichloromethane:methanol (95:5); HPLC: $t_R$=6.62, FR=0.5, column A, water:acetonitrile (1:1); MS: m/z= 553(M+1).

Analysis for $C_{26}H_{31}F_3N_4O_6$.0.4 $H_2O$: Calculated: C, 55.79; H, 5.73; N, 10.01 Found: C, 55.75; H, 5.66; N, 9.88

Example 32.a.: Except using a 5 h reaction time and washing with saturated sodium bicarbonate solution and brine; chromatography solvent: dichloromethane:ethyl acetate:methanol (gradient, 100:0:0, 50:50:0, 45:55:0, 40:60:0, to 36:54:10); TLC: $R_f$=0.11, dichloromethane:ethyl acetate (60:40); MS: m/z=669(M+1).

Example 32.b.: Except using a 1.5 h reaction time, partitioning the reaction mixture between saturated sodium bicarbonate solution and ethyl acetate. The ethyl acetate solution was washed (brine), dried and evaporated to give a product which was used without further purification; TLC: $R_f$=0.22, dichloromethane:methanol (95:5); MS: m/z= 555(M+1).

Example 33: R=bis(morpholinomethyl)methoxycarbonyl: Chromatography solvent: dichloromethane:methanol (gradient, 97:3 to 95:5), then trituration with hexane and ether; TLC: $R_f$=0.30, dichloromethane:methanol (95:5); MS: m/z= 652(M+1).

Analysis for $C_{31}H_{40}F_3N_5O_7$.0.7 $H_2O$: Calculated: C, 56.05; H, 6.28; N, 10,.54 Found: C, 55.98; H, 6.06; N, 10.25

Example 33.a.: Except the alcohol was added to the reaction mixture as a solution in methylene chloride, and the reaction was allowed to proceed overnight before it was diluted with methylene chloride, washed (saturated ammonium chloride solution, water, brine), dried, evaporated, and chromatographed twice; chromatography solvent: first column, dichloromethane:ethyl acetate:methanol (gradient, 60:40:0, 50:50:0, 50:50:1 to 90:0:10); second column, dichloromethanetethyl acetate (gradient, 60:40, 30:70 to 0:100); TLC: $R_f$=0.25, dichloromethane:methanol (95:5); MS: m/z=768(M+1), 766(M−1) by FAB.

Example 33.b.: Except dried, evaporated and used without further purification; TLC: $R_f$=0.59, chloroform:methanol (9:1); MS: m/z=654(M+1).

Example 34: R=4-tetrahydropyranyloxycarbonyl: Chromatography solvent: first .column, dichloromethane:methanol (gradient, 100:0, 98:2, 96:4), second column, dichloromethane:methanol (gradient, 100:0, 97.5:2.5), third column, dichloromethane:ethyl acetate (gradient, 100:0, 80:20); TLC: $R_f$=0.34, dichloromethane:methanol (95:5); HPLC: $t_R$=9.15, FR=1.0, column A, water:acetonitrile (1:1); MS: m/z=524(M+1).

Analysis for $C_{25}H_{28}F_3N_3O_6$.0.6 $H_2O$: Calculated: C, 56.20; H, 5.51; N, 7.86 Found: C, 56.26, H, 5.56; N, 7.86

Example 34.a.: Except the reaction mixture was diluted with methylene chloride, washed (10% aqueous hydrochloric acid, saturated sodium bicarbonate solution, brine), dried, evaporated and chromatographed twice; chromatography solvent: first column, dichloromethane:methanol (gradient, 100:0, 96:4, 95:5), second column, dichloromethane:ethyl acetate:methanol (gradient, 100:00:0, 95:5:0 [95:5]:5 [90:10]:5); TLC: $R_f$=0.40, dichloromethane:methanol (95:5); MS: m/z=640(M+1).

Example 34.b.: Except the ethyl acetate solution was washed (10% aqueous hydrochloric acid, water, saturated sodium bicarbonate solution, brine), dried and evaporated to give a product which was used without further purification; TLC: $R_f$=0.32, dichloromethane:methanol (95:5); MS: m/z 526(M+1).

EXAMPLES 35–40

Using similar procedures to that described in Example 1, the following compounds of formula I wherein $R^0$ is isopropyl, R is the indicated acyl group, $R^5$ is hydrogen and $R^6$ is phenyl were prepared by oxidation of the corresponding alcohols of formula II.

Example 35: R=carbamoylmethylaminocarbonyl: After overnight stirring, dilution of the reaction mixture with ethyl acetate afforded a suspension. The solid was filtered, washed (ether), dried under vacuum and triturated with methanol/ether to afford a white solid; TLC: $R_f$=0.29, dichloromethane:methanol (9:1); HPLC: $t_R$=6.09, FR=1, column A, water:acetonitrile (3:2); MS: m/z=496(M+1).

Analysis for $C_{22}H_{24}F_3N_5O_5$.1.25 $H_2O$: Calculated: C, 51.01; H, 5.16; N, 13.52 Found: C, 50.73; H, 5.05; N, 13.84

Example 36: R=2-methoxyethoxycarbonyl: Except using a 2 h reaction time; chromatography solvent: dichloromethane:ethanol (99:1); TLC: $R_f$=0.25, dichloromethane:ethanol (98:2); HPLC: $t_R$=6.09, FR=1, column A, water:acetonitrile (1:1); MS: m/z=498(M+1).

Analysis for $C_{23}H_{26}F_3N_3O_6$.0.25 $H_2O$: Calculated: C, 55.03; H, 5.32; N, 8.37 Found: C, 55.03; H, 5.70; N, 8.29

Example 37: R=acetyl: Chromatography solvent: dichloromethane:ethyl acetate (gradient, 100:0, 60:40, 50:50) then dichloromethane:isopropranol (95:5); TLC: $R_f$=0.09, dichloromethane:methanol (95:5); HPLC: $t_R$=5.47, FR=1, column A, water:acetonitrile (1:1); MS: m/z=438(M+1).

Analysis for $C_{21}H_{22}F_3N_3O_4$.0.3 $H_2O$: Calculated: C, 55.01; H, 5.46; N, 9.04 Found: C, 55.02; H, 5.31; N, 8.32

Example 38: R=cyanoacetyl: Except 45 min reaction time; chromatography solvent: first column, dichloromethane:methanol (98:2), second column, dichloromethane:isopropanol (97:3) then dichloromethane:methanol (9:1), then recrystallized from ethyl acetate/hexane; TLC: $R_f$=0.43, dichloromethane:methanol (96:4); HPLC: $t_R$=6.26, FR=1, column A, water:acetonitrile (1:1) MS: m/z=463(M+1).

Analysis for $C_{22}H_{21}F_3N_4O_4$.0.25 $H_2O$: Calculated: C, 56.59; H, 4.64; N, 12.00 Found: C, 56.64; H, 4.61; N, 11.85

Example 39: R=6-quinolylmethoxycarbonyl: Except omitting the hydrochloric acid wash; chromatography solvent: chloroform:methanol (first column, gradient 98:2, 97:3, second column, 98.5:1.5); TLC: $R_f$=0.27, chloroform:methanol (98:2); HPLC: $t_R$=6.77, FR=2, column A, water:acetonitrile (1:1); MS: m/z=581(M+1).

Analysis for $C_{30}H_{27}F_3N_4O_5$.0.75 $H_2O$: Calculated: C, 60.65; H, 4.84; N, 9.43 Found: C, 60.53; H, 4.75; N, 9.35

Example 40: R=3-methylisonicotinoyl: Chromatography solvent: chloroform:methanol (gradient, 60:1, 50:1, 40:1, 30:1); TLC: $R_f$=0.17, chloroform:methanol (20:1); HPLC: $t_R$=7.71, FR=1, column A, water:acetonitrile (1:1):

Analysis for $C_{26}H_{25}F_3N_4O_4$.0.5 $H_2O$: Calculated: C, 59.65; H, 5.01; N, 10.70 Found: C, 59.72; H, 5.17; N, 10.30

The corresponding alcohols of formula II for Examples 35–40 were prepared as follows:

Examples 35.a.–40.a.

2-(3-Acylamino-2-oxo-6-phenyl-1,2-dihydro-1-pyridyl)-N-( 2-tert-butyldimethysilyloxy-3,3,3-trifluoro-1-isopropylpropyl)-acetamides having the indicated acyl group R were prepared by acylating 2-(3-amino-2-oxo-6-phenyl-1-1,2-dihydro-1-pyridyl)-N-( 2-tert-butyldimethylsilyloxy-3,3,3-trifluoro-1-isopropylpropyl)-acetamide using the acylation method indicated or described.

Example 35.a.: R=carbamoylmethylaminocarbonyl: Acylation Method D using 1.5 equivalents triphosgene, 10 equivalents triethylamine and 2 equivalents glycinamide hydrochloride. After 20 min, the reaction mixture was dilute,] with dichloromethane, washed (three times with saturated ammonium chloride solution, then with brine), dried, evaporated, and dried under vacuum to afford the product which was used without further purification; TLC: $R_f$=0.16, dichloromethane:methanol (96:4); MS: m/z= 612(M+1).

Example 36.a.: R=2-methoxyethoxycarbonyl: Acylation Method D using 1.5 equivalents triphosgene, 7 equivalent triethylamine and 2.2 equivalents 2-methoxyethanol. After the cold reaction mixture was stirred 45 min, it was allowed to warm to ambient temperature over 3 h before it was diluted with dichloromethane, washed (three times with saturated ammonium chloride solution, then with brine), dried, evaporated and purified by chromatography: Chromatography solvent: dichloromethane:methanol (95:5); TLC: $R_f$=0.23, dichloromethane:ethyl acetate (9:1); MS: m/z=614(M+1).

Example 37.a.: R=acetyl: Acylation Method A using acetyl chloride and using the product isolated without chromatography; TLC: $R_f$=0.42, dichloromethane:methanol (95:5); MS: m/z=554(M+1).

Example 38.a.: R=cyanoacetyl. Acylation Method B, as follows: To a solution of the amine (1.05 g) in dry dimethylformamide was added cyanoacetic acid (0.79 g), 1-(3-dimethylaminopropyl)-3-ethyl-carbodimide hydrochloride (1.97 g), 1-hydroxybenzotriazole hydrate (1.39 g) and triethylamine (1.71 mL). After stirring overnight, the reaction mixture was diluted with ethyl acetate, washed (three times with 10% aqueous hydrochloric acid, twice with saturated sodium bicarbonate solution, water, and twice with brine), dried and evaporated before purification by chromatography. Chromatography solvent: dichloromethane:ethyl acetate (9:1); TLC: $R_f$=0.18, dichloromethane:ethyl acetate (9:1); MS: m/z=579(M+1).

Example 39.a.: R=6-quinolylmethoxycarbonyl: Acylation Method D using 2.2 equivalents of triethylamine and 2 equivalents of quinolin-6-ylcarbinol; chromatography solvent: chloroform:methanol (98:2); TLC: $R_f$=0.41, chloroform:methanol (97:3); MS: m/z=697(M+1).

Example 40.a.: R=3-methylisonicotinoyl: Acylation Method A as follows: The amine was added to a solution of 3-methylisonicotinoyl chloride hydrochloride (2.5 equivalents) in dry dimethylformamide; then triethylamine (2.2 equivalents) was added to the red solution, resulting in formation of a precipitate. After the reaction mixture was stirred overnight, it was worked up in a manner similar to that described for Acylation Method A. Chromatography solvent: first column, dichloromethane:methanol (gradient, 100:0, 98:2, 95:5), second column, dichloromethane:ethyl acetate (gradient, 100:0, 9:1, 8:2, 5:35) then dichloromethane:methanol (9:1); TLC: $R_f$=0.25, chloroform:methanol (20:1); MS: m/z=631(M+1).

The starting material 3-methylisonicotinoyl chloride hydrochloride was prepared as follows:
i. 3-Methylisonicotinic acid.

3,4-Lutidine (9.0 g) was dissolved in diphenyl ether (84 mL), under nitrogen, and immersed in a preheated oil bath (155° C.). Selenium dioxide (15 g) was added in 5 portions of 3.0, 2.0, 3.0, 3.5 and 3.5 grams over a 1 hour period. The reaction mixture exothermed vigorously following each addition. The reaction mixture, which turned dark brown, was heated at 155° C. for 0.5 h, then the reflux condenser was replaced with a distillation head. The temperature was raised to 195° C., but no water was distilled. After 35 min, the reaction mixture was cooled and filtered. The residue on the filter was washed with 200 mL hot water, in 5 portions. The combined aqueous washes were then washed ($CHCl_3$, 4×50 mL) and evaporated. The residue was dried under vacuum at 40° C. to afford 3-methylisonicotinic acid (61%); TLC: $R_f$=0.29, dichloromethane:methanol:acetic acid (90:7:3); MS: m/z=139(M+1).

ii. 3-Methylisonicotinoyl chloride hydrochloride.

To a suspension of 3-methylisonicotinic acid (0.676 g) in toluene was added thionyl chloride (0.5 mL), and the reaction mixture was heated under reflux 70 min. The resulting solution was decanted from a gummy residue on the bottom of the reaction flask, evaporated and further dried under high vacuum to afford 3-methylisonicotinoyl chloride hydrochloride which was used for the acylation without further purification.

Examples 35.b.–40.b.

2-(3-Acylamino-2-oxo-6-phenyl-1,2-dihydro-1-pyridyl)-N-(3,3,3-trifluoro-2-hydroxyisopropylpropyl)acetamides of formula II having the corresponding acyl group R, $R^0$ as isopropyl, $R^5$ as hydrogen and $R^6$ as phenyl were prepared by cleavage of the corresponding silyl ethers described above using a similar procedure to that described in Example 1.e., except as noted.

Example 35.b.: R=carbamoylmethylaminocarbonyl: Except using a 1 h reaction time and the diluted reaction mixture was washed with water and brine, resulting in the formation of a precipitate which was filtered, washed (ether) and dried under vacuum to afford the product as a white solid; TLC: $R_f$=0.28, dichloromethane:methanol (9:1); MS: m/z=498(M+1).

Example 36.b.: R=2-methoxyethoxycarbonyl: Except using a 2 h reaction time and the diluted reaction mixture was washed four times with brine:water (1:1) and once with brine. Chromatography solvent: dichloromethane:methanol (98.5:1.5); TLC: $R_f$=0.30, dichloromethane:methanol (97:3); MS: m/z=500(M+1).

Example 37.b.: R=acetyl: Except the diluted reaction mixture was washed only with water and brine, dried, evaporated and used without further purification; TLC: $R_f$=0.09, dichloromethane:methanol (95.5); MS: m/z=440(M+1).

Example 38.b.: R=cyanoacetyl: Except using a 2.5 h reaction time and the diluted reaction mixture was washed four times with brine:water (1:1) and once with brine. Chromatography solvent: dichloromethane:methanol (98:2); TLC: $R_f$=0.35, dichloromethane:methanol (96:4); MS: m/z=465(M+1).

Example 39.b.: R=6-quinolylmethoxycarbonyl: Except using a 1.5 h reaction time and washing the diluted reaction mixture twice with brine:water (1:1) and once with brine, and purifying the isolated solid by trituration with ethyl acetate/chloroform, rather than chromatography, to afford the product; TLC: $R_f$=0.31, chloroform:methanol (97:3); MS: m/z=583(M+1).

Example 40.b.: R=3-methylisonicotinoyl: Except the diluted reaction mixture was washed with water and brine and the isolated product was used without further purification; TLC: $R_f$=0.12, chloroform:methanol (20:1); MS: m/z=517(M+1).

EXAMPLES 41–44

Using similar procedures to that described in Example 1, the following compounds of formula I wherein $R^0$ is isopropyl, R is the indicated acyl group, $R^5$ is hydrogen and $R^6$ is phenyl were prepared by oxidation of the corresponding alcohols of formula II:

Example 41: R=4-methoxycarbonylbenzyloxycarbonyl: Except using a 2 h reaction time; chromatography solvent: dichloromethane:ethyl acetate (9:1); TLC: $R_f$=0.29, dichloromethane:ethyl acetate (9:1); NMR: 8.75 (d,1), 7.99 (d,2), 7.92 (d,1), 7.59 (d,2), 7.47–7.34 (m,6), 6.23 (d,1), 5.28 (s,2), 4.63 (t,1), 4.50 (AB q,2) 3.86 (s,3), 2.2–2.0 (m,1), 0.89 (d,3), 0.83 (d,3); MS: m/z=588(M+1).

Example 42: R=ethoxycarbonylmethoxycarbonyl: Except using a 4 h reaction time; chromatography solvent: dichloromethane:methanol (99:1); TLC: $R_f$=0.44, dichloromethane::methanol (98:2); NMR: 7.93 (d,1), 7.50–7.41 (m,5), 6.26 (d,1), 4.74 (s,2), 4.56 (AB q,2), 4.20 (q,2), 4.10 (d,1), 2.2–2.0 (m,1), 0.89 (d,3), 0.83 (d,3); MS: m/z=526(M+1).

Example 43:: R=methoxycarbonylmethylaminocarbonyl: Not chromatographed, but isolated and recrystallized from dichloromethane/petroleum ether; TLC: $R_f$=0.39, dichloromethane:methanol (95:5); NMR: 8.03 (d,1), 7.48–7.37 (m,5), 6.18 (d,1), 4.50 <AB q,2), 4.08 (d,1), 3.90 (s,3), 3.81 (s,3), 2.2–2.1 (m,1), 0.87 (d,3), 0.81 (d,3); MS: m/z=511(M+1).

Example 44: R=3-methoxycarbonylbenzyloxycarbonyl: Chromatography solvent: dichloromethane:methanol (gradient, 100:0, 7:3, 95:5); TLC: $R_f$=0.30, dichloromethane:ethyl acetate (9:1); NMR: 8.03 (s,1), 7.93 (t,2), 7.73 (d,1), 7.57 (t,1), 7.49–7.37 (m,5), 6.24 (d,1), 5.26 (s,2), 4.49 (AB q,2), 4.05 (d,1), 3.87 (s,3), 2.2–2.1 (m,1), 0.87 (d,3), 0.79 (d,3); MS: m/z=588(M+1).

The corresponding alcohols of formula II for Examples 41–44 were prepared as follows:

Examples 41.a.–44.a.

2-(3-Acylamino-2-oxo-6-phenyl-1,2-dihydro-1-pyridyl)-N-( 2-tert-butyldimethylsilyloxy-3,3,3-trifluoro-1-isopropylpropyl)acetamides having the indicated acyl group R were prepared from 2-(3-amino-2-oxo-6-phenyl-1,2-dihydro-1-pyridyl)-N-(2-tert-butyl-dimethylsilyloxy- 3,3,3-trifluoro-1-isopropylpropyl)acetamide using triphosgene, triethylamine and an alcohol of formula A.OH or an amine of formula $A.NH_2$ by Acylation Method D, as described in Example 22.f., except as otherwise noted or described. Certain of the requisite alcohols of formula A.OH which were not commercially available were prepared by the methods described.

Example 41.a.: R=4-methoxycarbonylbenzyloxycarbonyl: Except to a chilled solution of the amine (1.0 g) in dry dichloromethane (18 mL) was added triphosgene (0.29 g) and triethylamine (1.9 mL). After stirring the chilled mixture for 20 min, the alcohol (0.98 g) was added. The reaction mixture was stirred at 5° C. for 2 h before it was allowed to warm to ambient temperature over 4 h, diluted with dichloromethane (100 mL), washed (three times with saturated aqueous ammonium chloride solution and once with brine), dried and evaporated before purification by chromatography. Chromatography solvent: first column, dichloromethane:diethyl ether (97:3), second column, dichloromethane:ethyl acetate (9:1); TLC: $R_f$=0.48, dichloromethane:ethyl acetate (9:1); MS: m/z=704(M+1).

Example 42.a.: R=ethoxycarbonylmethoxycarbonyl: Except the reaction was carried out and worked up in a similar manner to that described in Example 41.a., but allowing the reaction mixture to stir 1.5 h before the cold bath was removed and it was allowed to warm to room temperature over 2 h before work up. Chromatography solvent: dichloromethane:ethyl acetate (9:1); TLC: $R_f$=0.48, dichloromethane:ethyl acetate (9:1); MS: m/z=642(M+1).

Example 43.a.: R=methoxycarbonylmethylaminocarbonyl: Except using a similar procedure to that described in Example 41.a., with a reaction time of 3.5 h; and the product was not chromatographed, but triturated successively with 10% aqueous hydrochloric acid, water and ether before drying under vacuum to afford the product; TLC: $R_f$=0.35, dichloromethane:methanol (95:5); MS: m/z=627(M+1).

Example 44.a.: R=3-methoxycarbonylbenzyloxycarbonyl: Except using a similar procedure to that described in Example 41.a., with a reaction time of 3.5 h. Chromatography solvent: dichloromethane:ethyl acetate (gradient, 100:0, 95:5, 93:7, 90:10), then rechromatographing the mixed fractions (gradient, 100:0, 95:5, 90:10); TLC: $R_f$=011, dichloromethane:ethyl acetate (9:1); MS: m/z=704(M+1).

The methyl 3-hydroxymethylbenzoate for the above procedure was obtained as follows, using literature procedures. (See U.S. Pat. No. 4,130,719; and Yoon et al., *J. Org. Chem.* (1973) 38(16), 2786–2792.)

To a suspension of 3-methoxycarbonylbenzoic acid (4.68 g, prepared by the method of Kasina and Nematollahi, *Tetrahedron Lett.* (1978) 1403) in tetrahydrofuran (12.5 mL) at 0° C. was added dropwise borane-tetrahydrofuran complex (1.0M in tetrahydrofuran, 25 mL) over 40 min. The reaction mixture, which had become a solution, was allowed to warm slowly to room temperature as it was stirred overnight. When examination by TLC after 24 h showed little conversion to the alcohol, the reaction mixture was cooled with an ice bath and the reaction quenched with water (20 mL). The mixture was saturated with potassium carbonate and the phases were separated. The organic phase was washed (saturated potassium carbonate solution) and evaporated. The aqueous phase was extracted with ethyl acetate; and the ethyl acetate solution was used to redissolve the residue from the tetrahydrofuran solution. The resulting ethyl acetate solution was washed (water), dried and evaporated to afford a portion of crude alcohol.

The original aqueous phase was acidified with 10% aqueous hydrochloric acid to pH 2, resulting in precipitation of unreacted acid as a white solid, which was filtered, washed with water and ether, and dried under vacuum to provided recovered starting acid (2.7 g).

To a suspension of the recovered acid (2.7 g) in tetrahydrofuran was added sodium borohydride (0.49 g), resulting in evolution of gas. To the mixture was added dropwise boron trifluoride etherate (2.05 mL) over 5 min, causing further gas evolution. The reaction mixture, which was heated to a gentle reflux by the exothermic reaction, was stirred 4 h, quenched with water (2.5 mL) and evaporated. The residue was partitioned between dichloromethane and water. After the aqueous phase was further extracted with dichloromethane, the combined extracts were washed (brine), dried and evaporated. The residue was partitioned between ethyl acetate and saturated sodium bicarbonate solution; and the organic phase was washed (brine), dried and evaporated to afford crude alcohol which was combined with the material obtained from the borane reduction for purification by chromatography, eluting with dichloromethane:ethyl acetate (gradient, 100:0, 95:5, 91.5:9.5, 91:1, 85:15) to afford methyl 3-hydroxymethylbenzoate; TLC: 0.42, dichloromethane:ethyl acetate (9:1); MS: m/z=167(M+1).

Examples 41.b.–44.b.

2-(3-Acylamino-2-oxo-6-phenyl-1,2-dihydro-1-pyridyl)-N-( 3,3,3-trifluoro-2-hydroxy-1-isopropylpropyl)acetamides of formula II having the indicated acyl group R, $R^0$ as isopropyl, $R^5$ as hydrogen and $R^6$ as phenyl were prepared by cleavage of the corresponding silyl ethers described above using a similar procedure to that described in Example 1.e., except as noted or described.

Example 41.b.: R=4-methoxycarbonylbenzyloxycarbonyl: Except using a 2 h reaction time and the diluted reaction mixture was washed 3 times with brine:water (1:1) and once with brine. The dried solution was evaporated and dried under vacuum to provide a product which was used without further purification; TLC: $R_f$=0.12, dichloromethane:ethyl acetate (9:1); MS: m/z=590(M+1).

Example 42.b.: R=ethoxycarbonylmethoxycarbonyl: Except a buffered deprotection was used. To a solution of the silyl ether (0.452 g) in dry tetrahydrofuran (7 mL) was added acetic acid (0.05 mL) and tetrabutylammonium fluoride (0.70 mL). After the reaction mixture was stirred 45 min (reaction deemed complete), it was diluted with ethyl acetate, washed (water, three times, then brine), dried and evaporated to a residue which was dried under vacuum to give a product which was used without further purification; TLC: $R_f$=0.28, dichloromethane:methanol (97:3); MS: m/z=528 (M+1).

Example 43.b.: R=methoxycarbonylmethylaminocarbonyl: Not chromatographed, but crystallized from ethyl acetate (with cooling for one crop), washed (water, then ether) and dried under vacuum; TLC: $R_f$=0.06, dichloromethane:ethyl acetate (60:40); MS: m/z=513 (M+1).

Example 44.b.: R=3-methoxycarbonylbenzyloxycarbonyl: Isolated and triturated with ether; TLC: $R_f$=0.05, dichloromethane:ethyl acetate (95:5); MS: m/z=590(M+1).

EXAMPLES 45–48

The following compounds of formula I wherein $R^0$ is isopropyl, R is the indicated acyl group which contains a carboxy moiety, is $R^5$ is hydrogen and $R^6$ is phenyl were prepared by hydrolysis of the ester groups of corresponding compounds of formula I in which the acyl group R contains an ester moiety, prepared as described in Examples 41–44, respectively. In each example, the hydrolysis was carried out using lithium hydroxide in aqueous tetrahydrofuran, followed by acidification, as described or indicated.

Example 45: R=4-carboxybenzyloxycarbonyl: To a solution of the starting ester (Example 41, 0.589 g) in dry tetrahydrofuran (8 mL) was added a solution of lithium hydroxide monohydrate (0.094 g) in water (2 mL). The biphasic mixture was rapidly stirred for 3 h. The mixture was diluted with water (5 mL) and the pH adjusted to about 3 with 10% aqueous hydrochloric acid to give a white precipitate. This mixture was extracted with ethyl acetate (3 times); and the combined extracts were washed (water, brine), dried, evaporated, and dried under vacuum. The product contained unhydrolyzed ester and was again subjected to the same reaction conditions for 5.5 h. The reaction mixture was worked-up as before to give a white solid which was crystallized from hot ethyl acetate/hexane to give the title acid as a white solid; TLC: $R_f$=0.41, dichloromethane:methanol:acetic acid (95.5:4:0.5); MS: m/z=574(M+1).

Analysis for $C_{28}H_{26}F_3N_3O_7$: Calculated: C, 58.65; H, 4.57; N, 7.33 Found: C, 58.87; H, 4.65; N, 7.13

Example 46: R=carboxymethoxycarbonyl: To a solution of the starting ester (Example 42, 0.586 g)in tetrahydrofuran (8 mL) and water (3 mL) was added lithium hydroxide monohydrate (0.10 g) to give a cloudy, biphasic mixture. After stirring for 45 min, the reaction was deemed complete. The reaction mixture was diluted with water (5 mL), acidified to about pH 3 with 10% aqueous hydrochloric acid, and extracted with ethyl acetate (three times). The combined extracts were washed (brine), dried, and evaporated. The residue was dried under vacuum to give a solid. The impure solid was crystallized from hot ethyl acetate/hexane to give the title product as an off-white powder; TLC: $R_f$=0.26, dichloromethane:methanol:acetic acid (89:10:1); MS: m/z=498(M+1).

Analysis for $C_{22}H_{22}F_3N_3O_7$: Calculated: C, 53.12; H, 4.46; N, 8.45 Found: C, 53.09; H, 4.57; N, 8.51

Example 47: R=carbamoylmethylaminocarbonyl: The ester (Example 43, 0.2 g) was dissolved in aqueous tetrahydrofuran (water:tetrahydrofuran, 20:80) such that the concentration was about 0.1 molar (4 mL); then lithium hydroxide monohydrate (2.2 equivalent) was added and the reaction mixture was stirred until the hydrolysis was deemed complete. The reaction mixture was diluted with water, washed with ether and acidified to about pH 2 with 10% aqueous hydrochloric acid. The resulting precipitate was filtered, washed (water) and dried under vacuum to afford the title product (77%); TLC: $R_f$=0.46, chloroform:methanol:acetic acid (85:10:5); MS: m/z=497(M+1).

Analysis for $C_{22}H_{23}F_3N_4O_6$·1.2 $H_2O$·0.35 $CH_3OH$: Calculated: C, 50.72; H, 5.10; N, 10,,59 Found: C, ,50.60; H, 4.72; N, 10.43

Example 48: R=3-carboxybenzyloxycarbonyl: The ester (Example 44) was hydrolyzed using a similar procedure to that of Example 47 except the crude product was purified by chromatography, eluting with dichloromethane:ethyl acetate:acetic acid (73:36:1), followed by redissolving the product in ethyl acetate, filtration, and evaporation to give the title acid as a solid; TLC: $R_f$=0.10, chloroform:methanol (9:1); MS: m/z=574(M+1).

Analysis for $C_{28}H_{26}F_3N_3O_7$: Calculated: C, 58.64; H, 4.57; N, 7.33 Found: C, 58.95; H, 4.90; N, 6.63

EXAMPLE 49

2-(3-Amino-2-oxo-6-phenyl-1,2-dihydro-1-pyridyl)-N-(3,3,3-trifluoro- 1-isopropyl-2-oxopropyl)acetamide.

To a solution of 2-(3-benzyloxycarbonylamino-2-oxo-6-phenyl- 1,2-dihydro-1-pyridyl)-N-(3,3,3-trifluoro-1-isopropyl-2-oxopropyl)acetamide (10 g) and anisole (6.6 g) in dichloromethane (100 mL) at 0° C. was added trifluoromethanesulphonic acid (9 mL, 15.3 g) while maintaining the temperature below 2° C. The reaction mixture was allowed to warm to room temperature in 30 min and kept at room temperature for a further 45 min before saturated aqueous sodium bicarbonate was added slowly to pH 7. Ethyl acetate was added, the phases separated and the aqueous phase extracted further with ethyl acetate. The combined organic extract was washed (brine), dried ($MgSO_4$) and evaporated. The crude product was purified by trituration with hexane followed by trituration with diethyl ether to give the title product (which can be recrystallized from dichloromethane/hexane) as a white solid (4.85 g); TLC: $R_f$=0.40, ethyl acetate; 300 MHz NMR: 0.78–0.91 (m,6), 2.07–2.30 (m,1), 4.39 (d,1), 4.49 (d,1), 4.61 (t,1), 5.17 (s,1), 5.98 (d,1), 6.51 (d,1), 7.28–7.41 (m,5), 8.68 (d,1); MS: m/z=396(M+1).

Analysis for $C_{19}H_{20}F_3N_3O_3$·0.25 $H_2O$: Calculated: C, 57.07; H, 5.17; N, 10,.51 Found: C, 57.25; H, 5.10; N, 10,,47

The benzyloxycarbonyl group can alternatively be removed using the following procedure:

To a solution of 2-(3-benzyloxycarbonylamino-2-oxo-6-phenyl-1,2-dihydro-1-pyridyl)-N-(3,3,3-trifluoro-1-isopropyl-2-oxopropyl)acetamide (22.2 g) in ethanol (500 mL) was added 10% (w/w) palladium on carbon (5.55 g). The mixture was shaken under a hydrogen atmosphere overnight. Catalyst was removed by filtration through diatomaceous earth. The filter pad was washed successively with ethanol and methanol. Concentration of the filtrate gave the crude product as an off-white solid (17.2 g). This material was combined with 0.61 g of product generated from a separate run, dissolved in a minimum volume of methanol, diethylether was added, and the mixture was allowed to stand overnight. The precipitate was collected and washed with ether to give the amine as an off-white solid (13.9 g).

The starting material ketone for the above preparation may be obtained as described in Example 1 or as follows:

a. 2-(3-Benzyloxycarbonylamino-2-oxo-6-phenyl-1,2-dihydro-1-pyridyl)-N-( 2-tert-butyldimethylsilyloxy-3,3,3-trifluoro-1-isopropylpropyl)acetamide.

To a slurry of 2-(3-amino-2-oxo-6-phenyl-1,2-dihydro-1-pyridyl)-N-( 2-tert-butyldimethylsilyoxy-3,3,3-trifluoro-1-isopropylpropyl)acetamide (20.0 g) (Example 14.a. or 22.e.) and sodium carbonate (9.53 g) in tetrahydrofuran (200 mL) and dimethylformamide (4 mL) at 0° C. was added benzyl chloroformate (10.2 mL) dropwise in 5 min. After warming to room temperature, the reaction mixture was stirred overnight, then filtered and the filtrates evaporated. Ethyl acetate was added and the solution washed (water, brine). The combined aqueous was back extracted with ethyl acetate and then the combined organic washed (brine) and evaporated. Chromatography, eluting with dichloromethane, gave the title compound as a near colorless oil (20.9 g); TLC: $R_f$=0.60, dichloromethane:ethyl acetate (5:1); 300 MHz MMR: 0.08 (s,3), O.1G (s,3), 0.82 (d,3), 0.85 (s,9), 0.92 (d,3), 1.70–1.76 (m,1), 3.82 (t,1), 3.70–4.00 (m,2), 4.25 (m,2), 4.60 (broad d,1), 5.19 (s,2), 6.22 (d,1), 7.25–7.50 (m,10), 7.64 (d,1), 7.92 (d,1), 8.54 (s, 1); MS: m/z=646(M+1).

b. 2-(3-Benzyloxycarbonylamino-2-oxo-6-phenyl-1,2-dihydro-1-pyridyl)-N-( 3,3,3-trifluoro-2-hydroxy-1-isopropylpropyl)acetamide.

To a solution of 2-(3-benzyloxycarbonylamino-2-oxo-6-phenyl-1,2-dihydro- 1-pyridyl)-N-(2-tert-butyldimethylsilyoxy-3,3,3-trifluoro-1-isopropylpropyl)acetamide (20.5 g) in dry tetrahydrofuran (120 mL) was added acetic acid (2 mL) followed by tetrabutylammonium fluoride (1M in tetrahydrofuran, 47.6 mL). After stirring for 5 min, the reaction mixture was diluted with ethyl acetate (1 L), washed (three times with water, brine), dried ($MgSO_4$) and evaporated to give the title product as a white solid (16.1 g) which was used without further purification; TLC: $R_f$=0.20, chloroform:ethyl acetate (20:1); 300 MHz NMR: 0.80 (d,3), 0.88 (d,3), 1.63–1.74 (m,1), 3.8 (t,1), 4.25–4.40 (m,1), 4.48–4.60 (broad d,1), 5.19 (s,2), 6.20 (d,1), 6.49 (d,1), 7.31–7.46 (m,10), 7.86 (d,1), 7.90 (d,1), 8.54 (s,1); MS: 532(M+1).

c. 2-(3-Benzyloxycarbonylamino-2-oxo-6-phenyl-1,2-dihydro-1-pyridyl)-N-( 3,3,3-trifluoro-1-isopropyl-2-oxopropyl)acetamide.

To a solution of 2-(3-benzyloxycarbonylamino-2-oxo-6-phenyl-1,2-dihyro- 1-pyridyl)-N-(3,3,3-trifluoro-2-hydroxy-1-isopropylpropyl)acetamide (10.4 g) in dry dimethyl sulfoxide (50 mL) and toluene (50 mL) was added 1-(3-dimethylaminopropyl)-3-ethylcarbodiimide hydrochloride (39 g). To this cooled mixture (3° C.) was added dichloroacetic acid (6 mL, 9.2 g) while maintaining the temperature below 10° C. The reaction mixture was warmed to room temperature in 30 min, then diluted with ethyl acetate (300 mL) and water (300 mL). The pH was adjusted to 6 with 1N HCl (10 mL), the phases separated and the organic phase washed (water and twice with brine), dried ($MgSO_4$) and evaporated to give the title product as a white solid (10.4 g) which was used without further purification; TLC: $R_f$=0.45, dichloromethane:ethyl acetate (5:1); 300 MHz NMR: 0.83 (d,3), 0.89 (d,3), 2.05–2.19 (m,1), 4.50 (q,1), 4.63 (t,3), 5.19 (s,2), 6.23 (d,1), 7.30–7.50 (m,10), 7.92 (d,1), 8.56 (s,1), 8.74 (d,1); MS: m/z=530(M+1).

2-(3-Benzyloxycarbonylamino-2-oxo-6-phenyl-1,2-dihydro-1-pyridyl)-N-( 3,3,3-trifluoro-2-hydroxy-1-isopropylpropyl)acetamide can alternatively be prepared as follows:

d. 3-Aza-4-phenylpent-3-enal dimethyl acetal.

Acetophenone (60.6 g) and aminoacetaldehyde dimethyl acetal (78.9 g) were dissolved in toluene (650 mL) in a 1 L round-bottomed flask. A Dean-Stark trap, fitted with a reflux condenser, was attached to the reaction vessel and the solution was brought to reflux. The trap was drained after 17 h, 41 h, and 48 h (30 mL each time). After 65 h, the reaction was cooled and volatiles were evaporated to leave a yellow liquid (103.3 g). Fractional distillation gave two major fractions: fraction 1, 10 5 g (60°–126° C. 20–24 Pa); fraction 2, 78.66 g (126°–130° C., 17–20 Pa). Fraction 1 contained a significant amount of acetophenone and amino acetaldyhyde dimethyl acetal. Fraction 2 contained less than 5% acetophenone and acetal, and was used directly in the next step. The NMR spectrum was obtained from a clean fraction of imine produced in a different run; 300 MHz NMR: 2.20 (s,6), 3.54 (d,2), 4.70 (t,1), 7.38–7.43 (m,3), 7.79–7.82 (m,2).

e. Dimethyl 4-aza-6,6-dimethoxy-3-phenylhex-2-enylidenemalonate.

A dry, 2 L, 3-necked flask was equipped with a mechanical stirrer, an addition funnel and a Claisen adapter fitted with a thermometer and a nitrogen inlet. To the reaction vessel was added a solution of lithium diisopropylamide (230 mL, 2.0M in hexane/tetrahydrofuran) and tetrahydrofuran (700 mL). To the cooled (5° C.) solution was added the crude material from Example 49.d. (78.5 g) in tetrahydrofuran (150 mL) over 30 min. The internal temperature was maintained at 5° C. during the addition and for 45 minutes thereafter. A solution of dimethyl methoxymethylenemalonate (70.5 g) in dry tetrahydrofuran (150 mL) was added dropwise over 30 min. The dark amber reaction mixture was allowed to warm to room temperature and was stirred overnight. The mixture was diluted with methylene chloride (2 L) and washed (saturated ammonium chloride). The aqueous washes were back extracted with methylene chloride. The combined methylene chloride layers were washed (brine) and dried ($MgSO_4$). Evaporation gave the crude diene ester as a red oil (147.6 g). This material was used without further purification. A separate iteration of this procedure provided a clean sample for characterization after chromatography; chromatography solvent: ethyl acetate:chloroform (5:95); TLC: $R_f$=0.32, ethyl acetate:chloroform:methanol (5:95:1); 300 MHz NMR: 3.33 (s,6), 3.48 (s,3), 3.68 (s,3), 4.63 (broad s,1), 6.17 (d,1), 7.33–7.35 (m,3), 7.52–7.54 (m,3), 7.90 (broad s,1); MS: m/z=350(M+1).

f. 1-(2,2-Dimethoxyethyl)-6-phenylpyrid-2-one-3-carboxylic acid.

A 3 L round-bottomed flask was equipped with a stir bar and fitted with a Claisen adapter holding a thermometer and a nitrogen inlet. The flask was charged with a solution of the product from Example 49.e. in methanol (1.5 L). Sodium methoxide (32.4 g) was added in one portion and caused a mild warming. After 3 h, aqueous sodium hydroxide (750 mL, 10% w/v) was added to the mixture in one portion. The mixture was stirred at room temperature for 2 h, the methanol was evaporated, and the aqueous residue was acidified with hydrochloric acid and extracted with methylene chloride. The extracts were washed (brine), dried (MgSO$_4$), and evaporated to give a red-brown oil (99.6 g) which partially solidified. This material was used without further purification. A sample of the pyridone, after purification, was characterized; TLC: R$_f$=0.41, methanol:chloroform:acetic acid (1.5:98:0.5); 300 MHz NMR: 3.13 (s,6), 4.14 (d,2), 4.63 (t,1), 6.64 (d,1), 7.51–7.58 (m,5), 8.41 (d,1).

g. 3-Benzyloxycarbonylamino-2-oxo-6-phenyl-1,2-dihydro-1-pyridyl-acetaldehyde dimethyl acetal.

An oven-dried, 3 L, three-necked flask was equipped with a mechanical stirrer, a thermometer and a reflux condenser capped with a nitrogen inlet. The reaction vessel was charged with a dioxane (1 L) solution of the product from Example 49.f (99.6 g). Diphenylphosphoryl azide (103.9 g) and triethylamine (39.8 g) were each added to the reaction vessel in one portion and washed down with dioxane (50 mL each). The resulting solution was heated at gentle reflux (100° C.) for 1 h. Gas evolution was vigorous at first but then subsided. The reaction mixture was cooled to 70° C., and benzyl alcohol (38.9 g) was added in one portion along with a dioxane wash (100 mL). The reaction was heated at reflux for 18 h, cooled and evaporated. The residual oil was dissolved in ethyl acetate (1 L) and washed with 1N hydrochloric acid:brine (1:1), followed by brine. The organic layer was dried (MgSO$_4$) and evaporated to give the crude mixture (249.5 g). This material was purified by chromatography, with ethyl acetate:dichloromethane as the eluent (gradient, 0:100, 5:95), to yield the amide (43.1 g); TLC: R$_f$=0.49, ethyl acetate:chloroform (5:95); 300 MHz NMR: 3.09 (s,6), 4.02. (d,2), 4.54 (t,1), 5.19 (s,2), 6.19 (d,1), 7.34–7.50 (m,5), 7.89 (d,1), 8.54 (s,1).

h. 3-Benzyloxycarbonylamino-2-oxo-6-phenyl-1,2-dihydro-1-pyridyl-acetaldehyde.

The product from Example 49.g. (43.1 g) was dissolved in a mixture of tetrahydrofuran (700 mL) and aqueous hydrochloric acid (225 mL 3N). The mixture was held at reflux under nitrogen for 3.5 h. The mixture was cooled and the tetrahydrofuran was evaporated. The aqueous residue was extracted with methylene chloride, washed (saturated aqueous sodium bicarbonate) and dried (MgSO$_4$). Evaporation gave the crude product as a tan solid. Trituration with ether (300 mL) gave the aldehyde as a white solid (27.3 g); TLC: R$_f$=0.32, ethyl acetate:dichloromethane (5:95); 300 MHz NMR: 4.66 (s,2), 5.19 (s,2), 6.28 (d,1), 7.32–7.49 (m,10), 7.94 (d,1), 8.61 (s,1), 9.50 (s,1); MS: m/z=363(M+1).

i. 3-Benzyloxycarbonylamino-2-oxo-6-phenyl-1,2-dihydro-1-pyridyl-acetic acid.

A 2 L, three-necked flask was equipped with a mechanical stirrer, an addition funnel and a Claisen adapter holding a thermometer and a reflux condenser capped with a nitrogen inlet. The flask was charged with a tetrahydrofuran (275 mL) solution of the product from Example 49.h. (40.5 g). The addition of tert-butanol (275 mL) caused precipitation of the aldehyde starting material. The reaction mixture was cooled to 15° C. with an ice-water bath, and 2-methyl-2-butene (250 mL) was added in one portion. A solution of sodium chlorite (80%, 88.5 g) and sodium dihydrogen phosphate monohydrate (108.0 g) in water (400 mL) was added dropwise to the reaction mixture over 45 min. The internal temperature was maintained at 20° C. during the addition. Stirring at room temperature was continued for 2 h. The mixture was partially evaporated to leave an aqueous suspension of white solid. The mixture was diluted with brine and extracted with chloroform. The combined extracts were dried (MgSO$_4$) and evaporated. The residue was dissolved in diethyl ether and evaporated to give an off-white solid, which was triturated with hexane:diethyl ether (9:1) to give the acid as an off-white solid (43.1 g); TLC: R$_f$=0.20, methanol:dichloromethane (2:98); 300 MHz NMR: 4.44 (s,2), 5.19 (s,2), 5.24 (d,1), 7.33–7.51 (m,10), 7.92 (d,1), 8.59 (s,1), 13.07 (broad s,1); MS: m/z=363(M+1). NMR showed that this material was pure but contained diethyl ether, which was not removed by prolonged drying in a vacuum oven.

j. 2-(3-Benzyloxycarbonylamino-2-oxo-6-phenyl-1,2-dihydro-1-pyridyl)-N-( 3,3,3-trifluoro-2-hydroxy-1-isopropylpropyl)acetamide.

To a solution of the acid of Example 49.i. (19.0 g), 1-hydroxybenzotriazole hydrate (13.6 g), 3-amino-1,1,1-trifluoro- 4-methyl-2-pentanol hydrochloride (11.5 g) and triethylamine (14.0 mL) in dimethyl-formamide (100 mL) was added 1-(3-dimethylaminopropyl)- 3-ethyl-carbodiimide hydrochloride (14.5 g). The mixture was stirred overnight diluted with 1N hydrochloric acid and extracted with ethyl acetate. The organics were washed (saturated sodium bicarbonate), dried, and evaporated to give a white solid. The solid was triturated with ether and dried in a vacuum oven overnight to yield the alcohol (20.85 g). The triturate was concentrated and the residue purified by flash chromatography (dichloromethane:methanol, 99:1) to yield additional alcohol (1.70 g).

The title compound of Example 49 can alternatively be prepared as follows:

To a solution of 2-(3-trifluoroacetylamino-2-oxo-6-phenyl-1,2-dihydro- 1-pyridyl)-N-(3,3,3-trifluoro-1-isopropyl-2-oxopropyl)acetamide (9.5 g) in tetrahydrofuran (92 mL) was added water (184 mL) followed by potassium carbonate (13.4 g). This mixture was allowed to stir overnight. A first crop of the amine (4.2 g) was obtained after filtration and washing with diethyl ether. The organic filtrates were evaporated, and the residue recrystallized from dichloromethane:hexane to give a second crop of the amine (2.9 g).

EXAMPLES 50–55

The following compounds of formula I wherein R$^0$ is isopropyl, R is the indicated acyl group, R$^5$ is hydrogen and R$^6$ is phenyl were prepared by acylation of 2-(3-amino-2-oxo-6-phenyl-1,2-dihydro-1-pyridyl)-N-( 3,3,3-trifluoro-1-isopropyl-2-oxopropyl)acetamide using the indicated acylation method, except as otherwise noted or described. Certain starting materials: which were not commercially available were prepared by the methods: described.

Example 50: R=3-methylpyrid-4-ylmethoxycarbonyl: Acylation Method D using 3-methylpyrid-4-ylcarbinol; chromatography solvent: first column, dichloromethane:methanol (gradient, 100:0, 97:3, 95:5), second column, dichloromethane:ethyl acetate:methanol (gradient, 100:0:0, 60:40:0, 60:39:1), third column, dichloromethane:ethyl acetate (gradient, 100:0, 60:40, 40:60, 0:100); TLC: R$_f$=0.31, dichloromethane:methanol (9:1); MS: m/z= 545(M+1).

Analysis for C$_{27}$H$_{27}$F$_3$N$_4$O$_5$.0.9 H$_2$O: Calculated: C, 57.83; H, 5.18; N, 9.99 Found: C, 57.96; H, 5.13; N, 9.86

The 3-methylpyrid-4-ylcarbinol was prepared as follows:

a. Ethyl 3-methylisonicotinate.

To a solution prepared by saturating absolute ethanol (25 mL) cooled in an ice bath (ca. 0° C.) with HCl gas was added 3-methylisonicotinic acid (Example 40.a.i.) (5.7 g). The yellow suspension was heated under reflux for 4.5 h, at which time esterification was complete. The reaction mixture was cooled and evaporated; and the residue was redissolved in water, affording a dark red solution. The aqueous phase was basified with sodium bicarbonate solution, resulting in formation of a precipitate. The mixture was then extracted with ether (solids still insoluble) and the ether phase was washed with brine, at which time the solids were filtered. The filtered ether solution was dried, evaporated and further dried under vacuum before purification by chromatography, eluting with dichloromethane:ethyl acetate (gradient, 100:0, 97:3) to afford the ester (42%); TLC:: 0.41, eluted twice, first hexane:ethyl acetate (6:1), then dichloromethane:methanol (9:1); MS: m/z=166(M+1).

b. 3-Methylpyrid-4-ylcarbinol.

A 500 mL, 3-necked round bottomed flask, equipped with a reflux condenser with a gas inlet tube, a dropping funnel, and a stopper was purged with nitrogen; and then lithium aluminum hydride (1.2 g) was weighed into it. The hydride was wet with distilled tetrahydrofuran (60 mL). The suspension was cooled in an ice bath (0° C.) before a solution of ethyl 3-methylisonicotinate (2.6 g) in tetrahydrofuran was added dropwise over 30 min. Following the addition, the reaction mixture was allowed to warm to room temperature. After one hour, the reduction was complete. The reaction mixture was again cooled in an ice bath before water (4 mL) was added very slowly to quench the reaction. 10% Aqueous sodium hydroxide solution (4 mL) and water (10 mL) were added, and the mixture was stirred for 0.5 h before diatomaceous earth was added. After further stirring, the mixture was filtered through more diatomaceous earth. The filtrate was evaporated, redissolved in dichloromethane and evaporated, and further dried under high vacuum. After storage overnight in the freezer, the milky residue was dissolved in ethyl acetate, dried, evaporated and further dried under high vacuum, before the oil was chromatographed, eluting with dichloromethane:methanol (gradient, 95:5, 92:8, 9:1), to afford the alcohol (6%); TLC: $R_f$=0.19, eluted twice, first hexane:ethyl acetate (6:1), then dichloromethane:methanol (9:1); MS: m/z=124(M+1).

Example 51: R=2-dimethylaminoethoxycarbonyl: Acylation Method D using 2-dimethylaminoethanol and diluting the reaction mixture with ethyl acetate before washing it with water, saturated sodium bicarbonate solution and brine. Chromatography solvent: dichloromethane:methanol (gradient, 100:0, 95:5, 9:1); TLC: $R_f$=0.21, dichloromethane:methanol (9:1); MS: m/z=311(M+1).

Analysis for $C_{24}H_{29}F_3N_4O_5$: Calculated: C, 56.47; H, 5.73; N, 10.97 Found: C, 56.44; H, 5.74; N, 10.89

Example 52: R=4-methoxyphenoxycarbonyl: Acylation Method A as follows: A solution of the amine in tetrahydrofuran was cooled in an ice bath and treated with 4-methoxyphenyl chloroformate, resulting in formation of a precipitate. The reaction mixture was allowed to warm to room temperature. After 1 h, the reaction mixture was diluted with ethyl acetate, washed (10% aqueous hydrochloric acid, water, saturated sodium bicarbonate solution and brine), dried and evaporated before purification by chromatography. Chromatography solvent: dichloromethane:ethyl acetate (gradient, 100:0, 9:1); TLC: $R_f$=0.67, dichloromethane:ethyl acetate (9:1); HPLC: $t_R$=17.14. FR=1, column A, water:acetonitrile (1:1); MS: m/z=415(M+1).

Analysis for $C_{27}H_{26}F_3N_3O_6$: Calculated: C, 59.45; H, 4.80; N, 7.70 Found: C, 59.63; H, 5.03; N, 7.28

Example 53: R=4-pyridylacetyl: Acylation Method B using 4-pyridylacetic acid hydrochloride. Upon quenching the reaction with water, a bit of the product precipitated and was filtered and redissolved in ethyl acetate. The filtrate was basified with sodium bicarbonate and extracted with ethyl acetate. The pH of the aqueous phase was further increased, and it was again extracted with ethyl acetate. The combined ethyl acetate solutions were washed (brine), dried and evaporated before purification by chromatography. Chromatography solvent: dichloromethane:methanol (9:1); TLC: $R_f$=0.38, dichloromethane:methanol (9:1); HPLC: $t_R$=7.41, FR=1, column A, water:acetonitrile (1:1); MS: m/z=515(M+1).

Analysis for $C_{26}H_{25}F_3N_4O_4 \cdot 0.55\ H_2O$: Calculated: C, 59 55; H 5 02; N 10.68 Found: C, 59.63; H, 4.99; N, 10.75

Example 54:: R=1-methylimidazol-4-ylacetyl: Acylation Method B as follows: To a solution of the 3-aminopyridine (0.308 g) in dry dimethylformamide (3.5 mL) was added 1-hydroxybenzotriazole hydrate (0.263 g), triethylamine (0.32 mL), 1-(3-dimethylaminopropyl)-3-ethyl-carbodiimide hydrochloride (0.373 g) and 1-methylimidazol-4-ylacetic acid (0.275 g); and the reaction mixture was stirred overnight, at which time the coupling was deemed complete. The reaction mixture was diluted with ethyl acetate, washed (three times with saturated sodium bicarbonate solution, then brine), dried and evaporated before purification by chromatography to afford the title compound as an off-white solid. Chromatography solvent: dichloromethane:methanol, (first column, 97:3), (second column, gradient, 98:2, 96:4); TLC: $R_f$=0.13, dichloromethane:methanol (96::4); HPLC: $t_R$=4.13, FR=3, column A, water:acetonitrile (2:3); MS: m/z=518(M+1).

Analysis for $C_{25}H_{26}F_3N_5O_4 \cdot 1.2\ H_2O$: Calculated: C, 55.70; H, 5.31; N, 12.99 Found: C, 55.68; H, 5.16; N, 12.90

Example 55: R=1-tert-butoxycarbonylimidazol-4-ylmethoxycarbonyl: Acylation Method D using 1-tert-butoxycarbonylimidazol- 4-ylcarbinol, but using tetrahydrofuran instead of dichloromethane as the reaction solvent and diluting the reaction mixture with ethyl acetate instead of dichloromethane. Chromatography solvent: first column, chloroform:methanol (97:3), second column dichloromethane:ethyl acetate:methanol (70:29.5:0.5); TLC: $R_f$=0.47, dichloromethane:ethyl acetate:methanol (50:48:2); MS: m/z=620(M+1).

The starting material alcohol for the acylation was obtained as follows, using a procedure from European Patent Application, Publication Number 284 174.

To a solution of 4-imidazolylcarbinol hydrochloride (1.01 g) in dry dichloromethane (5 mL) was added pyridine (1.82 mL) and di-tert-butyl dicarbonate (2.46 g). The resulting solution was stirred overnight, evaporated and resuspended/dissolved in 100 mL of ethyl acetate/tetrahydrofuran (9:1). The organic phase was washed (three times with water, brine), dried, evaporated and dried under high vacuum to give 1-tert-butoxycarbonylimidazol-4-ylcarbinol as a colorless oil; TLC: $R_f$=0.30, dichloromethane:ethyl acetate:methanol (50:49:1); MS: m/z=199(M+1).

EXAMPLE 56

2-[3-(4-Imidazolylmethoxycarbonylamino)-2-oxo-6-phenyl-1,2-dihydro-1-pyridyl]-N-( 3,3,3-trifluoro-1-isopropyl-2-oxopropyl)acetamide trifluoroacetate.

To a solution of 2-[3-(1-tert-butoxycarbonylimidazol- 4-ylmethoxycarbonylamino)-2-oxo-6-phenyl-1,2-dihydro-1-pyridyl]-N-( 3,3,3-trifluoro-1-isopropyl-2-oxopropyl)acetamide (0.134 g) in dry dichloromethane was added trifluoroacetic acid (0.018 mL). After stirring for 1 h, the reaction was not complete; so additional trifluoracetic acid (0.018 mL) was added. Following 17 h more stirring, the reaction was still incomplete. Additional trifluoroacetic acid (0.036 mL) was added and the reaction mixture was stirred 6 h (complete deprotection), evaporated and dried under high vacuum to give the title compound as a trifluoroacetate salt; TLC: $R_f$=0.10, dichloromethane:methanol (94:6); MS: 520(M+1).

Analysis for $C_{24}H_{24}F_3N_5O_5 \cdot 1.3\ CF_3CO_2H$: Calculated: C, 47.62; H, 3.79; N, 10.,40 Found: C, 47.62; H, 3.92; N, 10.10

EXAMPLE 57

2-[3-[4-(2-Dimethylaminoethoxycarbonyl) benzyloxycarbonylamino]-2-oxo- 6-phenyl-1,2-dihydro-1-pyridyl]-N-(3,3,3-trifluoro-1-isopropyl-2-oxopropyl)acetamide.

To a solution of 2-[3-(4-carboxybenzyloxycarbonylamino)-2-oxo- 6-phenyl-1,2-dihydro-1-pyridyl]-N-(3,3,3-trifluoro-1-isopropyl-2-oxopropyl)acetamide (0.281 g) in dry tetrahydrofuran (5 mL) was added 1-(3-dimethylaminopropyl)-3-ethylcarbodiimide hydrochloride (0,141 g), 1-hydroxybenzotriazole hydrate (0,066 g) and 2-dimethylaminoethanol (0.06 mL). The reaction mixture was stirred overnight before it was diluted with ethyl acetate, washed (twice with saturated sodium bicarbonate solution, then brine), dried and evaporated before purification by chromatography, eluting with dichloromethane:methanol (97:3), to afford the title compound; TLC: $R_f$=O.18, dichlormethane:methanol (97:3); HPLC: $t_R$=6.51, FR=1, column A, water:acetonitrile (3:2); MS: m/z=645(M+1).

Analysis for $C_{32}H_{35}F_3N_4O_7$: Calculated: C, 59.62; H, 5.47; N, 8.69 Found: C, 59.44; H, 5.69; N, 8.36

EXAMPLE 58

2-[3-[4-(N-methylsulfonylcarbamoyl)benzyloxycarbonylamino]-2-oxo-6-phenyl- 1,2-dihydro-1-pyridyl]-N-(3,3,3-trifluoro-1-isopropyl-2-oxopropyl)acetamide.

To a solution of 2-[3-(4-carboxybenzyloxycarbonylamino)-2-oxo- 6-phenyl-1,2-dihydro-1-pyridyl]-N-(3,3,3-trifluoro-1-isopropyl-2-oxopropyl)acetamide (0.387 g), 1-(3-dimethylaminopropyl)-3-ethylcarbodiimide hydrochloride (0.43 g) and 4-dimethylaminopyridine (0.27 g) in dry dichloromethane was added methanesulfonamide; and the reaction mixture was stirred for 5 days. The mixture was diluted with ethyl acetate, washed (three times with 10% aqueous hydrochloric acid, then brine), dried and evaporated before purification by chromatography, eluting with dichloromethane:ethyl acetate:methanol:acetic acid (50:48.9:1.0:0.1), to give the title compound; TLC: $R_f$=0.38, dichloromethane:ethyl acetate:methanol:acetic acid (50:48.9:1.0:0.1); HPLC: $t_R$=5.38, FR=2, column A, water:acetonitrile (7:3); MS: m/z=651(M+1).

Analysis for $C_{29}H_{29}F_3N_4O_8S$: Calculated: C, 53.53; H, 4.49; N, 8.61 Found: C, 54.08; H, 4.81; N, 8.26

EXAMPLE 59

2-(3-Benzyloxycarbonylamino-6-methyl-2-oxo-1,2-dihydro-1-pyridyl)-N-( 3,3,3-trifluoro-1-isopropyl-2-oxopropyl)acetamide.

Using a similar procedure to that described in Example 1, using chloroform:methanol (99:1) for elution in the chromatography, 2-(3-benzyloxycarbonylamino-6-methyl-2-oxo-1,2-dihydro-1-pyridyl)-N-( 3,3,3-trifluoro-2-hydroxy-1-isopropylpropyl)acetamide was oxidized to afford the title compound; TLC: $R_f$=0.32, chloroform:methanol (97:3); HPLC: $t_R$=4.60, FR=2.0, column B, acetonitrile:water (1:1); MS: m/z=468(M+1).

Analysis for $C_{22}H_{24}F_3N_3O_5 \cdot 0.4\ H_2O$: Calculated: C, 55.67; H, 5.27; N, 8.85 Found: C, 55.59; H, 5.31; N, 8.68

The intermediate 2-(3-benzyloxycarbonylamino-6-methyl-2-oxo- 1,2-dihydro-1-pyridyl)-N-(3,3,3-trifluoro-2-hydroxy-1-isopropylpropyl)acetamide may be prepared as follows:

a. 6-Methylpyrid-2-one-3-carboxylic acid.

A suspension of 6-methylpyrid-2-one-3-carbonitrile (Example 3.a.) (16.9 g) in 20% NaOH (w/w; 63 mL) was heated at 140°–145° C. overnight in a sealed bomb.. The cooled reaction mixture was acidified to about pH 8 with concentrated hydrochloric acid and extracted with dichloromethane (three times). The aqueous phase was acidified, precipitating a yellow solid which was filtered, washed with water, and dried overnight in a vacuum oven at about 80° C. The dried 6-methylpyrid-2-one-3-carboxylic acid (15.68 g) required no further purification; NMR: 2.38 (s,3), 6.54 (d,1, J=9), 8.27 (d,1, J=9), 13.27 (broad s, 1), 14.67 (broad s, 1); MS: m/z=154(M+1).

b. 3-Benzyloxycarbonylamino-6-methylpyrid-2-one.

Using a similar procedure to that described in Example 1.c. and using chloroform:ethyl acetate (80:20, then 70:30) for the chromatography, 6-methylpyrid-2-one-3-carboxylic acid was converted into 3-benzyloxycarbonylamino-6-methylpyrid-2-one; TLC: $R_f$=0.47, chloroform:methanol (97:3); MS: m/z=259(M+1).

c. Ethyl (3-Benzyloxycarbonylamino-6-methyl-2-oxo-1,2-dihydro-1-pyridyl)acetate.

Using a similar procedure to that of Example 1.d., above, 3-benzyloxycarbonylamino-6-methylpyrid-2-one (1.80 g) was added to a suspension of NaH (0.33 g) in dry dimethylformamide (50 mL). After the mixture had been stirred for 45 min, ethyl iodoacetate (1.48 g) was added; and the mixture was stirred overnight, diluted with 10% hydrochloric acid (300 mL) and extracted with ethyl acetate (3×150 mL). The organic phase was washed with brine (twice), dried and evaporated. The resulting yellow, waxy solid was chromatographed, eluting with ethyl acetate:dichloromethane (3:97), to give ethyl (3-benzyloxycarbonylamino-6-methyl-2-oxo-1,2-dihydro-1-pyridyl)acetate (1.28 g); TLC: $R_f$=0.52, dichloromethane:ethyl acetate (95:5); NMR: 1.21 (t,3, J=8.6), 2.26 (s,3), 4.16 (q,2, J=8.6), 4.84 (s,2), 5.15 (s,2), 6.20 (d,1, J=9), 7.32–7.43 (m,5), 7.76 (d,1, J=9), 8.38 (s,1); MS: m/z=345(M+1).

d. (3-Benzyloxycarbonylamino-6-methyl-2-oxo-1,2-dihydro-1-pyridyl)acetic acid.

Ethyl (3-benzyloxycarbonylamino-6-methyl-2-oxo-1,2-dihydro- 1-pyridyl)acetate (1.20 g) was dissolved in methanol (50 mL), and 20% NaOH (10 mL) was added. More methanol (25 mL) was added to facilitate stirring as white solid precipitated from the mixture. After stirring for 5 h, the mixture was evaporated, and the residue was partitioned between ethyl acetate and 10% hydrochloric acid. After the layers were separated, the aqueous phase was extracted further with ethyl acetate (twice). The combined organic extracts were washed with brine, dried and evaporated to give 1.43 g of crude product. Examination of this material showed a mixture of what was presumed to be the corresponding methyl carbamate along with the expected benzyl carbamate. The mixture proved to be inseparable by column chromatography and therefore was carried through to the next step without purification.

e. 2-(3-Benzyloxycarbonylamino-6-methyl-2-oxo-1,2-dihydro-1-pyridyl)-N-( 3,3,3-trifluoro-2-hydroxy-1-isopropylpropyl)acetamide.

A portion of the above mixture (1.10 g) was dissolved in dry dimethylformamide (25 mL) along with 3-amino-1,1,1- trifluro-4-methyl- 2-pentanol hydrochloride (0.72 g), 1-(3-dimethylaminopropylpropyl)- 3-ethylcarbodiimide hydrochloride (0.73 g) and 4-dimethylaminopyridine (0.93 g). The mixture was stirred overnight, diluted with 10% hydrochloric acid and extracted with ethyl acetate (three times). The extracts were washed with saturated sodium bicarbonate (twice) and brine, dried and evaporated to a white solid. Chromatography, eluting with acetone:dichloromethane (5:95), gave 2-(3-benzyloxycarbonyl-amino- 6-methyl-2-oxo-1,2-dihydro-1-pyridyl)-N-(3,3,3-trifluoro-2-hydroxy-1-isopropylpropyl)acetamide (0.80 g); TLC: $R_f$=0.48, dichloromethane:acetone (85:15); MS: m/z=470(M+1).

EXAMPLE 60

2-(3-Benzyloxycarbonylamino-6-methyl-2-oxo-5-phenyl-1,2-dihydro-1-pyridyl)-N-( 3,3,3-trifluoro-1-isopropyl-2-oxopropyl)acetamide.

Using a similar procedure to that described in Example 1, using chloroform:ethyl acetate for elution in the chromatography, 2-(3-benzyloxycarbonylamino-6-methyl-2-oxo-5-phenyl-1,2-dihydro-1-pyridyl)-N-( 3,3,3-trifluoro-2-hydroxy-1-isopropylpropyl)acetamide was oxidized to afford the title compound;. TLC: $R_f$=0.23, chloroform:ethyl acetate (20:1); HPLC: $t_R$=11.26, FR=2.0, column A, water:acetonitrile:tetrahydrofuran:trifluoroacetic acid (55:35:15:0.1); MS: m/z=544(M+1).

Analysis for $C_{28}H_{28}F_3N_3O_5$: Calculated: C, 61.87; H, 5.19; N, 7.73 Found: C, 61.75; H, 5.29; N, 7.44

The intermediate 2-(3-benzyloxycarbonylamino-6-methyl-2-oxo- 5-phenyl-1,2-dihydro-1-pyridyl)-N-(3,3,3-trifluoro-2-hydroxy- 1-isopropylpropyl)acetamide may be prepared as follows:

a. 6-Methyl-5-phenylpyrid-2-one-3-carbonitrile.

Using phenylacetone and Cyclization Method A, 6-methyl- 5-phenylpyrid-2-one-3-carbonitrile was obtained; MS: m/z=211(M+1).

Analysis for $C_{13}H_{10}N_2O$: Calculated: C, 74.27; H, 4.79; N. 13.32 Found: C, 74.10; H, 4.88; N, 13.15 b. 6-Methyl-5-phenylpyrid-2-one-3-carboxylic acid.

Using Hydrolysis Method A, 6-methyl-5-phenylpyrid-2-one- 3-carbonitrile was converted into 6-methyl-5-phenylpyrid-2-one-3-carboxylic acid; TLC: $R_f$=0.29, chloroform:methanol:acetic acid (50:1:trace); MS: m/z=230(M+1).

c. 3-Benzyloxycarbonylamino-6-methyl-5-phenylpyrid-2-one.

Using a similar procedure to that described in Example 1.c., 6-methyl-5-phenylpyrid-2-one-3-carboxylic acid was converted into 3-benzyloxycarbonylamino-6-methyl-5-phenylpyrid-2-one; purified by chromatography, eluting with chloroform:methanol (20:1), or by recrystallization from methanol; TLC: $R_f$=0.46, chloroform:methanol (20:1); MS: m/z=335(M+1).

d. 2-(3-Benzyloxycarbonylamino-6-methyl-2-oxo-5-phenyl-1,2-dihydro- 1-pyridyl)-N-(2-tert-butyldimethylsilyloxy-3,3,3-trifluoro-1-isopropylpropyl)acetamide.

Using a similar procedure to that described in Example 1.d., but using dichloromethane:ethyl acetate (20:1) for chromatography, 3-benzyloxycarbonylamino-6-methyl-5-phenylpyrid-2-one was converted into 2-(3-benzyloxycarbonylamino-6-methyl-2-oxo-5-phenyl-1,2-dihydro- 1-pyridyl)-N-(2-tert-butyldimethylsilyloxy-3,3,3-trifluoro-1-isopropylpropyl)acetamide; TLC: $R_f$=0.41, dichloromethane:ethyl acetate (20:1); MS: m/z=660(M+1).

e. 2-(3-Benzyloxycarbonylamino-6-methyl-2-oxo-5-phenyl-1,2-dihydro- 1-pyridyl)-N-(3,3,3-trifluoro-2-hydroxy-1-isopropylpropyl)acetamide.

Using a similar procedure to that described in Example 1.e., 2-(3-benzyloxycarbonylamino-6-methyl-2-oxo-5-phenyl-1,2-dihydro- 1-pyridyl)-N-(2-tert-butyldimethylsilyloxy-3,3,3-trifluoro-1-isopropylpropyl)acetamide was converted into 2-(3-benzyloxycarbonylamino- 6-methyl-2-oxo-5-phenyl-1,2-dihydro-1-pyridyl)-N-(3,3,3-trifluoro-2-hydroxy-1-isopropylpropyl)acetamide; chromatography solvent: chloroform:methanol (40:1); TLC: $R_f$=0.14, chloroform:ethyl acetate (20:1); MS: m/z=546(M+1).

EXAMPLE 61

2-[3-Benzyloxycarbonylamino-5-(3-fluorobenzyl)-2-oxo-1, 2-dihydro-1-pyridyl]-N-(3,3,3-trifluoro-1-isopropyl-2-oxopropyl)acetamide.

To a solution of 1-(3-dimethylaminopropyl)-3-ethylcarbodiimide hydrochloride (0.51 g) in dimethyl sulfoxide (2 mL), toluene (4 mL) and dichloroacetic acid (0.14 g) was added 2-[3-benzyloxycarbonyl-amino-5-(3-fluorobenzyl)-2-oxo-1,2-dihydro-1-pyridyl]-N-( 3,3,3-trifluoro-2-hydroxy-1-isopropylpropyl)acetamide (0.15 g). The mixture was allowed to stir overnight and was partitioned between ethyl acetate and saturated aqueous sodium bicarbonate. The organics were washed (brine), dried, evaporated, and purified using chromatography, with dichloromethane as the eluent to yield the title compound (80%); NMR: 0.79–0.97 (m,6), 2.21 (m,1), 4.06 (m, NHCH hydrate), 4.49–4.81 (m,3, NHCH keto, $CH_2CO$), 5.13 (s,2, $CH_2$), 6.95 (m, OH hydrate), 7.01–7.07 (m,3, phenyl), 7.22–7.40 (m,7, phenyl), 7.72 (m,1, pyridone), 7.82 (d,J=10.5, NH hydrate), 8.36 (s, NH hydrate), 8.40 (s, NH keto), 8.92 (d,J=6.5, NH keto form).

Analysis for $C_{28}H_{27}F_4O_5N_3$·0.25 $H_2O$: Calculated: C, 59.41; H, 4.90; N, 7.42 Found: C, 59.34; H, 4.84; N, 7.15

The intermediate 2-[3-benzyloxycarbonylamino-5-(3-fluorobenzyl)- 2-oxo-1,2-dihydro-1-pyridyl]-N-(3,3,3-trifluoro-2-hydroxy-1-isopropylpropyl)acetamide may be prepared as follows:

a. 3-Aminopyrid-2-one.

Ethanol (300 mL) was added to a mixture of 10% (w/w) palladium on carbon catalyst (1 g) and 3-nitropyrid-2-one (10 g). The mixture was hydrogenated at atmospheric pressure and room temperature for 8 h. The catalyst was removed by filtration, washed with ethanol, and the ethanol evaporated to give the amine as a brown crystalline solid (98%).

b. 3-Benzyloxycarbonylaminopyrid-2-one.

Benzyl chloroformate (13.085 g) was added dropwise to a stirred suspension of sodium carbonate (16.26 g) and 3-aminopyrid-2-one (7.67 g) in tetrahydrofuran. The mixture was stirred overnight, poured into ethyl acetate (400 mL), washed (saturated aqueous sodium bicarbonate, brine), dried and evaporated. The resulting residue was purified by crystallization from methanol to give the benzyl carbonate as a white crystalline solid (10.7 g).

The benzylcarbamate can alternatively be prepared as follows:

3-Carboxypyrid-2-one (5 g), diphenylphosphorylazide (9.9 g), benzyl alcohol (4.7 g), and triethylamine (3.6 g) were added to dioxane (50 mL). The mixture was allowed to stir at 90° C. for 20 h, was cooled, and the dioxane was evaporated. The residue was dissolved in ethyl acetate (400 mL), was washed (1N hydrochloric acid, brine), dried, evaporated and the resulting oil was purified by chromatography using ethyl acetate:dichloromethane (gradient, 0:100, 10:90, 20:80) as eluent to give the benzylcarbamate (6.2 g).

c. 3-Benzyloxycarbonylamino-5-iodopyrid-2-one.

To a stirred suspension of 3-benzyloxycarbonylaminopyrid-2-one (8.0 g) in dry dichloromethane (150 mL) was added N-iodosuccinimide (8.4 g). The mixture was allowed to stir overnight and the resulting precipitate was filtered to give the iodo compound (3.1 g). The filtrate was concentrated to 30 mL and purified by chromatography using ethyl acetate:dichloromethane as an eluent (gradient 0:100, 20:80, 25:75, 33:66, 50:50) to give additional iodo compound (5.7 g).

d. Ethyl 3-benzyloxycarbonylamino-5-iodo-2-oxo-1,2-dihydro-1-pyridylacetate.

A suspension of 3-benzyloxycarbonylamino-5-iodopyrid-2-one (2.0 g) in dimethylformamide (10 mL) was added to a suspension of NaH (0.156 g) in dimethylformamide (10 mL) maintaining the temperature between 15 and 25° C. After stirring for 20 min, ethyl iodoacetate (1.453 g) was added dropwise, maintaining the temperature below 20° C. The mixture was stirred at room temperature for 3 h, poured into iced 1N hydrochloric acid (100 mL) and extracted with ethyl acetate. The organic layer was washed (brine), dried, and evaporated to give a residue, which was purified by chromatography using ethyl acetate:dichloromethane as the eluent (gradient, 0:100, 3:97, 6:94) to give the ester (1.44 g).

e. Ethyl 3-benzyloxycarbonylamino-5-(3-fluorobenzyl)-2-oxo-1,2-dihydro-1-pyridylacetate.

To a solution of freshly activated zinc dust (0.39 g) was added 3-fluorobenzyl bromide (0.76 g) in tetrahydrofuran (10 mL), maintaining the temperature at 20° C. The solution was allowed to stir for 3 h and dichloro[1,1'-bis(diphenylphosphino)ferrocene]-palladium(II) (0.076 g) was added followed by a solution of ethyl 3-benzyloxycarbonylamino-5-iodo-2-oxo-1,2-dihydro-1-pyridylacetate (0.46 g) in tetrahydrofuran (10 mL), which was added dropwise. The mixture was stirred at room temperature for 5 h, at 50° C. for 4.5 h, and at room temperature overnight. It was poured into 1N hydrochloric acid and partitioned into ethyl acetate. The organic extracts were dried, evaporated, and the resulting oil was purified using chromatography with ethyl acetate:dichloromethane (gradient, 100, 5:95, 10:90) to give ethyl 2-[3-benzyloxycarbonylamino-5-( 3-fluorobenzyl)-2-oxo-1,2-dihydro-1-pyridyl]acetate (0.225 g).

f. 2-[3-Benzyloxycarbonylamino-5-(3-fluorobenzyl)-2-oxo-1,2-dihydro-1-pyridyl]-N-(3,3,3-trifluoro-2-hydroxy-1-isopropylpropyl)acetamide.

Aqueous 2N sodium hydroxide (1.25 mL) was added with stirring to a solution of ethyl 3-benzyloxycarbonylamino-5-( 3-fluoro-phenyl)-2-oxo-1,2-dihydro-1-pyridylacetate (0.22 g) in methanol (8 mL). The mixture was allowed to stir for 4 h, was evaporated, and the resulting residue was titrated with 1N hydrochloric acid and partitioned into ethyl acetate. The combined organic extracts were dried (MgSO$_4$) and evaporated to yield the crude acid (0.21 g).

To the crude acid (0.21 g) in dimethylformamide (35 mL) was added 3-amino-4-methyl-1,1,1-trifluoro-2-pentanol hydrochloride (0.117 g), dimethylaminopyridine (0.140 g) and 1-(3-dimethylamino-propyl)- 3-ethylcarbodiimide hydrochloride (0.113 g). The mixture was allowed to stir overnight, was added to 1N hydrochloric acid (100 mL), and was partitioned into ethyl acetate. The combined organic extracts were washed (saturated aqueous sodium bicarbonate, brine), dried, and evaporated to give a residue which was purified by chromatography, using ethyl acetate:dichloromethane (gradient, 0:100, 10:90, 20:80) as an eluent, to give 2-[3-benzyloxycarbonylamino- 5-(3-fluorobenzyl)-2-oxo-1,2-dihydro-1-pyridyl]-N-(3,3,3-trifluoro- 2-hydroxy-1-isopropyl-propyl)acetamide (0.155 g).

EXAMPLE 62

2-[3-Benzyloxycarbonylamino-2-oxo-5-(4-pivaloyloxybenzyl)-1,2-dihydro- 1-pyridyl]-N-(3,3,3-trifluoro-1-isopropyl-2-oxopropyl)acetamide.

2-[3-Benzyloxycarbonylamino-2-oxo-5-(4-pivaloyloxybenzyl)- 1,2-dihydro-1-pyridyl]-N-(3,3,3-trifluoro-2-hydroxy-1-isopropylpropyl)acetamide was oxidized using a similar procedure to that described in Example 61 to give the title compound; NMR: 0.77–0.97 (m,6), 1.30 (s,9), 2.20 (m,1), 4.50–4.75 (m,3, NHCH keto, CH$_2$CO), 5.13 (s,2), 6.95 (m, OH hydrate), 7.02 (d,2, J=8.5), 7.73 (m,1, pyridone), 7.22–7.73 (m,8), 7.74 (d, 3=10), 8.35 (s, NH hydrate), 8.37 (s, NH keto), 8.91 (d, J=6.5, NH keto).

Analysis for $C_{33}H_{36}N_3O_7F_3 \cdot 0.5\ H_2O$: Calculated: C, 60.72; H, 5.71; N, 6.44 Found: C, 60.81; H, 5.63; N, 6.14

The intermediate 2-[3-benzyloxy carbonylamino-2-oxo-5-( 4-pivaloyloxybenzyl)-1,2-dihydro-1-pyridyl]-N-(3,3,3-trifluoro- 2-hydroxy-1-isopropylpropyl)acetamide was prepared as follows:

a. tert-Butyl 3-benzyloxycarbonylamino-5-iodo-2-oxo- 1,2-dihydro-1-pyridylacetate.

A suspension of 3-benzyloxycarbonylamino-5-iodo-pyrid-2-one (5.0 g) in dimethylformamide (15 mL) was added to a stirred suspension of NaH (0.389 g), in dimethylformamide (10 mL), while maintaining the temperature between 15 and 25° C. After stirring for 1 h, a solution of tert-butyl bromoacetate (3.294 g), in dimethylformamide (5 mL) was added dropwise, while maintaining the reaction temperature below 20° C. The reaction mixture was stirred for 4 h at room temperature, poured into iced 1N HCl (100 mL) and extracted with ethyl acetate (200 mL). The organic layer was washed (saturated aqueous sodium bicarbonate, brine), dried, and evaporated. The resulting residue was purified by chromatography, eluting with dichloromethane:hexane (gradient, 0:100, 50:50, 100:0). The product-containing fractions were rechromatographed to give the desired ester as a red solid (4.3 g).

b. tert-Butyl 3-benzyloxycarbonylamino-2-oxo-5-( 4-pivaloyloxybenzyl)-1,2-dihydro-1-pyridylacetate.

A solution of 4-pivaloyloxybenzyl bromide (1.6 g) in tetrahydrofuran (10 mL) was added dropwise to freshly activated zinc dust (0,576 g) with stirring, maintaining the temperature at about 20° C. After 1 h, dichloro[1,1'-bis-(diphenylphosphino)ferrocene]-palladium(II) (0,112 g) was added followed by a solution of tert-butyl 3-benzyloxycarbonylamino-5-iodo-2-oxo-1,2-dihydro-1-pyridylacetate (0.714 g) in tetrahydrofuran (10 mL). The mixture was heated at 45°–50° C. for 5 h, stirred at room temperature overnight, poured into cold 1N hydrochloric acid (100 mL) and extracted with ethyl acetate. The combined extracts were dried and evaporated. The resulting residue was purified by chromatography, eluting with ethyl acetate:dichloromethane (0:100, 10:90), to give tert-butyl 3-benzyloxycarbonylamino-2-oxo-5-(4-pivaloyloxybenzyl)- 1,2-dihydro-1-pyridylacetate (0.35 g).

c. 2-[3-Benzyloxycarbonylamino-2-oxo-5-(4-pivaloyloxybenzyl)- 1,2-dihydro-1-pyridyl]-N-(3,3,3-trifluoro-2-hydroxy-1-isopropylpropyl] acetamide.

Trifluoroacetic acid (3 mL) was added dropwise to tert-butyl 3-benzyloxycarbonylamino-2-oxo-5-(4-pivaloyloxybenzyl)- 1,2-dihydro-1-pyridylacetate (0,320 g) with stirring. After 30 min, the reaction mixture was diluted with dichloromethane (50 mL) and evaporated, diluted with chloroform (50 mL) and evaporated, diluted with diethyl ether (50 mL) and evaporated twice, and dried under high vacuum to give the crude acid. (2RS,3SR)-3-Amino-4-methyl-1,1,1-trifluoro- 2-pentanol hydrochloride (0.149 g), 1-(3-dimethyl aminopropyl)-3-ethylcarbodiimide hydrochloride (0.143), and 4-dimethylaminopyridine (0.238 g) were added to a solution of the crude acid (0.32 g) in dimethylformamide and stirred overnight. The mixture was added to 1N HCl (100 mL), extracted with ethyl acetate (100 mL), washed (saturated aqueous sodium bicarbonate, brine), and evaporated to give a residue which was purified by chromatography, eluting with ethyl acetate:dichloromethane (0:100, 10:90), to give the alcohol (0.220 g).

The intermediate 4-pivaloyloxybenzyl bromide may be prepared as follows:

d. 4-Pivaloyloxybenzyl bromide.

N-Bromosuccinimide (3.43 g) and benzoyl peroxide (0.01 g) were added to a solution of 4-pivaloyloxytoluene (3.70 g) in carbon tetrachloride (100 mL). The mixture was irradiated (sun lamp) with heating (60° C.) for 0.5 h. The succinimide was removed by filtration and the carbon tetrachloride evaporated. The residue was purified by chromatography, eluting with hexane:dichloromethane (100:0, 90:10, 88:12, 30:20), to give the benzyl bromide (4.1 g).

The title compound can alternatively be prepared using a procedure similar to that outlined in Example 64 by substituting 4-pivaloyloxybenzyl bromide for 4-methoxycarbonylbenzyl bromide at the step corresponding to Example 64.b.

EXAMPLE 63

2-[3-Benzyloxycarbonylamino-2-oxo-5-(4-hydroxybenzyl)-1,2-dihydro- 1-pyridyl]-N-(3,3,3-trifluoro-1-isopropyl-2-oxopropyl]acetamide.

2-[3-Benzyloxycarbonylamino-2-oxo-5-(4-pivaloyloxybenzyl)- 1,2-dihydro-1-pyridyl]-N-(3,3,3-trifluoro-1-isopropyl-2-oxopropyl]acetamide was dissolved in methanol and excess 2N sodium hydroxide was added. The mixture was allowed to stir for 3 h, was evaporated, and partitioned between ethyl acetate and 1N hydrochloric acid. The organic layer was washed (brine), dried, evaporated and purified by chromatography, using dichloromethane:methanol (gradient, 99:1, 95:5) as the eluent, to give the title compound; NMR: 0.78–0.91 (m,6), 2.20 (m,1), 4.09 (m, NHCH hydrate), 4.50–4.77 (m,3, $CH_2CO$, NHCH keto), 5.13 (s,2), 6.68 (d,2, J=8), 6.95 (m, OH hydrate), 6.96 (d,2, J=8), 7.20 (m,1) 7.29–7.42 (m,5), 7.70 (m,1), 7.73 (d, J=10), 8.33 (s, NH hydrate), 8.37 (S, NH keto), 8.93 (d, J=6.5, NH keto), 9.24 (s,1, OH).

Analysis for $C_{28}H_{28}F_3N_3O_6 \cdot 0.75\ H_2O$: Calculated: C, 58.69; H, 5.19; N, 7.33 Found: C, 58.77; H, 5.28; N, 7.00

EXAMPLE 64

2-[3-Benzyloxycarbonylamino-5-(4-methoxycarbonylbenzyl)-2-oxo- 1,2-dihydro-1-pyridyl]-N-(3,3,3-trifluoro-1-isopropyl-2-oxopropyl)acetamide.

2-[3-Benzyloxycarbonylamino-5-(4-methoxycarbonylbenzyl)-2-oxo 1,2-dihydro-1-pyridyl]-N-(3,3,3-trifluoro-2-hydroxy-1-isopropylpropyl)acetamide was oxidized using a similar procedure to that described in Example 61 to give the title compound; NMR: 0.78–0.97 (m,6), 2.20 (m, 1), 3.84 (s,3, $CH_3$), 4.08 (m, NHCH hydrate), 4.62–4.78 (m, NHCH keto, $CH_2CO$), 5.11 (S, 2), 6.90 (m, OH hydrate), 7.27–7.40 (m, OH), 7.71 (m,1), 7.89 (d,2, J=8), 8.37 (s, NH hydrate), 8.40 (s, NH keto), 8.92 (d, J=6.5, NH keto).

Analysis for $C_{30}H_{30}F_3N_3O_7 \cdot 0.75\ H_2O$: Calculated: C, 58.58; H, 5.16; N, 6.83 Found: C, 58.62; H, 5.04; N, 6.90

The intermediate 2-[3-benzyloxycarbonylamino-5-(4-methoxy-carbonylbenzyl)-2-oxo-1,2-dihydro-1-pyridyl]-N-(3,3,3-trifluoro- 2-hydroxy-1-isopropylpropyl)acetamide was prepared as follows:

a. 2-(3-Benzyloxycarbonylamino-5-iodo-2-oxo-1,2-dihydro-1-pyridyl)-N-( 2-tert-butyldimethylsilyloxy-3,3,3-trifluoro-1-isopropylpropyl)acetamide.

A suspension of 3-benzyloxycarbonylamino-5-iodopyrid-2-one (1.0 g) in dimethylformamide (10 mL) was added to a suspension of sodium hydride (0.071 g), in dimethylformamide (5 mL) maintaining the temperature between 15 and 25° C. After stirring for 1 h, a solution of N-(2-tert-butyldimethylsiloxy-3,3,3-trifluoro-1-isopropylpropyl)-2-iodoacetamide (1.40 g) in dimethylformamide (5 mL) was added dropwise, maintaining the temperature below 20° C. The mixture was stirred for 2 h, poured into iced 1N HCl (100 mL) and extracted with ethyl acetate (200 mL). The organic layer was washed (saturated aqueous sodium bicarbonate, brine), dried, and evaporated. The resulting residue was purified by chromatography, eluting with dichloromethane, to give the iodoamide (1.74 g).

b. 2-[3-Benzyloxycarbonylamino-5-(4-methoxycarbonylbenzyl)-2-oxo- 1,2-dihydro-1-pyridyl]-N-(2-tert-butyldimethylsilyloxy- 3,3,3-trifluoro-1-isopropylpropyl)acetamide.

2-(3-Benzyloxycarbonylamino-5-iodo-2-oxo-1,2-dihydro- 1-pyridyl)-N-(2-tert-butyldimethylsilyloxy-3,3,3-trifluoro-1-isopropylpropyl)acetamide was coupled with 4-methoxycarbonylbenzyl bromide using a similar procedure to that described in Example 62.b. to give the 5-benzyl compound.

c. 2-[3-Benzyloxycarbonylamino-5-(4-methoxycarbonylbenzyl)- 2-oxo-1,2-dihydro-1-pyridyl]-N-(3,3,3.-trifluoro-2-hydroxy- 1-isopropylpropyl]acetamide.

A 1N solution of tetrabutylammonium fluoride (1.20 mL) in tetrahydrofuran *was added dropwise to a solution of 2-[3-benzyloxycarbonylamino- 5-(4-methoxycarbonylbenzyl)-2-oxo-1,2-dihydro-1-pyridyl]-N-(2-tert-butyldimethylsilyloxy-3,3,3-trifluoro- 1-isopropylpropyl)acetamide in tetrahydrofuran (5 mL) with stirring. After 15 min, the reaction mixture was diluted with ethyl acetate (100 mL), washed (1N HCl, saturated aqueous sodium bicarbonate, brine), dried, and evaporated. The resulting solid was purified by chromatography, eluting with ethyl acetate:dichloromethane (0:100, gradient 5:90 to 50:50), to give the alcohol (0.590 g).

EXAMPLE 65

2-[3-Benzyloxycarbonylamino-5-(4-fluorobenzyl)-2-oxo-1, 2-dihydro-1-pyridyl]-N-( 3,3,3-trifluoro-1-isopropyl-2-oxopropyl)acetamide.

Using a procedure similar to that outlined in Example 61, but substituting 4-fluorobenzyl bromide for 3-fluorobenzyl bromide in the step corresponding to Example 61.e., the title compound was obtained; mp 66°–72° C.

Analysis for $C_{28}H_{27}F_4N_3O_5 \cdot 0.75\ H_2O$: Calculated: C, 58.48; H, 5.00; N, 7.31 Found: C, 58.37; H, 4.83; N, 7.23

EXAMPLES 66–67

Using a procedure similar to that described in Example 61, the following compounds of formula I wherein $R^6$ is isopropyl, R is benzyloxycarbonylamino, $R^5$ is the indicated aryl containing group, and $R^6$ is hydrogen were prepared by oxidation of the corresponding alcohols of formula II:

Example 66: $R^5$=3-methylbenzyl.

Analysis for $C_{29}H_{30}F_3N_3O_5 \cdot 0.5\ H_2O$: Calculated: C, 61.48; H, 5.51; N, 7.42 Found: C, 61.55; H, 5.43; N, 7.41

Example 67: $R^5$=2-methylbenzyl: MS: m/z=557(M+1).

Analysis for $C_{29}H_{30}F_3N_3 \cdot 0.5\ H_2O$: Calculated: C, 61.48; H, 5.51; N, 7.42 Found: C, 61.31; H, 5.61; N, 7.14

The corresponding alcohols of formula II for Examples 66–67 were prepared as follows:

Examples 66.a.–67.a.

2-(3-Benzyloxycarbonylamino-5-iodo-2-oxo-1,2-dihydro-1-pyridyl)-N-( 2-tert-butyldimethylsilyloxy-3,3,3-trifluoro-1-isopropylpropyl)acetamide was coupled with a benzyl bromide possessing the requisite substitution using a procedure similar to that described in Example 64.b. to give the corresponding tert-butyldimethylsilyl ethers:

Example 66.a.: $R^5$=3-methylbenzyl.
Example 67.a.: $R^5$=2-methylbenzyl.

Examples 66.b.–67.b.

The corresponding alcohols of formula II were prepared from their tert-butyldimethylsilyl ethers using a procedure similar to that described in Example 64.c.

Example 66.b.: $R^5$=3-methylbenzyl.
Example 67.b.: $R^5$=2-methylbenzyl.

EXAMPLE 68

2-[3-Benzyloxycarbonylamino-2-oxo-5-(3-pivaloyloxybenzyl)-1,2-dihydro- 1-pyridyl]-N-(3,3,3-trifluoro-1-isopropyl-2-oxopropyl)acetamide.

Using a procedure similar to that described in Example 62 and substituting 3-pivaloyloxytoluene for 4-pivaloyloxytoluene at Example 62.d., the title compound was prepared; NMR: 1.29 (d,9), 3.72 (s,2 $CH_2$); MS: m/z=645(M+1).

Analysis for $C_{33}H_{36}F_3N_3O_7$.0.5 $H_2O$: Calculated: C, 60.31; H, 5.75; N, 6.39 Found: C, 60.30; H, 5.63; N, 6.23

EXAMPLE 69

2-[3-Benzyloxycarbonylamino-5-(3-hydroxybenzyl)-2-oxo-1,2-dihydro-1-pyridyl]-N-(3,3,3-trifluoro-1-iso-propyl-2-oxopropyl)acetamide.

2-[3-Benzyloxycarbonylamino-2-oxo-5-(3-pivaloyloxybenzyl)-1,2-dihydro- 1-pyridyl]-N-(3,3,3-trifluoro-1-isopropyl-2-oxopropyl)acetamide was hydrolyzed using a procedure similar to that described in Example 63 to afford the title compound; NMR: 3.60 (s, 2H), 9.32 (s,OH); MS: m/z=561(M+1).

Analysis for $C_{28}H_{28}F_3N_3O_6 \cdot H_2O$: Calculated: C, 58.23; H, 5.24; N, 7.28 Found: C, 58.45; H, 5.12; N, 6.99

EXAMPLE 70

2-[3-Benzyloxycarbonylamino-5-(3-acetoxybenzyl)-2-oxo-1,2-dihydro-1-pyridyl]-N-( 3,3,3-trifluoro-1-isopropyl-2-oxopropyl)acetamide.

2-[3-Benzyloxycarbonylamino-5-(3-hydroxybenzyl)-2-oxo- 1,2-dihydro-1-pyridyl]-N-(3,3,3-trifluoro-1-isopropyl-2-oxopropyl)acetamide was acylated using conditions similar to those described in Example 14.b., substituting acetic anhydride for phenylacetyl chloride, to give the title compound; NMR: 2.25 (s,3 and m,1), 6.95–7.41 (m,10); MS: m/z=602(M+1).

Analysis for $C_{30}H_{30}F_3N_3O_7$.0.5 $H_2O$: Calculated: C, 59.01; H, 5.12; N, 6.88 Found: C, 58.88; H, 5.15; N, 6.75

EXAMPLE 71

2-(5-Benzyl-3-benzyloxycarbonylamino-2-oxo-1,2-dihydro- 1-pyridyl)-N-(3,3,3-trifluoro-1-isopropyl-2-oxopropyl)acetamide.

2-(5-Benzyl-3-benzyloxycarbonylamino-2-oxo-1,2-dihydro- 1-pyridyl)-N-(3,3,3-trifluoro-2-hydroxy-1-isopropylpropyl)acetamide was oxidized using a procedure similar to that described in Example 61 to give the title compound; mp 58°–64° C.; NMR: 3.69 (s,2, $CH_2$), 5.12 (s,2, $CH_2$), 7.20–7.40 (m,11).

Analysis for $C_{28}H_{28}F_3N_3O_5$.0.75 $H_2O$: Calculated: C, 60.37; H, 5.34; N, 7.54 Found: C, 60.36; H, 5.35; N, 7.44

The intermediate 2-(5-benzyl-3-benzyloxycarbonylamino-2-oxo- 1,2-dihydro-1-pyridyl)-N-(3,3,3-trifluoro-2-hydroxy-1-isopropyl)acetamide was prepared as follows:

a. 2-(5-Benzyl-3-benzyloxycarbonylamino-2-oxo-1,2-dihydro-1-pyridyl)-N-( 2-tert-butyldimethylsiloxy-3,3,3-trifluoro-1-isopropylpropyl)acetamide.

2-(3-Benzyloxycarbonylamino-5-iodo-2-oxo-1,2-dihydro-1-pyridyl)-N-( 2-tert-butyldimethylsiloxy-3,3,3-trifluoro-1-isopropylpropyl)acetamide was coupled with benzyl bromide using a procedure similar to that described in Example 62.b. to give the 5-benzyl compound.

b. 2-(5-Benzyl-3-benzyloxycarbonylamino-2-oxo-1,2-dihydro-1-pyridyl)-N-( 3,3,3-trifluoro-2-hydroxy-1-isopropyl)acetamide.

2-(5-Benzyl-3-benzyloxycarbonylamino-2-oxo-1,2-dihydro- 1-pyridyl)-N-(2-tert-butyl-dimethylsiloxy-3,3,3-trifluoro-1-isopropylpropyl)-acetamide was deprotected using a procedure similar to that described in Example 64.c. to afford the corresponding alcohol.

The intermediate 2-(5-benzyl-3-benzyloxycarbonylamino-2-oxo- 1,2-dihydro-1-pyridyl)-N-(3,3,3-trifluoro-2-hydroxy-1-isopropyl)acetamide was alternatively prepared as follows:

c. 5-Benzyl-3-benzyloxycarbonylamino-pyrid-2-one.

3-Benzyloxycarbonylamino-5-iodopyrid-2-one was coupled with benzyl bromide using a procedure similar to that described in Example 62.b. to give the 5-benzyl compound.

d. Ethyl 5-benzyl-3-benzyloxycarbonylamino-2-oxo-1,2-dihydro- 1-pyridylacetate.

5-Benzyl-3-benzyloxycarbonylaminopyrid-2-one was alkylated using a procedure similar to that described in Example 61.d. to give the ester.

e. 2-(5-Benzyl-3-benzyloxycarbonylamino-2-oxo-1,2-dihydro-1-pyridyl)-N-( 3,3,3-trifluoro-2-hydroxy-1-isopropyl)acetamide.

Ethyl 2-(5-benzyl-3-benzyloxycarbonylamino-2-oxo-1,2-dihydro-1-pyridyl)acetate was subjected to a procedure similar to that described in Example 61.f. to yield the alcohol.

EXAMPLE 72

2-[3-Benzyloxycarbonylamino-5-(4-trifluoromethylbenzyl)-2-oxo- 1,2-dihydro-1-pyridyl]-N-(3,3,3-trifluoro-1-isopropyl-2-oxopropyl)acetamide.

Using a procedure similar to that outlined in Example 61, but substituting 4-trifluoromethylbenzyl bromide for 3-fluorobenzyl bromide in the step corresponding to Example 61.e., the title compound was obtained; mp 61°–65° C.

Analysis for $C_{29}H_{27}F_6N_3O_5 \cdot H_2O$: Calculated: C, 55.33; H, 4.64; N, 6.67 Found: C, 55.23; H, 4.54; N, 6.63

EXAMPLE 73

2-(2-Oxo-6-phenyl-3-succinimidomethoxycarbonylamino-1,2-dihydro- 1-pyridyl)-N-(3,3,3-trifluoro-1-isopropyl-2-oxopropyl)acetamide.

To a suspension of 2-(3-amino-2-oxo-6-phenyl-1,2-dihydro- 1-pyridyl)-N-(3,3,3-trifluoro-1-isopropyl-2-oxopropyl)acetamide (0.50 g) in dichloromethane (15 mL) cooled in an ice bath, was added dropwise a solution of bis(trichloromethyl) carbonate (0.198 g) in dichloromethane (7 mL). The reaction mixture was stirred 15 min in the ice bath, 15 min with the ice bath removed, then the reaction was cooled to a temperature of less than 4° C. A solution of triethylamine (0.95 mL) in dichloromethane was added dropwise and the mixture was stirred for 25 min. A solution of N-hydroxymethyl succinimide (0.338 g) in dichloromethane (2 mL) was added dropwise and the mixture was stirred 3 h. Bis(trichloromethyl) carbonate (0.032 g) was added and the mixture stirred 1 h. The reaction mixture was diluted with dichloromethane (15 mL) and washed with saturated aqueous ammonium chloride (4 times). The aqueous solutions were combined and extracted with dichloromethane. The combined dichloromethane extracts were washed with brine, dried and evaporated to yield a solid (0.6 g) which was purified by chromatography, eluting with acetonitrile:dichloromethane (2:8), followed by trituration with diethyl ether and drying overnight under high vacuum (75° C. at 13.3 Pa) to give the title compound as an off white powder (0.27 g); mp 216°–218° C. (dec); TLC: $R_f$=0.53, dichloromethane:methanol (9:1); NMR: 0.82 (d,3, J=6.6), 0.88 (d,3, J=6.7), 2.12 (m,1), 2.70 (s,4), 4.5 (m,3), 5.45 (s,2), 6.23 (d,1, J=7.7), 7.42 (m,5), 7.85 (d,1, J=7.6), 9.40 (s,1), 9.72 (d,1, J=6.9); IR(KBr): 1725, 1645, 1610 cm ; MS: m/z=551(M+1), 549(M−1) by FAB.

Analysis for $C_{25}H_{25}F_3N_4O_7$: Calculated: C, 54.55; H, 4.58; N, 10.18 Found: C, 54.30; H, 4.59; N, 10.14

EXAMPLE 74

2-(3-Acetylamino-2-oxo-1,2-dihydro-1-pyridyl)-N-(3,3,3-trifluoro- 1-isopropyl-2-oxopropyl)acetamide.

2-(3-Acetylamino-2-oxo-1,2-dihydro-1-pyridyl)-N-(3,3, 3-trifluoro- 2-hydroxy-1-isopropylpropyl)acetamide was oxidized using a procedure similar to that described in Example 61 to yield the title compound; mp 76°–80° C.; NMR: 0.81–1.24 (m,6), 2.12 (s,3), 2.22 (m,1), 4.13 (m, NHCH hydrate), 4.53–4.89 (m, $CH_2CO$, NHCH keto), 6.22 (m,1), 6.91 (m, OH hydrate), 7.30(m,1), 8.21 (d,1, J=7.5), 8.93 (d, $CH_2CONH$), 9.24 (s, $NHCOCH_3$), 9.26 (s, $NHCOCH_3$).

Analysis for $C_{15}H_{18}F_3N_{34}\cdot H_2O$: Calculated: C, 47.49; H, 5.31; N, 11.08 Found: C, 47.79; H, 5.16; N, 11.07

The intermediate 2-(3-acetylamino-2-oxo-1,2-dihydro-1-pyridyl)-N-( 3,3,3-trifluoro-2-hydroxyl-1-isopropylpropyl)acetamide can be prepared as follows:
a. Ethyl 3-amino-2-oxo-1,2-dihydro-1-pyridylacetate.

Ethyl 3-nitro-2-oxo-1,2-dihydro-1-pyridylacetate was reduced using a procedure similar to that outlined in Example 61.a. to give the amine.
b. Ethyl 3-acetylamino-2-oxo-1,2-dihydro-1-pyridylacetate.

Ethyl 3-amino-2-oxo-1,2-dihydro-1-pyridylacetate was acylated using a procedure similar to Acylation Method A, substituting acetic anhydride for the acid chloride, to give the acetylamino compound.
c. 2-(3-Acetylamino-2-oxo-1,2-dihydro-1-pyridyl)-N-(3,3, 3-trifluoro- 2-hydroxy-1-isopropylpropyl)acetamide.

Ethyl 3-acetylamino-2-oxo-1,2-dihydro-1-pyridylacetate was subjected to a procedure similar to that described in Example 61.f. to yield the amide.

EXAMPLE 75

2-(3-Amino-2-oxo-1,2-dihydro-1-pyridyl)-N-(3,3,3-trifluoro-1-isopropyl- 2-oxopropyl)acetamide.

2-(3-Nitro-2-oxo-1,2-dihydro-1-pyridyl)-N-(3,3,3-trifluoro-1-isopropyl- 2-oxopropyl)acetamide was hydrogenated using a procedure similar to that shown in Example 61.a. to yield the title compound; mp 135° C. (dec); NMR: 0.77–0.95 (m,6), 2.02–2.21 (m,1), 4.07 (m, NHCH hydrate), 4.40–4.74 (m, NHCH keto), 5.05 (s br, $NH_2$), 6.02 (m,1), 6.42 (m,1), 6.78 (m,1), 6.95 (m, OH hydrate), 8.63 (d, J=7).

Analysis for $C_{13}H_{16}F_3N_3O_3\cdot0.5\ H_2O$: Calculated: C, 47.6; H, 5.2; N, 12.8 Found: C, 47.6; H, 5.5; N, 11.8

The intermediate 2-(3-nitro-2-oxo-1,2-dihydro-1-pyridyl)-N-( 3,3,3-trifluoro-1-isopropyl-2-oxopropyl)acetamide was prepared as follows:
a. Ethyl 3-nitro-2-oxo-1,2-dihydro-1-pyridylacetate.

3-Nitropyrid-2-one was alkylated using a procedure similar to that described in Example 61.d. to yield the ester.
b. 2-(3-Nitro-2-oxo-1,2-dihydro-1-pyridyl)-N-(3,3,3-trifluoro-2-hydroxy- 1-isopropylpropyl)acetamide.

Ethyl 3-nitro-2-oxo-1,2-dihydro-1-pyridylacetate was subjected to a procedure similar to that described in Example 61.f. to yield the amide.

The nitro acid intermediate used in Example 75.b. alternatively can be prepared as follows:
i. 3-Nitro-2-oxo-1,2-dihydro-1-pyridylacetic acid.

A solution of concentrated sulphuric acid (10 mL) in water (90 mL) was added dropwise to a solution of 1-allyl-3-nitropyrid-2-one (4.0 g) in acetone (40 mL) at about 0° C. Potassium permanganate (17.42 g) was added in portions to the stirred reaction mixture at 0° C. After 2 h, sodium bisulphate (9.25 g) was added portionwise at 0° C. The solution was filtered and the salts washed with water. The acetone was evaporated from the combined filtrates and the resulting aqueous solution was extracted with ethyl acetate. The combined extracts were dried and evaporated to give the nitro acid (2.45 g).

The intermediate 1-allyl-3-nitropyrid-2-one may be prepared as follows:
ii. 1-Allyl-3-nitropyrid-2-one.

3-Nitropyrid-2-one was alkylated with allyl bromide using a procedure similar to that described in Example 61.d.
c. 2-(3-Nitro-2-oxo-1,2-dihydro-1-pyridyl)-N-(3,3,3-trifluoro- 1-isopropyl-2-oxopropyl)acetamide.

2-(3-Nitro-2-oxo-1,2-dihydro-1-pyridyl)-N-(3,3,3-trifluoro- 2-hydroxy-1-isopropylpropyl)acetamide was oxidized using a procedure similar to that described in Example 61 to yield the ketone; mp 60°–65° C.; NMR: 0.80–1.02 (m,6), 2.24 (m,1), 4.08 (m, NHCH hydrate), 4.66–4.99 (m, NHCH, $CH_2CO$), 6.48 (m,1), 6.95 (m, OH hydrate), 8.02 (d, J=10, NH hydrate), 8.15 (m,1), 8.45 (m,1), 9.03 (d, J=6.5, NH keto).

Analysis for $C_{13}H_{14}F_3N_3O_5\cdot H_2O$: Calculated: C, 42.51; H, 4.39; N, 11.44 Found: C, 42.95; H, 4.08; N, 11.24

EXAMPLE 76

2-[3-(3-phenylpropionylamino)-2-oxo-1,2-dihydro-1-pyridyl]-N-(3,3,3-trifluoro-1-isopropyl-2-oxopropyl)acetamide.

To a stirred suspension of 2-(3-amino-2-oxo-1,2-dihydro-1-pyridyl)-N-(3,3,3-trifluoro-1-isopropyl-2-oxopropyl)acetamide (0.399) in dichloromethane at 0° C. was added 3-phenylpropionyl chloride (0.247 g) and triethylamine (0.247 g). The mixture was allowed to stir for 2 h, was diluted with dichloromethane (100 mL), washed (1N hydrochloric acid, saturated aqueous sodium bicarbonate, brine), dried, and evaporated to give a residue which was purified by chromatography, using methanol:dichloromethane as an eluent (gradient, 0.5:99.5, 2:98), to yield the title compound; mp 154°–155° C.; NMR: 0.80–0.98 (m,6), 2.21 (m,1), 4.09(m, NHCH hydrate), 4.52–4.82 (m, NHCH keto, CH$_2$CO), 6.23 (m), 7.15–7.34 (m), 7.91 (d, J=10, NH hydrate), 8.24 (dd,1, J=7.5, 1.5), 8.93 (d, NH keto), 9.26 (s, NH hydrate), 9.29 (s, NH keto).

Analysis for C$_{22}$H$_{24}$F$_3$N$_3$O$_4$.0.25 H$_2$O: Calculated: C, 57.95; H 5.42; N 9.22 Found: C, 57.98; H 5.55; N 8.90

EXAMPLE 77

2-(3-Phenylacetylamino-2-oxo-1,2-dihydro-1-pyridyl)- N-(3,3,3-trifluoro-1-isopropyl-2-oxopropyl)acetamide.

2-(3-Amino-2-oxo-1,2-dihydro-1-pyridyl)-N-(3,3,3-trifluoro-1-isopropyl- 2-oxopropyl)acetamide was acylated using a procedure similar to that described in Example 76, substituting phenylacetyl chloride for 3-phenylpropionyl chloride, to give the title compound; mp 70°–72° C.

Analysis for C$_{21}$H$_{22}$F$_3$N$_3$O$_4$.0.50 H$_2$O: Calculated: C, 56.50; H, 5.19; N, 9.41 Found: C, 56.61; H, 5.28; N, 9.34

EXAMPLES 78–80

Using a procedure similar to that described in Example 76, the following compounds of Formula I wherein R$^0$ is isopropyl, R is the indicated acyl group, R$^5$ is hydrogen and R$^6$ is hydrogen were prepared by acylation of 2-(3-amino-2-oxo-1,2-dihydro-1-pyridyl)-N-( 3,3,3-trifluoro-1-isopropyl-2-oxopropyl)acetamide with the requisite acid chloride:

Example 78: R=ethoxymalonyl: mp 126°–128° C.; NMR: 1.19 (t,3, J=7.1, CH$_2$CH$_3$), 3.64 (s,2, COCH$_2$CO), 4.12 (q,2, J=7.1, CH$_2$CH$_3$); MS: m/z=434(M+1).

Analysis for C$_{18}$H$_{22}$F$_3$N$_3$O$_6$.0.25 H$_2$O: Calculated: C, 49.37; H, 5.18; N, 9.60 Found: C, 49.18; H, 5.21; N, 9.37

Example 79: R=methoxyoxalyl: mp 74°–79° C.; NMR: 3.84 (s,3, (CO$_2$CH$_3$); MS: m/z=406(M+1).

Analysis for C$_{16}$H$_{18}$F$_3$N$_3$O$_6$.0.75 H$_2$O: Calculated: C, 45.88; H, 4.69; N, 10.03 Found: C, 46.01; H, 4.85; N, 10.00

Example 80: R= methoxysuccinyl.

Analysis for C$_{18}$H$_{22}$F$_3$N$_3$O$_6$.0.75 H$_2$O: Calculated: C, 48.38; H, 5.30; N, 9.40 Found: C, 48.15; H, 5.28; N, 9.06

EXAMPLES 81–83

Using a procedure similar to that described in Example 63, the following acids of Formula I wherein R$^0$ is isopropyl, R is the indicated acyl group, and R$^5$ and R$^6$ are hydrogen were prepared by hydrolysis of the corresponding esters described in Examples 78–80:

Example 81: R=hydroxymalonyl: NMR: 3.48 (d,2); MS: m/z=406(M+1).

Analysis for C$_{16}$H$_{18}$ F$_3$O$_3$O$_6$.2 H$_2$O: Calculated: C, 43.38; H, 4.32; N, 9.37 Found: C, 43.51; H, 4.53; N, 9.34

Example 82: R=hydroxyoxalyl; mp 168°–170° C.; MS: m/z=392(M+1).

Analysis for C$_{15}$H$_{16}$F$_3$N$_3$O$_6$.0.33 H$_2$O: Calculated: C, 45.35; H, 4.22; N, 10.58 Found: C, 45.33; H, 4.19; N, 10.36

Example 83: R=hydroxysuccinyl: mp 98°–100° C.; NMR: 2.25 (d,2, J=6.0), 2.67 (m,2); MS: m/z=420(M+1).

Analysis for C$_{17}$H$_{20}$N$_3$O$_6$F$_3$.H$_2$O.HCl: Calculated: C, 43.09; H, 4.89; N, 8.87 Found: C, 43.41; H, 4.56; N, 8.61

EXAMPLE 84

2-(3-Benzyloxyoxalylamino-2-oxo-1,2,-dihydro-1-pyridyl)-N-(3,3,3-trifluoro-1-isopropyl-2-oxopropyl)acetamide.

2-(3-Hydroxyoxalylamino-2-oxo-1,2-dihydro-1-pyridyl)-N-(3,3,3-trifluoro- 1-isopropyl-2-oxopropyl)acetamide (0.15 g), benzyl alcohol (0.49 mL), 4-dimethylaminopyridine (0.14 g), and 1-(3-dimethylaminopropyl)-3-ethylcarbodiiide hydrochloride (0.98 g) were combined in dimethylformamide (4 mL) and allowed to stir for 72 h. The mixture was partitioned between ethyl acetate and 1N hydrochloric acid, and the organic layer was subsequently washed (saturated aqueous sodium bicarbonate, water, brine), dried, evaporated, and purified using chromatography, with ethyl acetate:dichloromethane (gradient, 10:90, 15:85, 20:80, 30:70) as the eluent, to give the title compound as an off white solid (0.037 g); MS: m/z=482(M+1).

Analysis for C$_{22}$H$_{22}$F$_3$N$_3$O$_6$.0.5 H$_2$O: Calculated: C, 53.88; H, 4.73; N, 8.57 Found: C, 54.02; H, 4.78; N, 8.30

EXAMPLE 85

2-(3-Aminooxalylamino-2-oxo-1,2-dihydro-1-pyridyl)- N-(3,3,3-trifluoro-1-isopropyl-2-oxopropyl)acetamide.

2-(3-Hydroxyoxalylamino-2-oxo-1,2-dihydro-1-pyridyl)-N-(3,3,3-trifluoro- 1-isopropyl-2-oxopropyl)acetamide (0.26 g), the ammonium salt of 1-hydroxybenzotriazole (0.20 g, Bajusz, S. FEBS Lett. (1977), 76, 91), and 1-(3-dimethylaminopropyl)-3-ethylcarbodiimide hydrochloride (0.14 g) were combined in dimethylformamide (5 mL) and allowed to stir overnight. The mixture was partitioned between ethyl acetate and 1N hydrochloric acid, and the organic layer was subsequently extracted (saturated aqueous sodium bicarbonate, water, brine), dried, evaporated and purified using chromatography, with ethyl acetate:dichloromethane (gradient, 1:1, 3:1, ethyl acetate) as the eluent, to give the title compound as a white solid; mp 258°–260° C.; NMR: 8.15 (s,1, NH$_2$), 8.45 (s,1, NH$_2$), 9.92 (s,1, NH); MS: m/z=391(M+1).

Analysis for C$_{15}$H$_{17}$F$_3$N$_4$O$_5$.0.50 H$_2$O: Calculated: C, 45.12; H, 4.54; N, 14.03 Found: C, 45.42; H, 4.63; N, 13.78

EXAMPLE 86

2-(3-Benzylaminooxalylamino-2-oxo-1,2-dihydro-1-pyridyl)-N-(3,3,3-trifluoro-1-isopropyl-2-oxopropyl)acetamide.

2-(3-Hydroxyoxalylamino-2-oxo-1,2-dihydro-1-pyridyl)-N-(3,3,3-trifluoro- 1-isopropyl-2-oxopropyl)acetamide, 1-(3-dimethylaminopropyl)-3-ethylcarbodiimide hydrochloride, and benzylamine (1:1.2:1.2) were combined with 4-dimethylaminopyridine (catalyst) in dimethylformamide and the mixture was allowed to stir overnight. The mixture was poured into ethyl acetate, washed (1N hydrochloric acid, water, brine), dried, evaporated and purified by chromatography to give the title compound; mp 160°–164° C.; NMR: 4.39 (d,2, J=6.4, CH$_2$O), 9.69 (t,1, J=6.4, CH$_2$NHCO); MS: m/z=481(M+1).

Analysis for C$_{22}$H$_{23}$F$_3$N$_4$O$_5$.0.25 H$_2$O: Calculated: C, 54.49; H, 4.88; N, 11.55 Found: C, 54.66; H, 4.97; N, 11.34

EXAMPLE 87

2-[3-(4-Chlorophenoxycarbonylamino)-2-oxo-1,2-dihydro-1-pyridyl]-N-(3,3,3-trifluoro-1-isopropyl-2-oxopropyl)acetamide.

2-[3-(4-Chlorophenoxycarbonylamino)-2-oxo-1,2-dihydro-1-pyridyl]-N-( 3,3,3-trifluoro-2-hydroxy-1-isopropylpropyl)acetamide was oxidized using a procedure similar to that described in Example 61 to give the title compound; mp 137°–139° C.; MS: m/z=474(M+1).

Analysis for $C_{20}H_{19}ClF_3N_3O_5$: Calculated: C, 50.70; H, 4.04; N, 8.87 Found: C, 50.60; H, 4.11; N, 8.81

The intermediate 2-[3-(4-chlorophenoxycarbonylamino)-2-oxo-1,2-dihydro-1-pyridyl]-N-(3,3,3-trifluoro-2-hydroxy-1-isopropylpropyl)acetamide was prepared as follows:
a. 2-(3-Amino-2-oxo-1,2-dihydro-1-pyridyl)-N-(3,3,3-trifluoro-2-hydroxy- 1-isopropylpropyl)acetamide.

2-(3-Nitro-2-oxo-1,2,-dihydro-1-pyridyl)-N-(3,3,3-trifluoro-2-hydroxy- 1-isopropylpropyl)acetamide was hydrogenated using a procedure similar to that described in Example 61 to give the amine.
b. 2-[3-(4-Chlorophenoxycarbonylamino)-2-oxo-1,2-dihydro-1-pyridyl]-N-( 3,3,3-trifluoro-2-hydroxy-1-isopropylpropyl)acetamide.

2-(3-Amino-2-oxo-1,2-dihydro-1-pyridyl)-N-(3,3,3-trifluoro-2-hydroxy- 1-isopropylpropyl)acetamide was acylated using a procedure similar to that described in Example 14.a., except sodium carbonate (2 equivalents) was used as a base instead of triethylamine and 4-chlorophenyl chloroformate was used in place of phenylacetyl chloride, to give the 4-chlorophenoxy compound.

EXAMPLES 88–94

Using procedures similar to that described in Example 87, the following compounds of Formula I, wherein $R^0$ is isopropyl, R is the indicated acyl group and $R^5$ and $R^6$ are hydrogen, were prepared by substituting the requisite acid chloride in the steps corresponding to Example 87.b.

Example 88: R=4-methoxyphenoxycarbonyl: mp 74°–87° C.; NMR: 3.76 (s,3); MS: m/z=470(M+1).

Analysis for $C_{21}H_{22}F_3N_3O_6 \cdot 0.5\ H_2O$: Calculated: C, 52.72; H, 4.85; N, 8.78 Found: C, 52.61; H, 4.82; N, 8.61

Example 89: R=isobutoxycarbonyl: mp 68°–84° C.; NMR: 0.93 (m, OCH$_2$CHCH$_3$), 1.90 (m,1, OCH$_2$CH), 3.87 (m,2, OCH$_2$CH); MS: m/z=420(M+1).

Analysis for $C_{13}H_{24}F_3N_3O_5 \cdot 0.5\ H_2O$: Calculated: C, 50.47; H, 5.88; N, 9.81 Found: C, 50.45; H, 5.85; N, 9.56

Example 90: R=4-methylphenoxycarbonyl: mp 72°–82° C. NMR: 2.31 (s, CH$_3$); MS: m/z=454(M+1).

Analysis for $C_{21}H_{22}F_3N_3O_5 \cdot 0.5\ H_2O$: Calculated: C, 54.55; H, 5.01; N, 9.09 Found: C, 54.39; H, 5.07; N, 8.95

Example 91: R=4-fluorophenoxycarbonyl: mp 147°–150° C.; MS: m/z=458(M+1).

Analysis for $C_{20}H_{19}F_4N_3O_5$: Calculated: C, 52.52; H, 4.19; N, 9.19 Found: C, 52.30; H, 4.26; N, 9.13

Example 92: R=phenoxycarbonyl: mp 74°–76° C.

Analysis for $C_{20}H_{20}F_3N_3O_5 \cdot 0.5\ H_2O$: Calculated: C, 53 57; H 4 72; N, 9.37 Found: C, 53.66; H, 4.66; N, 9.20

Example 93: R=cyclopentyloxycarbonyl: mp 71°–76° C.; NMR: 1.55–1.84 (m,8, CH$_2$), 5.07 (m,1, OCH).

Analysis for $C_{19}H_{24}F_3N_3O_5 \cdot 0.5\ H_2O$: Calculated: C, 51.80; H, 5.72; N, 9.50 Found: C, 51.62; H, 5.74; N, 9.30

Example 94: R=benzyloxycarbonyl: mp 58°–61° C.

Analysis for $C_{21}H_{22}F_3N_3O_5 \cdot 0.33\ H_2O$: Calculated: C, 54.55; H, 5.01; N, 9.09 Found: C, 54.86; H, 5.04; N, 8.65

EXAMPLE 95

2-[2-Oxo-3-(3-phenylureido)-1,2-dihydro-1-pyridyl]- N- (3,3,3-trifluoro-1-isopropyl-2-oxopropyl)acetamide.

2-[2-Oxo-3-(3-phenylureido)-1,2-dihydro-1-pyridyl]-N-(3,3,3-trifluoro- 2-hydroxy-1-isopropylpropyl)acetamide was oxidized using a procedure similar to that described in Example 61 to give the title compound; mp 94°–106° C.; NMR: 7.25 (m,3, phenyl), 7.45 (m,2, phenyl).

Analysis for $C_{20}H_{21}F_3N_4O_4 \cdot 0.33\ H_2O$: Calculated: C, 54.05; H, 4.91; N, 12.61 Found: C, 54.36; H, 5.02; N, 12.34

The intermediate 2-[2-oxo-3-(3-phenylureido)-1,2-dihydro-1-pyridyl]-N-( 3,3,3-trifluoro-2-hydroxy-1-isopropylpropyl)acetamide was prepared as follows:

2-(3-Amino-2-oxo-1,2-dihydro-1-pyridyl)-N-(3,3,3-trifluoro-2-hydroxy- 1-isopropylpropyl)acetamide (0.43 g) and phenylisocyanate (0.175 g) were combined in dichloromethane (5 mL) and allowed to stir overnight. The mixture was poured into ethyl acetate, washed (saturated aqueous sodium bicarbonate, brine), evaporated, and purified using chromatography, eluting with ethyl acetate:dichloromethane (gradient, 0:100, 50:50, 100:0), to give the urea (0.54 g).

EXAMPLE 96

2-(2-Oxo-6-phenyl-3-ureido-1,2-dihydro-1-pyridyl)-N-(3,3,3-trifluoro-1-isopropyl-2-oxopropyl)acetamide.

To a solution of 2-(3-amino-2-oxo-6-phenyl-1,2-dihydro-1-pyridyl)-N-(3,3,3-trifluoro-1-isopropyl-2-oxopropyl)acetamide (0.30 g) in tetrahydrofuran (5 mL), cooled to 0° C., was added, dropwise, chlorosulfonyl isocyanate (0.12 g). The reaction mixture was stirred for 10 min, neutralized with saturated aqueous sodium bicarbonate solution (1 mL), diluted with ethyl acetate (10 mL), and the organic phase washed (water, brine), dried (MgSO$_4$) and evaporated. Purification by chromatography, using an eluant of methylene chloride:methanol (30:1), followed by overnight vacuum-drying (50° C. at 27 Pa), yielded the title product as a white solid (0.23 g); mp 227°–230° C. (dec); TLC: R$_f$=0.16, dichloromethane:methanol (20:1); 300 MHz NMR: 0.88 (2d,6), 2.15 (m,1), 4.50 (q,2), 4.65 (d,1), 6.18 (d,1), 6.40 (broad s,2), 7.40 (m,5), 8.08 (d,1), 8.35 (s,1), 8.75 (d,1); IR(KBr): 3470 (broad), 3360, 2980, 1760, 1700, 1535, 1490, 1210, 1160, 1020 cm$^{-1}$; MS: m/z=439(M+1).

Analysis for $C_{20}H_{21}F_3N_4O_4 \cdot 0.25\ H_2O$: Calculated: C, 54.24; H, 4.89; N, 12.65 Found: C, 154.12; H, 4.76; N, 12.66

EXAMPLE 97

2-(5-Benzyl-3-methoxyoxalylamino-2-oxo-1,2-dihydro-1-pyridyl)-N-(3,3,3-trifluoromethyl-1-isopropyl-2-oxopropyl)acetamide.

2-(3-Amino-5-benzyl-2-oxo-1,2-dihydro-1-pyridyl)-N-(3,3,3-trifluoromethyl- 1-isopropyl-2-oxopropyl)acetamide was acylated using a procedure similar to that outlined in Example 79 to give the title compound; mp 155°–157° C.; NMR: 3.82 (s,3, CH$_3$OCO); MS: m/z=496(M+1).

Analysis for $C_{23}H_{24}F_3N_3O_6$: Calculated: C, 55.76; H, 4.88; N, 8.48 Found: C, 55.64; H, 4.97; N, 8.47

The intermediate amine (which is also an Example of the invention) was prepared as follows:

a. 2-(3-Amino-5-benzyl-2-oxo-1,2-dihydro-1-pyridyl)-N-(3,3,3-trifluoromethyl- 1-isopropyl-2-oxopropyl)acetamide 2-(5-Benzyl-3-benzyloxycarbonylamino-2-oxo-1,2-dihydro-1-pyridyl)-N-( 3,3,3-trifluoromethyl-1-isopropyl-2-oxopropyl)acetamide was hydrogenolyzed using conditions similar to those outlined in Example 61.a., except the reaction was carried out at 3 bar in a shaking hydrogenator for 12 h, to give the amine.

EXAMPLE 98

2-(5-Benzyl-3-hydroxyoxalylamino-2-oxo-1,2-dihydro- 1-pyridyl)-N-(3,3,3-trifluoromethyl-1-isopropyl-2-oxopropyl)acetamide.

2-(5-Benzyl-3-methoxyoxalylamino-2-oxo-1,2-dihydro-1-pyridyl)-N-( 3,3,3-trifluoromethyl-1-isopropyl-2-oxopropyl)acetamide was hydrolysed using a procedure similar to that outlined in Example 63 to give the title compound; mp 82°–93° C.; MS: m/z=482(M+1).

Analysis for $C_{22}H_{22}F_3N_3O_6$.0.5 $H_2O$: Calculated: C, 54.89; H 4.61; N, 8.73 Found: C, 54.64; H 4.69; N, 8.66

EXAMPLE 99

2-(3-Aminooxalylamino-5-benzyl-2-oxo-1,2-dihydro-1-pyridyl)-N-(3,3,3-trifluoromethyl-1-isopropyl-2-oxopropyl)acetamide.

2-(5-Benzyl-3-methoxyoxalylamino-2-oxo-1,2-dihydro-1-pyridyl)-N-( 3,3,3-trifluoromethyl-1-isopropyl-2-oxopropyl)acetamide (0.35 g) and concentrated ammonium hydroxide (1 mL) were combined in methanol (1 mL) and allowed to stir for 3 h. The mixture was poured into ethyl acetate, washed (1N hydrochloric acid), dried, evaporated, and purified by chromatography, eluting with ethyl acetate:dichloromethane (gradient, 25:75, 50:50, 75:25), to give the title compound as a white solid (0.21 g); mp 147°–156° C.; NMR: 8.13 (m,2, $NH_2COCO$); MS: m/z=481(M+1).

Analysis for $C_{22}H_{23}F_3N_4O_5$.0.5 $H_2O$: Calculated: C, 53.99; H, 4.94; N, 11.45 Found: C, 54.18; H, 5.08; N, 11.63

EXAMPLE 100

2-[5-Benzyl-3-(methylaminooxalyl)amino-2-oxo-1,2-dihydro-1-pyridyl]-N-(3,3,3-trifluoromethyl-1-isopropyl-2-oxapropyl)acetamide.

2-(5-Benzyl-3-methoxyoxalylamino-2-oxo-1,2-dihydro-1-pyridyl)-N-( 3,3,3-trifluoromethyl-1-isopropyl-2-oxopropyl)acetamide (0.15 g) and 40% aqueous methylamine (2 mL) were combined in methanol (2 mL) and allowed to stir for 2 h. The mixture was poured into ethyl acetate, washed (1N hydrochloric acid, saturated aqueous sodium bicarbonate, brine), dried, evaporated, and purified by chromatography, eluting with ethyl acetate:dichloromethane (gradient, 50:50, 75:25), to give the title compound as a white solid (0.11 g); mp 177°–179° C.; NMR: 2.71 (d,3, J=4.8, $CH_3NH$); MS: m/z=495(M+1).

Analysis for $C_{22}H_{25}F_3N_4O_5$: Calculated: C, 55.87; H, 5.10; N, 11.33 Found: C, 55.67; H, 5.20; N, 11.02

EXAMPLE 101

2-[3-Benzyloxycarbonylamino-5-(3-trifluoroacetylaminobenzyl)-2-oxo-1,2-dihydro-1-pyridyl]-N-(3,3,3-trifluoro-1-isopropyl-2-oxopropyl)acetamide.

2-[3-Benzyloxycarbonylamino-5-(3-trifluoroacetylaminobenzyl)- 2-oxo-1,2-dihydro-1-pyridyl]-N-(3,3,3-trifluoro-2-hydroxy-1-isopropylpropyl)acetamide was oxidized using a procedure similar to that outlined in Example 61 to give the title compound; MS: m/z=655(M+1).

Analysis for $C_{30}H_{28}F_6N_4O_6$.0.5 $H_2O$: Calculated: C, 54.30; H, 4.40; N, 8.44 Found: C, 54.36; H, 4.41; N, 8.40

The intermediate 2-[3-benzyloxycarbonylamino-5-(3-trifluoroacetylaminobenzyl)- 2-oxo-1,2-dihydro-1-pyridyl]-N-(3,3,3-trifluoro- 2-hydroxy-1-isopropylpropyl)acetamide was prepared as follows:

a. N-Trifluoroacetyl-m-toluidine.

m-Toluidine was acylated using a procedure similar to Acylation Method A, but substituting trifluoroacetic anhydride for the acid chloride, to give the amide.

b. 3-(Trifluoroacetylamino)benzyl bromide.

N-Trifluoroacetyl-m-toluidine was brominated using a procedure similar to that outlined in Example 62.d. to give the benzyl bromide.

c. tert-Butyl 3-benzyloxycarbonylamino-5-(3-trifluoroacetylaminobenzyl)- 2-oxo-1,2-dihydro-1-pyridylacetate.

3-(Trifluoroacetylamino)benzyl bromide was coupled with tert-butyl 3-benzyloxycarbonylamino-5-iodo-2-oxo-1, 2-dihydro-1-pyridylacetate using a procedure similar to that outlined in Example 62.b. to give the benzyl substituted tert-butyl ester.

d. 2-[3-Benzyloxycarbonylamino-5-(3-trifluoroacetylaminobenzyl)- 2-oxo-1,2-dihydro-1-pyridyl]-N-(3,3,3-trifluoro-2-hydroxy-1-isopropylpropyl)acetamide.

tert-Butyl 3-benzyloxycarbonylamino-5-(3-trifluoroacetylaminobenzyl)- 2-oxo-1,2-dihydro-1-pyridylacetate was subjected to a procedure similar to that outlined in Example 61.f. to give the alcohol.

EXAMPLE 102

2-[5-(3-Aminobenzyl)-3-methoxycarbonylamino-2-oxo-1,2-dihydro-1-pyridyl]-N-(3,3,3-trifluoro-1-isopropyl-2-oxopropyl)acetamide.

2-[3-Benzyloxycarbonylamino-5-(3-trifluoroacetylaminobenzyl)- 2-oxo-1,2-dihydro-1-pyridyl]-N-(3,3,3-trifluoro-1-isopropyl-2-oxopropyl)acetamide (0.19 g), and 1N sodium hydroxide (3 mL) were combined in methanol and allowed to stir for 6 h. The methanol was evaporated, the residue was dissolved in ethyl acetate, dried, evaporated, and purified by chromatography, eluting with ethyl acetate:dichloromethane (gradient, 0:100, 5:95), to give the title compound (0.070 g).

Analysis for $C_{22}H_{25}F_3N_4O_6$.0.66 $H_2O$: Calculated: C, 53.44; H, 5.37; N, 11.33 Found: C, 53.57; H, 5.33; N, 11.18

EXAMPLES 103–121

Using a similar procedure to that described in Example 1, the following compounds of formula I wherein $R^0$ is isopropyl, R is the indicated acyl group, $R^5$ is hydrogen and $R^6$ is phenyl were prepared by oxidation of the corresponding alcohols of formula II.

Example 103: R=2-benzyloxycarbonylphenylacetyl: Chromatography solvent: ethyl acetate:dichloromethane (30:70); TLC: $R_f$=0.6, ethyl acetate:dichloromethane (30:70).

Example 104: R=2-methoxycarbonylphenylacetyl: Chromatography solvent: ethyl acetate:hexane (gradient, 30:70 to 100:0); TLC: $R_f$=0.5, methanol:dichloromethane (5:95); MS: m/z=572(M+1).

Analysis for $C_{29}H_{28}F_3N_3O_6 \cdot H_2O$: Calculated: C, 59.08; H, 5.12; H, 7.12 Found: C, 59.06; H, 5.09; N, 7.08

Example 105: R=(diethoxyphosphoryl)methylaminocarbonyl: Chromatography solvent: methanol:dichloromethane (0:100, 2.5:97.5, 5:95, 7:93); TLC: $R_f$=0.52, methanol:dichloromethane (10:90); MS: m/z=589(M+1).

Analysis for $C_{25}H_{32}F_3N_4O_7 \cdot 0.75\ H_2O$: Calculated: C, 49.88; H, 5.61; N, 9.31 Found: C, 49.75; H, 5.38; N, 8.95

Example 106: R=4-methoxycarbonylphenylacetyl: Chromatography solvent: ethyl acetate:dichloromethane (gradient, 0:100, 10:90); TLC: $R_f$=0.46, ethyl acetate:dichloromethane (20:80); MS: m/z=572(M+1).

Example 107: R=3-methoxycarbonylphenylacetyl: Chromatography solvent: ethyl acetate:dichloromethane (gradient, 0:100, 20:80, 40:60); TLC: $R_f$=0.28, ethyl acetate:dichloromethane (20:80); MS: m/z=572(M+1).

Example 108: R=4-pyridylmethylaminocarbonyl: Chromatography solvent: methanol:dichloromethane (10:90); TLC: $R_f$=0.25, methanol:dichloromethane (10:90); MS: m/z=530(M+1).

Analysis for $C_{26}H_{26}F_3N_5O_4$: Calculated: C, 58.98; H, 4.95; N, 13.23 Found: C, 58.93; H, 4.93; N, 13.46

Example 109: R=3-pyridylmethylaminocarbonyl: Chromatography solvent: methanol:dichloromethane (gradient, 0:100 to 20:80); MS: m/z=530(M+1).

Analysis for $C_{26}H_{26}F_3N_5O_5 \cdot 0.75\ H_2O$: Calculated: C, 57.51; H, 5.10; N, 12.90 Found: C, 57.52; H, 5.03; N, 12.21

Example 110: R=2-(4-pyridyl)ethoxycarbonyl: Chromatography solvent: methanol:dichloromethane (gradient, 3:97 to 5:95); MS: m/z=55(M+1).

Analysis for $C_{27}H_{27}F_3N_4O_5 \cdot 0.3\ H_2O$: Calculated: C, 58.97; H, 5.06; N, 10.19 Found: C, 58.95; H, 4.98; N, 10.13

Example 111: R=2-morpholinoethylaminocarbonyl: Chromatography solvent: methanol:dichloromethane (10:90); MS: m/z=552(M+1).

Analysis for $C_{26}H_{32}F_3N_5O_5$: Calculated: C, 56.62; H, 5.85; N, 12.70 Found: C, 56.35; H, 6.06; N, 12.98

Example 112: R=ethoxycarbonylaminocarbonyl: Chromatography solvent: methanol:dichloromethane (5:95); MS: m/z=511(M+1).

Analysis for $C_{23}H_{25}F_3N_4O_6 \cdot H_2O$: Calculated: C, 52.27; H, 5.15; N, 10.60 Found: C, 52.08; H, 4.93; N, 10.74

Example 113: R=3-methoxycarbonylanilinocarbonyl: Chromatography solvent: ethyl acetate:dichloromethane (10:90); MS: m/z=587(M+1).

Example 114: R=2-benzyloxycarbonylanilinocarbonyl: Chromatography solvent: ethyl acetate:dichloromethane (gradient, 10:90, 20:80); TLC: $R_f$=0.66, ethyl acetate:dichloromethane (25:75); MS: m/z=649(M+1).

Example 115: R=4-(dimethoxyphosphoryl)benzyloxycarbonyl: Chromatography solvent: methanol:dichloromethane (5:95); TLC: $R_f$=0.4, methanol:dichloromethane (10:90); MS: m/z=638(M+1). Analysis for $C_{29}H_{31}F_3N_3PO_8 \cdot 0.25\ H_2O$: Calculated: C, 54.25; H, 4.94; N, 6.54 Found: C, 54.14; H 5.00; N 6.43

Example 116: R=2-pyridylaminocarbonyl: Chromatography solvent: methanol:dichloromethane (gradient, 0:100 to 10:90); TLC: $R_f$=0.65, methanol:dichloromethane (10:90); MS: m/z=516(M+1).

Analysis for $C_{25}H_{24}F_3N_5O_4 \cdot 0.75\ H_2O$: Calculated: C, 56.76; H, 4.86; N, 13.24 Found: C, 56.71; H, 4.80; N, 13.16

Example 117: R=2-(2-pyridyl)ethoxycarbonyl: MS: m/z=545(M+1).

Analysis for $C_{27}H_{27}F_3N_4O_5 \cdot 0.5\ H_2O$: Calculated: C, 58.59; H, 5.10; N, 10.12 Found: C, 59.38; H, 4.94; N, 10.06

Example 118: R=2-(2-tert-butoxycarbonylaminothiazol-4-yl)-ethoxycarbonyl: Chromatography solvent: ethyl acetate; MS: m/z=666(M+1).

Example 119: R=1-methylpiperid-4-yloxycarbonyl: Chromatography solvent: methanol:dichloromethane (gradient, 5:95 to 15:85); MS: m/z=537(M+1).

Analysis for $C_{26}H_{31}F_3N_4O_5 \cdot H_2O$: Calculated: C, 56.31; H, 6.00 N, 10.10 Found: C, 56.31; H, 5.70; N, 9.97

Example 120: R=2-piperidinoethylaminocarbonyl: Chromatography solvent: methanol:dichloromethane:ammonium hydroxide (10:89:1); MS: m/z=550(M+1).

Analysis for $C_{27}H_{34}F_3N_5O_4 \cdot 0.75\ H_2O$: Calculated: C, 56.68; H, 6.43; N, 12.24 Found: C, 56.67; H, 6.21; N, 12.11

Example 121: R=5-methylpyrid-2-ylmethoxycarbonyl: Chromatography solvent: methanol:dichloromethane (5:95); MS: m/z=545(M+1).

Analysis for $C_{27}H_{27}F_3N_4O_5 \cdot 0.5\ H_2O$: Calculated: C, 58.59; H, 5.10; N, 10.12 Found: C, 58.54; H, 5.00; N, 10.06

The corresponding alcohols of Formula II for Examples 103–121 were prepared as follows:

EXAMPLES 103.a.–121.a.

2-(3-Acylamino-2-oxo-6-phenyl-1,2-dihydro-1-pyridyl)-N-(2-tert-butyldimethylsilyloxy- 3,3,3-trifluoro-1-isopropylpropyl)acetamides having the indicated acyl group R were prepared by acylation of 2-(3-amino-2-oxo-6-phenyl-1,2-dihydro-1-pyridyl)-N-(2-tert-butyldimethylsilyloxy- 3,3,3-trifluoro-1-isopropylpropyl)acetamide using the Acylation Method noted:

Example 103.a.: R=2-benzyloxycarbonylphenylacetyl: Acylation Method B; Chromatography solvent: diethyl ether:hexane (gradient 30:70, 40:60); TLC: $R_f$=0.7, diethyl ether (40:60); MS: m/z=764(M+1).

The 2-benzyloxycarbonylphenylacetic acid for the acylation described in 103.a. was prepared as follows:

To a solution of homophthalic acid (15 g) in dimethylformamide (40 mL) was added potassium carbonate (34 g) and then benzyl bromide (21 mL). The resulting solution was allowed to stir for 12 h. The mixture was diluted with ether, washed (saturated aqueous sodium bicarbonate, water, 1N hydrochloric acid), dried, and evaporated to give an oil which was dissolved in tetrahydrofuran (240 mL) and $H_2O$ (120 mL). To this was added lithium hydroxide and the solution was allowed to stir for 2 h and was acidified to pH 2. The product was extracted into ether and dried. The solvent was evaporated and the resulting oil was crystallized from ether/hexane to yield the mono-benzyl acid (3.7 g); TLC: $R_f$=0.5, ether; MS: m/z=271(M+1).

Example 104.a.: R=2-methoxycarbonylphenylacetyl: Acylation Method B; chromatography solvent: diethyl ether:hexane; (gradient, 60:40 to 100:0), TLC: $R_f$=0.8, methanol:dichloromethane (5:95); MS: m/z=688(M+1).

The 2-methoxycarbonylphenylacetic acid for the acylation described in Example 104.a. was prepared as follows:

Using a procedure similar to that described in Example 103.a.i., for preparing the acid, but substituting methyl iodide for benzyl bromide, the mono-methyl acid was prepared; chromatography solvent: methanol:dichloromethane (10:90), TLC: $R_f$=0.5, methanol:dichloromethane (15:85); MS: m/z=195(M+10).

Example 105.a.: R=(diethoxyphosphoryl)methylaminocarbonyl: Acylation Method D; TLC: $R_f$=0.19, methanol:dichloromethane (4:96); MS: m/z=705(M+1).

The amine for the acylation was prepared as follows.
i. Benzyloxycarbonylaminomethylphosphonic acid.

To a solution of aminomethylphosphonic acid (2.5 g) in 2N aqueous sodium hydroxide (23 mL) containing sodium carbonate (4.77 g) and sodium bicarbonate (3.78 g) at 50° C. was added benzyl chloroformate (9.64 mL), portionwise over 1 h. The resulting solution was allowed to stir overnight. The solution was diluted with water (100 mL) and the pH lowered to 1. The product was extracted into ethyl acetate and the organic solvent dried ($MgSO_4$). The solvent was evaporated and the product crystallized from ethyl acetate to provide the carbamate (4.64 g); MS: m/z=246(M+1).

ii. Diethyl benzyloxycarbonylaminomethylphosphonate.

A solution of benzyloxycarbonylaminomethylphosphonic acid (3.0 g) and triethyl orthoformate (40 mL) was heated to 90° C. for 48 h. The reaction was diluted with ethyl acetate and washed with 1N hydrochloric acid. The mixture was dried ($MgSO_4$) and evaporated to give an oil which was chromatographed, eluting with ethanol:ethyl acetate (gradient, 0.25:99.75 to 2:98), to yield the diethyl phosphonate (1.3 g); TLC: $R_f$=0.36, ethanol:ethyl acetate (0.5:99.5); MS: m/z=302(M+1).

iii. Diethyl aminomethylphosphonate.

To a solution of diethyl benzyloxycarbonylaminomethyl phosphonate (3.56 g) in tetrahydrofuran (125 mL) and ethanol (100 mL) was added 10% (w/w) palladium on carbon (15% by weight) and the mixture was shaken under a hydrogen atmosphere (2.8 bar) overnight. The catalyst was removed by filtration and the solvent evaporated. The resulting oil was chromatographed, eluting with methanol:dichloromethane (gradient, 1:99 to 10:90), to yield the amine (0.45 g); TLC: $R_f$=0.38, methane:dichloromethane (10:90); MS: m/z=168(M+1).

Example 106.a.: R=4-methoxycarbonylphenylacetyl: Acylation Method B; chromatography solvent: ethyl acetate:dichloromethane (gradient, 0:100, 10:90); TLC: $R_f$=0.59 methanol:dichloromethane (5:95); MS: m/z=688(M+1).

The 4-methoxycarbonylphenylacetic acid for the acylation was prepared as follows:
i. Methyl 4-hydroxyphenylacetate.

To a solution of 4-hydroxyphenylacetic acid (10 g) in methylene chloride (66 mL) and methanol (26 mL) was added p-toluenesulfonic acid (1.25 g), and the resulting solution was heated at reflux overnight. The solvent was evaporated, the residue dissolved in ethyl acetate, and the the solution washed ($H_2O$), dried ($MgSO_4$), and evaporated to give crude methyl 4-hydroxyphenylacetate (10.4 TLC: $R_f$=0.72, ethyl acetate:dichloromethane (10:90); MS: m/z=167(M+1).

ii. Methyl 4-trifluoromethylsulfonyloxyphenylacetate.

To a solution of methyl 4-hydroxyphenyl acetate (5 g) and triethylamine (3.97 g) in methylene chloride (60.2 mL) was added a solution of N-phenyltrifluoromethanesulfonimide (13.97 g) in methylene chloride (20 mL), and the resulting mixture was allowed to stir overnight. The reaction was diluted with ethyl acetate, washed (1N hydrochloric acid), dried ($MgSO_4$), evaporated, and the resulting oil was purified by chromatography, eluting with ethyl acetate:dichloromethane:hexane (gradient, 30:15:55, 15:15:70), to afford the trifluoromethylsulfonyloxy compound (8.56 g); TLC: $R_f$=0.68; MS: m/z=299(M+1).

iii. Methyl 4-methoxycarbonylphenylacetate.

To a solution of methyl 4-trifluoromethylsulfonyloxyphenylacetate (6 g) dissolved in dimethyl sulfoxide (30 mL) and methanol (5 mL) was added 1,3-bis(diphenylphosphino)propane (0.25 g) and bis(triphenylphosphine)palladium(II) chloride (0.43 g). The reaction was placed under a carbon monoxide atmosphere and the solution heated at 60° C. for 24 h. The reaction was diluted with ethyl acetate, washed (1N hydrochloric acid, water, brine), dried ($MgSO_4$), and evaporated to give an oil which was purified by chromatography, eluting with diethyl ether:hexane (7:3), to afford the di-ester (3.15 g); TLC: $R_f$=0.32, diethyl ether:hexane (30:70).

iv. 4-Methoxycarbonylphenylacetic acid.

To a solution of methyl 4-methoxycarbonylphenylacetate (3.15 g) dissolved in tetrahydrofuran (100 mL), methanol (25 mL) and water (25 mL) at 0° C. was added lithium hydroxide (0.7 g) and the solution was allowed to stir for 2 h. The solution was acidified to pH 2.5 and the product extracted into ethyl acetate. The organic layer was dried ($MgSO_4$) and evaporated to give an oil which was crystallized from hexane to give the mono-acid; TLC: $R_f$=0.65, methanol:dichloromethane (20:80); MS: m/z=195(M+1).

Example 107.a.: R=3-methoxycarbonylphenylacetyl: Acylation Method B; TLC: $R_f$=0.73, methanol:dichloromethane (5:45); MS: m/z=688(M+1).

The 3-methoxycarbonylphenylacetic acid for the acylation was prepared using procedures similar to those described in Example 106.a.i.–.iv., except 3-hydroxyphenylacetic acid was substituted for 4-hydroxyphenylacetic acid in the step corresponding to 106.a.i:

i. Methyl 3-hydroxyphenylacetate: TLC: $R_f$=0.87, ethyl acetate:dichloromethane (10:90); MS: m/z=167(M+1).

ii. Methyl 3-trifluoromethylsulfonyloxyphenylacetate: Chromatography solvent: diethyl ether:hexane (gradient 10:90, 40:60); TLC: $R_f$=0.5, diethyl ether:hexane (25:75); MS: m/z=299(M+1).

iii. Methyl 3-methoxycarbonylphenylacetate: Chromatography solvent: diethyl ether:hexane (30:70); TLC: $R_f$=0.2, diethyl ether:hexane (30:70).

iv. 3-Methoxycarbonylphenylacetic acid: TLC: $R_f$=0.54, methanol:dichloromethane (20:80); MS: m/z=195(M+1).

Example 108.a.: R=4-pyridylmethylaminocarbonyl: Acylation Method D; chromatography solvent: methanol:dichloromethane (10:90); TLC: $R_f$=0.15, methanol:dichloromethane (5:95); MS: m/z=646(M+1).

Example 109.a.: R=3-pyridylmethylaminocarbonyl: Acylation Method D; chromatography solvent: methanol:dichloromethane (5:95); TLC: $R_f$=0.25, methanol:dichloromethane (5:95); MS: m/z=646(M+1).

Example 110.a.: R=2-(4-pyridyl)ethoxycarbonyl: Acylation Method D; chromatography solvent: ethyl acetate; MS: m/z=661(M+1).

Example 111.a.: R=2-morpholinoethylaminocarbonyl: Acylation Method D; chromatography solvent: methanol:dichloromethane (10:90); TLC: $R_f$=0.3, methanol:dichloromethane (10:90); MS: m/z=668(M+1).

Example 112.a.: R=ethoxycarbonylaminocarbonyl: Acylation Method C; chromatography solvent: methane:dichloromethane (10:90); TLC: $R_f$=0.4, ethyl acetate:dichloromethane (10:90); MS: m/z=627(M+1).

Example 113.a.: R=3-methoxycarbonylanilinocarbonyl: Acylation Method C; chromatography solvent: methanol:dichloromethane (5:95); TLC: $R_f$=0.5, methanol:dichloromethane (5:95); MS: m/z=703(M+1).

Example 114.a.: R=2-benzyloxycarbonylanilinocarbonyl: Acylation Method D; chromatography solvent: diethyl ether; MS: m/z=765(M+1).

Example 115.a.: R=4-(dimethoxyphosphoryl)benzyloxycarbonyl: Acylation Method D; chromatography solvent: ethyl acetate; TLC: $R_f$=0.25, ethyl acetate; MS: m/z=754(M+1).

The alcohol for the acylation was prepared as follows:
i. 4-Iodobenzyl alcohol.

To a solution of 4-iodobenzoic acid (22 g) in tetrahydrofuran (450 mL) was added borane dimethylsulfide complex (35.5 mL, 10M in tetrahydrofuran), and the solution was allowed to stir overnight. The reaction was quenched by addition of methanol, and the solvent was evaporated. The residue was dissolved in ethyl acetate and filtered. The solvent was evaporated to give a solid, which was recrystallized from ether to yield a white solid, which was chromatographed, eluting with ether, to give 4-iodobenzyl alcohol (15.1 g).

ii. 4-(tert-Butyldimethylsilyloxymethyl)iodobenzene.

To a solution of 4-iodobenzyl alochol (7 g) in dimethylformamide (30 mL) was added imidazole (4.08 g) and tert-butyl-dimethylsilyl chloride (5.28 g) and the solution allowed to stir for 0.25 h. The reaction mixture was diluted with ethyl acetate, washed (saturated aqueous ammonium chloride, water, brine), dried (MgSO4), and evaporated; and the resulting material was chromatographed, eluting with ether:hexane (20:80), to give the tert-butyldimethylsilyl ether as a white solid (8.76 g).

iii. Dimethyl 4-(tert-butyldimethylsiloxymethyl)phenylphosphonate.

To a solution of 4-(tert-butyldimethylsiloxymethyl)iodobenzene (6.96 g) in dimethylformamide (90 mL) was added dimethyl phosphite (2.64 g) and diisopropylethylamine (4.53 mL). The mixture was placed under an argon atmosphere and tetrakis(triphenylphosphine)palladium(O) (0.9 g) was added. The solution was heated for 2 h at 80° C., and the solvent was evaporated. The residue was dissolved in ethyl acetate, washed (water, brine), dried (MgSO$_4$), and evaporated. The product was purified by chromatography, eluting with ethyl acetate, to give the phosphonate (3.45 g) as an oil; TLC: $R_f$=0.35, ethyl acetate; MS: m/z=331(M+1).

iv. Dimethyl 4-(hydroxymethyl)phenylphosphonate.

To a solution of dimethyl 4-(tert-butyldimethylsiloxymethyl)phenylphosphonate (3.4 g) in tetrahydrofuran (20 mL) was added acetic acid (0.6 mL) and tetrabutylammonium floride (15 mL, 1M in THF), and the resulting solution was allowed to stir for 1 h. The solvent was evaporated and the residue dissolved in ethyl acetate, washed (saturated aqueous ammonium chloride, brine), dried (MgSO$_4$), and evaporated. The product was purified by chromatography (ethyl acetate) to provide the alcohol (1.5 g); TLC: $R_f$=0.15, ethyl acetate; MS: m/z=217(M+1).

Example 116.a.: R=2-pyridylaminocarbonyl: Acylation Method D; TLC: $R_f$=0.65, methanol:dichloromethane (10:90); MS: m/z=632(M+1).

Example 117.a.: R=2-(2-pyridyl)ethoxycarbonyl: Acylation Method D; chromatography solvent: ethyl acetate:dichloromethane (gradient, 20:80, 40:60); TLC: $R_f$=0.6, ethyl acetate; MS: m/z=661(M+1).

Example 118.a.: R=2-[2-(tert-butoxycarbonylamino)thiazol-4-yl]ethoxycarbonyl: Acylation Method D; chromatography solvent: ethyl acetate:hexane (50:50); MS: m/z=782(M+1).

The alcohol for the acylation was prepared as follows:
i. Ethyl 2-tert-butoxycarbonylamino-4-thiazoleacetate.

To a solution of ethyl 2-amino-4-thiazoleacetate (4.66 g) in tetrahydrofuran (100 mL) was added di-tert-butyl dicarbonate (5.9 g), and the solution was allowed to reflux for 4 h. The solvent was evaporated, and the residue was redissolved in ethyl acetate, washed (saturated aqueous ammonium chloride, brine), dried (MgSO$_4$), and evaporated. The product was purified by chromatography, eluting with ether, to provide a mixture of monoprotected and diprotected compounds (9.65 g); MS: m/z=287(M+1), monoprotected, m/z=387(M+1), diprotected.

ii. 2-(2-tert-Butoxycarbonylaminothiazol-4-yl)ethanol.

To the crude product from step i. (9.65 g) in tetrahydrofuran (200 mL) at –78° C. was added dropwise a solution of diisobutylaluminum hydride (75 mL, 1M in toluene). The mixture was allowed to warm to room temperature and then recooled to –78° C. The reaction was quenched by addition of ethyl acetate and then brought to room temperature. The mixture was diluted with ethyl acetate, washed (saturated aqueous sodium potassium tartrate), dried (MgSO$_4$), and evaporated to give an oil which was purified by chromatography, eluting with diethyl ether, to give the alcohol (0.97 g); MS: m/z=245(M+1).

Example 119.a.: R=1-methylpiperid-4-yloxycarbonyl: Acylation Method D; chromatography solvent: methanol:dichloromethane (10:90); MS: m/z=653(M+1).

Example 120.a.: R=2-piperidinoethylaminocarbonyl: Acylation Method D; chromatography solvent: ethyl acetate; TLC: $R_f$=0.15, ethyl acetate.

Example 121.a.: R=5-methylpyrid-2-ylmethoxycarbonyl: Acylation Method D; chromatography solvent: methanol:dichloromethane (5:95); MS: m/z=661(M+1).

EXAMPLES 103.b.–121.b.

The following alcohols of formula II wherein $R^0$ is isopropyl, R is the indicated acyl group, $R^5$ is hydrogen and $R^6$ is phenyl were prepared by deprotection of the corresponding tert-butyldimethylsilyl ethers using a procedure similar to either that outlined in Example 1.e. or that outlined in Example 19.b. as noted.

Example 103.b.: R=2-benzyloxycarbonylphenylacetyl: Deprotection as in Example 19.b.; chromatography solvent: ethyl acetate:dichloromethane (20:80); TLC: $R_f$=0.35, methanol:dichloromethane (5:95);

Example 104.b.: R=2-methoxycarbonylphenylacetyl: Deprotection as in Example 19.b.; TLC: $R_f$=0.5, diethyl ether.

Example 105.b.: R=(diethoxyphosphoryl)methylaminocarbonyl: Deprotection as in Example 1.e.; chromatography solvent: methanol:dichloromethane (gradient, 3:97, 7:93); TLC: $R_f$=0.38, methanol:dichloromethane (10:90); MS: m/z=591(M+1).

Example 106.b.: R=4-methoxycarbonylphenylacetyl: Deprotection as in Example 19.b.; TLC: $R_f$=0.33, ethyl acetate:dichloromethane (20:80); MS: m/z=574(M+1).

Example 107.b.: R=3-methoxycarbonylphenylacetyl: Deprotection as in Example 19.b.; TLC: $R_f$=0.19, ethyl acetate:dichloromethane (20:80); MS: m/z=574(M+1).

Example 108.b.: R=4-pyridylmethylaminocarbonyl: Deprotection as in Example 1.e.; chromatography solvent: methanol:dichloromethane (10:90); TLC: $R_f$=0.15, methanol:dichloromethane (10:90); MS: m/z=532(M+1).

Example 109.b.: R=3-pyridylmethylaminocarbonyl: Deprotection as in Example 1.e.; chromatography solvent: methanol:dichloromethane (10:90); TLC: $R_f$=0.1, methanol:dichloromethane (5:95); MS: m/z=532(M+1).

Example 110.b.: R=2-(4-pyridyl)ethoxycarbonyl: Deprotection as in Example 1.e.; chromatography solvent: ethyl acetate; MS: m/z=547(M+1).

Example 111.b.: R=2-morpholinoethylaminocarbonyl: Deprotection as in Example 1.e.; chromatography solvent: methanol:dichloromethane (5:95); TLC: $R_f$=0.5, methanol:dichloromethane (5:95).

Example 112.b.: R=ethoxycarbonylaminocarbonyl: Deprotection as in Example 1.e.; chromatography solvent: ethyl acetate:dichloromethane (10:90); MS: m/z=513(M+1).

Example 113.b.: R=3-methoxycarbonylanilinocarbonyl: Deprotection as in Example 1.e.; chromatography solvent: methanol:dichloromethane (5:95); TLC: $R_f$=0.18, methanol:dichloromethane (5:95); MS: m/z=589(M+1).

Example 114.b.: R=2-benxyloxycarbonylanilinocarbonyl: Deprotection as in Example 19.b.; chromatography solvent: ethyl acetate:dichloromethane (25:75); TLC: $R_f$=0.5, ethyl acetate:dichloromethane (25:75); MS: m/z=651(M+1).

Example 115.b.: R=4-(dimethoxyphosphoryl)benzyloxycarbonyl: Deprotection as in Example 1.e.; chromatography solvent: methanol:dichloromethane (10:90); TLC: $R_f$=0.45, methanol:dichloromethane (10:90); MS: m/z=640(M+1).

Example 116.b.: R=2-pyridylaminocarbonyl: Deprotection as in Example 1.e.; chromatography solvent: methanol:dichloromethane (5:95); TLC: $R_f$=0.55, methanol:dichloromethane (10:90); MS: m/z=518(M+1).

Example 117.b.: R=2-(2-pyridyl)ethoxycarbonyl: Deprotection as in Example 19.b.; chromatography solvent: ethyl acetate; TLC: $R_f$=0.4, ethyl acetate; MS: m/z=547(M+1).

Example 118.b.: R=2-(2-tert-butoxycarbonylaminothiazol-4-yl)-ethoxycarbonyl: Deprotection as in Example 1.e.; chromatography solvent: ethyl acetate; MS: m/z=668(M+1).

Example 119.b.: R=1-methylpiperid-4-yloxycarbonyl: Deprotection as in Example 1.e.; chromatography solvent: methanol:dichloromethane (gradient, 10:90, 20:80); MS: m/z=539(M+1).

Example 120.b.: R=2-piperidinoethylaminocarbonyl: Deprotection as in Example 1.e.; chromatography solvent: methanol:dichloromethane (gradient, 10:90, 15:85); MS: m/z=552(M+1).

Example 121.b.: R=6-methylpyrid-2-ylmethoxycarbonyl: Deprotection as in Example 1.e.; chromatography solvent: methanol:dichloromethane (5:95); MS: m/z=547(M+1).

EXAMPLE 122

2-[3-(2-Carboxyphenylacetylamino)-2-oxo-6-phenyl-1,2-dihydro- 1-pyridyl]-N-(3,3,3-trifluoro-1-isopropyl-2-oxopropyl)acetamide.

To 2-[3-(2-Benzyloxycarbonylphenylacetylamino)-2-oxo-6-phenyl- 1,2-dihydo-1-pyridyl]-N-(3,3,3-trifluoro-1-isopropyl-2-oxopropyl)acetamide (0.6 g) in methanol (50 mL) was added 10% (w/w) palladium on carbon (0.2 g), and the mixture was shaken under a hydrogen atmosphere (3.4 bar) for 3 h. The catalyst was filtered and the solvent evaporated to give a solid which was chromatographed, eluting with methanol:dichloromethane (gradient, 2:98 to 10:90), to give the title compound (0.5 g); TLC: $R_f$=0.25, methanol:dichloromethane (10:90); MS: m/z=588(M+1).

Analysis for: $C_{28}H_{26}F_3O_6N_3 \cdot 0.5$ $H_2O$: Calculated: C, 59.36; H 4.80; N 7.41 Found: C, 59.40; H, 4.91; N, 7.28

EXAMPLE 123

2-[3-[3-(2-Carboxyphenyl)ureido]-2-oxo-6-phenyl-1,2-dihydro-1-pyridyl]-N-(3,3,3-trifluoro-1-isopropyl-2-oxopropyl)acetamide.

2-[3-[3-(2-Benzyloxycarbonylphenyl )ureido]-2-oxo-6-phenyl-1,2- dihydro-1-pyridyl]-N-(3,3,3-trifluoro-1-isopropyl-2-oxopropyl)-acetamide was hydrogenolyzed using a procedure similar to that outlined in Example 122 to give the title compound; chromatography solvent: methanol:dichloromethane (gradient, 5:95, 10:90); MS: m/z=559(M+1).

Analysis for: $C_{27}H_{25}F_3N_4O_6 \cdot 0.75$ $H_2O$: Calculated: C, 56.69; H, 4.67; N, 9.79 Found: C, 56.62; H, 4.61; N, 9.63

EXAMPLES 124–126

The following compounds of formula I wherein $R^0$ is isopropyl, R is the indicated acyl group which contains a carboxy moiety, $R^5$ is hydrogen and $R^6$ is phenyl were prepared by hydrolysis of the ester groups of corresponding compounds of formula I in which the acyl group R contains an ester moiety, prepared as described in Examples 106, 107, and 113, respectively. In each example, the hydrolysis was carried out using a procedure similar to that described in Example 106.a.iv. to give the acid:

Example 124: R=4-carboxyphenylacetyl: Chromatography solvent: methanol:dichloromethane (gradient, 0:0:100, 35:5:60); TLC: $R_f$=0.45, methanol:dichloromethane (20:80); MS: m/z=558(M+1).

Analysis for: $C_{27}H_{26}F_3N_3O_6$: Calculated: C, 60.32; H, 4.70; N, 7.54 Found: C, 60.52; H, 4.87; N, 7.22

Example 125: R=3-carboxyphenylacetyl: Chromatography solvent: methanol:ethyl acetate:dichloromethane (gradient, 0:0:100, 5:35:10, 10:35:55); TLC: $R_f$=0.43, methanol:dichloromethane (20:80), MS: m/z=558(M+1).

Analysis for: $C_{27}H_{26}F_3N_3O_6$: Calculated: C, 60.32; H, 4.70; N, 7.54 Found: C, 60.04; H, 4.81; N, 7.32

Example 126: R=3-carboxyanilinocarbonyl: MS: m/z=559(M+1).

Analysis for: $C_{27}H_{25}F_3N_4O_6 \cdot 0.5$ $H_2O$: Calculated: C, 57.14; H, 4.62; N, 9.87 Found: C, 57.24; H, 4.65; N, 9.70

EXAMPLE 127

2-[2-Oxo-[3-(1-oxopyrid-4-ylmethyl)ureido]-6-phenyl-1,2-dihydro-1-pyridyl]-N-(3,3,3-trifluoro-1-isopropyl-2-oxopropyl)acetamide.

2-[2-Oxo-6-phenyl-3-[3-(4-pyridylmethyl)ureido]-1,2-dihydro- 1-pyridyl]-N-(3,3,3-trifluoro-1-isopropyl-2-oxopropyl)-acetamide (0.83 g) was combined with dioxirane (40 mL, 0.035M, Murry *J. Org. Chem.* (1985), 2847) in acetone (10 mL), and the mixture was allowed to stir for 0.5 h. The solvent was evaporated and the residue purified by chromatography, eluting with methanol:dichloromethane (gradient, 10:90, 20:80), to provide the title compound (0.42 g); TLC: $R_f$=0.5, methanol:dichloromethane (20:80); MS: m/z=546(M+1).

Analysis for $C_{26}H_{26}F_3N_5O_5 \cdot 0.5$ $H_2O$: Calculated: C, 56.32; H, 4.91; N, 12.63 Found: C, 56.13; H, 4.92; N, 11.69

EXAMPLE 128

2-[2-Oxo-3-[3-(1-oxopyrid-3-ylmethyl)ureido]-6-phenyl-1,2-dihydro-1-pyridyl]-N-(3,3,3-trifluoro-1-isopropyl-2-oxopropyl)-acetamide.

2-[2-Oxo-6-phenyl-3-[3-(3-pyridylmethyl)uriedo]-1,2-dihydro- 1-pyridyl]-N-(3,3,3-trifluoro-1-isopropyl-2-oxopropyl)acetamide was oxidized using a procedure similar to that described in Example 127 to give the title compound; chromatography solvent: methanol:dichloromethane (gradient, 10:90, 20:80); TLC: R$_f$=0.35, methanol:dichloromethane (20:80); MS: m/z=546(M+1), 544(M−1) by FAB.

Analysis for C$_{26}$H$_{26}$F$_3$N$_5$O$_5$.H$_2$O: Calculated: C, 55.53; H, 5.23; N, 12.10 Found: C, 55.70; H, 5.03; N, 11.72

EXAMPLE b 129

2-[2-Oxo-3-[3-(1-oxopyrid-2-yl)ureido]-6-phenyl-1,2-dihydrol-1-pyridyl]-N-(3,3,3-trifluoro-1-isopropyl-2-oxopropyl)-acetamide.

2-[2-Oxo-6-phenyl-3-[3-(2-pyridyl)ureido]-1,2-dihydro-1-pyridyl]-N-( 3,3,3-trifluoro-1-isopropyl-2-oxopropyl)acetamide was oxidized using a procedure similar to that described in Example 127 to give the title compound; chromatography solvent: methanol:dichloromethane (10:90); MS: m/z=532(M+1), 530(M−1) by FAB.

Analysis for C$_{25}$H$_{24}$F$_3$N$_5$O$_5$: Calculated: C, 56.50; H, 4.55; N, 13.18 Found: C, 54.66; H, 4.64; N, 12.72

EXAMPLE 130

2-[2-Oxo-6-phenyl-3-[4-(N-phenylsulfonylcarbamoyl)phenylacetylamino]-1,2-dihydro-1-pyridyl]-N-(3,3,3-trifluoro-1-isopropyl-2-oxopropyl)acetamide.

2-[2-Oxo-6-phenyl-3-[4-(N-phenylsulfonylcarbamoyl)phenylacetylamino]- 1,2-dihydro-1-pyridyl]-N-(3,3,3-trifluoro-2-hydroxy- 1-isopropylpropyl)acetamide was oxidized using a procedure similar to that described in Example 61 to give the title compound; chromatography solvent: methanol:dichloromethane (gradient, 1:99, 3:97); TLC: R$_f$=0.3, methanol:dichloromethane (5:95); MS: m/z=695 (M−1) by FAB.

The intermediate alcohol was prepared as follows:
a. 2-[3-(4-Carboxyphenylacetylamino)-2-oxo-6-phenyl-1,2-dihydro- 1-pyridyl]-N-(3,3,3-trifluoro-2-hydroxy-1-isopropylpropyl)acetamide.

2-[3-(4-Methoxycarbonylphenylacetylamino)-2-oxo-6-phenyl-1,2-dihydro- 1-pyridyl]-N-(2-tert-butyldimethylsilyloxy-3,3,3-trifluoro-1-isopropylpropyl)acetamide (1.0 g) was dissolved in tetrahydrofuran:methanol:water (4:1:1) and cooled to 0° C. Lithium hydroxide (0.312 g) was added and the mixture was allowed to stir for 6 h. The mixture was cooled to −78° C. for 12 h and then allowed to warm to room temperature for 4 h. The mixture was diluted with water and 1N hydrochloric acid to pH 2, extracted with ethyl acetate, dried, evaporated and crystallized from ethyl acetate/hexane to give the hydroxy acid (0.75 g).

b. 2-[2-Oxo-6-phenyl-3-[4-(N-phenylsulfonylcarbamoyl)phenylacetylamino]- 1,2-dihydro-1-pyridyl]-N-(3,3,3-trifluoro-2-hydroxy-1-isopropylpropyl)acetamide.

To a solution of 2-[3-(4-carboxyphenylacetylamino)-2-oxo- 6-phenyl-1,2-dihydro-1-pyridyl]-N-(3,3,3-trifluoro-2-hydroxy-1-isopropylpropyl)acetamide (0.52 g), benzenesulfonamide (0.16 g) and 4-dimethylaminopyridine (0.13 g) dissolved in dichloromethane (43 mL) and dimethylformamide (3 mL) was added 1-(3-dimethylaminopropyl)-3-ethylcarbodiimide (0.2 g), and the mixture was allowed to stir for 5 days. The mixture was diluted with ethyl acetate, washed (1N hydrochloric acid), dried (MgSO$_4$), evaporated, and the resulting material chromatographed, eluting with dichloromethane:methanol (gradient, 0:100, 2.5:97.5, 5:95), to provide material which was rechromatographed, eluting with ethyl acetate:dichloromethane (gradient, 25:75.0, 30:70:0; 0:99:1, 0:97.5:2.5, 0:95:5), to provide the alcohol (0.32 g); TLC: R$_f$=0.74, methanol:dichloromethane (15:85); MS: m/z=699(M+1), 697(M−1) by FAB.

EXAMPLE 1.31

2-[2-Oxo-6-phenyl-3-[3-(N-phenylsulfonylcarbamoyl)phenylacetylamino]- 1,2-dihydro-1-pyridyl]-N-(3,3,3-trifluoro-1-isopropyl-2-oxopropyl)acetamide.

Using a procedure similar to that described in Example 130, substituting 2-[3-(3-methoxycarbonylphenylacetylamino)-2-oxo-6-phenyl- 1,2-dihydro-1-pyridyl]-N-(2-tert-butyldimethylsilyloxy- 3,3,3-trifluoro-1-isopropylpropyl)acetamide for 2-[3-(4-methoxycarbonylphenylacetylamino)- 2-oxo-6-phenyl-1,2,-dihydro-1-pyridyl]-N-( 2-tert-butyldimethylsilyloxy-3,3,3-trifluoro-1-isopropylpropyl)acetamide at the step corresponding to Example 130.a., the title compound was prepared; TLC: R$_f$=0.5, methanol:dichloromethane (20:80); MS: m/z=697(M+1), 695(M−1) by FAB.

Analysis for C$_{22}$H$_{22}$F$_3$N$_7$O$_4$. H$_2$O: Calculated: C, 50.47; H, 4.62; N, 18.73 Found: C, 50.71; H, 4.37; N, 18.70

EXAMPLE 132

2-[2-Oxo-6-phenyl-3-(tetrazol-5-ylacetylamino)-1,2-dihydro-1-pyridyl]-N-(3,3,3-trifluoro-1-isopropyl-2-oxopropyl)acetamide.

2-[2-Oxo-6-phenyl-3-(1-triphenylmethyltetrazol-5-ylacetylamino)- 1,2-dihydro-1-pyridyl)-N-(3,3,3-trifluoro-2-hydroxy-1-isopropylpropyl)acetamide was oxidized using a procedure similar to that outlined in Example 61. The material obtained from extraction and solvent removal was redissolved in tetrahydrofuran and treated with 1N hydrochloric acid to remove the triphenylmethyl protecting group. The solution was allowed to stir for 0.5 hr. The product was extracted into ethyl acetate, dried, evaporated and chromatographed, eluting with methanol:dichloromethane (gradient, 5:95 to 30:70) to give the title compound; TLC: R$_f$=0.5, methanol:dichloromethane (20:80); MS: m/z=506(M+1).

Analysis for C$_{22}$H$_{22}$F$_3$N$_7$O$_4$.H$_2$O: Calculated: C, 50.47; H, 4.62; N, 18.73 Found: C, 50.71; H, 4.37; N, 18.70

The intermediate alcohol was prepared as follows:
a. Ethyl 1-triphenylmethyltetrazol-5-ylacetate.

To a solution of ethyl 5-tetrazolylacetate (1 g) (Lofquist et al. *J. Amer. Chem. Soc.* (1958), 80, 3908) in pyridine (6 mL) was added triphenylmethyl chloride (2.2 g) and the resulting solution allowed to stir for 3 h. The solvent was evaporated and the product crystallized from ether/hexane to give ethyl 3-triphenylmethyltetrazol-5-ylacetate as a white solid (2 g); TLC: R$_f$=0.5, ether:hexane (50:50).

b. 1-Triphenylmethyltetrazol-5-ylacetic acid.

To a solution of ethyl 1-triphenylmethyltetrazol-5-ylacetate (1.95 g) in tetrahydrofuran (12 mL), methanol (4 mL), and H$_2$O (4 mL) was added lithium hydroxide (0.61 g) and the resulting solution was allowed to stir for 2 h. The solution was acidified to pH 2, the product extracted into dichloromethane, dried, and evaporated to give the acid as a white solid (1.61 g); TLC: R$_f$=0.2, ether.

c. 2-[2-Oxo-6-phenyl-3-(1-triphenylmethyltetrazol-5-ylacetylamino)- 1,2-dihydro-1-pyridyl]-N-(2-tert-butyldimethylsilyloxy-3,3,3-trifluoro- 1-isopropylpropyl)acetamide.

2-(3-Amino-2-oxo-6-phenyl-1,2-dihydro-1-pyridyl)-N-(2-tert-butyldimethylsilyloxy- 3,3,3-trifluoro-1-isopropylpropyl)acetamide was acylated using a procedure similar to Acylation Method B, with 2-(3-triphenylmethyltetrazol-5-yl)acetic acid as an acylating agent, to give the amide; chromatography solvent: diethyl ether:hexane (70:30); TLC: $R_f$=0.5, diethyl ether.

d. 2-[2-Oxo-6-phenyl-3-(1-triphenylmethyltetrazol-5-ylacetylamino)- 1,2-dihydro-1-pyridyl]-N-(3,3,3-trifluoro-2-hydroxy-1-isopropylpropyl)acetamide.

The tert-butyldimethylsilyl group was removed from 2-[2-oxo-6-phenyl-3-(1-triphenylmethyltetrazol-5-ylacetylamino)-1,2,-dihydro- 1-pyridyl]-N-(2-tert-butyldimethylsilyloxy-3,3,3-trifluoro- 1-isopropylpropyl)acetamide using a procedure similar to that outlined in Example 1.e. to give the alcohol; chromatography solvent: ethyl acetate:dichloromethane (30:70); TLC: $R_f$=0.5, ethyl acetate:dichloromethane (30:70).

EXAMPLE 133

2-[2-Oxo-6-phenyl-3-[3-(5-tetrazolyl)ureido]-1,2-dihydro-1-pyridyl]-N-(3,3,3-trifluoro-1-isopropyl-2-oxopropyl)acetamide.

2-[2-Oxo-6-phenyl-3-[3-(1-triphenylmethyltetrazol-5-yl)ureido]- 1,2-dihydro-1-pyridyl)-N-(3,3,3-trifluoro-2-hydroxy-1-isopropylpropyl)acetamide was subjected to a procedure similar to that outlined in Example 132 to give the title compound; chromatography solvent: methanol:dichloromethane (10:90); MS: m/z=507(M+1), 505(M−1) by FAB.

Analysis for $C_{21}H_{21}F_3N_8O_4 \cdot 0.75\ H_2O$: Calculated: C, 48.51; H, 4.36; N, 21.,55 Found: C, 48.35; H, 4.12; N, 21.17

The intermediate 2-[2-oxo-6-phenyl-3-[3-(1-triphenylmethyltetrazol- 5-yl)ureido]-1,2-dihydro-1-pyridyl)-N-(3,3,3-trifluoro-2-hydroxy-1-isopropylpropyl)acetamide was prepared as follows:

a. 2-[2-Oxo-6-phenyl-3-[3-(5-tetrazolyl)ureido]-1,2-dihydro-1-pyridyl]-N-( 2-tert-butyldimethylsilyloxy-3,3,3-trifluoro-1-isopropylpropyl)acetamide.

2-(3-Amino-2-oxo-6-phenyl-1,2-dihydro-1-pyridyl)-N-(2-tert-butyldimethylsilyloxy- 3,3,3-trifluoro-1-isopropylpropyl)acetamide was combined with 5-aminotetrazole using a procedure similar to Acylation Method D to give the urea; chromatography solvent: methanol:dichloromethane (15:85); TLC: $R_f$=0.2, ethyl acetate; MS: m/z=623(M+1), 621(M−1) by FAB.

b. 2-[2-Oxo-6-phenyl-3-[3-(1-triphenylmethyltetrazol-5-yl)ureido]- 1,2-dihydro-1-pyridyl]-N-(2-tert-butyldimethylsilyloxy-3,3,3-trifluoro-1-isopropylpropyl)acetamide.

To a solution of 2-[2-oxo-6-phenyl-3-[3-(5-tetrazolyl)ureido]- 1,2-dihydro-1-pyridyl]-N-(2-tert-butyldimethylsilyloxy-3,3,3-trifluoro-1-isopropylpropyl)acetamide (0.15 g) in pyridine (2 mL) was added triphenylmethyl chloride (0.13 g) and the resulting solution was allowed to stir for 3 h. The pyridine was evaporated and the residue was dissolved in ethyl acetate, washed (H$_2$O, brine), dried (MgSO$_4$), and evaporated. The product was purified by chromatography, with diethyl ether as the eluent, to give the triphenylmethyl compound; TLC: $R_f$=0.7, diethyl ether; MS: m/z=864(M−1) by FAB.

c. 2-[2-Oxo-6-phenyl-3-[3-(1-triphenylmethyltetrazol-5-yl)ureido]- 1,2-dihydro-1-pyridyl]-N-(3,3,3-trifluoro-2-hydroxy-1-isopropylpropyl)acetamide.

2-[2-Oxo-6-phenyl-3-[3-(1-triphenylmethyltetrazol-5-yl)ureido]- 1,2-dihydro-1-pyridyl]-N-(2-tert-butyldimethylsilyloxy-3,3,3-trifluoro-1-isopropylpropyl)acetamide was subjected to a procedure similar to that described in Example 1.e. to give the alcohol; chromatography solvent: diethyl ether; TLC: $R_f$=0.2, diethyl ether.

EXAMPLE 134

2-[3-[2-(2-Aminothiazol-5-yl)ethoxycarbonylamino]-2-oxo-6-phenyl-1,2-dihydro-1-pyridyl]-N-(3,3,3-trifluoro-1-isopropyl-2-oxopropyl)acetamide.

To 2-[3-[2-(2-tert-butoxycarbonylaminothiazol-5-yl)ethoxycarbonylamino]- 2-oxo-6-phenyl-1,2-dihydro-1-pyridyl]-N-(3,3,3-trifluoro-1-isopropyl-2-oxopropyl)acetamide (0.9 g) in methylene chloride (5 mL) was added trifluoroacetic acid (1 mL), and the resulting solution was allowed to stir for 3 h. The solvents were evaporated and the residue chromatographed, eluting with methanol:methylene chloride (5:95), to give the title compound (0.46 g); MS: m/z=566(M+1).

EXAMPLE 135

2-[2-Oxo-6-phenyl-3-(3-phenylsulfonylureido)-1,2-dihydro-1-pyridyl]-N-(3,3,3-trifluoro-1-isopropyl-2-oxopropyl)acetamide.

To 2-(3-amino-2-oxo-6-phenyl-1,2-dihydro-1-pyridyl)-N-(3,3,3-trifluoro- 1-isopropyl-2-oxopropyl)acetamide (0.5 g) in dichloromethane (40 mL) was added benzenesulfonyl isocyanate (0.23 g), and the resulting solution was allowed to stir for 1 h. The solvent was evaporated and the product was purified by chromatography to provide the title compound (0.7 g); chromatography solvent: methanol:dichloromethane (5:95); TLC: $R_f$=0.6, methanol:dichloromethane (10:90); MS: m/z=579(M+1), 577(M−1) by FAB.

Analysis for $C_{26}H_{25}F_3N_4O_6S \cdot 0.5\ H_2O$: Calculated: C, 53.15; H, 4.46; N, 9.54 Found: C, 53.07; H, 4.48; N, 9.40

EXAMPLES 136–145

Using a similar procedure to that described in Example 1, the following compounds of Formula I wherein $R^0$ is isopropyl, $R^5$ is hydrogen, $R^6$ is phenyl and R has the indicated value were prepared by oxidation of the corresponding alcohols of formula II.

Example 136: R=methoxymalonyl: Chromatography solvent: dichloromethane:methanol (98:2), then recrystallized from ethyl acetate/hexane; mp 164.5°–167° C. TLC: $R_f$=0.63, chloroform:methanol (9:1); NMR: 0.84 (d,3, J=6.7), 0.89 (d,3, J=6.7), 2.16 (m,1), 3.65 (s,3), 3.70 (s,2), 4.23–4.86 (m,2), 6.22 (d,1, J=7.6), 7.34–7.50 (m,5), 8.30 (d,1, J=7.7), 8.76 (d,1), 9.81 (s,1); IR(KBr): 1645, 1605, 1600, 1530 cm$^{-1}$; MS: m/z=496(M4.1).

Analysis for $C_{23}H_{24}F_3N_3O_6 \cdot 0.25\ H_2O$: Calculated: C, 55.26; H, 4.94; N, 8.40 Found: C, 55.21; H, 4.88; N, 8.33

Example 137: R=methoxysuccinyl: Purified by recrystallization from ethyl acetate:2-butanone (10:1); mp 173°–175° C.; TLC: $R_f$=0.35, dichloromethane:methanol (20:1); 300 MHz NMR: 0.89 (2d,6), 2.20 (m,1), 2.58 (t,2), 2.75 (t,2), 3.60 (s,3), 4.50 (q,2), 4.63 (t,1), 6.20 (d,1), 7.43 (m,5), 8.27

(d,1), 8.76 (d,1), 9.45 (s,1); IR(KBr): 3320 (broad), 1745, 1650, 1530, 1375, 1220, 1155, 700 cm$^{-1}$; MS: m/z=510(M+1).

Analysis for $C_{24}H_{26}F_3N_3O_6 \cdot 0.50\ H_2O$: Calculated: C, 55.60; H, 5.25; N, 8.10 Found: C, 55.71; H, 5.06; N, 7.99

Example 138: R=oxazolidin-2-on-3-ylacetyl: Chromatography solvent: dichloromethane:methanol (20:1), then recrystallization from ethyl acetate; mp 172°–182° C.; TLC: $R_f$=0.4, dichloromethane:methanol (95:5); NMR: 0.83 (d,3), 0.89 (d,3), 2.15 (m,1), 3.61 (t,2), 4.14 (s,2), 4.37 (t,2), 4.46 (d,1), 4.56 (d,1), 4.63 (dd,2), 6.21 (d,1), 7.3–7.5 (m,6), 8.26 (d,1), 8.75 (d,1), 9.67 (s,1); IR(KBr): 1740, 1530 cm$^{-1}$; MS: m/z=523(M+1).

Analysis for $C_{24}H_{25}F_3N_4O_6$: Calculated: C, 55.17; H, 4.82; N, 101.72 Found: C, 54.84; H, 4.82; N, 10.56

Example 139: R=dimethylaminosuccinyl: Chromatography solvent: dichloromethane:methanol (98:2); mp 167°–170° C. (dec); TLC: $R_f$=0.35, dichloromethane:methanol (20:1); NMR: 0.88 (2d,6), 2.18 (m,6), 2.65 (2d,4), 2.85 (s,3), 3.00 (s,3), 4.52 (q,2), 4.65 (t,1), 6.22 (d,1), 7.45 (m,5), 8.30 (d,1), 8.77 (d,1), 9.35 (s,1); IR(KBr): 3300, 1760, 1650, 1530 cm$^{-1}$; MS: m/z=523(M+1).

Analysis for $C_{24}H_{29}F_3N_4O_5 \cdot 0.75\ H_2O$: Calculated: C, 56.02; H, 5.73; N, 10.45 Found: C, 56.07; H, 5.46; N, 10.31

Example 140: R=2-benzoxazolinon-3-ylacetyl: Purified by trituration with dietyl ether:hexane (5:95), then with ethyl acetate; mp 252°–254° C. (dec); TLC: $R_f$=0.63, chloroform:methanol (9:1); NMR: 0.86 (d,3, J=6.7), 0.92 (d,3, J=6.8), 2.16 (m,1), 4.5–4.75 (m,3), 6.20 (d,1, J=7.7), 7.1–7.34 (m,4), 7.34–7.56 (m,5), 8.22 (d,1, J=7.7), 8.77 (d,1, J=6.5), 10.05 (s,1); IR(KBr): 1775, 1700, 1650, 1610 cm$^{-1}$; MS: m/z=571(M+1).

Analysis for $C_{25}H_{25}F_3N_4O_6$: Calculated: C, 58.97; H, 4.42; N, 9.82 Found: C, 58.76; H, 4.55; N, 9.81

Example 141: R=succinimidoacetyl: Chromatography solvent: dichloromethane:ethyl acetate (1:1); mp 217°–222° C. (dec); TLC: $R_f$=0.42, ethyl acetate; NMR: 0.84 (d,3), 0.90 (d,3), 2.14 (m,1), 2.73 (s,4), 4.35 (s,1), 6.19 (d,1, J=7.6), 7.49 (m,5), 8.20 (d,1, J=7.6), 8.76 (d,1, J-7.0), 9.91 (s,1); IR(KBr): 1710, 1645, 1600 cm$^{-1}$; MS: m/z=535(M+1).

Analysis for $C_{25}H_{25}F_3N_4O_6$: Calculated: C, 56.18; H, 4.71; N, 10.66 Found: C, 55.98; H, 4.85; N, 10.31

Example 142: R=2-pyrrolidinon-1-ylacetyl: Chromatography solvent: dichloromethane:methanol (96:4), then preparative (thick layer) TLC, dichloromethane:methanol (9:1); mp 198.5°–200.5° C.; TLC: $R_f$=0.65, chloroform:methanol (9:1); NMR: 0.82 (d,3), 0.88 (d,3), 1.95 (broad t,2), 2.15 (m,1), 2.22 (broad t,2, J=7.5), 3.39 (broad t,2, J=6.7), 6.19 (d,1, J=7.4), 7.41 (m,5), 8.23 (d,1, J=7.6), 8.73 (d,1, J=6.7), 9.53 (s,1); MS: m/z=521(M+1).

Analysis for $C_{25}H_{27}F_3N_4O_5$: Calculated: C, 57.69; H, 5.23; N, 10.76 Found: C, 57.42; H, 5.27; N, 10.71

Example 143: R=phthalimidoacetyl: Chromatography solvent: dichloromethane:methanol (98:2), then trituration with diethyl ether; mp 229°–230° C.; TLC: $R_f$=0.68, dichloromethane:methanol (9:1); 300 MHz NMR: 0.85 (d,3, J=6.7), 0.91 (d,3, J=6.7), 2.33 (m,1), 6.20 (d,1, J=7.7), 7.40 (m,5), 7.92 (m,4), 8.19 (d,1, J=7.6), 8.78 (d,1, J=7.0), 10.05 (s,1); IR(KBr): 1720, 1650 cm$^{-1}$; MS: m/z=583(M+1).

Analysis for $C_{29}H_{25}F_3N_4O_6$: Calculated: C, 59.79; H, 4.32; N, 9.62 Found: C, 59.41; H, 4.33; N, 9.59

Example 144: R=cis-hexahydrophthalimidoacetyl: Chromatography solvent: dichloromethane:tetrahydrofuran (9:1); mp 126°–131° C.; TLC: $R_f$=0.61, dichloromethane:tetrahydrofuran (8:2); NMR: 0.82 (d,3, J=6.8), 0.88 (d,3, J=6.7), 1.36 (broad d,4), 1.72 (broad d,4), 2.14 (m,1), 2.98 (broad t,2), 4.32 (s,2), 6.16 (d,1 J=7.7), 7.38 (m,5), 8.18 (d,1 J=7.7), 8.72 (d,1J=7.1), 9.88 (s,1); IR(KBr): 1710, 1645, 1520 cm$^{-1}$; EI MS: m/z=588(M).

Analysis for $C_{29}H_{31}F_3N_4O_6 \cdot 0.5\ H_2O$: Calculated: C, 58.29; H, 5.40; N, 9.38 Found: C, 58.46; H, 5.36; N, 9.32

Example 145: R=methoxyoxalyl: Chromatography solvent: dichloromethane:methanol (98:2); mp 227°–228° C.; TLC: $R_f$=0.30, dichloromethane:methanol (95:5); NMR: 0.82 (d,3 J=6.8), 0.87 (d,3 J=6.7), 2.12 (m,1), 3.94 (s,3), 6.29 (d,1, J=8.0), 7.41 (m,5), 8.26 (d,1, J=7.6), 8.75 (d,1, J=6.9), 9.72 (s,1); IR(KBr): 1755, 1710, 1642 cm$^{-}$; MS: m/z=482(M+1).

Analysis for $C_{22}H_{22}F_3N_3O_6 \cdot 0.25\ H_2O$: Calculated: C, 54.38; H, 4.67; N, 8.65 Found: C, 54.28; H, 4.64; N, 8.55

The corresponding alcohols of formula II for Examples 136–145 were prepared as follows:

EXAMPLES 136.a.–145.a.

2-(3-Acylamino-2-oxo-6-phenyl-1,2-dihyro-1-pyridyl-N-(2-tert-butyldimethylsilyloxy- 3,3,3-trifluro-1-isopropylpropyl)acetamides having the indicated acyl group R were prepared from 2-(3-amino-2-oxo- 6-phenyl-1,2-dihydro-1-pyridyl)-N-(2-tert-butyl-dimethylsilyloxy- 3,3,3-trifluoro-1-isopropylpropyl)acetamide using the indicated acylation method, except as otherwise noted or described.

Example 136.a.: R=methoxymalonyl: Acylation Method A using methyl malonyl chloride and using sodium carbonate instead of triethylamine; not purified, but used directly; TLC: $R_f$=0.69, dichloromethane:methanol (9:1); MS: m/z=612(M+1).

Example 137.a.: R=methoxysuccinyl: Acylation Method A using methyl succinoyl chloride and using sodium carbonate instead of triethylamine; not purified, but used directly; TLC: $R_f$=0.46, dichloromethane:methanol (95:5); MS: m/z=626(M+1).

Example 138.a.: R=oxazolidin-2-on-3-ylacetyl: Acylation Method B using oxazolindin-2-on-3-ylacetic acid (K. Potts *J. Org. Chem.* (1980), 45, 4985); used directly without further purification; TLC: $R_f$=0.6, dichloromethane:ethyl acetate (1:1); MS: m/z=639(M+1).

Example 139.a.: R=dimethlyaminosuccinyl: Acylation Method B using N,N-dimethylsuccinamic acid; used directly without purification; TLC: $R_f$=0.32, dichloromethane:ethyl acetate (3:1); MS: m/z=639(M+1).

Example 140.a.: R=2-benzoxazolinon-3-ylacetyl: Acylation Method B using 2-benzoxazolinon-3-ylacetic acid (K. Potts *J. Org. Chem.* (1980), 45, 4985); used directly without further purification; TLC: $R_f$=0.84, dichloromethane:methanol (9:1); MS: m/z=687(M+1).

Example 141.a.: R=succinimidoacetyl: Acylation Method B using succinimidoacetic acid (Sheehan and Loubach *J. Amer. Chem. Soc.* (1975), 173, 4376); used directly without purification; TLC: $R_f$=0.40, toluene:ethyl acetate (1:1); MS: m/z=651(M+1).

Example 142.a.: R=2-pyrrolidinon-1-ylacetyl: Acylation Method B using 2-pyrrolidinon-1-ylacetyl acid (prepared from the methyl ester); obtained as a 48:52 mixture with methyl 2-pyrrolidinon-1-ylacetate and not purified, but used directly; TLC: $R_f$=0.42, ethyl acetate; MS: m/z=637(M+1).

Example 143.a.: R=phthalimidoacetyl: Acylation Method B using phthalimidoacetic acid (Nefkins et al. *Recueil* (1960), 79, 688); used directly without purification; TLC: $R_f$=0.70, toluene:ethyl acetate (1:1); MS: m/z=699(M+1).

Example 144.a.: R=cis-hexahydrophthalimidoacetyl: Acylation Method B using cis-hexahydrophthalimidoacetic acid (T. Nagase *Chem. Pharm. Bull.* (1964), 37, 1175); used directly without purification; TLC: $R_f$=0.56, toluene:ethyl acetate (1:1); MS: m/z=705(M+1).

Example 145.a.: R=methoxyoxalyl: Acylation Method A using methyl oxalyl chloride and using sodium carbonate instead of triethylamine; used directly without purification; TLC: $R_f$=0.85, dichloromethane:methanol (95:5); MS: m/z=598(M+1).

EXAMPLES 136.b.–145.b.

The following alcohols of formula II having the indicated acyl group R, in which $R^0$ is isopropyl, $R^5$ is hydrogen and $R^6$ is phenyl were prepared by cleavage of the corresponding silyl ethers described above using a similar procedure to that described in Example 19.b. (fluoride buffered with acetic acid).

Example 136.b.: R=methoxymalonyl: Used directly without further purification; TLC: $R_f$=0.53, dichloromethane:methanol (9:1); MS: m/z=498(M+1).

Example 137.b.: R=methoxysuccinyl: Chromatography solvent: dichloromethane:methanol (99:1); TLC: $R_f$=0.31, dichloromethane:methanol (95:5); MS: m/z=512(M+1).

Example 138.b.: R=oxazolidin-2-on-3-ylacetyl: Chromatography solvent: dichloromethane:ethyl acetate (gradient, 1:1 to 1:3); TLC: $R_f$=0.25, dichloromethane:methanol (20:1); MS: m/z=525(M+1).

Example 139.b.: R=dimethylaminosuccinyl: Chromatography solvent: dichloromethane:methanol (99:1); TLC: $R_f$=0.32, dichloromethane:methanol (20:1); MS: m/z=525(M+1).

Example 140.b.: R=2-benzoxazolinon-3-ylacetyl: Chromatography solvent: dichloromethane:ethyl acetate (gradient, 3:1, 2:1); TLC: $R_f$=0.67, dichloromethane:ethyl acetate (1:1); MS: m/z=573(M+1).

Example 141.b.: R=succinimidoacetyl: Chromatography solvent: dichloromethane:ethyl acetate (1:2); TLC: $R_f$=0.54, dichloromethane:methanol (9:1); MS: m/z=537(M+1).

Example 142.b.: R=2-pyrrolidinon-1-ylacetyl: Chromatography solvent: dichloromethane:methanol (96:4); TLC: $R_f$=0.54, dichloromethane:methanol (9:1); MS: m/z=523(M+1).

Example 143.b.: R=phthalimidoacetyl: Chromatography solvent: dichloromethane:methanol (98:2); TLC: $R_f$=0.58, dichloromethane:methanol (9:1); MS: m/z=585(M+1).

Example 144.b.: R=cis-hexahydrophthalimidoacetyl: Chromatography solvent: dichloromethane:ethyl acetate (3:2); TLC: $R_f$=0.51, dichloromethane:methanol (9:1); MS: m/z=590(M+1).

Example 145.b.: R=methoxyoxalyl: Chromatography solvent: dichloromethane:methanol (95:5); TLC: $R_f$=0.23, dichloromethane:methanol (95:5); MS: m/z=484(M+1).

EXAMPLE 146

2-(3-Methanesulfonylacetylamino-2-oxo-6-phenyl-1,2-dihydro-1-pyridyl)-N-(3,3,3-trifluoro-1-isopropyl-2-oxopropyl)acetamide.

A flask was charged with 2-(3-amino-2-oxo-6-phenyl-1,2-dihydro-1-pyridyl)-N-(3,3,3-trifluoro-1-isopropyl-2-oxopropyl)acetamide (0.30 g), methanesulfonylacetic acid (0.14 g), 1-(3-dimethylaminopropyl)-3-ethylcarbodiimide hydrochloride (0.19 g), 4-dimethylaminopyridine (0.12 g), and methylene chloride (8 mL); and the mixture was stirred. Over the next 15 min the initial suspension became completely soluble, and the reaction mixture was stirred overnight. The reaction mixture was diluted with ethyl acetate (25 mL), acidified with 1N aqueous hydrochloric acid, and the organic phase washed (water, brine), dried (MgSO$_4$) and evaporated to yield a yellow/green solid (0.35 g), which was purified by chromatography, eluting with dichloromethane:tetrahydrofuran (9:1), followed by drying overnight under high vacuum at 50° C. to yield an off-white solid (0.16 g); TLC: $R_f$=0.29, dichloromethane:methanol (20:1); NMR: 0.82 (2d,6), 2.17 (m,1), 3.15 (s,3), 4.55 (m,3), 4.62 (s,2), 6.25 (d,1), 7.42 (m,5), 8.32 (d,1), 8.76 (d,1), 10.0 (S,1); IR(KBr): 3280, 2940, 1770, 1690, 1640, 1530, 1310, 1215, 1150 cm$^{-1}$; MS: m/z=516(M+1).

Analysis for $C_{22}H_{24}F_3N_3O_6$: Calculated: C, 51.26; H, 4.69; N, 8.15 Found: C, 51.54; H, 4.80; N, 8.29

EXAMPLE 147

2-(3-Methoxycarbonylamino-2-oxo-6-phenyl-1,2-dihydro-1-pyridyl)-N-(3,3,3-trifluoro-1-isopropyl-2-oxopropyl)acetamide.

To a suspension of 2-(3-amino-2-oxo-6-phenyl-1,2-dihydro-1-pyridyl)-N-(3,3,3-trifluoro-1-isopropyl-2-oxopropyl)acetamide (0.10 g) and anhydrous sodium carbonate (0.60 g) in tetrahydrofuran (1.5 mL) was added a 1.5 mL tetrahydrofuran solution of methyl chloroformate (0.30 g), and the mixture was stirred overnight. The reaction mixture was diluted with ethyl acetate (5 mL), acidified with 1N aqueous hydrochloric acid, and the organic phase washed (water, brine), dried (MgSO$_4$) and evaporated to yield a light-yellow foam (0.08 g). Silica (preparative-plate) chromatography, eluting with methylene chloride:ethyl acetate (6:1), followed by drying overnight under high vacuum at 40° C., yielded an off-white solid (0.04 g); mp 204°–206° C. (dec); TLC: $R_f$=0.24, dichloromethane:ethyl acetate (4:1); NMR: 0.90 (2d,6), 2.20 (m,1), 3.70 (s,3), 4.50 (q,2), 4.65 (t,1), 6.25 (d,1), 7.40 (m,5), 7.90 (d,1), 8.40 (s,1), 8.75 (d,1); IR(KBr): 3380, 3280, 1730, 1680, 1645, 1520, 1370, 1200, 1160 cm$^{-1}$; MS: m/z=454(M+1).

Analysis for $C_{21}H_{22}F_3N_3O_5$: Calculated: C, 55.63; H, 4.89; N, 9.27 Found: C, 55.41; H, 4.91; N, 8.93

EXAMPLE 148

2-(3-Hydroxymalonylamino-2-oxo-6-phenyl-1,2-dihydro-1-pyridyl)-N-(3,3,3-trifluoro-1-isopropyl-2-oxopropyl)acetamide.

A solution of 2-(3-methoxymalonylamino-2-oxo-6-phenyl-1,2-dihydro-1-pyridyl)-N-(3,3,3-trifluoro-1-isopropyl-2-oxopropyl)-acetamide (0.87 g) in methanol (10.7 mL) was treated with 1N sodium hydroxide (3.52 mL). After 1.5 h of stirring the reaction was diluted with water (40 mL), made acidic (pH 1) by addition of 1N hydrochloric acid, and was extracted with ethyl acetate (40 mL). The extract was washed with brine, dried and evaporated to give a solid. Purification was by reverse phase flash chromatography of the sodium salt over octadecylsilane coated support (from REGIS), using methanol:water (1:1) as the eluent. The appropriate fractions were combined, the methanol evaporated and the product precipitated by addition of 1N hydrochloric acid. Filtration and drying overnight (75° C. at 13.3 Pa) gave the title compound as a white solid (0.846 g); mp 203°–205° C. (dec); TLC: $R_f$=0.5, on ODS reversed phase plates, methanol:water (65:35) adjusted to pH 6.7 with 0.1% aqueous ammonium acetate; NMR: 0.84 (d,3, J=6.7), 0.90 (d,3, J=6.8), 2.14 (m,1), 3.59 (s,2), 4.51 (dd,2), 4.65 (d,1, J=6.5), 6.21 (d,1, J=7.6), 7.42 (m,5), 8.30 (d,1, J=7.2), 8.76 (d,1, J=7.0), 9.82 (s,1); IR(KBr): 1640, 1535, 1500 cm$^{-1}$; MS: m/z=482(M+1).

Analysis for $C_{22}H_{22}F_3N_3O_6 \cdot 0.1\ H_2O$: Calculated: C, 54.68; H, 4.63; N, 8.70 Found: C, 54.73; H, 4.62; N, 8.70

EXAMPLES 149–150

Using similar procedures to that described in Example 148, the following acids of formula I wherein $R^0$ is isopropyl, $R^5$ is hydrogen, $R_6$ is phenyl and R has the indicated values were prepared by hydrolysis of the corresponding esters of formula I described in Examples 137 and 145, respectively.

Example 149: R=hydroxysuccinyl: Purified by trituration with hexane; mp 213° C. (dec); TLC: $R_f$=0.54, on ODS reversed phase plates, methanol:water (60:40); 300 MHz NMR: 0.88 (2d,6), 2.15 (m,1), 3.00 (t,2), 3.20 (t,2), 4.50 (m,2), 4.65 (t,1), 6.20 (t?,1), 7.43 (m,5), 8.25 (d,1), 8.75 (d,1), 9.40 (s,1), 12.15 (broad s,1), IR(KBr): 3310 (broad), 2990, 1765, 1680, 1645, 1530, 1400, 1150 cm$^{-1}$; MS: m/z=496(M+1).

Analysis for $C_{23}H_{24}F_3N_3O_6 \cdot 0.5\ H_2O$: Calculated: C, 54.70; H, 4.99; N, 8.32 Found: C, 54.98; H, 4.84; N, 8.33

Example 150: R=hydroxyoxalyl: Purified by trituration with ethyl acetate; mp 216°–218° C. (dec); TLC: $R_f$=0.64, on ODS reversed phase plates, methanol:water (65:35).adjusted to pH 5.7 with 0.1% aqueous ammonium acetate; NMR: 0.84 (d,3, J=6.8), 0.90 (d,3, J=6.7), 2.15 (m,1), 4.53 (q,2), 4.64 (t,1), 6.32 (t,1, J=7.6), 7.43 (m,5), 8.30 (d,1, J=7.6), 8.78 (d,1, J=7.0), 9.75 (s,1); IR(KBr): 1760, 1690, 1680, 1640 cm$^{-1}$; MS: m/z=468(M+1).

Analysis for $C_{21}H_{20}F_3N_3O_6 \cdot 0.5\ H_2O$: Calculated: C, 52.94; H, 4.44; N, 8.82 Found: C, 53.19; H, 4.38; N, 8.73

EXAMPLES 151–152

Using a similar procedure to that described in Example 1, the following compounds of formula I wherein $R^0$ is isopropyl, $R^5$ is hydrogen, $R^6$ is phenyl and R has the indicated value were prepared by oxidation of the corresponding alcohols of formula II.

Example 151: R=oxazolidin-2-on-3-ylmethoxycarbonyl: Chromatography solvent: dichloromethane:ethyl acetate (3:1); mp 159°–161° C. (with gas evolution); TLC: $R_f$=0.66, ethyl acetate; NMR: 0.82 (d,3, J=6.8), 0.88 (d,3, J=6.7), 2.13 (m,1), 3.72 (t,2, J=7.9), 4.32 (t,2, J=7.9), 4.49 (d,1, J=9.5), 4.82 (t,2, J=6.9), 5.32 (s,2), 8.22 (d,1, J=7.6), 7.4–7.5 (m,5), 7.87 (d,1, J=7.6), 8.82 (s,1), 8.74 (d,1, J=6.5); IR(KBr): 1775, 1650, 1610 cm$^{-1}$; MS: m/z=539(M+1).

Analysis for $C_{24}H_{25}F_3N_4O_7$: Calculated: C, 53.53; H, 4.68; N, 10.40 Found: C, 53.51; H, 4.68; N, 10.29

Example 152: R=5-methyl-1,3-dioxacyclohex-5-yl-methoxycarbonyl: Chromatography solvent: dichloromethane:methanol (99:1); mp 82°–84° C.; TLC: $R_f$=0.28, dichloromethane:methanol (20:1); NMR: 0.88 (2d,6), 2.18 (m,1), 3.45 (d,2), 3.85 (d,2), 4.15 (s,2), 4.50 (q,2), 4.65 (2d,2), 4.90 (d,1), 6.25 (d,1), 7.42 (m,5), 7.95 (d,1), 8.0 (d,1); IR(KBr): 3320 (broad), 2980, 1740, 1650, 1610, 1530, 1500, 1210, 1165 cm$^{-1}$; MS: m/z=554(M+1).

Analysis for $C_{26}H_{30}F_3N_3O_7 \cdot 0.33\ H_2O$: Calculated: C, 55.82; H, 5.52; N, 7.51 Found: C, 55.83; H, 5.55; N, 7.16

The corresponding alcohols of formula II for Examples 151–152 were prepared as follows.

Examples 151.a.–152.a.

2-(3-Acylamino-2-oxo-6-phenyl-1,2-dihydro-1-pyridyl)-N-( 2-tert-butyldimethylsilyloxy-3,3,3-trifluoro-1-isopropylpropyl)acetamides having the indicated acyl group R were prepared from 2-(3-amino-2-oxo-6-phenyl-1,2-dihydro-1-pyridyl)-N-(2-tert-butyldimethylsilyloxy- 3,3,3-trifluoro-1-isopropylpropyl)acetamide using triphosgene, triethylamine and an alcohol of formula A.OH by Acylation Method D, as described in Example 22.f.

Example 151.a.: R=oxazolidin-2-on-3-ylmethoxycarbonyl: Using oxazolidin-2-on-3-ylcarbinol (Endo et al. *Macromol. Chem.* (1968), 112, 49–57; *Chem. Abstr.* (1968), 69, 3198, Abstract 3190x); used directly without purification; TLC: $R_f$=0.79, dichloromethane:methanol (9:1); MS: m/z=655(M+1).

Example 152.a.: R=5-methyl-1,3-dioxacyclohex-5-yl-methoxycarbonyl: From 5-methyl-1,3-dioxacyclohex-5-yl-carbinol; used directly without purification; TLC: $R_f$=0.61, dichloromethane:ethyl acetate (4:1); MS: m/z=670(M+1).

EXAMPLES 151.b.–152.b.

The following alcohols of formula II having the indicated acyl group R, in which $R^0$ is isopropyl, $R^5$ is hydrogen and $R^6$ is phenyl, were prepared by cleavage of the corresponding silyl ethers described above. The cleavage was carried out using a similar procedure to that described in Example 19.b. (fluoride buffered with acetic acid).

Example 151.b.: R=oxazolidin-2-on-3-ylmethoxycarbonyl: Used directly without purification; TLC: $R_f$=0.46, dichloromethane:methanol (9:1); MS: m/z=424(M+1) for isocyanate resulting from elimination of oxazolidin-2-on-3-ylcarbinol.

Example 152.b.: R=5-methyl-1,3-dioxacyclohex-5-yl-methoxycarbonyl: Chromatography solvent: dichloromethane:ethyl acetate (4:1); TLC: $R_f$=0.28, dichloromethane:methanol (20:1); MS: m/z=556(M+1).

EXAMPLE 153

2-[3-[2,2-bis(hydroxymethyl)propoxycarbonylamino]-2-oxo-6-phenyl-1,2-dihydro-1-pyridyl]-N-(3,3,3-trifluoro-1-isopropyl-2-oxopropyl)acetamide.

To a solution of 2-[3-(5-methyl-1,3-dioxacyclohex-5-yl-methoxy-carbonylamino)- 2-oxo-6-phenyl-1,2-dihydro-1-pyridyl]-N-(3,3,3-trifluoro- 1-isopropyl-2-oxopropyl)acetamide (0.35 g) in methylene chloride (6 mL), cooled to 0° C. , was added dropwise 1.27 mL of a 10M methylene chloride solution of boron trichloride, and the reaction mixture allowed to warm to room temperature over 30 min. The reaction mixture was quenched by pouring into 25 mL of a 15% aqueous sodium chloride solution and stirring 15 min. Ethyl acetate (10 mL) was added, and the organic phase washed with brine, dried (MgSO$_4$) and evaporated. Chromatography, using as eluant methylene chloride:methanol (20:1), followed by overnight vacuum-drying (50° C. at 27 Pa) yielded the title compound as a white solid (0.25 g); mp 94°–97° C. (dec); TLC: $R_f$=0.11, dichloromethane:methanol (95:5); 300 MHz NMR: 0.80 (s,3), 0.85 (s,3), 2.15 (m,1), 3.32 (2d,4), 3.98 (s,2), 4.4–4.6 (m,4), 4.65 (t,]), 6.25 (dd,1), 7.43 (m,5), 7.90 (d,1), 8.40 (d,1), 8.75 (d,1); IR(KBr): 3400

(broad), 2980, 1700, 1650, 1600, 1525, 1215 cm$^{-1}$; MS: m/z=542(M+1).

Analysis for $C_{25}H_{30}F_3N_3O_7 \cdot 0.5\ H_2O$: Calculated: C, 54.54; H, 5.68; N, 7.63 Found: C, 54.76; H 5.68; N 7.50

EXAMPLES 154–158

The following compounds of formula I wherein $R^0$ is isopropyl, R is the indicated acyl group, $R^5$ is hydrogen and $R^6$ is phenyl were prepared by acylation of 2-(3-amino-2-oxo-6-phenyl-1,2-dihydro-1-pyridyl)-N-( 3,3,3-trifluoro-1-isopropyl-2-oxopropyl)acetamide using the acylating agent and the Acylation Method noted.

Example 154: R=2-methylphenylcarbonyl: Acylation Method A using 2-methylbenzoyl chloride. Chromatography solvent: hexane:ethyl acetate (2:1); TLC: $R_f$=0.60, dichloromethane:methanol (96:4); MS: m/z=514(M+1).

Analysis for $C_{27}H_{26}F_3N_3O_4 \cdot 0.3\ H_2O$: Calculated: C, 62.49; H, 5.17; N, 8.10 Found: C, 62.41; H, 5.31; N, 7.91

Example 155: R=pyrid-4-ylcarbonyl: Acylation Method A using isonicotinoyl chloride hydrochloride and eliminating the work-up wash with 10% hydrochloric acid; purified by precipitation from acetone:hexane. TLC: $R_f$=0.31, dichloromethane:methanol (96:4); MS: m/z=501(M+1).

Analysis for $C_{25}H_{23}F_3N_4O_4 \cdot 0.65\ H_2O$: Calculated: C, 58.63; H, 4.78; N, 10.94 Found: C, 58.66; H, 4.81; N, 10.98

Example 156: R=4-fluorophenoxycarbonyl: Acylation Method A using 4-fluorophenyl chloroformate; purified by chromatographing twice, eluting the first column with dichloromethane:methanol (96:4) and eluting the second with dichloromethane:ethyl acetate (97:3); TLC: $R_f$=0.13, dichloromethane:ethyl acetate (97:3); MS: m/z=534(M+1).

Analysis for $C_{26}H_{23}F_4N_3O_5 \cdot 0.35\ H_2O$: Calculated: C, 57.85; H, 4.43; N, 7.78 Found: C, 57.89; H, 4.47; N, 7.83

Example 157: R=4-bromophenoxycarbonyl: Acylation Method A using 4-bromophenyl chloroformate. Chromatography solvent: Dichloromethane:ethyl acetate (97:3); TLC: $R_f$=0.17, dichloromethane:ethyl acetate (97:3); MS: m/z= 594 (M+1) for $^{79}$Br.

Analysis for $C_{26}H_{23}BrF_3N_3O_5 \cdot 0.3\ H_2O$: Calculated: C, 52.07; H, 3.97; N, 7.01 Found: C, 52.07; H, 4.05; N, 6.84

Example 158: R=4-(dimethylamino)phenoxycarbonyl: Acylation Method D using 4-dimethylaminophenol purified by chromatographing twice, eluting the first column with hexane:ethyl acetate (2:1), then dichloromethane:ethyl acetate (2:1), and eluting the second column with dichloromethane:methanol (99:1). TLC: $R_f$=0.30, dichloromethane:methanol (99:1); MS: m/z=559(M+1).

Analysis for $C_{28}H_{29}F_3N_4O_5 \cdot 0.2\ H_2O$: Calculated: C, 59.82; H, 5.27; N, 9.97 Found: C, 59.79; H, 5.36; N, 9.80

The 4-dimethylaminophenol was prepared as follows:

A mixture of 4-methylaminophenol sulfate (1.00 g) and potassium carbonate (0.88 g) in dry tetrahydrofuran (29 mL) was stirred for 45 minutes at room temperature before iodomethane (0.36 mL) was added. After the reaction was stirred for 18 h, TLC showed incomplete reaction. Dimethylformamide (5 mL) was added to make the reaction mixture homogeneous and stirring was continued. After a total of 42 h, the reaction was evaporated and the residue was suspended in ethyl acetate (75 mL). The suspension was washed (saturated sodium bicarbonate, brine), dried, evaporated and dried under vacuum to give the crude product as an oil. The oil was preadsorbed onto silica gel; and chromatography, eluting with hexane:ethyl acetate (2:1), gave 4-dimethylaminophenol as a white solid (0.26 g); TLC: $R_f$=0.35, hexane:ethyl acetate (2:1); MS: m/z=138(M+1).

EXAMPLE 159

2-[3-(4-Aminophenylacetylamino)-2-oxo-6-phenyl-1,2-dihydro-1-pyridyl]-N-(3,3,3-trifluoro-1-isopropyl-2-oxopropyl)acetamide hydrochloride.

2-[3-(4-Nitrophenylacetylamino)-2-oxo-6-phenyl-1,2-dihydro-1-pyridyl]-N-( 3,3,3-trifluoro-1-isopropyl-2-oxopropyl)acetamide (0.318 g) was dissolved in absolute ethanol (5 mL). To the solution was added 10% (w/w) palladium on carbon (0.051 g) and the mixture was stirred under a hydrogen atmosphere overnight. The mixture was filtered through diatomaceous earth and evaporated to give a yellow-orange oil. The crude oil was purified by chromatography, eluting with dichloromethane:methanol (gradient, 98.5:1.5, 92:8). The amine was dissolved in dichloromethane and hydrogen chloride gas was bubbled through the solution. Evaporation gave the salt, which was purified by trituration with ether:dichloromethane, followed by crystallization from ethyl acetate:hexane:ether to give the title compound as a tan powder; free base TLC: $R_f$=0.45, dichloromethane: methanol (96:4); MS: m/z=529(M+1).

Analysis for $C_{27}H_{27}F_3N_4O_4 \cdot 1.0\ HCl \cdot 0.5\ H_2O$: Calculated: C, 56.50; H, 5.09; N, 9.76 Found: C, 56.36; H, 5.25; N, 9.71

The starting nitro compound was prepared by using Acylation Method A (but excluding triethyl amine), using N-succinimidyl 4-nitrophenylacetate and 2-(3-amino-2-oxo-6-phenyl-1,2-dihydro- 1-pyridyl)-N-(3,3,3-trifluoro-1-isopropyl-2-oxopropyl)-acetamide and used without purification; TLC: $R_f$=0.41, dichloromethane:methanol (97.3); MS: m/z=559(M+1).

EXAMPLE 160

2-(3-Aminoacetylamino-2-oxo-6-phenyl-1,2-dihydro-1-pyridyl)-N-(3,3,3-trifluoro-1-isopropyl-2-oxopropyl)acetamide.

Using a procedure similar to that described in Example 49 for removal of the benzyloxycarbonyl group with trifluoromethane sulfonic acid, and purifying by trituration with ether:dichloromethane followed by partitioning between water and ethyl acetate, drying, evaporating, and drying under vacuum, 2-(3-benzyloxycarbonylaminoacetylamino-2-oxo- 6-phenyl-1,2-dihydro-1-pyridyl)-N-(3,3,3-trifluoro-1-isopropyl-2-oxopropyl)acetamide was converted into the title compound; TLC: $R_f$=0.47, dichloromethane:methanol (9:1); MS: m/z=453(M+1).

Analysis for $C_{21}H_{23}F_3N_4O_4 \cdot 0.5\ H_2O$: Calculated: C, 54.66; H, 5.24; N, 12.14 Found: C, 54.70; H, 5.19, N, 11.82

The starting material ketone was prepared as follows:

a. 2-(3-Benzyloxycarbonylaminoacetylamino-2-oxo-6-phenyl-1,2-dihydro- 1-pyridyl)-N-(2-tert-butyldimethylsilyloxy-3,3,3-trifluoro- 1-isopropylpropyl)acetamide.

Using N-benzyloxycarbonylglycine and a procedure similar to that described in Acylation Method B, the amide was prepared. Chromatography solvent: Dichloromethane:methanol (99:1, 90:10); TLC: $R_f$=0.38, dichloromethane:methanol (98:2); MS: m/z=703(M+1).

b. 2-(3-Benzyloxycarbonylaminoacetylamino-2-oxo-6-phenyl-1,2-dihydro- 1-pyridyl)-N-(3,3,3-trifluoro-2-hydroxy-1-isopropylpropyl)acetamide.

Cleavage of the silyl ether of 2-(3-benzyloxycarbonylaminoacetylamino- 2-oxo-6-phenyl-1,2-dihydro-1-pyridyl)-N-(2-tert-butyldimethylsilyloxy- 3,3,3-trifluoro-1-isopropylpropyl)acetamide was carried out using a similar procedure to that described in Example 1.e. The alcohol was purified by trituration with dichloromethane; TLC: $R_f$=0.32, dichloromethane:methanol (96:4); MS: m/z=589(M+1).

c. 2-(3-Benzyloxycarbonylaminoacetylamino-2-oxo-6-phenyl-1,2-dihydro- 1-pyridyl)-N-(3,3,3-trifluoro-1-isopropyl-2-oxopropyl)acetamide.

Using a similar procedure to that described in Example 1, 2-(3-benzyloxycarbonylaminoacetylamino-2-oxo-6-phenyl-1,2-dihydro- 1-pyridyl)-N-(3,3,3-trifluoro-2-hydroxy-1-isopropylpropyl)acetamide was oxidized to give the ketone which was purified by trituration with dichloromethane followed by chromatography, eluting with dichloromethane:methanol (98:2, 90:10); TLC: $R_f$=0.37, dichloromethane:methanol (96:4); MS: m/z=587(M+1).

EXAMPLE 161

2-(3-Amino-5-methyl-2-oxo-6-phenyl-1,2-dihydro-1-pyridyl)-N-(3,3,3-trifluoro-1-isopropyl-2-oxopropyl)acetamide.

2-(3-benzyloxycarbonylamino-5-methyl-2-oxo-6-phenyl-1,2-dihydro- 1-pyridyl)-N-(3,3,3-trifluoro-1-isopropyl-2-oxopropyl)acetamide was subject to conditions similar to those described in Example 49. The resulting mixture was purifying by trituration with ether to give the title compound; TLC: $R_f$=0.08, chloroform:methanol (98:2); MS: m/z=410(M+1).

Analysis for $C_{20}H_{22}F_3N_3O_3 \cdot 0.9\ H_2O$: Calculated: C, 56.44; H, 5.64; N, 9.87 Found: C, 56.66; H, 5.33; N, 9.86

EXAMPLE 162

2-[3-Amino-6-(3,5-dimethoxyphenyl)-2-oxo-1,2-dihydro-1-pyridyl]-N-(3,3,3-trifluoro-1-isopropyl-2-oxopropyl)acetamide.

2-[3-Benzyloxycarbonylamino-6-(3,5-dimethoxyphenyl)-2-oxo-1,2-dihydro- 1-pyridyl]-N-(3,3,3-trifluoro-1-isopropyl-2-oxopropyl)acetamide was subjected to the conditions described in Example 159, except with shaking under a 2.7 bar hydrogen atmosphere, to give the title compound. Chromatography solvent: Dichloromethane:methanol (98:2, 95:5); TLC: $R_f$=0.35, dichloromethane:methanol (95:5); MS: m/z=456(M+1).

Analysis for $C_{21}H_{24}F_3N_3O_5 \cdot 0.65\ H_2O$: Calculated: C, 53.99; H, 5.46; N, 9.00 Found: C, 53.94; H, 5.41; N, 8.75

EXAMPLE 163

2-(3-Dimethylaminooxycarbonylamino-2-oxo-6-phenyl-1,2-dihydro-1-pyridyl)-N-(3,3,3-trifluoro-1-isopropyl-2-oxopropyl)acetamide.

Using a procedure similar to that described in Example 73 and substituting N,N-dimethylhydroxylamine for N-hydroxymethyl succinimide, the title compound was prepared: Chromatography solvent: dichloromethane:acetonitrile; TLC: $R_f$=0.55, dichloromethane:methanol (90:10); MS: m/z=483(M+1).

Analysis for $C_{22}H_{25}F_3N_4O_5$: Calculated: C, 54.76; H, 5.22; N, 11.61 Found: C, 54.54; H, 5.22; N, 11.56

EXAMPLES 164–167

Using a procedure similar to that described in Example 1, the following compounds of formula I wherein $R^0$ is isopropyl, R is the indicated acyl group, $R^5$ is hydrogen and $R^6$ is phenyl were prepared by oxidation of the corresponding alcohols of formula II.

Example 164: R=2,6-dichloropyrid-4-ylmethoxycarbonyl: Chromatography solvent: dichloromethane:methanol (99.5:0.5, 99:1); TLC: $R_f$=0.39, dichloromethane:methanol (98:2); MS: m/z=600(M+1).

Analysis for $C_{26}H_{23}Cl_2F_3N_4O_5 \cdot 0.5\ H_2O$: Calculated: C, 51.32; H, 3.97; N, 9.20 Found: C, 51.31; H, 3.84; N, 8.99

Example 165: R=2-thenyloxycarbonyl: Chromatography solvent: dichloromethane:methanol (99.5:0.5, 99:1, 98.5:1.5); TLC: $R_f$=0.51, dichloromethane:methanol (98:2); MS: m/z=536(M+1).

Analysis for $C_{25}H_{24}F_3N_3O_5S \cdot 0.7\ H_2O$: Calculated: C, 54.77; H, 4.67; N, 7.66 Found: C, 54.72; H, 4.85; N, 7.40

Example 166: R=3-thenyloxycarbonyl: Chromatography solvent: dichloromethane:methanol (99.5:0.5, 99:1, 98.5:0.5); TLC: $R_f$=0.52, dichloromethane:methanol (98:2); MS: m/z=536(M+1).

Analysis for $C_{25}H_{24}F_3N_3O_5S \cdot 0.7\ H_2O$: Calculated: C, 54.77; H, 4.67; N, 7.66 Found: C, 54.69; H, 4.70; N, 7.41

Example 167: R=trifluoroacetyl: Not chromatographed but purified by trituration with diethyl ether followed by recrystallization with ethyl acetate:hexane; TLC: $R_f$=0.30, dichloromethane:methanol (96:4); MS: m/z=492(M+1).

Analysis for $C_{21}H_{19}F_6N_3O_4 \cdot 0.25\ H_2O$: Calculated: C, 50.80; H, 3.96; N, 8.47 Found: C, 50.74; H, 3.97; N, 8.44

EXAMPLES 164.a.–167.a.

2-(3-Acylamino-2-oxo-6-phenyl-1,2-dihydro-1-pyridyl)-N-(2-tert-butyldimethylsilyloxy- 3,3,3-trifluoro-1-isopropyl)acetamides having the indicated acyl group R were prepared by acylation of 2-(3-amino- 2-oxo-6-phenyl-1,2-dihydro-1-pyridyl)-N-(2-tert-butyldimethylsilyloxy- 3,3,3-trifluoro-1-isopropyl)acetamide using the Acylation Method and the acylating agent noted.

Example 164.a.: R=2,6-dichloropyrid-4-ylmethoxycarbonyl: Acylation Method D with 2,6-dichloropyrid-4-yl-carbinol; chromatography solvent: dichloromethane:methanol (99:1); TLC: $R_f$=0.95, dichloromethane:methanol (9:1); MS: m/z=716(M+1).

Example 165.a.: R=2-thenyloxycarbonyl: Acylation Method D with 5 equivalents of 2-thienylcarbinol; chromatography solvent: dichloromethane:methanol (99.5:0.5) (first column) and dichloromethane:acetone (99.5:0.5) (second column); TLC: $R_f$=0.80, dichloromethane:methanol (98:2); MS: m/z=652(M+1).

Example 166.a.: R=3-thenyloxycarbonyl: Acylation Method D with 5 equivalents of 3-thienylcarbinol; chromatography solvent: dichloromethane:methanol (99.5:0.5) (two columns); TLC: $R_f$=0.76, dichloromethane:methanol (98:2); MS: m/z=652(M+1).

Example 167.a.: R=trifluoroacetyl: Acylation method A with trifluoroacetic anhydride, and dichloromethane in place of tetrahydrofuran; used without further purification; TLC: $R_f$=0.55, dichloromethane:methanol (99:1); MS: m/z=608(M+1).

EXAMPLES 164.b.–167.b.

The following alcohols of formula II wherein $R^0$ is isopropyl, is the indicated acyl group, $R^5$ is hydrogen and $R^6$ is phenyl were prepared by deprotection of the corresponding tert-butyldimethylsilyl ethers using a procedure similar to either that outline in Example 1.e. or that outlined in Example 19.b. as noted.

Example 164.b.: R=2,6-dichloropyrid-4-ylmethoxycarbonyl: Deprotection as in Example 1.e.; chromatography solvent: dichloromethane:methanol (99:1, 98:2, 95:5); TLC: $R_f$=0.47, dichloromethane:methanol (95:5); MS: m/z= 602(M+1).

Example 165.b.: R=2-thenyloxycarbonyl: Deprotection as in Example 1.e.; chromatography solvent: dichloromethane:methanol (gradient, 99.5:0.5, 99:1, 98.5:1.5); TLC: $R_f$=0.37, dichloromethane:methanol (98:2); MS: m/z= 538(M+1).

Example 166.b.: R=3-thenyloxycarbonyl: Deprotection as in Example 1.e.; chromatography solvent: dichloromethane:methanol (gradient, 99.5:0.5, 99:1, 98.5:1.5); TLC: $R_f$=0.37, dichloromethane:methanol (98:2); MS: m/z= 538(M+1).

Example 167.b.: R=trifluoroacetyl: Deprotection as in Example 19.b. and used without purification; TLC: $R_f$=0.25, dichloromethane:methanol (96:4); MS: m/z=494(M+1).

EXAMPLE 168

2-(2-Oxo-6-phenyl-3-pyruvoylamino-1,2-dihydro-1-pyridyl)-N-(3,3,3-trifluoro-1-isopropyl-2-oxopropyl)acetamide.

2-(3-Amino-2-oxo-6-phenyl-1,2-dihydro-1-pyridyl)-N-(3,3,3-trifluoro- 1-isopropyl-2-oxopropyl)acetamide was subjected to procedure similar to Acylation Method B, but substituting: dichloromethane for tetrahydrofuran, 4-dimethylaminopyridine for 1-hydroxybenzotriazole, and pyruvic acid for 4-methoxyphenyl acetic acid. After 72 h, dichloromethane was added and the mixture was washed (water, brine), dried (magnesium sulfate) and evaporated. Chromatography, eluting with dichloromethane:methanol (gradient, 99.5:0.5, 99:1), gave the title compound as a pale yellow solid; TLC: $R_f$=0.44, dichloromethane:methanol (98:2); MS: m/z=466(M+1).

Analysis for $C_{22}H_{22}F_3N_3O_5$·0.6 $H_2O$: Calculated: C, 55.48; H, 4.91; N, 8.82 Found: C, 55.43; H, 4.83; N, 8.77

EXAMPLE 169

2-[3-(4-Aminobenzoylamino)-2-oxo-6-phenyl-1,2-dihydro-1-pyridyl]-N-(3,3,3-trifluoro-1-isopropyl-2-oxopropyl)acetamide.

To a suspension of 2-[3-(4-nitrobenzoylamino)-2-oxo-6-phenyl- 1,2-dihydro-1-pyridyl]-N-(3,3,3-trifluoro-1-isopropyl-2-oxopropyl)acetamide (0.38 g) in ethanol (20 mL), was added tin(II) chloride dihydrate (0.79 g). This mixture was heated to reflux for 1 h then cooled to ambient temperature. The reaction mixture was poured into water and the pH adjusted to 7–8 with saturated sodium bicarbonate. The aqueous layer was extracted with ethyl acetate, and the organic extract washed (water, brine), dried (magnesium sulfate), and evaporated. The crude solid was triturated with diethyl ether:hexane (1:1), then further purified by chromatography, eluting with dichloromethane:methanol (gradient, 99.5:0.5, 99:1, 98.5:1.5), to give the title compound as a pale yellow solid; TLC: $R_f$=0.32, dichloromethane:methanol (98:2); MS: m/z=515(M+1).

Analysis for $C_{26}H_{25}F_3N_4O_4$·0.40 $H_2O$ Calculated: C, 59.85; H, 4.98; N, 10.73 Found: C, 59.74; H, 5.08; N, 10.57

The intermediate nitro compound was prepared as follows:

2-(3-Amino-2-oxo-6-phenyl-1,2-dihydro-1-pyridyl)-N-(3,3,3-trifluoro- 1-isopropyl-2-oxopropyl)acetamide and 4-nitrobenzoic acid were subjected to a procedure simlar to Acylation Method B, omitting 1-hydroxybenzotriazole hydrate and adding 4-dimethylaminopyridine. After stirring 24 h, dichloromethane was added and the organic layer was washed (1N hydrochloric acid, saturated sodium chloride), dried (magnesium sulfate), and evaporated. Chromatography, eluting with dichloromethane:methanol (gradient, 99.5:0.5, 99:1), gave the nitro compound as a yellow solid; TLC: $R_f$=0.48, dichloromethane:methanol (98:2); MS: m/z= 545(M+1).

EXAMPLES 170–172

The following compounds of formula I wherein $R^0$ is isopropyl, R is benzyloxycarbonyl, $R^5$ is hydrogen and $R^6$ is the indicated heteroaryl group were prepared using a procedure similar to that outline in Example 49 steps d.–j., which correspond to steps a.–g. below.

Example 170: $R^6$=3-pyridyl: Using a procedure similar to that described in Example 1, 2-[3-benzyloxycarbonylamino-2-oxo-6-(3-pyridyl)- 1,2-dihydro-1-pyridyl]-N-(3,3,3-trifluoro-2-hydroxy-1-isopropylpropyl)acetamide was oxidized to give the title compound; purified by crystallization from ethyl acetate; TLC: $R_f$=0.80, dichloromethane:methanol (90:10); MS: m/z=531(M+1).

Analysis for $C_{26}H_{25}F_3N_4O_5$·1.5 $H_2O$: Calculated: C, 56.01; H, 5.06; N, 10.05 Found: C, 55.98; N, 5.13; N, 10.24

The intermedicate alcohol was prepared as follows:

a. 3-Aza-4-(3-pyridyl)pent-3-enal dimethyl acetal.

Using a procedure similar to that described in Example 49.d., 3-acetylpyridine and aminoacetaldehyde dimethyl acetal were converted to the imine, a yellow oil; bp 150°–157° C. (120 Pa).

b. 3-Ethoxycarbonyl-2-oxo-6-(3-pyridyl)-1,2-dihydro-1-pyridylacetaldehyde dimethyl acetal.

Using a procedure similar to that described in Example 49.e., but employing diethyl ethoxymethylenemalonate (in place of dimethyl methoxymethylenemalonate), including a methanol addition prior to the extractive work-up to complete the cyclization, and purifying the product by dry-column chromatography, eluting with ethyl acetate:hexane (gradient, 40:60, 50:50, 60:40, 70:30, 80:20, 100:0) then ethyl acetate:ethanol (90:10), the pyridone was obtained (as a mixture of methyl and ethyl esters); TLC: $R_f$=0.15, ethyl acetate; MS: m/z=333(M+1) (ethyl ester), 319(M+1) (methyl ester).

c. 1-(2,2-Dimethoxyethyl)-6-(3-pyridyl)pyrid-2-one-3-carboxylic acid.

Using a procedure similar to that described in Example 49.f., but omitting the sodium methoxide addition and using the following modified work-up procedure, the acid was obtained. On completion of hydrolysis, water was added followed by 6N hydrochloric acid to pH 6. On standing for 10 min, the acid crystallized and was collected by filtration, washed with water and dried overnight under vacuum. Additional acid was obtained by extraction of the aqueous phase with dichloromethane, which was dried (magnesium sulfate), evaporated, and further dried under vacuum overnight. The two crops were combined and used without further purification; TLC: $R_f$=0.10, ethyl acetate; MS: m/z= 305(M+1).

d. 3-Benzyloxycarbonylamino-2-oxo-6-(3-pyridyl)-1,2-dihydro-1-pyridylacetaldelyde dimethyl acetal.

Using a procedure similar to that described in Example 49.g., but omitting the acid wash, and purifying by dry-column chromatography, eluting with ethyl acetate:hexane (gradient, 50:50, 60:40, 80:20, 100:0), the benzyloxycarbonylamino compound was obtained; TLC: $R_f$=0.40, ethyl acetate; MS: m/z=410(M+1).

e. 3-Benzyloxycarbonylamino-2-oxo-6-(3-pyridyl)-1,2-dihydro-1-pyridylacetaldehyde.

Using a procedure similar to that described in Example 49.h., but purifying by chromatography, eluting with ethyl acetate, the aldehyde was obtained; TLC: $R_f$=0.20, dichloromethane:methanol (96:4); MS: m/z=364(M+1).

f. 3-Benzyloxycarbonylamino-2-oxo-6-(3-pyridyl)-1,2-dihydro-1-pyridylacetic acid.

Using a procedure similar to that described for Example 49.i., but with the following modified work-up, the acid was prepared. Upon completion of the oxidation, dichloromethane, followed by 6N hydrochloric acid to pH 3–4, were added. The aqueous phase was separated and further extracted with dichloromethane. The combined organic extracts were washed (water), dried (magnesium sulfate), evaporated, and the resultant oil was triturated with diethyl ether to produce a pale-yellow solid, which was collected by filtration and dried under vacuum overnight; TLC: $R_f$=0.10, dichloromethane:methanol (90:10); MS: m/z=380(M+1).

g. 2-[3-Benzyloxycarbonylamino-2-oxo-6-(3-pyridyl)-1,2-dihydro-1-pyridyl] -N-(3,3,3-trifluoro-2-hydroxy-1-isopropylpropyl)acetamide.

3-Benzyloxycarbonylamino-2-oxo-6-(3-pyridyl)-1,2-dihydro-1-pyridylacetic acid was subject to a procedure similar to that described for Example 171.g., but employing the following modified work-up, to give the alcohol. On addition of ethyl acetate and 1N aqueous sodium hydroxide to the reaction mixture, the product crystallized in the organic phase. The aqueous layer phase was rapidly separated and the organic phase allowed to stand. The aqueous layer was further extracted with ethyl acetate, again separating the organic phase rapidly as product crystallized. The organic phases were combined and allowed to stand 2–3 h. A first crop of the crystals was collected by filtration and washed with ethyl acetate. The combined ethyl acetate layers were evaporated to give a dark-red oil, which on trituration with diethyl ether yielded a second crop of solid. The second crop was collected by filtration, washed with ethyl acetate, then combined with the first crop and dried under vacuum overnight; TLC: $R_f$=0.50, dichloromethane:methanol (90:10); MS: m/z=533(M+1).

Example 171:

$R^6$=2-thienyl: 2-[3-Benzyloxycarbonylamino-2-oxo-6-(2-thienyl)-1,2-dihydro -1-pyridyl]-N-(3,3,3-trifluoro-2-hydroxy-1-isopropylpropyl)acetamide was subjected to a procedure similar to that described in Example 1, but purifying by chromatography, with dichloromethane:methanol (98:2) as the eluent, to give the title compound as a white solid; TLC: $R_f$=0.55, dichloromethane:methanol (96:4); MS: m/z=536(M+1).

Analysis for $C_{25}H_{24}F_3N_3O_5S.0.75 H_2O$: Calculated: C, 54.69; H, 4.68; N, 7.65 Found: C, 54.69; H, 4.52; N, 7.55

The intermediate alcohol was prepared as follows:

a. 3-Aza-4-(2-thienyl)pent-3-enal dimethyl acetal.

Using a procedure similar to that described in Example 49.d., 2-acetylthiophene and aminoacetaldehyde dimethyl acetate were converted to the imine, a pale yellow oil; bp 133°–42° C. (47–67 Pa).

b. 3-Methoxycarbonyl-2-oxo-6-(2-thienyl)-1,2-dihydro-1-pyridylacetaldehyde dimethyl acetal.

The imine from Example 171.a. was subjected to a procedure similar to that described in Example 49.e., but employing a methanol addition prior to the extractive work-up to complete cyclization, and purifying the product by dry-column chromatography, with ethyl acetate:hexane (gradient, 40:60, 50:50, 60:40) as the eluent, to give the pyridone as a dark-orange oil; TLC: $R_f$=0.20, ethyl acetate:hexane (50:50).

c. 1-(2,2-Dimethoxyethyl)-6-(2-thienyl)pyrid-2-one-3-carboxylic acid.

Using a procedure similar to that described in Example 49.f., but omitting the sodium methoxide addition, the acid was obtained as a dark-orange oil and used without purification; TLC: $R_f$=0.10, ethyl acetate:hexane (50:50); MS: m/z=310(M+1).

d. 3-Benzyloxycarbonylamino-2-oxo-6-(2-thienyl)-1,2-dihydro-1-pyridylacetaldehyde dimethyl acetal.

Using a procedure similar to that described in Example 49.g., but purifying by dry-column chromatography, with ethyl acetate:hexane (gradient, 20:80, 30:70, 40:60) as the eluent, the benzyloxycarbonyl compound was obtained; TLC: $R_f$=0.30, ethyl acetate:hexane; MS: m/z=415(M+1).

e. 3-Benzyloxycarbonylamino-2-oxo-6-(2-thienyl)-1,2-dihydro-1-pyridylacetaldehyde.

The following procedure, based on that described by Huet F. et al., *Synthesis* (1978) 63, was used to prepare the aldehyde.

To a stirred solution of the product from Example 171.d. (9.3 g) in chloroform (200 mL) was added silica gel (36.4 g), followed by 3N hydrochloric acid (18.6 mL). The mixture was stirred for 3 days, filtered through magnesium sulfate, washed with chloroform and evaporated. A second iteration of this procedure was required to complete the hydrolysis. Dry-column chromatography, with ethyl acetate:hexane (gradient, 20:80, 30:70, 100:0) as the eluent, followed by a second dry column, with ethyl acetate:hexane (gradient, 30:70, 0:60, 50:50) as the eluent, gave the aldehyde as a yellow solid (2.8 g); TLC: $R_f$=0.30, ethyl acetate:hexane; MS: m/z=369(M+1).

f. 3-Benzyloxycarbonylamino-2-oxo-6-(2-thienyl)-1,2-dihydro-1-pyridylacetic acid.

The product from Example 171.e. was subjected to a procedure similar to that described in Example 49.i., with the following modifications to the work-up. Upon completion of the reaction, dichloromethane, followed by 1N hydrochloric acid, was added. The organic phase was separated, washed (water), dried (magnesium sulfate), and evaporated. Chromatography, with dichloromethane:methanol (gradient, 100:0, 95:5) as the eluent, gave the acid as a beige solid; TLC: $R_f$=0.15, dichloromethane:methanol (90:10); MS: m/z=385(M+1).

g. 2-[3-Benzyloxycarbonylamino-2-oxo-6-(2-thienyl)-1,2-dihydro-1pyridyl] -N-(3,3,3-trifluoro-2-hydroxy-1-isopropylpropyl)acetamide.

To a solution of the product from Example 171.f., 3-amino-1,1,1-trifluoro-4-methyl-2-pentanol hydrochloride, 1-hydroxybenzotriazole hydrate and triethylamine in dimethylformamide was added 1-(3-dimethylaminopropyl)-3-ethylcarbodiimide hydrochloride. This mixture was stirred overnight. Ethyl acetate and 1.0N sodium hydroxide were added, and the aqueous phase was separated and further extracted with ethyl acetate. The combined organic layers were washed (1:1 brine:water), dried (magnesium sulfate), and evaporated. Chromatography, with dichloromethane:methanol (98:2) as the eluent, gave alcohol as a white solid; TLC: $R_f$=0.25, dichloromethane:methanol (98:2); MS: m/z=538(M+1).

Example 172:

$R^6$=2-furyl: 2-[3-Benzyloxycarbonylamino-6-(2-furyl)-2-oxo-1,2-dihydro-1-pyridyl]-N-(3,3,3-trifluoro-2-hydroxy-1-isopropyl-propyl)acetamide was subjected to a procedure similar to that described in Example 1, but purifying by chromatography, with dichloromethane:methanol (98:2) as the eluent, to give the title compound; TLC: $R_f$=0.55, dichloromethane:methanol (96:4); MS: m/z=520(M+1).

Analysis for $C_{25}H_{24}F_3N_3O_6$.0.1 $H_2O$: Calculated: C, 57.60; H, 4.68; N, 8.06 Found: C, 57.39; H, 4.78; N, 7.98

The intermediate alcohol was prepared as follows:

a. 3-Aza-4-(2-furyl)pent-3-enal dimethyl acetal.

Using a procedure similar to that described in Example 49.d., 2-acetylfuran and aminoacetaldehyde dimethyl acetal were converted to the imine, a pale yellow oil; bp 92°–102° C. (93–106 Pa).

b. 6-(2-Furyl)-3-methoxycarbonyl-2-oxo-1,2-dihydro-1-pyridylacetaldehyde dimethyl acetal.

The imine from 172.a. was subjected to a procedure similar to that described in Example 49.e., but employing a methanol addition to complete cyclization prior to extractive work-up, and purifying the product by dry-column chromatography, with ethyl acetate:hexane (gradient, 40:60, 50:50, 60:40) as the eluent, to give the pyridone as a dark-orange oil; TLC: $R_f$=0.20, ethyl acetate:hexane (50:50); MS: m/z=308(M+1).

c. 1-(2,2-Dimethoxyethyl)-6-(2-furyl)pyrid-2-one-3-carboxylic acid.

Using a procedure similar to that described in Example 49.f., but omitting the sodium methoxide addition, the acid was obtained as a dark-orange oil and used without purification; TLC: $R_f$=0.10, ethyl acetate:hexane (50:50); MS: m/z=294(M+1).

d. 3-Benzyloxycarbonylamino-6-(2-furyl)-2-oxo-1,2-dihydro-1-pyridylacetaldehyde dimethyl acetal.

Using a procedure similar to that described in Example 49.g., but purifying by dry-column chromatography, with ethyl acetate:hexane (gradient, 20:80, 30:70, 40:60) as the eluent, the benzyloxycarbonyl compound was obtained; TLC: $R_f$=0.60, ethyl acetate:hexane (50:50); MS: m/z=399(M+1).

e. 3-Benzyloxycarbonylamino-6-(2-furyl)-2-oxo-1,2-dihydro-1-pyridylacetaldehyde.

3-Benzyloxycarbonylamino-6-(2-furyl)-2-oxo-1,2-dihydro-1-pyridylacetaldehyde dimethyl acetal was subjected to a procedure similar to that described in Example 171.e. Dry-column chromatography, with ethyl acetate:hexane (gradient, 10:90, 20:80, 30:70) as the eluent, gave the aldehyde as a white solid; TLC: $R_f$=0.20, ethyl acetate:hexane (30:70); MS: m/z=353(M+1).

f. 3-Benzyloxycarbonylamino-6-(2-furyl)-2-oxo-1,2-dihydro-1-pyridylacetic acid.

The product from Example 172.e. was subjected to a procedure similar to that described in Example 49.i., with the following modifications to the work-up. After stirring the reaction mixture for 1 h, the solid was collected by filtration, washed (water, diethyl ether), and dried overnight under vacuum to give the acid, which was used without purification; TLC: $R_f$=0.15, dichloromethane:methanol (90:10); MS: m/z=369(M+1).

g. 2-[3-Benzyloxycarbonylamino-6-(2-furyl)-2-oxo-1,2-dihydro-1pyridyl] -N-(3,3,3-trifluoro-2-hydroxy-1-isopropylpropyl)acetamide.

3-Benzyloxycarbonylamino-6-(2-furyl)-2-oxo-1,2-dihydro-1-pyridylacetic acid was subjected to a procedure similar to that described in Example 171.g. to give the alcohol as a white solid; chromatography solvent: dichloromethane:methanol (98:2); TLC: $R_f$=0.65, dichloromethane:methanol (90:10); MS: m/z=522(M+1).

EXAMPLES 173–175

The following compounds of formula I wherein $R^0$ is isopropyl, R is hydrogen, $R^5$ is hydrogen and $R^6$ is the indicated heteroaryl group were prepared by removal of the benzyloxycarbonyl group from the corresponding compounds of formula I described in Examples 170–172, using a procedure similar to the one described in Example 49, with exceptions as noted:

Example 173:

$R^6$=3-pyridyl: Addition of trifluoromethanesulfonic acid to a stirred suspension of the urethane in dichloromethane caused deposition of title product as a sticky mass. Sodium bicarbonate solution was added to pH 8, and the reaction mixture was extracted with ethyl acetate. The combined organic extracts were washed (1:1 brine:water), dried (magnesium sulphate), and evaporated. The resulting solid was triturated with hexane, diethyl ether, purified by chromatography, with dichloromethane:methanol (gradient, 95:5 90:10 80:20) as the eluent, and trituration with refluxing ethyl acetate. Cooling overnight, gave the title compound, which was collected by filtration and dried under vacuum; TLC: $R_f$=0.40, dichloromethane:methanol (90:10); MS: m/z=397(M+1).

Analysis for $C_{18}H_{19}F_3N_4O_3$.1.2 $H_2O$:
Calculated: C, 51.72; H, 5.16; N, 13.40
Found: C, 51.64; H, 5.25; N, 13.11

Example 174:

$R^6$=2-thienyl: Purified by trituration with hexane, then diethyl ether; TLC: $R_f$=0.30, dichloromethane:methanol (9:1); MS: m/z=402(M+1).

Analysis for $C_{17}H_{18}F_3N_3O_3S$.0.75 $H_2O$: Calculated: C, 49.21; H, 4.74; N, 10.13 Found: C, 48.99; H, 4.48; N, 9.79

Example 175:

$R^6$=2-furyl: Purified by trituration with hexane, then diethyl ether; TLC: $R_f$=0.50, dichloromethane:methanol (90:10); MS: m/z=386(M+1).

Analysis for $C_{17}H_{18}F_3N_3O_4$.0.55 $H_2O$: Calculated: C, 51.66; H, 4.87; N, 10.63 Found: C, 52.07; H, 5.04; N, 10.23

EXAMPLES 176–178

The following compounds of formula I wherein $R^0$ is isopropyl, R is trifluoroacetyl, $R^5$ is hydrogen and $R^6$ is the indicated heteroaryl group were prepared from the corresponding amines of formula I described in Examples 173–175 using Acylation Method A, with the exceptions noted:

Example 176:

R=3-pyridyl: Omitting addition of triethylamine, employing dichloromethane in place of tetrahydrofuran, and purifying by chromatography, with dichloromethane:methanol (96:4) as the eluent, the title compound was prepared; TLC:

$R_f$=0.55, dichloromethane:methanol (90:10); MS: m/z=493(M+1).

Analysis for $C_{20}H_{18}F_6N_4O_4 \cdot CF_3CO_2H \cdot H_2O$: Calculated: C, 42.32; H, 3.39; N, 8.97 Found: C, 42.01; H, 3.13; N, 8.74

Example 177:

R=$^2$-thienyl: Omitting addition of triethylamine, employing dichloromethane in place of tetrahydrofuran, and purifying by chromatography, with dichloromethane:methanol (98:2) as the eluent, the title compound was prepared; TLC: $R_f$=0.40, dichloromethane:methanol (96:4); MS: m/z=498(M+1).

Analysis for $C_{19}H_{17}F_6N_3O_4S$: Calculated: C, 145.88; H, 3.44; N, 8.45 Found: C, 45.51; H, 3.66; N, 8.25

Example 178:

R=$^2$-furyl: Omitting addition of triethylamine, employing dichloromethane in place of tetrahydrofuran, and purifying by chromatography, with dichloromethane:methanol (98:2) as the eluent, the title compound was prepared; TLC: $R_f$=0.45, dichloromethane:methanol (96:4); MS: m/z=482(M+1).

Analysis for $C_{19}H_{17}F_6N_3O_5$: Calculated: C, 47.41; H, 3.56; N, 8.73 Found: C, 47.07; H, 3.73; N, 8.49

EXAMPLE 179

2-[2-Oxo-6-phenyl-3-[3-(3-pyridylmethyl)thioureido]-1,2-dihydro-1-pyridyl] -N-(3,3,3-trifluoro-1-isopropropyl-2-oxopropyl)acetamide.

A slurry of 2-(3-amino-2-oxo-6-phenyl-1,2-dihydro-1-pyridyl)-N-(3,3,3-trifluoro-1 -isopropropyl-2-oxopropyl)acetamide (0.30 g), 3-picolyl isothiocyanate hydrobromide (0.178 g) and triethylamine (0.21 mL) in dry tetrahydrofuran (3 mL) was heated at 60° C. for 4 h. Additional 3-picolyl isothiocyanate (0.36 g) and triethylamine (0.04 mL) were added, and the reaction was allowed to stir for 64 h. Additional isothiocyanate (0.16 g) was: added and the reaction was heated at 60° C. for 3 hours and isothiocyanate (0.17 g) was again added. Three hours later, isothiocyanate (0.17 g) and triethylamine (0.02 mL) were added and the reaction was heated overnight. Ethyl acetate was added and the mixture was washed (water:sodium phosphate monobasic monohydrate:sodium phosphate dibasic (95 mL:5 g:5 g), water, brine), dried and evaporated. The residue was purified by chromatography, with dichloromethane:methanol (98:2) as the eluent, followed by trituration with methyl tert-butyl ether to yield the title compound (0.148 g); mp 124.5°–127° C.; TLC: $R_f$=0.61, dichloromethane:methanol (90:10); MS: m/z=546(M+1).

Analysis for $C_{26}H_{26}F_3N_5O_3S \cdot 0.5 H_2O$: Calculated: C, 56.31; H, 4.91; N, 12.63 Found: C, 56.00; H, 4.72; N, 12.60

EXAMPLES 180–183

Using a procedure similar to that described in Example I, the following compounds of formula I wherein $R^0$ is isopropyl, R is the indicated acyl group, $R^5$ is hydrogen and $R^6$ is phenyl were prepared by oxidation of the corresponding alcohols of formula II.

Example 180:

R=methoxyacetyl: Product was isolated directly from workup with no chromatographic purification; TLC: $R_f$=0.25, methanol:dichloromethane (5:95); MS: m/z=468(M+1).

Analysis for $C_{22}H_{24}F_3N_3O_5 \cdot 1.0 H_2O$: Calculated: C, 54.43: H, 5.40; N, 8.66 Found: C, 54.46; H, 5.42; N, 8.69

Example 181:

R=pyrazinylominocarbonyl: Chromatography solvent: methanol:dichloromethane (gradient, 1:99, 7:93); TLC: $R_f$=0.41, methanol:dichloromethane (5:95); MS: m/z=517(M+1).

Analysis for $C_{24}H_{23}F_3N_6O_4 \cdot 0.8 H_2O$: Calculated: C, 54.29; H, 4.67; N, 15.83 Found: C, 54.37; H, 4.83; N, 15.49

Example 182:

R=pyrid-4-yldimethylmethoxycarbonyl: Chromatography solvent: methanol:dichloromethane (1:99); TLC: $R_f$=0.30, methanol:dichloromethane (3:97); MS: m/z=559(M+1).

Analysis for $C_{28}H_{29}F_3N_4O_5$: Calculated: C, 60.21; H, 5.23; N, 10.03 Found: C, 59.95; H, 5.48; N, 9.60

Example 183:

R=morpholinoacetyl: Chromatography solvent: methanol:dichloromethane (4:96), followed by trituration with diethylether; TLC: $R_f$=0.29, methanol:dichloromethane (4:96); MS: m/z=523(M+1).

Analysis for $C_{25}H_{29}F_3N_4O_5 \cdot 0.1 H_2O$: Calculated: C, 57.27; H, 5.61; N, 10.69 Found: C, 56.97; H, 5.59; N, 10.60

The corresponding alcohols of Formula II for examples 180–183 were prepared as follows:

EXAMPLES 180.a.–183.a.

2-(3-Acylamino-2-oxo-6-phenyl-1,2-dihydro-1-pyridyl)-N-(2-tert-butyldimethylsilyloxy -3,3,3-trifluoro-1-isopropylpropyl)-acetamides having the indicated acyl group R were prepared by acylation of 2-(3-amino-2-oxo-6-phenyl-1,2-dihydro-1-pyridyl)-N-(2-tert -butyldimethylsilyloxy-3,3,3-trifluoro-1-isopropylpropyl)acetamide using the Acylation Method noted:

Example 180.a.:

R=methoxyacetyl: Acylation Method A, with sodium carbonate in place of triethylamine; used without further purification; TLC: $R_f$=0.64, methanol:dichloromethane (5:95); MS: m/z=584(M+1).

Example 181.a.:

R=pyrazinylaminocarbonyl: Acylation Method D; chromatography solvent: methanol:dichloromethane (gradient, 0.5:99.5, 2:98); TLC: $R_f$=0.52, methanol:dichloromethane (5:95); MS: m/z=633(M+1).

Example 182.a.:

R=pyrid-4-yldimethylmethoxycarbonyl: Acylation Method D. The required alcohol was prepared using a literature procedure; *J. Chem. Soc. Perkin Trans. I* (1985), 213. Chromatography: First column, methanol:dichloromethane (2:98); second column, methanol:dichloromethane (99:1); third column, methanol:diethyl ether:dichloromethane (0.5:25:74.5); fourth column, methanol:diethyl ether:dichloromethane (0.5:25:74.5); TLC: $R_f$=0.43, methanol:diethylether:dichloromethane (0.5:25:74.5); MS: m/z=675(M+1).

Example 183.a.:

R=morpholinoacetyl: Acylation Method B; the reaction mixture was diluted with water and the resulting solid was washed with saturated aqueous sodium bicarbonate and water and dried under vacuum at 40° C.; TLC: $R_f$=0.43, methanol:dichloromethane (4:96); MS: m/z=639(M+1).

The morpholinoacetic acid used in Example 183.a. was prepared as follows:

Ethyl morpholinoacetate (5.0 g) in ethanol (115 mL) was added to a solution of sodium hydroxide (1.27 g) in water (12 mL) and the mixture was allowed to stir for 1 h. The mixture was evaporated, dissolved in water (125 mL), and extracted with ethyl acetate. The aqueous phase was acidified with 10% hydrochloric acid (pH 2) and lyophilized to give a brown oil. The oil was dried under vacuum to yield morpholinoacetic acid hydrochloride, which was used directly for the acylation above.

EXAMPLES 180.b.–183.b.

The following alcohols of Formula II wherein $R^0$ is isopropyl, R is the indicated acyl group, $R^5$ is hydrogen and $R^6$ is phenyl were prepared by deprotection of the corresponding tert-butyldimethylsilylethers using a procedure similar to that described in Example 1.e., unless otherwise noted:

Example 180.b.:

R=methoxyacetyl: Deprotection as in Example 19.b.; used without further purification; TLC: $R_f$=0.26, methanol:dichloromethane (5:95); MS: m/z=470(M+1).

Example 181.b.:

R=pyrazinylaminocarbonyl: Chromatography solvent: methanol:dichloromethane (gradient, 0.5:99.5, 5:95); TLC: $R_f$=0.35, methanol:dichloromethane (5:95); MS: m/z=519(M+1).

Example 182.b.:

R=pyrid-4-yldimethylmethoxycarbonyl: TLC: $R_f$=0.12, methanol:diethylether:dichloromethane (1:25:75); MS: m/z=561(M+1).

Example 183.b.:

R=morpholinoacetyl: Chromatography solvent: methanol:dichloromethane (gradient, 0:100, 2:98); TLC: $R_f$=0.30, methanol:dichloromethane; MS: m/z=525(M+1).

EXAMPLE 184

2-(3-Benzyloxycarbonylamino-2-oxo-6-phenyl-1,2-dihydro-1-pyridyl)-N-(1-ethyl-3,3,3-trifluoro -2-oxopropyl)acetamide.

2-(3-Benzyloxycarbonylamino-2-oxo-6-phenyl-1,2-dihydro-1-pyridyl) -N-(1-ethyl-3,3,3-trifluoro-2-hydroxypropyl)acetamide was oxidized using a procedure similar to that outlined in Example 1 to give the title compound, which was purified by chromatography, with methanol:dichloromethane (5:95) as the eluent; TLC: $R_f$=0.55, methanol:dichloromethane (5:95); MS: m/z=516(M+1).

Analysis for $C_{26}H_{24}F_3O_5N_3$: Calculated: C, 60.58; H, 4.69; N, 8.15 Found: C, 60.05; H, 4.76; N, 7.97

The intermediate alcohol was prepared as follows:
a. 1,1,1-Trifluoro-3-nitro-2-pentanol.

A mixture of 1-nitropropane (10 mL), trifluoroacetaldehyde ethyl hemiacetal (20.2 mL), and potassium carbonate (15.4 g) was stirred at 25° C. for 48 h. The solution was made acidic by addition of 1N hydrochloric acid and the product extracted into dichloromethane. The solution was dried (MgSO$_4$) and the solvent evaporated to give an oil, which was distilled (60° C., 133 Pa) to provide 1,1,1-trifluoro-3-nitro-2-pentanol (15 g) as a mixture of diastereoisomers; MS: m/z=188(M+1).

b. 3-Amino-1,1,1-trifluoro-2-pentanol hydrochloride.

To a solution of 1,1,1-trifluoro-3-nitro-2-pentanol (3 g) in ethanol (100 mL) was added 10% (w/w) palladium on carbon (1 g) and the resulting mixture shaken under a hydrogen atmosphere (4 bar) for 3 days. The catalyst was removed by filtration and the solvent evaporated. To the resulting oil was added a saturated solution of ethanolic hydrochloric acid (5 mL) and the solvent was evaporated. Addition of ether gave a white solid which was collected and washed with ether to provide 3-amino-1,1,1-trifluoro-2-pentanol hydrochloride (1.3 g) as a white solid; MS: m/z=158(M+1–Cl); TLC: $R_f$=0.1, methanol:dichloromethane (10:90).

c. 2-(3-Benzyloxycarbonylamino-2-oxo-6-phenyl-1,2-dihydro-1-pyridyl) -N-(1-ethyl-3,3,3-trifluoro-2-hydroxypropyl)acetamide.

Using a procedure similar to that described in Example 49.j., but substituting 3-amino-1,1,1-trifluoro-2-pentanol hydrochloride for 3-amino-1,1,1-trifluoro-4-methyl-2-pentanol hydrochloride, the hydroxy amide was prepared. The crude material was crystallized from ether to yield a white solid; TLC: $R_f$=0.60, methanol:dichloromethane, (10:90); MS: m/z=518(M+1).

EXAMPLE 185

2-[3-Benzyloxycarbonylamino-6-(3-carboxyphenyl)-2-oxo-1,2-dihydro-1-pyridyl] -N-(3,3,3-trifluoro-1-isopropyl-2-oxopropyl)acetamide.

2-[3-Benzyloxycarbonylamino-6-(3-methoxycarbonylphenyl)-2 -oxo-1,2-dihydro-1-pyridyl]-N-(3,3,3-trifluoro-1-isopropyl-2oxopropyl)acetamide was hydrolyzed using a procedure similar to that described in Example 45 to give the title compound: Chromatography solvent: ethanol:dichloromethane:acetic acid (3:96.5:0.5); TLC: $R_f$=0.45, ethanol:dichloromethane:acetic acid, (3:96.5:0.5): MS: m/z=574(M+1).

Analysis for $C_{28}H_{26}F_3N_3O_7$·0.5 $H_2O$: Calculated: C, 57.73; H, 4.67; N, 7.21 Found: C, 57.78; H, 4.70; N, 7.19

The intermediate 2-[3-benzyloxycarbonylamino-6-(3-methoxycarbonyl-phenyl) -2-oxo-1,2-dihydro-1-pyridyl]-N-(3,3, 3-trifluoro-1-isopropyl-2 -oxopropyl)acetamide was prepared as follows:
a. Methyl 3-acetylbenzoate.

To a solution of 3-acetylbenzoic acid (4.10 g) in dimethylformamide (50 mL) was added potassium carbonate (3.63 g) and methyl iodide (5.2 mL) and the mixture was allowed to stir for 18 h. Water was added and the mixture was extracted with ethyl acetate. The combined organic extracts were washed with brine, dried, evaporated, and dried under vacuum, to give the ester as a brown oil (4.10 g); TLC: $R_f$=0.36, hexane:ethyl acetate (6:1); MS: m/z=179(M+1).

b. 6-(3-Methoxycarbonylphenyl)-3-nitropyrid-2-one.

A solution of methyl 3-acetylbenzoate (4.01 g) and dimethylformamide dimethylacetal (8.97 mL) in acetonitrile (100 mL) was allowed to reflux for 18 h. The mixture was evaporated and dried under vacuum to give a brown solid. This solid (4.16 g) was dissolved in dimethylformamide (50 mL), and the ammonium salt of nitro acetamide (2.90 g, prepared as described in *J. Org. Chem.* (1958), 113) was added. The mixture was heated to 100° C. for 24 h., cooled and diluted with water. The resulting precipitate was collected, washed with water, and dried under vacuum to give the pyridone (1.75 g); TLC: $R_f$=0.20, methanol:ethyl acetate:dichloromethane (2:3:95); MS: m/z=275(M+1).

c. 3-Amino-6-(3-methoxycarbonylphenyl)pyrid-2-one.

A solution of 6-(3-methoxycarbonylphenyl)-3-nitropyrid-2-one (0.12M, in dimethylformamide) was added to 10% (w/w) palladium on carbon (10% by weight) and the mixture was shaken under hydrogen (3.5 bar) for 18 h. The catalyst was removed by filtration and the resulting solution was evaporated and dried under vacuum to give the amine; TLC: $R_f$=0.21, methanol:ethyl acetate:dichloromethane (3:3:94); MS: m/z=245(M+1).

d. 3-Benzyloxycarbonylamino-6-(3-methoxycarbonylphenyl)pyrid-2-one.

3-Amino-6-(3-methoxycarbonylphenyl)pyrid-2-one was acylated with benzyl chloroformate using conditions similar to those described in Acylation Method A. The crude material was triturated with methanol and crystallized from dimethylformamide and water to give the benzyloxycarbonylamino-compound; TLC: $R_f$=0.62, methanol:ethyl acetate:dichloromethane (3:3:94); MS: m/z=379(M+1).

e. 2-[3-Benzyloxycarbonylamino-6-(3-methoxycarbonylphenyl)-2-oxo-1,2-dihydro-1-pyridyl]-N-(2-tert-butyldimethylsilyloxy-3,3,3-trifluoro-1-isopropylpropyl)acetamide.

3-Benzyloxycarbonylamino-6-(3-methoxycarbonylphenyl)pyrid-2-one was subjected to a procedure similar to that described in Example 1.d. The crude material was purified by chromatography, with ethyl acetate:dichloromethane (1.5:98.5) as the eluent, to yield the N-alkylated pyridone; TLC: $R_f$=0.19, ethyl acetate:dichloromethane (1.5:98.5); MS: m/z=704(M+1).

f. 2-[3-Benzyloxycarbonylamino-6-(3-methoxycarbonylphenyl) -2-oxo-1,2-dihydro-1-pyridyl]-N-(3,3,3-trifluoro-2-hydroxy-1-isopropylpropyl)acetamide.

2-[3-Benzyloxycarbonylamino-6-(3-methoxycarbonylphenyl) -2-oxo-1,2-dihydro-1-pyridyl]-N-(2-tert-butyldimethylsilyloxy-3,3,3 -trifluoro-1-isopropylpropyl)acetamide was subjected to a procedure similar to that described in Example 1.e. The crude material was purified by chromatography, with ethanol:diethylether:dichloromethane (1:10:89) as the eluent, to give the alcohol; TLC: $R_f$=0.15, ethanol:diethylether:dichloromethane (1:10:89); MS: m/z=590(M+1).

g. 2-[3-Benzyloxycarbonylamino-6-(3-methoxycarbonylphenyl) -2-oxo-1,2-dihydro-1-pyridyl]-N-(3,3,3-trifluoro-1-isopropyl-2oxopropyl)acetamide.

2-[3-Benzyloxycarbonylamino-6-(3-methoxycarbonylphenyl) -2-oxo-1,2-dihydro-1-pyridyl]-N-(3,3,3-trifluoro-2-hydroxy-1-isopropylpropyl)acetamide was subjected to an oxidation procedure similar to that described in Example 1. The crude material was purified by chromatography, with ethanol:diethylether:dichloromethane (1:10:89) as the eluent, to give the ketone (which is also an example of the invention); TLC: $R_f$=0.30, ethanol:diethylether:dichloromethane (1:10:89); MS: m/z=588(M+1).

EXAMPLE 186

2-[3-Benzyloxycarbonylamino-6-(4-carboxyphenyl)-2-oxo-1,2-dihydro-1-Pyridyl] -N-(3,3,3-trifluoro-1-isopropyl-2-oxopropyl)acetamide.

2-[3-Benzyloxycarbonylamino-6-(4-methoxycarbonylphenyl) -2-oxo-1,2-dihydro-1-pyridyl]-N-(3,3,3-trifluoro-1-isopropyl-2-oxopropyl)acetamide was hydrolyzed using a procedure similar to that described in Example 45 to give the title compound, which crystallized from hot ethyl acetate-:hexane; TLC: $R_f$=0.43,methanol:dichloromethane:acetic acid, (5:94.5:0.5): MS: m/z=574(M+1).

Analysis for $C_{28}H_{26}F_3N_3O_7$: Calculated: C, 58.64; H, 4.57; N, 7.33 Found: C, 58.37; H, 4.57; N, 7.30

The intermediate 2-[3-benzyloxycarbonylamino-6-(4-methoxycarbonyl -phenyl)-2-oxo-1,2-dihydro-1-pyridyl]-N-(3,3, 3-trifluoro-1-isopropyl-2 -oxopropyl)acetamide was prepared as follows:

a. Methyl 4-acetylbenzoate.

To a solution of 4-acetylbenzoic acid (4.10 g) in dimethylformamide (50 mL) was added potassium carbonate (3.63 g) and methyl iodide (5.2 mL) and the mixture was allowed to stir for 18 h. Water was added and the mixture was extracted with ethyl acetate. The combined organic extracts were washed with brine, dried, evaporated, and dried under vacuum, to give the ester as a brown oil; TLC: $R_f$=0.33, hexane:ethyl acetate (6:1); MS: m/z=179(M+1).

b. 6-(4-Methoxycarbonylphenyl)-3-nitropyrid-2-one.

Using a procedure similar to that described in Example 185.b., but substituting methyl 4-acetylbenzoate for methyl 3-acetylbenzoate, the nitro pyridone was prepared; TLC: $R_f$=0.14, methanol:ethyl acetate:dichloromethane (2:3:95); MS: m/z=275(M+1).

c. 3-Amino-6-(4-methoxycarbonylphenyl)pyrid-2-one.

6-(4-Methoxycarbonylphenyl)-3-nitropyrid-2-one was subjected to a procedure similar to that outlined in Example 185.c. to give the amine; TLC: $R_f$=0.23, methanol:dichloromethane (3:97); MS: m/z=245(M+1).

d. 3-Benzyloxycarbonylamino-6-(4-methoxycarbonylphenyl)pyrid-2-one.

3-Amino-6-(4-methoxycarbonylphenyl)pyrid-2-one was acylated with benzyl chloroformate using conditions similar to those described in Acylation Method A. After stirring overnight, the mixture was evaporated, suspended in ethyl acetate, and washed with saturated sodium bicarbonate solution. Solids suspended in the aqueous layers were removed by filtration, and dried to give a mixture of the starting amine and the benzyloxycarbonylamino pyridone. This material was subjected to a second iteration of the acylation procedure. The ethyl acetate from the above extraction was washed (1N hydrochloric acid, brine), dried and evaporated to give crude material. This residue was combined with the material- isolated from the second iteration and purified by chromatography, with methanol:ethyl acetate:dichloromethane (gradient, 0:5:95, 1:0:99, 2:0:98) as the eluent. The recovered solid was crystallized from dimethylformamide and water. The resulting material was washed (water, diethyl ether) and dried under vacuum to give the benzyloxycarbonylamino compound; TLC: $R_f$=0.52, methanol:dichloromethane (3:97); MS: m/z= 379(M+1).

e. 2-[3-Benzyloxycarbonylamino-6-(4-methoxycarbonylphenyl)-2-oxo-1,2 -dihydro-1-pyridyl]-N-(2-tert-butyldimethylsilyloxy-3,3,3-trifluoro-1-isopropylpropyl)acetamide.

3-Benzyloxycarbonylamino-6-(4-methoxycarbonylphenyl)pyrid-2-one was subjected to a procedure similar to that described in Example 1.d. The crude material was purified by chromatography: First column, ethyl acetate:dichloromethane (3:97); secound column, ethyl acetate:dichloromethane (2:98); third column, ethyl acetate:dichloromethane (3:97); to yield the N-alkylated pyridone; TLC: $R_f$=0.20, ethyl acetate:dichloromethane (3:97); MS: m/z= 704(M+1).

f. 2-[3-Benzyloxycarbonylamino-6-(4-methoxycarbonylphenyl) -2-oxo-1,2-dihydro-1-pyridyl]-N-(3,3,3-trifluoro-2-hydroxy-1-isopropylpropyl)acetamide.

2-[3-Benzyloxycarbonylamino-6-(4-methoxycarbonylphenyl) -2-oxo-1,2-dihydro-1-pyridyl]-N-(2-tert-butyldimethylsilyloxy-3,3,3 -trifluoro-1-isopropylpropyl)acetamide was subjected to a procedure similar to that described in Example 1e. The crude material was crystallized from ethyl acetate and hexane to give the alcohol; TLC: $R_f$=0.35, methanol:dichloromethane (3:97); MS: m/z= 590(M+1).

g. 2-[3-Benzyloxycarbonylamino-6-(4-methoxycarbonylphenyl) -2-oxo-1,2-dihydro-1-pyridyl]-N-(3,3,3-trifluoro-1-isopropyl-2oxopropyl)acetamide.

2-[3-Benzyloxycarbonylamino-6-(4-methoxycarbonylphenyl) -2-oxo-1,2-dihydro-1-pyridyl]-N-(3,3,3-trifluoro-2-hydroxy-1-isopropylpropyl)acetamide was subjected to an oxidation procedure similar to that described in Example 1. The crude material was crystallized from ethyl acetate and hexane to give the ketone (which is also an example of the invention); TLC: $R_f$=0.46, methanol:dichloromethane (2:98); MS: m/z=588(M+1).

EXAMPLE 187

2-[3-[3-Tris(acetoxymethyl)methylureido]-2-oxo-6-phenyl-1,2-dihydro -1-pyridyl]-N-(3,3,3-trifluoro-1-isopropyl-2-oxopropyl)acetamide.

2-[3-[3-Tris(acetoxymethyl)methylureido]-2-oxo-6-phenyl -1,2-dihydro-1-pyridyl]-N-(3,3,3-trifluoro-2-hydroxy-1-isopropylpropyl)acetamide was oxidized using a procedure similar to that outlined in Example 1 to give crude material, which was purified by chromatography, with acetonitrile:dichloromethane (20:80) as the eluent, to give the title compound; TLC: $R_f$=0.62, methanol:chloroform (10:90); MS: m/z=669(M+1).

Analysis for $C_{30}H_{35}F_3N_4O_{10}$: Calculated: C, 53.89; H, 5.28; N, 8.38 Found: C, 53.57; H, 5.31; N, 8.32

The intermediate 2-[3-[3-tris(acetoxymethyl)methylureido]-2 -oxo-6-phenyl-1,2-dihydro-1-pyridyl]-N-(3,3,3-trifluoro-2-hydroxy -1-isopropylpropyl)acetamide was prepared as follows:

a. 2-[3-[3-Tris(hydroxymethyl)methylureido]-2-oxo-6-phenyl -1,2-dihydro-1-pyridyl]-N-(2-tert-butyldimethylsilyloxy-3,3,3 -trifluoro-1-isopropylpropyl)acetamide.

A solution of triphosgene (0.450 g) in dichloromethane (6 mL) was added dropwise to a 3° C. solution of 2-(3-amino-2-oxo-6 -phenyl-1,2-dihydro-1-pyridyl)-N-(2-tert-butyldimethylsilyloxy -3,3,3-trifluoro-1-isopropylpropyl)acetamide (1.5 g) in dichloromethane (6 mL) The mixture was allowed to stir for 10 min at 3° C. 10 min at room temperature and was then cooled to 3° C. Triethylamine (2.2 mL) as a solution in dichloromethane (2 mL) was added dropwise maintaining the internal temperature below 5° C. The mixture was stirred for 15 min and was added dropwise to a room temperature suspension of tris(hydroxymethyl)methylamine (0.728 g) in tert-butanol (50 mL). The mixture was allowed to stir at room temperature for 75 min, was diluted with ethyl acetate and washed with saturated brine. The saturated brine was extracted with ethyl acetate and the combined organic layers were washed with saturated brine, dried and evaporated to yield the urea, (2.49 g). The crude material was used without further purification; TLC: $R_f$=0.40, chloroform:methanol (90:10); MS: m/z=659 (M+1).

b. 2-[3-[3-Tris(acetoxymethyl)methylureido]-2-oxo-6-phenyl -1,2-dihydro-1-pyridyl]-N-(2-tert-butyldimethylsilyloxy-3,3,3-trifluoro-1-isopropylpropyl)acetamide.

A solution of 2-[3-[3-tris-(hydroxymethyl)methylureido] 2-oxo-6-phenyl-1,2-dihydro-1-pyridyl]-N-(2-tert-butyldimethylsilyloxy -3,3,3-trifluoro-1-isopropylpropyl)acetamide (1.5 g), acetic anhydride (1.1 mL), triethylamine (1.6 mL) and 4-dimethylaminopyridine (0.045 g) in dichloromethane (7 mL) was stirred for 1 h. The mixture was diluted with ethyl acetate (75 mL), washed (10% acetic acid, half saturated sodium hydrogen carbonate, water, saturated brine), dried and evaporated to yield the triacetate (2.39 g). The material was used without further purification; TLC: $R_f$=0.75 chloroform:methanol (90:10); MS: m/z=785(M+1).

c. 2-[3-[3-Tris(acetoxymethyl)methylureido]-2-oxo-6-phenyl -1,2-dihydro-1-pyridyl]-N-(3,3,3-trifluoro-2-hydroxy-1-isopropylpropyl) acetamide.

2-[3-[3-Tris(acetoxymethyl)methylureido]-2-oxo-6-phenyl -1,2-dihydro-1-pyridyl]-N-(2-tert-butyldimethylsilyloxy-3,3,3-trifluoro-1-isopropylpropyl)acetamide was subjected to a procedure similar to that described in Example 19.b. to yield the alcohol, which was purified by chromatography, with dichloromethane:acetonitrile (80:20) as the eluent; TLC: $R_f$=0.42, chloroform:methanol (90:10); MS: m/z=671 (M+1).

EXAMPLE 188

2-[3-[3-Tris(hydroxymethyl)methylureido]-2-oxo-6-phenyl-1,2-dihydro -1-pyridyl]-N-(3,3,3-trifluoro-1-isopropyl-2-oxopropyl)acetamide.

A solution of lithium hydroxide monohydrate (0.419 g) in water (5 mL) was added to a solution of 2-[3-[3-tris(acetoxymethyl)methylureido] -2-oxo-6-phenyl-1,2-dihydro-1-pyridyl]-N-(3,3,3, -trifluoro-1-isopropyl-2-oxopropyl)acetamide (1.11 g) in tetrahydrofuran (6 mL) and the cloudy mixture was allowed to stir for 1 h. The mixture was diluted with half saturated potassium phosphate monobasic and extracted with ethyl acetate. The ethyl acetate was washed with saturated brine, dried and evaporated. The residue was purified by chromatography, with dichloromethane:methanol (95:5) as the eluent, to yield the title compound (0.592 g); mp 148°–151° C.; TLC: $R_f$=0.23, chloroform:methanol (90:10); MS: m/z=543 (M+1).

Analysis for $C_{24}H_{29}F_3N_4O_7 \cdot 0.5\ H_2O$: Calculated: C, 52.33; H, 5.48; N, 10.16 Found: C, 52.20; H, 5.50; N, 9.98

EXAMPLE 189

2-(3-Ethylamino-2-oxo-6-phenyl-1,2-dihydro-1-pyridyl)-N-(3,3,3 -trifluoro-1-isopropyl-2-oxopropyl)acetamide.

To a solution of 2-(3-amino-2-oxo-6-phenyl-1,2-dihydro -1-pyridyl-N-(3,3,3-trifluoro-1-isopropyl-2-oxopropyl)acetamide (0.305 g) and 2,6-lutidine (0.1 mL) in dimethylformamide (4.5 mL) was added ethyl iodide (0.09 mL). After 20 hours, further charges of 2,6-lutidine (0.1 mL) and ethyl iodide (0.09 mL) were made. After 5 hours, the reaction mixture was added to ethyl acetate and water and the organic phase was separated, washed (brine), dried ($MgSO_4$), and evaporated. Chromatography (twice), eluting with dichloromethane:methanol (gradient, 99.5:0.5 99:1) gave the title compound (68 mg) as a yellow solid; TLC: $R_f$=0.42, dichloromethane:methanol (98:2); MS: m/z=424(M+1).

Analysis for $C_{21}H_{24}F_3N_3O_3$: Calculated: C, 59.56; H, 5.71; N, 9.92 Found: C, 59.17; H, 5.76; N, 9.52

EXAMPLE 190

2-(2-Oxo-3-phenethylamino-6-phenyl-1,2-dihydro-1-pyridyl) -N-(3,3,3-trifluoro-1-isopropyl-2-oxopropyl)acetamide.

Using a procedure similar to that described for Example 189, but using 2-phenethyl bromide and sodium iodide in place of ethyl iodide, omitting the second addition of reagents and purifying by chromatography, eluting with dichloromethane:methanol (gradient, 99.5:1, 97:3), the title product was obtained as a light yellow foam; TLC: $R_f$=0.41, dichloromethane:methanol (98:2); MS: m/z=500(M+1).

Analysis for $C_{27}H_{28}F_3N_3O_3$.0.4 $H_2O$: Calculated: C, 63.99; H, 5.72; N, 8.29 Found: C, 63.93; H, 5.62; N, 8.29

EXAMPLES 191–196

The following compounds of Formula I wherein $R^0$ is isopropyl, $R^5$ is hydrogen, $R^6$ is phenyl and R is the indicated value were prepared by oxidation of the corresponding alcohols of formula II using a procedure similar to that which follows:

To a solution of an alcohol of Formula II wherein $R^0$ is isopropyl, $R^5$ is hydrogen, $R^6$ is phenyl and R is the indicated value (0.2 millimolar in dimethylsulfoxide:toluene, 1:1) is added 1-(3-dimethylaminopropyl)-3-ethylcarbodiimide hydrochloride (10 equivalents) and dichloroacetic acid (5 equivalents). After overnight stirring, the reaction mixture is diluted with ethyl acetate; washed (10% hydrochloric acid, saturated aqueous sodium bicarbonate, brine), dried and evaporated to give material which is purified using chromatography, eluting with the indicated solvent, except as otherwise noted, to provide the product.

Example 191:

R=benzylsulfonyl: Chromatography solvent: dichloromethane:ethyl acetate (95:5), and drying overnight in a vacuum oven; mp 192°–193° C.; TLC: $R_f$=0.29, methanol:dichloromethane (5:95); NMR: 0.85 (d,3), 0.90 (d,3), 2.14 (m,1), 4.57 (m,5), 6.10 (d,1), 7.24 (d,1), 7.36 (m,10), 8.74 (d,1), 8.82 (s,1); MS: m/z=550(M+1).

Analysis for $C_{26}H_{26}F_3N_3O_5$: Calculated: C, 56.82; H, 4.77; N, 7.65 Found: C, 56.46; H, 5.03; N, 7.50

Example 192:

R=2-(2-pyridyl)ethylsulfonyl: Chromatography solvent: methanol:dichloromethane (2:98), followed by trituration with methyl tert-butyl ether; mp 80°–86° C; TLC: $R_f$=0.43, methanol:dichloromethane (5:95); NMR: 0.76 (d,3), 0.84 (d,3), 2.21 (m,1), 3.24 (t,2), 3.83 (t,2), 4.44 (d,1), 4.58 (d,1), 6.25 (d,1), 7.46 (m,7), 7.74 (dd,1), 8.48 (d,1), 8.73 (d,1), 9.13 (s,1); MS: m/z=565(M+1).

Analysis for $C_{26}H_{27}N_4O_5S$.0.3 methyl tert-butyl ether: Calculated: C, 54.88; H, 5.33; N, 9.31 Found: C, 54.78; H, 5.41; N, 8.94

Example 193:

R=8-quinolylsulfonyl: Chromatography solvent: dichloromethane:tetrahydrofuran (20:1); TLC: $R_f$=0.39, dichloromethane:methanol (5:1); MS: m/z=587(M+1).

Analysis for $C_{28}H_{25}F_3N_4O_5S$.1.0 $H_2O$: Calculated: C, 55.62; H, 4.50; N, 9.43 Found: C, 55.97; H, 4.46; N, 9.15

Example 194:

R=butylsulfonyl: Chromatography solvent: dichloromethane:methanol (95:5); TLC: $R_f$=0.45, dichloromethane:methanol (20:1); MS: m/z=516(M+1).

Analysis for $C_{23}H_{28}F_3N_3O_5S$.0.25 $H_2O$: Calculated: C, 53.12; H, 5.52; N, 8.08 Found: C, 53.17; H, 5.64; N, 8.01

Example 195:

R=4-nitrobenzylsulfonyl: Chromatography solvent: dichloromethane:methanol (gradient, 100:0, 99:1, 98:2); TLC: $R_f$=0.45, dichloromethane:methanol (95:5); MS: m/z=595 (M+1).

Analysis for $C_{26}H_{25}F_3N_4O_7S$: Cyalculated: C, 52.52; H, 4.24; N, 9.42 Found: C, .52.17; H, 4.27; N, 9.49

Example 196:

R=3-pyridylsulfonyl: Purified by chromatography, with methanol:dichloromethane (2:98) as the eluent for three columns and ethyl acetate:hexane (3:1) as the eluent for a fourth column; TLC: $R_f$=0.35, ethyl acetate:hexane (3:1); MS: m/z=537(M+1).

Analysis for $C_{24}H_{23}F_3N_4O_5S$.1.5 $H_2O$: Calculated: C, 51.15; H, 4.65; N, 9.94 Found: C, 51.18; H, 4.59; N, 9.37

The intermediate alcohols of Formula II used in Examples 191–196 were prepared as follows.

EXAMPLES 191.a.–196.a.

tert-Butyldimethylsilyl ethers of the alcohols of Formula II wherein $R^0$ is isopropyl, $R^5$ is hydrogen, $R^6$ is phenyl and R is the indicated value were prepared using the following general procedure:

2-(3-Amino-2-oxo-6-phenyl-1,2-dihydro-1-pyridyl)-N-(2-tert -butyldimethylsilyloxy-3,3,3-trifluoro-1-isopropylpropyl)acetamide is sulfonylated, using triethylamine and the required sulfonyl chloride in tetrahydrofuran. The solution is stirred overnight, diluted with ethyl acetate, washed (10% hydrochloric acid, saturated aqueous sodium bicarbonate, brine), dried and evaporated to give the sulfonamide, which is purified using chromatography, eluting with the indicated solvent, except as otherwise noted.

Example 191.a.:

R=benzylsulfonyl: The product was used without additional purification; TLC: $R_f$=0.82, toluene:ethyl acetate (2:1); MS: m/z=666(M+1).

Example 192.a.:

R=2-(2-pyridyl)ethylsulfonyl: The product was used without additional purification; TLC: $R_f$=0.42, toluene:ethyl acetate (1:1); MS: m/z=681(M+1).

Example 193.a.:

R= 8-quinolylsulfonyl: Chromatography solvent: dichloromethane:methanol (25:1); TLC: $R_f$=0.51, dichloromethane:methanol (20:1); MS: m/z=731(M+1).

Example 194.a.:

R=butylsulfonyl; The product was used without additional purification; TLC: $R_f$=0.68, toluene:ethyl acetate (2:1); MS: m/z=632(M+1).

Example 195.a.:

R=4-nitrobenzylsulfonyl: Pyridine was used in place of triethylamine and the product was used without additional purification; TLC: $R_f$=0.63, dichloromethane:ethyl acetate (70:30); MS: m/z=711(M+1).

Example 196.a.:

R=3-pyridylsulfonyl: Using dichloromethane in place of tetrahydrofuran and using the, hydrochloride of 3-pyridylsulfonyl chloride, with two equivalents of base employed. The resulting material was a mixture of mono- and bis-sulfonylation products. The mixture was used directly in Example 196.b.

The required sulfonyl chloride for Example 196.a. was prepared by a method similar to that described by T. F. Mich, in U.S. Pat. No. 4,315,014, for the preparation of 2-(4-pyridyl)ethylsulfonyl chloride hydrochloride: Purified by trituration with carbon tetrachloride, acetonitrile, and diethyl ether.

EXAMPLES 191.b.–196.b.

The alcohols of Formula II wherein $R^0$ is isopropyl, $R^5$ is hydrogen, $R^6$ is phenyl and R is the indicated value were prepared using the following general procedure (acetic acid buffered fluoride):

The corresponding tert-butyldimethylsilyl ether prepared in Examples 191.a.–196.a. is dissolved in tetrahydrofuran and treated with tetrabutylammonium fluoride (1M in tetrahydrofuran, 1.1 equivalents) and glacial acetic acid (1 equivalent). The mixture is stirred for 4.5 hours, diluted with ethyl acetate, washed (water, brine), dried and evaporated to give the product, which is used without further purification, except as otherwise noted.

Example 191.b.:

R=benzylsulfonyl: TLC: $R_f$=0.31, toluene:ethyl acetate (2:1); MS: m/z=552(M+1).

Example 192.b.:

R=2-(2-pyridyl)ethylsulfonyl: Chromatographed, eluting with methanol:dichloromethane (3:97), followed by trituration with hexane; TLC: $R_f$=0.33, methanol:dichloromethane (5:95); MS: m/z=567(M+1).

Example 193.b.:

R=8-quinolylsulfonyl: TLC: $R_f$=0.16, dichloromethane:methanol (20:1); MS: m/z=589(M+1).

Example 194.b.:

R=butylsulfonyl: Chromatographed, eluting with dichloromethane:methanol (98:2); TLC: $R_f$=0.5, dichloromethane:methanol (95:5); MS: m/z=518(M+1).

Example195.b.:

R=4-nitrobenzylsulfonyl: TLC: $R_f$=0.51, dichloromethane:-ethyl acetate (70:30); MS: m/z=597(M+1).

Example 196.b.:

R=3-pyridylsulfonyl: The product was a a mixture of mono- and bis-sulfonyl compounds. The mixture was dissolved in tetrahydrofuran and treated with 1N NaOH at 60° C. for 1.5 hours. Ethyl acetate was added followed by 1N hydrochloric acid to pH 2. The mixture was diluted with water and the organic layer was dried (MgSO$_4$), evaporated and purified by chromatography, with methanol:dichloromethane (3:97) as the eluent, to give the mono-sulfonyl compound; TLC: $R_f$=0.40, methanol:dichloromethane (10:90); MS: m/z=539(M+1).

The intermediate 2-(3-amino-2-oxo-6-phenyl-1,2-dihydro -1-pyridyl)-N-(2-tert-butyldimethylsilyloxy-3,3,3-trifluoro-1-isopropylpropyl)acetamide used in Examples 191.a.–196.a. was prepared as described above at Example 22.a.–22.e.; see also preparations described at Example 1.a.–1.h. and Example 14.a.

EXAMPLE 197

2-(3-Methoxycarbonylmethylsulfonylamino-2-oxo-6-phenyl-1,2-dihydro -1-pyridyl)-N-(3,3,3-trifluoro-1-isopropyl-2-oxopropyl)acetamide.

To a solution of 2-(3-amino-2-oxo-6-phenyl-1,2-dihydro-1 -pyridyl)-N-(3,3,3-trifluoro-1-isopropyl-2-oxopropyl)acetamide (0.50 g) in tetrahydrofuran (6 mL), cooled to 0° C., was added, dropwise, methyl chlorosulfonylacetate (0.29 g). Immediately, triethylamine (0.38 g) was added dropwise to the reaction mixture, generating a color change from light orange to green. After 10 min stirring, the reaction mixture was diluted with 25 mL ethyl acetate and acidified with 1N aqueous hydrochloric acid. The organic phase was washed (water, brine), dried (magnesium sulfate) and evaporated to yield 0.60 g of an orange foam. Chromatography, using acidic silica gel and eluant of methylene chloride:tetrahydrofuran (20:1), followed by overnight vacuum-drying (40° C., 27 Pa), yielded a light-yellow foam (0.35 g); mp 165°–168° C.; TLC: $R_f$=0.33, dichloromethane:tetrahydrofuran (9:1, trace acetic acid); NMR: 0.90 (2d,6), 2.20 (m,1), 3.70 (s,3), 4.4–4.6 (s and m, 4), 4.65 (t,1), 6.20 (d,1), 7.45 (m,6), 8.75 (d,1), 9.35 (s,1); MS: m/z=532(M+1).

Analysis for $C_{22}H_{24}F_3N_3O_7S$: Calculated: C, 49.72; H, 4.55; N, 7.91 Found: C, 50.55; H, 4.79; N, 7.55

The intermediate 2-(3-amino-2-oxo-6-phenyl-1,2-dihydro-1 -pyridyl)-N-(3,3,3-trifluoro-1-isopropyl-2-oxopropyl)acetamide may be prepared as described above at Example 49 (and the subparts thereunder); see also Example 22.a.–22.b. and Example 167.

EXAMPLES 198–202

Using a procedure similar to that described in Example 197, the following compounds of Formula I wherein $R^0$ is isopropyl, $R^5$ is hydrogen, $R^6$ is phenyl and R has the indicated value were prepared by sulfonylation of 2-(3-amino-2-oxo-6-phenyl-1,2-dihydro-1-pyridyl)-N -(3,3,3-trifluoro-1-isopropyl-2-oxopropyl)acetamide with the corresponding sulfonyl chloride. Except as otherwise noted, the product was purified by chromatography over silica gel.

Example 198:

R=methylsulfonyl: Chromatography on acidic silica gel, with dichloromethane:tetrahydrofuran (20:1) as the eluent; TLC: $R_f$=0.37, dichloromethane:tetrahydrofuran (9:1, with 2.5% acetic acid); 300 MHz NMR: 0.90 (2d,6), 2.15 (m,1), 3.10 (s,3), 4.50 (q,2), 4.63 (t,1), 6.20 (d,1), 7.40 (m,6), 8.75 (d,1), 8.95 (s,1); MS: m/z=471(M+1).

Analysis for $C_{20}H_{22}F_3N_3O_5S$: Calculated: C, 50.74; H, 4.68; N, 8.88 Found: C, 51.25; H, 4.89; N, 8.48

Example 199:

R=methylsulfonylmethylsulfonyl: Purified by trituration with ethyl acetate; TLC: $R_f$=0.2, methanol:dichloromethane (5:95); 300 MHz NMR: 0.84 (d,3), 0.89 (d,3), 2.15 (m,1), 3.22 (s,3), 4.48 (q,2), 4.64 (t,1), 5.36 (s,2), 6.23 (d,1), 7.41 (m,6), 8.75 (d,1), 9.71 (s,1); MS: m/z=552(M+1).

Analysis for $C_{21}H_{24}F_3N_3O_7S_2$: Calculated: C, 45.73; H, 4.38; N, 7.62 Found: C, 45.41; H, 4.40; N, 7.59

Example 200:

R=aminosulfonyl: Recrystallized from hexane:ethyl acetate (1:10); TLC: $R_f$=0.22, dichloromethane:methanol (20:1); MS: m/z=475(M+1).

Analysis for $C_{19}H_{21}F_3N_4O_5S.0.25\ H_2O$: Calculated: C, 47.65; H, 4.52; N, 11.70 Found: C, 47.73; H, 4.46; N, 11.60

Example 201:

R=benzylaminosulfonyl: Purified by trituration with diethyl ether; TLC: $R_f$=0.26, dichloromethane:methanol (20:1); MS: m/z=565(M+1).

Analysis for $C_{26}H_{27}F_3N_4O_5S.0.25\ H_2O$: Calculated: C, 55.31; H, 4.82; N, 9.92 Found: C, 54.91; H, 4.88; N, 9.74

Example 202:

R=trifluoromethylsulfonyl: Chromatography solvent: dichloromethane:methanol (40:1); TLC: $R_f$=0.17, dichloromethane:methanol (20:1); MS: m/z=528(M+1).

Analysis for $C_{20}H_{19}F_6N_3O_5S$: Calculated: C, 45.54; H, 3.63; N, 7.97 Found: C, 45.49; H, 3.68; N, 7.76

EXAMPLES 203–215

Using a procedure similar to that described in Example 7, except replacing triethylamine with pyridine, the following compounds of Formula I wherein $R^0$ is isopropyl, $R^5$ is hydrogen, $R^6$ is phenyl and R has the indicated value were prepared by sulfonylation of 2-(3-amino-2-oxo-6-phenyl-1,2-dihydro-1-pyridyl)-N-(3,3,3-trifluoro-1-isopropyl-2-oxopropyl)acetamide with the corresponding sulfonyl chloride and purified by chromatography over silica gel, except as otherwise indicated. If the sulfonyl chloride was a pyridine hydrochloride, an extra equivalent of base was used.

Example 203:

R=phenylsulfonyl: Chromatography solvent: dichloromethane:tetrahydrofuran (20:1); TLC: $R_f$=0.31, dichloromethane:methanol (20:1); MS: m/z=536(M+1).

Analysis for $C_{25}H_{24}F_3N_3O_5S$: Calculated: C, 56.07; H, 4.52; N, 7.85 Found: C, 55.82; H, 4.66; N, 7.58

Example 204:

R=4-chlorophenylsulfonyl: Chromatography solvent: dichloromethane:tetrahydrofuran (20:1); TLC: $R_f$=0.30, dichloromethane:methanol (20:1); MS: m/z=570(M+1).

Analysis for $C_{25}H_{23}Cl_1F_3N_3O_5S$: Calculated: C, 52.68; H, 4.07; N, 7.37 Found: C, 52.71; H, 4.25; N, 7.12

Example 205:

R=4-methoxyphenylsulfonyl: Chromatography solvent: dichloromethane:tetrahydrofuran (7:1); TLC: $R_f$=0.18, dichloromethane:tetrahydrofuran (5:1); MS: m/z=566(M+1).

Analysis for $C_{26}H_{26}F_3N_3O_6S.0.25\ H_2O$: Calculated: C, 54.78; H, 4.69; N, 7.37 Found: C, 54.80; H, 4.69; N, 7.39

Example 206:

R=anilinosulfonyl: Chromatography solvent: dichloromethane:acetonitrile (80:20); TLC: $R_f$=0.42, dichloromethane:ethyl acetate (70:30); MS: m/z=551(M+1).

Analysis for $C_{25}H_{25}F_3N_4O_5S.0.5\ H_2O$: Calculated: C, 53.66; H, 4.68; N, 10.01 Found: C, 53.76; H, 4.68; N, 9.97

Example 207:

R=butylaminosulfonyl: Purified by trituration with methyl tert-butyl ether; TLC: $R_f$=0.57, dichloromethane:ethyl acetate (70:30); MS: m/z=531(M+1).

Analysis for $C_{23}H_{29}F_3N_4O_5S$: Calculated: C, 52.07; H, 5.51; N, 10.56 Found: C, 51.92; H, 5.52; N, 10.51

Example 208:

R=methylaminosulfonyl: Purified by trituration with methyl tert-butyl ether; TLC: $R_f$=0.29, dichloromethane:ethyl acetate (70:30); MS: m/z=489(M+1).

Analysis for $C_{20}H_{23}F_3N_4O_5S$: Calculated: C, 49.18; H, 4.74; N, 11.47 Found: C, 49.11; H, 4.75; N, 11.42

Example 209:

R=cyclohexylaminosulfonyl: Purified by trituration with methyl tert-butyl ether; TLC: $R_f$=0.58, dichloromethane:ethyl acetate (70:30); MS: m/z=557(M+1).

Analysis for $C_{25}H_{31}F_3N_4O_5S$: Calculated: C, 53.95; H, 5.61; N, 10.06 Found: C, 53.57; H, 5.59; N, 9.97

Example 210:

R=4-nitrophenylsulfonyl: Chromatography solvent: dichloromethane:methanol (20:1); TLC: $R_f$=0.25, dichloromethane:tetrahydrofuran:acetic acid (100:10:1); MS: m/z=581(M+1).

Analysis for $C_{25}H_{23}F_3N_4O_7S.0.25\ H_2O$: Calculated: C, 51.33; H, 4.05; N, 9.58 Found: C, 51.20; H, 3.72; N, 9.41

Example 211:

R=4-acetylaminophenylsulfonyl: Chromatography solvent: dichloromethane:methanol (20:1); TLC: $R_f$=0.12, dichloromethane:methanol (20:1); MS: m/z=593(M+1).

Analysis for $C_{27}H_{27}F_3N_4O_6S.1.0\ H_2O$: Calculated: C, 53.11; H, 4.80; N, 9.18 Found: C, 53.31; H, 4.83; N, 8.94

Example 212:

R=4-pyridylmethylsulfonyl: Chromatography solvent: dichloromethane:methanol (99:1 to 98:2); TLC: $R_f$=0.26, dichloromethane:methanol (95:5); MS: m/z=551(M+1).

Analysis for $C_{25}H_{25}F_3N_4O_5S.0.5\ H_2O$: Calculated: C, 53.66; H, 4.68; N, 10.01 Found: C, 53.70; H, 4.60; N, 9.87

Example 213:

R=3-pyridylmethylsulfonyl: Chromatography solvent: dichloromethane:methanol (99:1); TLC: $R_f$=0.28, dichloromethane:methanol (95:5); MS: m/z=551(M+1).

Analysis for $C_{25}H_{25}F_3N_4O_5S$: Calculated: C, 53.66; H, 4.68; N, 10.01 Found: C, 53.75; H, 4.48; N, 9.98

Example 214:

R=tert-butylaminosulfonyl: Chromatography solvent: dichloromethane:ethyl acetate (70:30); TLC: $R_f$=0.55, dichloromethane:ethyl acetate (70:30); MS: m/z= 531(M+1).

Analysis for $C_{23}H_{29}F_3N_4O_5S$: Calculated: C, 52.07; H, 5.51; N, 10.56 Found: C, 52.19; H, 5.51; N, 10.52

Example 215:

R=4-carboxyphenylsulfonyl: Reverse phase chromatography solvent: methanol:water (50:50); RP-TLC: $R_f$=0.36, methanol:water (65:35); MS: m/z=580(M+1).

Analysis for $C_{26}H_{24}F_3N_3O_7S$: Calculated: C, 53.88; H, 4.17; N, 7.25 Found: C, 53.95; H, 4.19; N, 7.17

EXAMPLE 216

2-(2-Oxo-6-phenyl-3-sulfoamino-1,2-dihydro-1-pyridyl)-N-(3,3,3-trifluoro-1-isopropyl-2-oxopropyl)acetamide sodium salt.

Using a procedure similar to that described in Example 197 except that the sulfonyl chloride and triethylamine were replaced by a preformed complex of sulfur trioxide/triethylamine, the title compound was prepared. Purification was performed by ion-exchange chromatography on DOWEX 50, sodium form, with methanol:water (1:10) as the eluant. The appropriate fractions were combined, the methanol and triethylamine evaporated and the remaining solution lyophilized. The residual solid was partially dissolved in warm ethyl acetate, the solid was filtered and the solution evaporated to give a white solid; mp 140° C. (dec); RP-TLC: $R_f$=0.67, methanol:water (65:35); MS: m/z=474(M−1 for free acid), m/z=496(M−1 for sodium salt) by FAB.

Analysis for $C_{19}H_{19}F_3N_3O_6SNa.1.0 H_2O$: Calculated: C, 44.27; N, 4.10; N, 8.15 Found: C, 44.01; N, 4.15; N, 7.84

EXAMPLE 217

2-(3-Carboxymethylamino-2-oxo-6-phenyl-1,2-dihydro-1-pyridyl)-N-(3,3,3-trifluoro-1-isopropyl-2-oxopropyl)acetamide.

2-(3-Methoxycarbonylmethylsulfonylamino-2-oxo-6-phenyl-1,2-dihydro-1-pyridyl)-N-(3,3,3-trifluoro-1-isopropyl-2-oxopropyl)acetamide was dissolved in methanol and treated with 1N sodium hydroxide. The mixture was diluted with water, acidified with 1N hydrochloric acid and extracted with ethyl acetate. The organic layers were washed (brine), dried and evaporated to give a solid, which was purified by reverse phase chromatography, with methanol:water (1:1) as the eluent. The resulting material was triturated with hexane to give the title compound; RP-TLC: $R_f$=0.58, methanol:water (65:35); 300 MHz NMR: 0.85 (2d,6), 2.15 (m,1), 4.30 (s,2), 4.50 (q,2), 4.65 (t,1), 6.25 (d,1), 7.45 (m,6), 7.75 (d,1), 9.20 (broad s, 1); MS: m/z= 518(M+1).

Analysis for $C_{21}H_{22}F_3N_3O_7S$: Calculated: C, 48.74; H, 4.28; N, 8.12 Found: C, 48.79; H, 4.52; N, 7.85

EXAMPLE 218

2-[3-(4-Aminophenylsulfonylamino)-2-oxo-6-phenyl-1,2-dihydro-1-pyridyl] -N-(3,3,3-trifluoro-1-isopropyl-2-oxopropyl)acetamide.

2-[3-(4-Nitrophenylsulfonyl)-2-oxo-6-phenyl-1,2-dihydro-1-pyridyl] -N-(3,3,3-trifluoro-1-isopropyl-2-oxopropyl)acetamide (167 mg) and 10% (w/w) palladium on carbon (42 mg) in a mixture of absolute ethanol (3 mL) and N,N-dimethylformamide (0.5 mL) was shaken under hydrogen (3.5 bar). After 24 hours and 28 hours, 32 mg and 42 mg respectively of 10% (w/w) palladium on carbon, were added. After 32 hours the reaction mixture was filtered through diatomatious earth and the solvent evaporated. The residue was dissolved in tetrahydrofuran, filtered through diatomaceous earth and the solvent evaporated. This residue was dissolved in dichloromethane and the product was precipitated by the addition of hexane to yield the title compound (105 mg) as a hemi-hydrate; mp 140°–142° C. (dec); TLC: $R_f$=0.41; dichloromethane:methanol (95:5); MS: m/z=563(M−1) by FAB.

Analysis for $C_{26}H_{27}F_3N_4O_5S.0.5 H_2O$: Calculated: C, 54.44; H, 4.92; N, 9.77 Found: C, 54.65; H, 4.88; N, 9.79

EXAMPLE 219

2-[3-(4-Aminobenzylsulfonylamino)-2-oxo-6-phenyl-1,2-dihydro-1-pyridyl] -N-(3,3,3-trifluoro-1-isopropyl-2-oxopropyl)acetamide.

2-[3-(4-Nitrophenylsulfonyl)-2-oxo-6-phenyl-1,2-dihydro-1-pyridyl]-N-(3,3,3-trifluoro-1-isopropyl-2-oxopropyl)acetamide (0.20 g), 10% (w/w) palladium on carbon (0.05 g), and 2.5 mL absolute ethanol were combined and shaken under hydrogen (3.5 bar). After 4 hours the reaction mixture was filtered through diatomaceous earth and evaporated to yield 0.15 g of a light yellow solid. Chromatography, eluting with dichloromethane:methanol (40:1), followed by overnight vacuum drying, (50° C. 27 Pa) yielded the title compound (0.08 g) as an off-white solid; mp 110°–113° C.; TLC: $R_f$=0.19, dichloromethane:methanol (20:1); MS: m/z= 551(M+1).

Analysis for $C_{25}H_{25}F_3N_4O_5S.0.75 H_2O$: Calculated: C, 53.23; H, 4.74; N, 9.93 Found: C, 53.50; H, 4.68; N, 9.62

EXAMPLE 220

2-[3-(4-Trifluoroacetylaminophenylsulfonylamino)-2-oxo-6-phenyl-1,2-dihydro-1-pyridyl]-N-(3,3,3-trifluoro-1-isopropyl-2-oxopropyl)acetamide.

2-[3-(4-Aminophenylsulfonyl)-2-oxo-6-phenyl-1,2-dihydro-1-pyridyl]-N-(3,3,3-trifluoro-1-isopropyl-2-oxopropyl)acetamide was acylated using a procedure similar to that described in Example 191.a., except substituting trifluoroacetic anhydride for the sulfonyl chloride and dichloromethane for tetrahydrofuran, to give the title compound: Chromatography solvent: dichloromethane:methanol (30:1); TLC: $R_f$=0.33, dichloromethane:tetrahydrofuran:acetic acid (100:10:1); MS: m/z=647(M+1).

Analysis for $C_{27}H_{24}F_6N_4O_6S$: Calculated: C, 50.16; H, 3.74; N, 8.67 Found: C, 50.42; H, 3.87; N,8.46

EXAMPLES 221–251

Using a procedure similar to that described in Example 197, except replacing triethylamine with pyridine, the following compounds of Formula I wherein $R^0$ is isopropyl, $R^5$ is hydrogen, $R^6$ is phenyl and R has the indicated value were prepared by sulfonylation of 2-(3-amino-2-oxo-6-phenyl-1,2-dihydro-1-pyridyl)-N-(3,3,3-trifluoro-1-isopropyl-2-oxopropyl)acetamide using the corresponding sulfonyl chloride and purified by chromatography over silica gel, except as otherwise indicated.

Example 221:

R=trifluoromethylsulfonyl: Chromatography solvent: dichloromethane:methanol (40:1); TLC: $R_f$=0.17, dichloromethane:methanol (20:1); NMR: 8.75 (s,1), 7.45 (m,7), 6.22 (d,2), 4.63 (m,1), 4.50 (dd,2), 2.16 (m,1), 0.88 (dd,6); MS: m/z=528(M+1).

Analysis for $C_{20}H_{19}F_6N_3O_5S$: Calculated: C, 45.54; H, 3.63; N, 7.97 Found: C, 45.64; H, 3.66; N, 7.78

Example 222:

R=3-nitrophenylsulfonyl: Chromatography solvent: dichloromethane:methanol (30:1); TLC: $R_f$=0.5, dichloromethane:methanol:acetic acid (99:10:1); NMR: 10.20 (s,1), 8.65 (m,2), 8.47 (d,1), 8.30 (d,1), 7.85 (dd,1), 7.47 (m,5), 7.30 (d,1), 6.18 (d,1), 4.58 (dd,1), 4.35 (dd,2), 2.14 (m,1), 0.82 (dd,6); MS: m/z=581(M+1).

Analysis for $C_{25}H_{23}N_4O_7F_3S$: Calculated: C, 51.72; H, 3.99; N, 9.65 Found: C, 51.80; H, 4.08; N, 9.57

Example 223:

R=isopropylaminosulfonyl: Chromatography solvent: dichloromethane:tetrahydrofuran (85:15), followed by trituration with diethyl ether; TLC: $R_f$=0.44, dichloromethane:methanol (20:1); NMR: 8.73 (d,1), 8.32 (s,1), 7.58 (m,1), 7.43 (m,6), 6.72 (d,1), 4.63 (dd,1), 4.50 (dd,2), 3.40 (m,1), 2.15 (m,1), 1.05 (m,1), 0.89 (d,3), 0.83 (d,3); MS: m/z=517(M+1).

Analysis for $C_{22}H_{27}F_3N_4O_5S$: Calculated: C, 51.16; H, 5.27; N, 10.85 Found: C, 50.90; H, 5.24; N, 10.77

Example 224:

R=4-(N,N-dimethylcarbamoylmethyl)phenylsulfonyl: Purified by trituration with diethyl ether; TLC: $R_f$=0.21, dichloromethane:methanol (20:1); NMR (DMSO/$D_2O$): 7.88 (d,2), 7.42 (m,8), 6.16 (d,1), 4.42 (dd,2), 4.05 (d,1), 3.80 (s,2), 3.03 (s,3), 2.84 (s,3), 2.15 (m,1), 0.85 (dd,6); MS: m/z=621(M+1).

Analysis for $C_{29}H_{31}F_3N_4O_6S\cdot 0.50\ H_2O$: Calculated: C, 55.32; H, 5.12; N, 8.90 Found: C, 55.33; H, 5.13; N, 8.83

Example 215:

R=benzoylaminosulfonyl: Purified by trituration with methyl tert-butyl ether; TLC: $R_f$=0.36, dichloromethane:methanol (9:1); NMR (DMSO/$D_2O$): 6.25 (d,1, J=7.7), 4.55 (d,1, J=16.5), 4.40 (d,1, J=16.5), 4.02 (d,1, J=2.9), 2.22 (m,1), 0.84 (d,3, J=6.8), 0.76 (d,3, J=6.8); MS: FAB m/z=579(M+1), 577(M−1).

Analysis for $C_{26}H_{25}F_3N_4O_6S$: Calculated: C, 53.98; H, 4.36; N, 9.68 Found: C, 53.65; H, 4.44; N, 9.67

Example 226:

R=methoxycarbonylaminosulfonyl: Purified by sequential trituration, first with diethyl ether:hexanes (1:1) then with methyl tert-butyl ether; TLC: $R_f$=0.20, dichloromethane:methanol (9:1); NMR (DMSO/$D_2O$): 7.44 (m,6), 6.25 (d,1, J=7.5), 4.56 (d,1, J=16.4), 4.42 (d,1, J=16.4), 4.04 (d,1, J=2.6), 3.65 (s,3), 2.23 (m,1), 0.85 (d,3, J=6.6), 0.78 (d,3, J=6.7); MS: FAB m/z=533(M+1), 531(M−1).

Analysis for $C_{21}H_{23}F_3N_4O_7S\cdot 0.5\ H_2O$: Calculated: C, 46.58; H, 4.47; N, 10.35 Found: C, 46.77; H, 4.39; N, 10.29

Example 227:

R=2,2,2-trifluoroethylsulfonyl: Purified by trituration with methyl tert-butyl ether:hexanes; TLC: $R_f$=0.83, dichloromethane:tetrahydrofuran:acetic acid (100:10:1); NMR (DMSO/$D_2O$): 7.45 (m,6), 6.28 (d,1, J=7.6), 4.52 (m,4), 4.05 (d,1, J=2.6), 2.23 (m,1), 0.86 (d,3, J=6.8), 0.79 (d,3, J=6.8); MS: m/z=542(M+1).

Analysis for $C_{21}H_{21}F_6N_3O_5S\cdot 0.5\ H_2O$: Calculated: C, 45.82; H, 4.03; N, 7.63 Found: C, 46.11; H, 4.02; N, 7.60

Example 228:

R=2,2,2-trifluoroethylaminosulfonyl: Purified by trituration with diethyl ether:ethyl acetate (20:1); TLC: $R_f$=0.75, dichloromethane:tetrahydrofuran (9:1);: NMR (DMSO/$D_2O$): 7.44 (m,6), 6.23 (d,1, J=7.6), 4.56 (d,1, J=16.5), 4.31 (d,1, J=16.5), 4.06 (d,1, J=2.9), 3.71 (q,2, J=9.6), 2.24 (m,1), 0.86 (d,3, J=6.8), 0.79 (d,3, J=6.8); MS: m/z=557(M+1).

Analysis for $C_{21}H_{22}F_6N_4O_5S\cdot 0.5\ H_2O$: Calculated: C, 44.60; H, 4.10; N, 9.91 Found: C, 44.56, H, 3.92; N, 9.98

Example 229:

R=acetylaminosulfonyl: Reverse phase chromatography solvent: methanol:water (50:50); TLC: $R_f$=0.27, dichloromethane:methanol (90:10); NMR: 7.70 (d,1, J=7.6), 7.43 (m,5), 6.24 (d,1, J=7.6), 4.56 (d,1, J=16.4), 4.41 (d,1, J=16.4), 4.04 (d,1), 2.22 (m,1), 1.96 (s,3), 0.85 (d,3, J=6.8), 0.78 (d,3, J=6.8); MS: FAB m/z=517(M+1), 515(M−1).

Analysis for $C_{21}H_{23}N_4O_6S\cdot 1.0\ H_2O$: Calculated: C, 47.19; H, 4.71; N, 10.48 Found: C, 47.13; H, 4.62; N, 10.52

Example 230:

R=ethoxycarbonylaminosulfonyl: Purified by trituration using hexane:diethyl ether (5:1); TLC: $R_f$=0.16, dichloromethane:methanol (10:1); NMR (DMSO/$D_2O$): 7.44 (m,6), 6.26 (d,1), 4.48 (dd,2), 4.12 (q,2), 4.05 (d,1), 2.25 (m,1), 1.80 (t,3), 0.85 (d,3), 0.78 (d,3); MS: m/z=FAB 547(M+1), 545(M−1).

Analysis for $C_{22}H_{25}F_3N_4O_7S$: Calculated: C, 48.35; H, 4.61; N, 10.25 Found: C, 48.16, H, 4.69; N, 10.06

Example 231:

R=cyanomethylsulfonyl: Chromatography solvent: dichloromethane:methanol (9:1), followed by trituration with diethylether; TLC: $R_f$=0.5, dichloromethane:methanol (9:1); NMR (DMSO/$D_2O$): 7.47 (m,6), 6.24 (d,1, J=7.5), 4.57 (d,1, J=16.3), 4.42 (d,1, J=16.3), 4.06 (d,1, J=2.9), 2.22 (m,1), 0.86 (d,3, J=6.8), 0.78 (d,3, J=6.8); MS: m/z=499(M+1).

Analysis for $C_{21}H_{21}F_3N_4O_5S\cdot 0.25\ H_2O$: Calculated: C, 50.15; H, 4.31; N, 11.14 Found: C, 50.14; H, 4.10; N, 11.01

EXAMPLE 232

2-[3-(3-Aminophenylsulfonylamino)-2-oxo-6-phenyl-1,2-dihydro-1-pyridyl]-N-(3,3,3-trifluoro-1-isopropyl-2-oxopropyl)acetamide.

Using a procedure similar to that described in Example 29, 2-[3-(3-nitrophenylsulfonylamino)-2-oxo-6-phenyl-1,2-dihydro-1-pyridyl]-N-(3,3,3-trifluoro-1-isopropyl-2-oxopropyl)acetamide was converted into the title compound. Chromatography solvent: dichloromethane:methanol (40:1); TLC: $R_f$=0.20, dichloromethane:methanol (20:1); NMR:

9.43 (s,1), 8.62 (d,1), 7.48 (m,6), 7.18 (dd,1), 7.09 (dd,1), 7.03 (d,1), 6.77 (dd,1), 6.15 (d,1), 5.62 (broad s,2), 4.63 (m,1), 4.45 (dd,2), 2.15 (m,1), 0.87 (dd,6); MS: m/z=551(M+1).

Analysis for $C_{25}H_{25}N_4O_5F_3S$: Calculated: C, 54.54; H, 4.58; N, 10.18 Found: C, .54.56; H, 4.74; N, 10.06

EXAMPLE 233

2-[3-(3-Acetylaminophenylsulfonylamino)-2-oxo-6-phenyl-1,2-dihydro-1-pyridyl]-N-(3,3,3-trifluoro-1-isopropyl-2-oxopropyl)acetamide.

Using a procedure similar to that described in Example 197.1., except replacing trifluoroacetic anhydride with acetic anydride, 2-[3-(3-aminophenylsulfonylamino)-2-oxo-6-phenyl-1,2-dihydro-1-pyridyl] -N-(3,3,3-trifluoro-1-isopropyl-2-oxopropyl)acetamide was converted into the title compound. Chromatography solvent: dichloromethane:methanol (35:1); TLC: $R_f$=0.24, dichloromethane:methanol (20:1); NMR (DMSO/$D_2O$): 8.22 (s,1) 7.73 (d,1), 7.60 (d,1), 7.5 (br m, 7), 6.16 (d,1), 4.40 (m,2), 4.02 (d,1), 2.12 (m,1), 2.09 (s,3), 0.80 (d,2); MS: m/z=593(M+1).

Analysis for $C_{27}H_{27}F_3N_4O_6S.0.50\ H_2O$: Calculated: C, 53.91; H, 4.69; N, 9.31 Found: C, 54.07; H, 4.86; N, 9.10

EXAMPLE 234

2-[3-[4-(N-Methylsulfonylcarbamoyl)phenylsulfonylamino]-2-oxo-6-phenyl-1,2-dihydro-1-pyridyl]-N-(3,3,3-trifluoro-1-isopropyl-2-oxopropyl)acetamide.

A solution of 2-[3-(4-carboxyphenylsulfonylamino)-2-oxo-6-phenyl-1,2-dihydro-1-pyridyl]-N-(3,3,3-trifluoro-1-isopropyl-2oxopropyl)acetamide (0.600 g), methanesulfonamide (0.1983 g), 1-(3-dimethylaminopropyl)-3-ethylcarbodiimide hydrochloride (0.2327 g), and 4-dimethylaminopyridine (0.1472 g) in dichloromethane (4.5 mL) was stirred. After 4 hours and 7 hours, 0.0167 g and 0.0172 g of 1-(3-dimethylaminopropyl)-3-ethylcarbodiimide hydrochloride was added respectively and stirring was continued for 24 hours. Methanesulfonamide (0.0180 g) was added, the solution was stirred for 25 hours. The reaction was diluted with ethyl acetate (100 mL), and was washed (0.1N hydrochloric acid (twice), water, brine), dried (sodium sulfate) and evaporated to give an orange brown solid. Reverse phase chromatography, eluting with methanol:water (40:60), followed by evaporation of the methanol and additon of 1N hydrochloric acid precipitated the title compound as a white powder (0.196 g). RP-TLC $R_f$=0.66, methanol:water 65:35 pH 6.7; NMR (DMSO/$D_2O$): 8.06 (s,4), 7.64 (d,1), 7.41 (m,6), 6.16 (d,1), 4.48 (d,1), 4.32 (d,1), 4.03 (d,1), 3.37 (s,3), 2.21 (m,1), 0.82 (d,3), 0.75 (d,3); MS: m/z=657(M+1).

Analysis for $C_{27}H_{27}F_3N_4O_8S_2.1.0\ H_2O$: Calculated: C, 48.07; H, 4.33; N, 8.30 Found: C, 47.80; H, 4.29; N, 8.20

EXAMPLES 235–236

Using a procedure similar to that described in Example 234, except replacing methanesulfonamide with the required sulfonamide, the following compounds of Formula I wherein $R^0$ is isopropyl, $R^5$ is hydrogen, $R^6$ is phenyl and R has the indicated value were prepared.

Example 235:

R=4-[N-(4-chlorophenylsulfonyl)carbamoyl]phenylsulfonyl: Chromatography solvent: dichloromethane:methanol (50:1); TLC: $R_f$=0.31, dichloromethane:methanol:acetic acid (100:5:1); NMR: 9.87 (s,1), 8.70 (d,1), 8.01 (d,2), 7.91 (m,4), 7.57 (d,2), 7.38 (m,6), 6.13 (d,1), 4.60 (m,1), 4.38 (dd,2), 2.12 (m,1), 0.85 (dd,6); MS: FAB m/z=751(M−1), 753(M+1).

Analysis for $C_{32}H_{28}C_1F_3N_4O_8S_2.1.0\ H_2O$: Calculated: C, 49.84; H, 3.92; N, 7.27 Found: C, 49.63; H, 3.77; N, 7.09

Example 236:

R=4-[N-(2-methylphenylsulfonyl)carbamoyl]phenylsulfonyl: Reverse phase chromatography solvent: methanol:water (40:60); RP-TLC: $R_f$=0.48, methanol:water (65:35 at pH 6.7); NMR: 10.01 (s,1), 8.68 (d,1), 8.02 (m,1), 7.35 (m,1), 6.12 (d,1), 4.59 (dd,1), 4.44 (d,1), 4.33 (d,1), 2.61 (s,3), 2.11 (m,1), 0.85 (d,3). 0.79 (d,3); MS: m/z=733(M+1).

Analysis for $C_{33}H_{31}F_3N_4O_8S_2.0.5H_2O$: Calculated: C, 53.45; H, 4.35; N, 7.55 Found: C, .53.37; H, 4.44; N, 7.73

EXAMPLE 237

2-[3-(4-Methylsulfonylaminophenylsulfonylamino)-2-oxo-6-phenyl-1,2-dihydro-1-pyridyl]-N-(3,3,3-trifluoro-1-isopropyl-2-oxopropyl)acetamide.

Using a procedure similar to that described in Example 220, except using methanesulfonyl chloride in place of trifluoroacetic anhydride, the title compound was prepared. Chromatography solvent: dichloromethane:tetrahydrofuran (20:1); TLC: R#=0.23, dichloromethane:tetrahydrofuran:acetic acid (99:10:1); NMR: 10.45 (s,1), 9.60 (s,1), 8.70 (d,1), 7.90 (d,2), 7.37 (d,2), 6.14 (d,1), 4.60 (dd,1), 4.41 (dd,2), 3.15 (s,3), 2.15 (m,1), 0.88 (dd,6); MS: m/z=629(M+1).

Analysis for $C_{26}H_{27}F_3N_4O_7S_2.0.05\ C_{15}H_{24}O$: Calculated: C, 50.22; H, 4.44; N, 8.76 Found: C, 50.20; H, 4.49; N, 8.69

EXAMPLE 238

2-[3-(4-Methoxycarbonylaminophenylsulfonylamino)-2-oxo-6-phenyl-1,2-dihydro-1-pyridyl]-N-(3,3,3-trifluoro-1-isopyropyl-2-oxopropyl)acetamide.

Using a procedure similar to that described in Example 220, except using methyl chloroformate in place of trifluoroacetic anhydride, and purification by trituration using hexane:diethyl ether (2:1), the title compound was obtained; TLC: $R_f$=0.26, chloroform:tetrahydrofuran:acetic acid (99:10:1); NMR (DMSO/$D_2O$): 10.12 (s,1), 7.85 (d,2), 7.62 (d,2), 7.40 (m,6), 6.15 (d,1), 4.40 (q,2), 4.03 (d,1), 2.22 (m,1), 0.83 (d,3), 0.76 (d,3); MS: m/z=609(M+1).

Analysis for $C_{27}H_{27}F_3N_4O_7S.0.5\ H_2O$: Calculated: C, 52.51; H, 4.56; N, 9.22 Found: C, 52.63; H, 4.57; N, 8.87

EXAMPLES 239–240

Using a procedure similar to that described in Example 197, except using pyridine in place of triethylamine, the following compounds of Formula I wherein $R^0$ is isopropyl, $R^5$ and $R^6$ are each hydrogen and R has the indicated value were prepared by sulfonylation of 2-(3-amino-2-oxo-1,2-dihydro-1-pyridyl)-N-(3,3,3-trifluoro-1-isopropyl-2-oxopropyl)acetamide (Example 75 in European Patent Application, Publication Number 509769) with the corresponding sulfonyl chloride. Except as otherwise noted, the product was purified by chromatography over silica gel.

Example 239:

R=4-acetylaminophenylsulfonyl: Chromatography solvent: dichloromethane:methanol (gradient 98:2 to 95:5); TLC: $R_f$=0.46, dichloromethane:methanol (90:10); NMR: 10.31 (s,1), 9.35 (s,1), 8.87 (d,1, J=6.7), 7.78 (d,2), 7.70 (d,2), 7.29 (m,2), 6.17 (t,1, J=7.1), 4.63 (m,3), 2.18 (m,1), 2.06 (s,3), 0.94 (d,3, J=6.8), 0.91 (d,3, J=6.8); MS: m/z= 417(M+1).

Analysis for $C_{21}H_{23}F_3N_4O_6S$: Calculated: C, 48.84; H, 4.49; N, 10.85 Found: C, 48.80; H, 4.56; N, 10.50

Example 240:

R=benzylsulfonyl: Purified by recrystallization from ethyl acetate; TLC: $R_f$=0.41, dichloromethane:methanol (95:5); NMR: 8.95 (d,1, J=6.5), 8.74 (s,1), 7.40 (dd,1), 7.33 (s,5), 7.18 (dd,1, J=1.7, 7.3), 6.17 (t,1, J=7.1),, 4.55 (s,2), 2.21 (m,1), 0.97 (d,3, J=6.8), 0.95 (d,3, J=6.8); MS: m/z=474(M+1).

Anaylsis for: $C_{20}H_{22}F_3N_4O_5S$: Calculated: C, 50.74; H, 4.68; N, 8.88 Found: C, 50.76; H, 4.67; N, 8.86

EXAMPLE 241

2-(3-Methylamino-2-oxo-6-phenyl-1,2-dihydro-1-pyridyl)-N-(3,3,3-trifluoro-1-isopropyl-2-oxopropyl)acetamide.

Using a procedure similar to that described above under Example 49.j. for the basic hydrolysis of the analogous 3-(N-trifluoroacetylamino) compound to the 3-amino-compound, but using the following extractive work-up, the title compound was prepared from 2-[3-(N-trifluoroacetyl-N-methylamino)-2-oxo-6-phenyl -1,2-dihydro-1-pyridyl]-N-(3,3,3-trifluoro-1-isopropyl -2-oxopropyl)acetamide. On completion of hydrolysis, ethyl acetate and brine were added. The organic phase was separated, washed (brine), dried (MgSO$_4$), and evaporated. The resultant solid was triturated with diethyl ether, chromatographed, eluting with dichloromethane:methanol (96:4), and dried overnight under vacuum to give the title product as a white solid; TLC: $R_f$=0.20, dichloromethane:methanol (96:4); MS: m/z= 410(M+1).

Analysis for $C_{20}H_{22}F_3N_3O_3.0.5\ H_2O$: Calculated: C, 57.41; H, 5.54; N, 10.04 Found: C, 57.42; H, 5.34; N, 9.78

The starting material was prepared as follows.

a. 2-[3-(N-Trifluoroacetyl-N-methylamino)-2-oxo-6-phenyl-1,2 -dihydro-1-pyridyl)-N-(3,3,3-trifluoro-1-isopropyl-2-oxopropyl)acetamide.

To a solution of 2-(3-trifluoroacetylamino-2-oxo-6-phenyl -1,2-dihydro-1-pyridyl]-N-(3,3,3-trifluoro-1-isopropyl-2-oxopropyl)acetamide (Example 167 above) (200 mg)in dimethylformamide (2 mL) was added sodium carbonate (128 mg) and methyl iodide (130 µL). The mixture was stirred in a stoppered vessel overnight. Ethyl acetate and brine were added. The organic phase was separated, washed (brine), dried (MgSO$_4$), and evaporated. Chromatography, eluting with dichloromethane:methanol (98:2), gave the title product (80 mg) as a white solid; TLC: $R_f$=0.15, dichloromethane:methanol (98:2); MS: m/z=506(M+1).

EXAMPLE 242

2-[3-(4-Fluorobenzylamino)-2-oxo-6-phenyl-1,2-dihydro-1-pyridyl] -N-(3,3,3-trifluoro-1-isopropyl-2-oxopropyl)acetamide.

2-[3-[N-(4-Fluorobenzyl)-N-trifluoroacetylamino]-2-oxo-6 -pheny-1,2-dihydro-1-pyridyl]-N-(3,3,3-trifluoro-1-isopropyl-2oxopropyl)acetamide was subjected to a procedure similar to that described in Example 241, but purifying by chromatography, eluting with dichloromethane:methanol (gradient, 99.5:0.5, 99:1), to give the title compound; TLC: $R_f$=0.45, dichloromethane:methanol (98:2); MS: m/z= 504(M+1).

Analysis for $C_{26}H_{25}F_4N_3O_3.0.3\ H_2O$: Calculated: C,61.36; H, 5.07; N, 8.25 Found: C,61.45; H, 5.00; N, 8.23

The starting material was prepared as follows.

a. 2-[3-[N-Trifluoroacetyl-N-(4-fluorobenzyl)amino]-2-oxo-6-phenyl -1,2-dihydro-1-pyridyl]-N-(3,3,3-trifluoro-1-isopropyl-2-oxopropyl)acetamide Using a procedure similar to that described for Example 241.a. except using 4-fluorobenzyl bromide and sodium iodide in place of methyl iodide and purifying by chromatography, eluting with dichloromethane:methanol (gradient, 99.5:0.5, 98:2), the title product was prepared as a colorless gum; TLC: $R_f$=0.29, dichloromethane:acetone (95:5); MS: m/z=600(M+1).

EXAMPLE 243

2-[3-[N-Trifluoroacetyl-N-(4-methoxybenzyl)amino]-2-oxo-6 -phenyl-1,2-dihydro-1-pyridyl]-N-(3,3,3-trifluoro-1-isopropyl-2-oxopropyl)acetamide was subjected to a procedure similar to that described in Example 241, but purifying by chromatography, eluting with dichloromethane:methanol (gradient, 99:1, 98:2), to give the title compound as a white solid; TLC: $R_f$=0.24, dichloromethane:methanol (98:2); MS: m/z=516(M+1).

Analysis for $C_{27}H_{28}F_3N_3O_4.0.5\ H_2O$: Calculated: C, 61.83; H, 5.57; N, 8.01 Found: C, 61.58; H, 5.57; N, 7.77

The starting material was prepared as follows.

a. 2-[3-[N-(4-Methoxybenzyl)-N-trifluoroacetylamino]-2-oxo-6-phenyl -1,2-dihydro-1-pyridyl]-N-(3,3,3-trifluoro-1-isopropyl-2-oxopropyl)acetamide.

Using a procedure similar to that described for Example 241.a., except using 4-methoxybenzyl bromide and sodium iodide in place of methyl iodide and purifying by chromatography, eluting with dichloromethane:methanol (99:1), the title compound was prepared; TLC: $R_f$=0.33, dichloromethane:methanol (98:2); MS: m/z=612(M+1).

EXAMPLE 244

2-(3-Benzylamino-2-oxo-6-phenyl-1,2-dihydro-1-pyridyl)-N-(3,3,3 -trifluoro-1-isopropyl-2-oxopropyl)acetamide.

2-[3-(N-Benzyl-N-trifluoroacetylamino)-2-oxo-6-phenyl-1,2 -dihydro-1-pyridyl)-N-(3,3,3-trifluoro-1-isopropyl-2-oxopropyl)acetamide was subjected to a procedure similar to that described for Example 241, but purifying by chromatography, eluting with dichloromethane:methanol (gradient, 99.5:0.5, 98:2), to give the title compound as a white solid; TLC: $R_f$=0.45, dichloromethane:methanol (98:2); MS: m/z::486(M+1).

Analysis for $C_{26}F_{26}F_3N_3O_3.0.2\ H_2O$: Calculated: C, 63.84; H, 5.44; N, 8.59 Found: C, 63.86; H, 5.68; N, 8.31

The starting material was prepared as follows.

a. 2-[3-(N-Trifluoroacetyl-N-benzylamino)-2-oxo-6-phenyl-1,2-dihydro -1 -pyridyl)-N-(3,3,3-trifluoro- 1-isopropyl-2-oxopropyl)acetamide.

Using a procedure similar to that described for Example 241.a., except employing benzyl bromide and sodium iodide in place of methyl iodide, heating the reaction mixture at 50° C. and purifying by chromatography, eluting with dichloromethane:methanol (99:1), the title product was prepared; $R_f$=0.35, dichloromethane:methanol (98:2); MS: m/z= 582(M+1).

EXAMPLE 245

2-[3-(2,2,2-Trifluoroethoxycarbonylamino-2-oxo-6-phenyl-1,2-dihydro-1 -pyridyl]-N-(3,3,3-trifluoro-1-isopropyl-2-oxopropylpropyl)acetamide.

To a solution of 2-(3-amino-2-oxo-6-phenyl-1,2-dihydro -1-pyridyl)-N-(3,3,3-trifluoro-1-isopropyl-2-oxopropyl)acetamide (400 mg) in dichloromethane (8 mL) at 0° C. was added pyridine (320 mg) followed by 2,2,2-trifluoroethyl chloroformate (180 µL). After 1 hour the reaction mixture was diluted with diethyl ether and quenched with ice. The phases were separated; and the organic phase was washed (dilute hydrochloric acid, brine), dried and evaporated to afford a gummy solid. This solid was triturated with diethyl ether:hexanes (10 mL, 1:1) to afford a white powder which was collected by filtration and dried under vacuum to yield the title compound (388 mg); mp 196°–198° C.; TLC: $R_f$=0.68, chloroform:methanol (20:1); NMR (DMSO/$D_2O$): 7.91 (d,1, J=8.19), 7.30–7.50 (m,5), 6.29 (d,1, J=8.19), 4.83 (d,1, J=9), 4.75 (d,1, J=9), 4.71 (d,1, J=16), 4.47 (d,1, J=16.4), 2.23 (m,1), 0.86 (d,3, J=6.7), 0.80 (d,3, J=6.7); MS: m/z=522(M+1).

Analysis for $C_{22}H_{21}F_6N_3O_5 \cdot 0.5\ H_2O$: Calculated: C, 49.82; H, 4.18; N, 7.92 Found: C, 49.96; H, 4.21; N, 7.80

The intermediate 2,2,2-trifluoroethyl chloroformate was prepared using a procedure similar to that described in U.S. Pat. No. 3,852,464, except that bis(trichloromethyl) carbonate was used in place of phosgene.

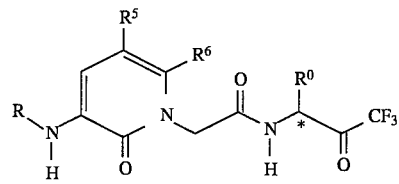

I

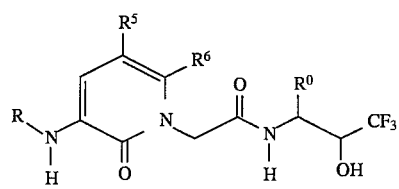

II

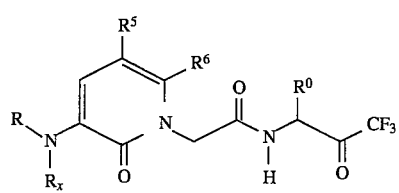

Vb

SCHEME I

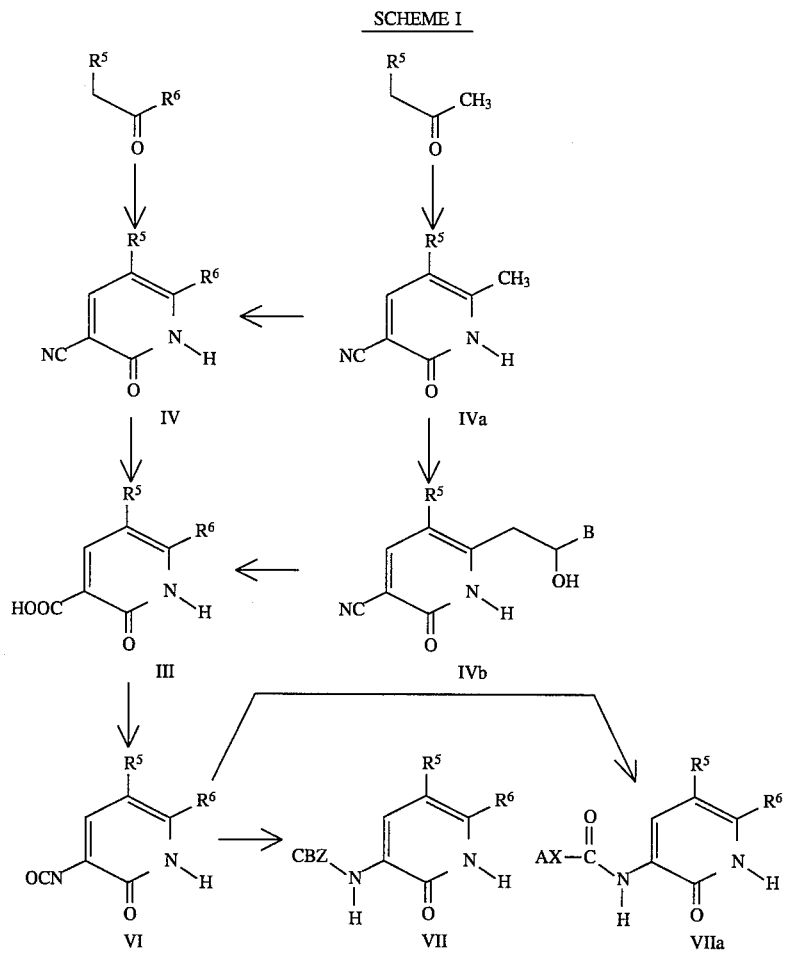

SCHEME II
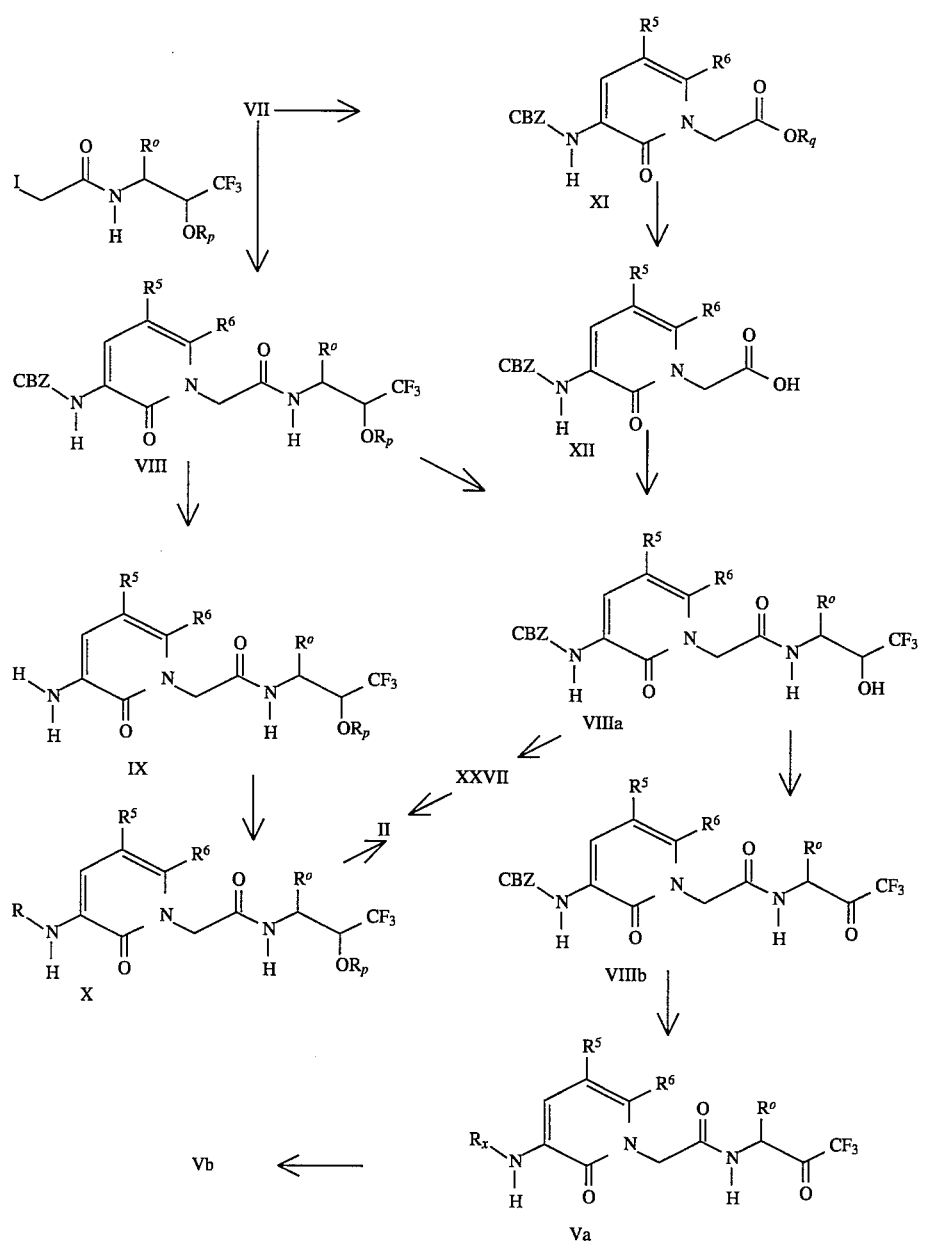
SCHEME III
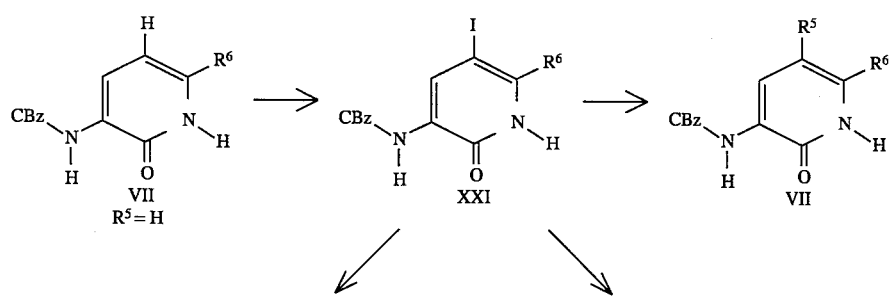

-continued
SCHEME III
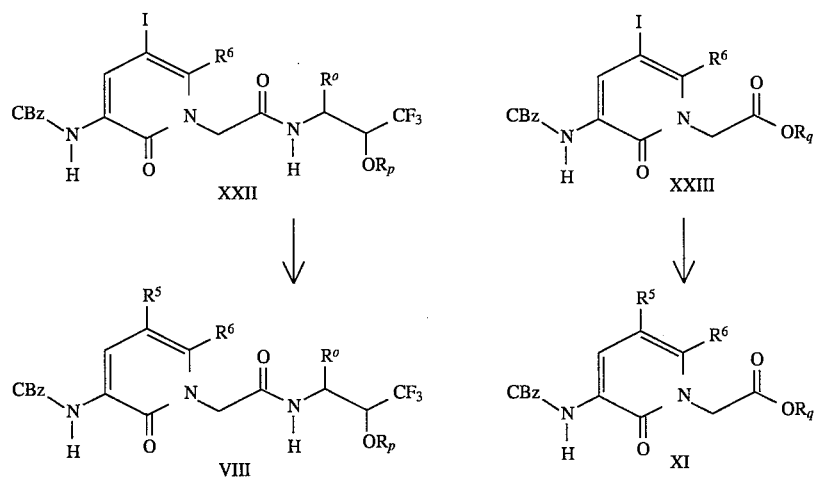
SCHEME IV
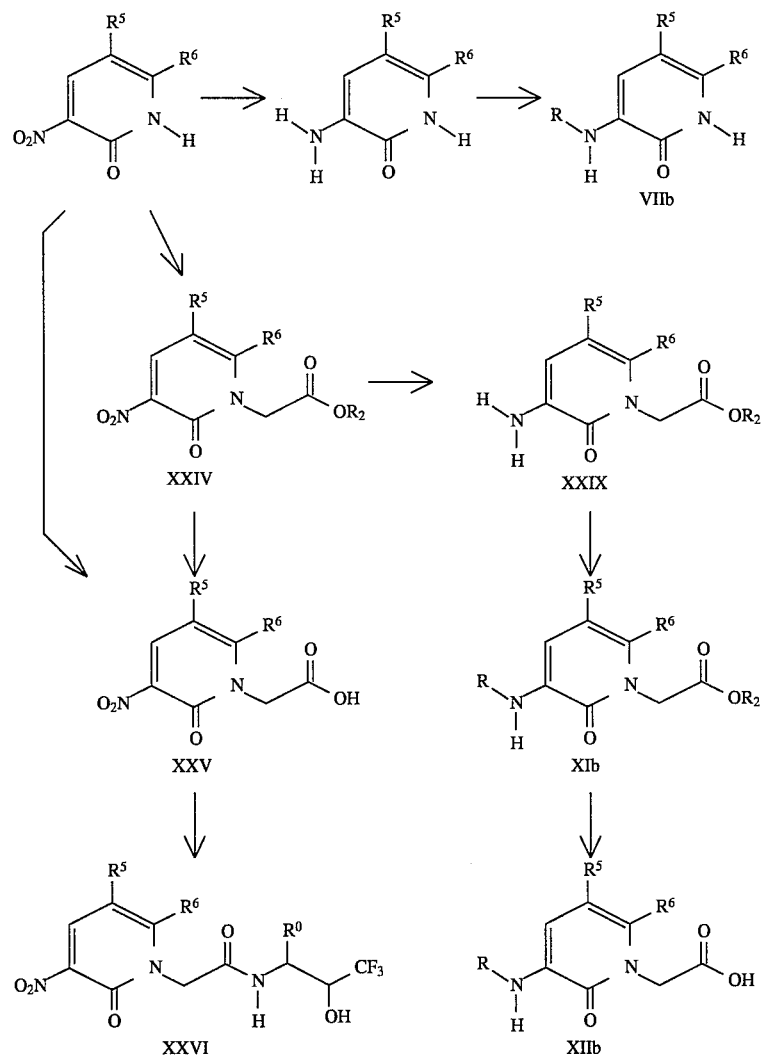

-continued
SCHEME IV

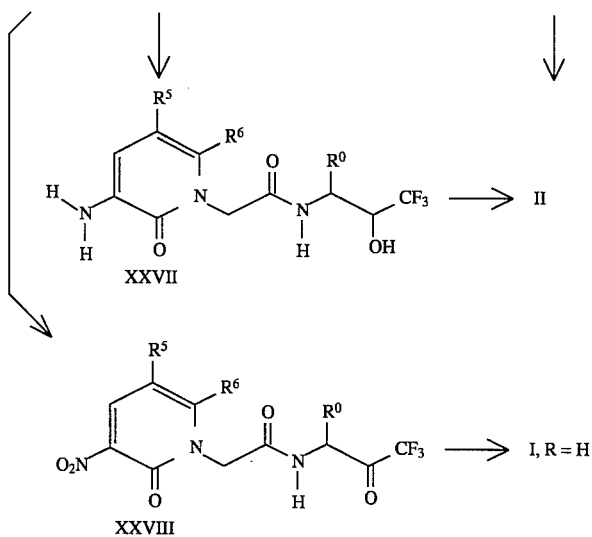

What is claimed is:
1. A compound of formula I:

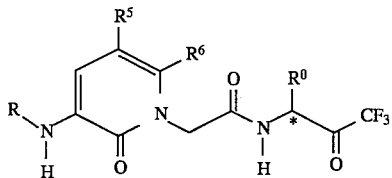

wherein:

$R^0$ is (1–5C)alkyl;

R is hydrogen; or

R is an acyl group of formula A.X.CO- in which A.X- , taken together, is hydrogen, trifluoromethyl, 2,2,2-trifluoroethoxy, amino, methoxyamino, 2,2,2-trifluoroethylamino, RbRcN.O—, RaOCONH—, $R^1$SO$_2$NH—, RaOCO—, RbRcNCO— or RaCO—; or R is an acyl group of formula A.X.C(=J)- in which J is oxygen or sulfur;

X is a direct bond, imino, oxy or thio; and

A is as defined below or

A is tetrahydropyran-4-yl, 1-methylpiperid-4-yl, or 5-methyl-1,3-dioxacyclohex-5-ylmethyl; or R is a sulfonyl group of formula D.W.SO$_2$— in which D.W-, taken together, is hydroxy, amino, di(lower alkyl)amino, 2,2,2-trifluoroethylamino, 2,2,2-trifluoroethyl, 3,3,3-trifluoropropyl or trifluoromethyl; or W is a direct bond, imino, carbonylimino, oxycarbonylimino or iminocarbonylimino; and D is as defined below; or R is a group G as defined below;

The group A, D or G is (1–6C)alkyl, (3–6C)cycloalkyl, (3–6C)cycloalkyl-(1–3C)alkyl, aryl, aryl(1–3C)alkyl, heteroaryl or heteroaryl(1–3C)alkyl, wherein any heteroaryl is a radical attached via a ring carbon selected from furyl, imidazolyl, tetrazolyl, pyridyl (or its N-oxide), thienyl, pyrimidinyl (or its N-oxide), indolyl, quinolyl (or its N-oxide), thiazolyl and pyrazinyl, and further wherein an aryl or heteroaryl moiety may bear one or more halogeno, nitro, methyl or trifluoromethyl groups and further wherein the group A, D or G may bear one or more substituents selected from a group consisting of hydroxy, lower alkoxy, lower acyloxy, COORa, CH$_2$COORa, CONRbRc, CH$_2$CONRbRc, COO(CH$_2$)$_2$NReRf, cyano, SO $R^1$, CONRdSO$_2R^1$, NReRf, NRgCHO, NRgCOR$^2$, NRgCOOR$^2$, NRhCQNRiRj, NRkSO$_2R^3$, SO$_2$NRlRm, SO$_2$NRnCOR$^4$ and P(O)(ORa)$_2$ in which Q is oxygen or sulfur;

Ra–Rn are independently hydrogen, benzyl or lower alkyl; or, independently, a group NRbRc, NReRf, NRiRj or NRlRm is a cyclic radical selected from a group consisting of 1-pyrrolidinyl, piperidino, morpholino or 1-piperazinyl which may bear a lower alkyl substituent at the 4-position; or, independently, a group NReRf is a cyclic radical selected from a group consisting of 2-pyrrolidinon-1-yl, succinimido, oxazolidin-2-on-3-yl, 2-benzoxazolinon-3-yl, phthalimido and cis-hexahydrophthalimido; and $R^1$–$R^4$ are independently trifhoromethyl, (1–6C)alkyl, (3–6C)cycloalkyl, aryl or heteroaryl, wherein heteroaryl is a radical attached via a ring carbon selected from furyl, imidazolyl, tetrazolyl, pyridyl (or its N-oxide), thienyl, pyrimidinyl (or its N-oxide), indolyl, quinolyl (or its N-oxide), thiazolyl and pyrazinyl, in which the aryl or heteroaryl may bear one or more substituents selected from a group consisting of lower alkyl, hydroxy, lower alkoxy, halogeno or trifluoromethyl; and Each of $R^5$ and $R^6$ is, independently, hydrogen or lower alkyl; or One of $R^5$ and $R^6$ is hydrogen or methyl and the other of $R^5$ and $R^6$ is a radical of formula B.Y- in which B is aryl or heteroaryl, wherein heteroaryl is a radical attached via a ring carbon selected from furyl, imidazolyl, tetrazolyl, pyridyl (or fits N-oxide), thienyl, pyrimidinyl (or its N-oxide), indolyl, quinolyl (or its N-oxide), thiazolyl and pyrazinyl, which aryl or heteroaryl independently may bear one or more of the substituents defined for A, D or G or an aryl or heteroaryl moiety thereof;

Y is a direct bond, methylene, ethylene or trans-vinylene;

provided that no aliphatic carbon is bonded to more than one nitrogen or oxygen, except as part of a cyclic ketal or where the nitrogen bears a carbonyl group; or, for a compound of formula I which is acidic or basic, a pharmaceutically acceptable salt thereof.

2. A compound as claimed in claim 1 wherein $R^0$ is ethyl or isopropyl; D.W-, taken together, is amino, 2,2,2-trifluoroethylamino or 2,2,2-trifluoroethylimino; W is a direct bond or imino; G is (1–3C)alkyl, aryl(1-C)alkyl or heteroaryl(1–2C)alkyl which may bear one or more substituents as defined in claim 1 for G or a part thereof;

(1–6C)alkyl or (1–10C)alkyl is methyl, ethyl, propyl, isopropyl, butyl, isobutyl, t-butyl, pentyl, 3-methylbutyl, 1-ethylpropyl, hexyl or 4-methylpentyl; (3–6C)cycloalkyl is cyclopropyl, cyclopentyl or cyclohexyl; the (1–3C)alkyl portion of (3–6C)cycloalkyl-(1–3C)alkyl, aryl(1–3C)alkyl or heteroaryl(1-3C)alkyl is methylene, ethylene or trimethylene; aryl is phenyl, indenyl, indanyl or naphthyl; lower alkyl is methyl, ethyl, propyl, isopropyl, butyl, isobutyl or t-butyl; lower acyloxy is acetoxy; lower alkoxy is methoxy, ethoxy, propoxy, isoproxy or t-butoxy; halogeno is bromo, chloro or fluoro;

COORa is carboxy or methoxycarbonyl; CONRbRc is carbamoyl or N,N-dimethylcarbamoyl; NRgCHO is formylamino; $NRgCOR^2$ is acetylamino or trifluoroacetylamino; and $CONRdSO_2R^1$ is N-phenylsulfonylcarbamoyl or N-(4-chlorophenylsulfonyl)carbamoyl.

3. A compound as claimed in claim 2 wherein $R^0$ is isopropyl; J is oxygen; X is a direct bond, imino or oxy; A is methyl, ethyl, phenyl, benzyl, phenethyl, pyridyl, thienyl, 5-tetrazolyl, thiazolyl, pyridylmethyl, thenyl, 5-tetrazolylmethyl, 2-(pyridyl)ethyl, 2-(thienyl)ethyl or 2-(thiazolyl)ethyl wherein the phenyl or heteroaryl group may bear one or two halogeno or methyl groups and further wherein the group A may bear a substituent selected from hydroxy, methoxy, t-butoxy, acetoxy, pivaloyloxy, carboxy, methoxycarbonyl, ethoxycarbonyl, carbamoyl, dimethylcarbamoyl, 2-(dimethylamino)ethoxycarbonyl, cyano, methylsulfonyl, phenylsulfonyl, N-methylsulfonylcarbamoyl, N-phenylsulfonylcarbamoyl, amino, dimethylamino, oxazolidin-2-on-3-yl, acetylamino, trifluoroacetylamino, ureido, methylsulfonyl, sulfamoyl, dimethylphosphoryl or diethylphosphoryl; D is methyl, ethyl, isopropyl, tert-butyl, cyclohexyl, phenyl, benzyl, phenethyl, pyridyl, thienyl, 5-tetrazolyl, thiazolyl, quinolyl, pyridylmethyl, thenyl, 5-tetrazolylmethyl, 2-(pyridyl)ethyl, 2-(thienyl)ethyl or 2-(thiazolyl)ethyl wherein the phenyl or heteroaryl group may bear one or two halogeno or methyl groups and further wherein the group D may bear a substituent selected from hydroxy, methoxy, t-butoxy, acetoxy, pivaloyloxy, carboxy, methoxycarbonyl, ethoxycarbonyl, carbamoyl, dimethylcarbamoyl, 2-(dimethylamino)ethoxycarbonyl, cyano, methylsulfonyl, phenylsulfonyl, N-methylsulfonylcarbamoyl, N-phenylsulfonylcarbamoyl, N-(4-chlorophenylsulfonyl)carbamoyl, methylsulfonylamino, amino, dimethylamino, oxazolidin-2-on-3-yl, acetylamino, trifluoroacetylamino, ureido, methylsulfonyl, sulfamoyl, dimethylphosphoryl or diethylphosphoryl; and G is methyl, ethyl, benzyl, phenethyl, pyridyl, pyridylmethyl, thenyl, 5-tetrazolylmethyl, or 2-(pyridyl)ethyl, wherein the phenyl or heteroaryl group may bear one or two halogeno or methyl groups and further wherein the group G may bear a substituent selected from hydroxy, methoxy, acetoxy, carboxy, methoxycarbonyl, ethoxycarbonyl, carbamoyl, dimethylcarbamoyl, phenylcarbamoyl, pyridylcarbamoyl, methylsulfonylamino, amino, dimethylamino, acetylamino, nicotinoylamino, or trifluoroacetylamino.

4. A compound as claimed in claim 1, 2 or 3 wherein R is hydrogen, trifluoroacetyl, hydroxyoxalyl, methoxycarbonyl, ethoxycarbonyl, isopropoxycarbonyl, 4-fluorophenoxycarbonyl, 4-bromophenoxycarbonyl, 4-methoxyphenoxycarbonyl, benzyloxycarbonyl, 4-fluorobenzyloxycarbonyl, 4-pyridylmethoxycarbonyl, 3-methylpyrid-4-ylmethoxycarbonyl, 2,6-dimethylpyrid-4-ylmethoxycarbonyl, 2-pyridylmethoxycarbonyl, 6-methylpyrid-2-ylmethoxycarbonyl, 2-dimethylaminoethoxycarbonyl, acetyl, carbamoylmethylaminocarbonyl, 4-(N-phenylsulfonylcarbamoyl)phenylacetyl, sulfo, aminosulfonyl, dimethylaminosulfonyl, trifluoromethylsulfonyl, methylsulfonyl (which may bear a methoxycarbonyl, carboxy or ethylsulfonyl substituent), methylaminosulfonyl, isopropylaminosulfonyl, butylsulfonyl, butylaminosulfonyl, tert-butylaminosulfonyl, cyclohexylaminosulfonyl, phenylsulfonyl (in which the phenyl may bear a chloro, nitro, amino, acetylamino, trifluoroacetylamino, methoxy, carboxy, N-(4-chlorophenylsulfonyl)carbamoyl, or methylsulfonylamino substituent at the 3- or 4-position), anilino, pyridylsulfonyl, quinolylsulfonyl, benzylsulfonyl (in which the phenyl ring may bear a nitro or amino substituent at the 3- or 4-position), pyridylmethylsulfonyl, 2-(pyridyl)ethylsulfonyl, benzylaminosulfonyl, methyl, ethyl, benzyl, phenethyl or pyridylmethyl.

5. A compound as claimed in any one of claims 1–3 in which $R^5$ is hydrogen and $R^6$ is hydrogen.

6. A compound as claimed in any one of claims 1–3 in which $R^5$ is benzyl, the phenyl ring of which may bear a 3-fluoro, 4-fluoro, 4-trifluoromethyl, 4-methoxycarbonyl, 3-acetoxy, 3-hydroxy, 3-pivaloyloxy, 4-hydroxy, 4-pivaloyloxy, 3-trifluoroacetylamino or 3-amino substituent, and $R^6$ is hydrogen.

7. A compound as claimed in any one of claims 1–3 in which $R^5$ is hydrogen, and $R^6$ is 2-furyl, 2-thienyl, 3-pyridyl or phenyl in which the phenyl may bear one or two halogeno, trifluoromethyl, methyl, hydroxy, methoxy, tert-butoxy, methoxycarbonyl or carboxy substituents.

8. A compound as claimed in claim 7 wherein $R^6$ is phenyl, 4-fluorophenyl or 2-thienyl.

9. A compound as claimed in claim 1 selected from (a) 2-[3-[3-(carbamoylmethyl)ureido]-2-oxo-6-phenyl-1,2-dihydro -1-pyridyl]-N-(3,3,3-trifluoro-1-isopropyl-2-oxopropyl)acetamide;

(b) 2-(3-amino-2-oxo-6-phenyl-1,2-dihydro-1-pyridyl)-N-(3,3,3-trifluoro-1-isopropyl -2-oxopropyl)acetamide;

(c) 2-[3-(4-bromophenoxycarbonylamino)-2-oxo-6-phenyl-1,2-dihydro -1-pyridyl]-N-(3,3,3-trifluoro-1-isopropyl-2-oxopropyl)acetamide;

(d) 2-[3-(4-aminophenylacetyl)-2-oxo-6-phenyl-1,2-dihydro -1-pyridyl]-N-(3,3,3-trifluoro-1-isopropyl-2-oxopropyl)acetamide;

(e) 2-[2-oxo-6-(2-thienyl)-3-trifluoroacetylamino-1,2-dihydro -1-pyridyl]-N-(3,3,3-trifluoro-1-isopropyl-2-oxopropyl)acetamide;

(f) 2-[3-(4-acetylaminophenylsulfonyl)-2-oxo-6-phenyl-1,2-dihydro -1-pyridyl]-N-(3,3,3-trifluoro-1-isopropyl-2-oxopropyl)acetamide;

(g) 2-[3-[N-(4-chlorophenylsulfonyl)carbamoyl]-2-oxo-6-phenyl -1,2-dihydro-1-pyridyl]-[-(3,3,3-trifluoro-1-isopropyl-2oxopropyl)acetamide;

(h) 2-[3-[N-(2-methylphenylsulfonyl)carbamoyl]-2-oxo-6-phenyl -1,2-dihydro-1-pyridyl]-N-(3,3,3-trifluoro-1-isopropyl-2oxopropyl)acetamide; and (i) 2-[3-(2,2,2-trifluoroethoxycarbonylamino-2-oxo-6-phenyl -1,2-dihydro-1-pyridyl]-N-(3,3,3-trifluoro-1-isopropyl-2oxopropylpropyl)acetamide;

or a pharmaceutically acceptable salt thereof.

10. A salt as claimed in claim 1 selected from (a) for an acidic compound of formula I, an alkalai metal salt, an alkaline earth metal salt, an aluminum salt, an ammonium salt, or a salt made from an organic base which affords a pharmaceutically acceptable cation; and (b) for a basic compound of formula I, an acid-addition salt made with an acid which provides a pharmaceutically acceptable anion.

11. A method of administering a compound of claim 1, or a pharmaceutically acceptable salt thereof, to a human is need thereof for treatment of a disease or condition in which human leukocyte elastase is implicated.

12. A pharmaceutical composition comprising a compound as defined in claim 1, or a pharmaceutically acceptable salt thereof, and a pharmaceutically acceptable diluent or carrier.

13. A compound of formula II:

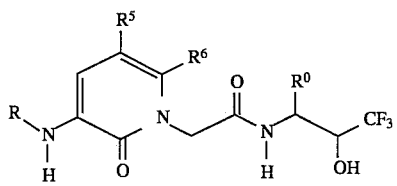

(II)

wherein $R^0$, $R^5$ and $R^6$ are defined as in claim 1 or a salt thereof.

14. A compound of formula Vb:

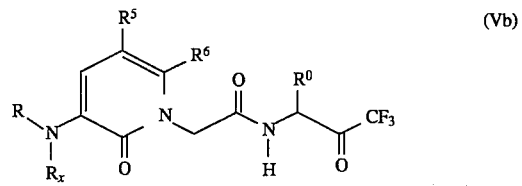

(Vb)

wherein R has a value defined for G in claim 1; $R^0$, $R^5$ and $R^6$ are defined as in claim 1; and Rx is a group which protects and activates a primary amino group for substitution, or a salt thereof.

* * * * *